United States Patent
Neuteboom et al.

(10) Patent No.: US 9,540,627 B2
(45) Date of Patent: Jan. 10, 2017

(54) METHODS AND COMPOSITIONS FOR ISOLATING, IDENTIFYING AND CHARACTERIZING MONOCOT PLASTIDIC ACCASE HERBICIDE TOLERANT MUTATIONS USING A MODEL SYSTEM

(71) Applicant: BASF SE, Ludwigshafen (DE)

(72) Inventors: Leon Neuteboom, Morrisville, NC (US); Sherry R. Whitt, Raleigh, NC (US); John A. McElver, Durham, NC (US); Jill M. Stevenson-Paulik, Cary, NC (US); S. Luke Mankin, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/357,691

(22) PCT Filed: Nov. 13, 2012

(86) PCT No.: PCT/US2012/064831
§ 371 (c)(1),
(2) Date: May 12, 2014

(87) PCT Pub. No.: WO2013/074524
PCT Pub. Date: May 23, 2013

(65) Prior Publication Data
US 2014/0377835 A1    Dec. 25, 2014

Related U.S. Application Data

(60) Provisional application No. 61/559,618, filed on Nov. 14, 2011.

(51) Int. Cl.
*C12N 9/00* (2006.01)
*C12N 15/82* (2006.01)

(52) U.S. Cl.
CPC ............. *C12N 9/93* (2013.01); *C12N 15/8274* (2013.01); *C12Y 604/01002* (2013.01); *C12Y 604/01* (2013.01)

(58) Field of Classification Search
None
See application file for complete search history.

(56) References Cited

U.S. PATENT DOCUMENTS 5,925,805 A * 7/1999 Ohlrogge ................. C12N 9/93
435/419
6,306,636 B1    10/2001 Haselkorn et al.

OTHER PUBLICATIONS

Powles et al., Resistance and World Grains, CRC Press (2001), Boca Raton Florida, pp. 31-33.*
Beetham et al., "A Tool for Functional Plant Genomics: Chimeric RNA/DNA Oligonucleotides Cause In Vivo Gene-Specific Mutations," Proc Natl Acad Sci USA, vol. 96, pp. 8774-8778, 1999.
Chugh, A. and Eudes, F., "Study of Uptake of Cell Penetrating Peptides and Their Cargoes in Permeabilized Wheat Immature Embryos," FEBS J. vol. 275, pp. 2403-2414, 2008.

(Continued)

*Primary Examiner* — Alexander Kim
(74) *Attorney, Agent, or Firm* — Mark S. Scott

(57) ABSTRACT

The present invention relates compositions and methods for identifying, isolating, and characterizing herbicide tolerant mutations in monocot plastidic acetyl-CoA carboxylases using a model system.

12 Claims, 105 Drawing Sheets

(56) References Cited

OTHER PUBLICATIONS

Delye et al., "An Isoleucine Residue Within the Carboxyltransferase Domain of Multidomain Acetyl-Coenzyme A Carboxylase is a Major Determinant of Sensitivity to Aryloxyphenoxypropionate but not to Cyclohexanedione Inhibitors," Plant Physiol, vol. 132, pp. 1716-1723, 2003.

Delye et al., "Molecular Bases for Sensitivity to Acetyl-Coenzyme A Carboxylase Inhibitors in Black-Grass," Plant Physiol, vol. 137, pp. 794-806, 2005.

Gietz et al., "Improved Method for High Efficiency Transformation of Intact Yeast Cells," Nucl Acids Res, vol. 20, p. 1425, 1992.

Hasslacher et al., "Acetyl-CoA Carboxylase from Yeast is an Essential Enzyme and is Regulated by Factors that Control Phospholipid Metabolism," J Biol Chem, vol. 268, No. 15, pp. 10946-10952, 1993.

Joachimiak et al., "Wheat Cytosolic Acetyl-CoA Carboxylase Complements an ACC1 Null Mutation in Yeast," Proc Natl Acad Sci USA, vol. 94, No. 18, pp. 9990-9995, 1997.

Liu et al., "Single-Site Mutations in the Carboxyltransferase Domain of Plastid Acetyl-CoA Carboxylase Confer Resistance to Grass-Specific Herbicides," Proc Natl Acad Sci USA, vol. 104, No. 9, pp. 3627-3632, 2007.

Mumberg et al., "Yeast Vectors for the Controlled Expression of Heterologous Proteins in Different Genetic Backgrounds," Gene, vol. 156, pp. 119-122, 1995.

Nikolau et al., "Plant Biotin-Containing Carboxylases," Arch Biochem Biophys, vol. 414, pp. 211-222, 2003.

Nikolskaya et al., "Herbicide Sensitivity Determinant of Wheat Plastid Acetyl-CoA Carboxylase is Located in a 400-Amino Acid Fragment of the Carboxyltransferase Domain," Proc Natl Acad Sci USA, vol. 96, No. 25, pp. 14647-14651, 1999.

Podkowinski et al., Expression of Cytosolic and Plastid Acetyl-Coenzyme A Carboxylase Genes in Young Wheat Plants, Plant Physiol, vol. 131, No. 2, pp. 763-772, 2003.

Schneiter et al., A Yeast Acetyl Coenzyme A Carboxylase Mutant Links Very-Long-Chain Fatty Acid Synthesis to the Structure and Function of the Nuclear Membrane-Pore Complex, Mol Cell Biol, vol. 16, pp. 7161-7172, 1996.

Shivrain et al., Gene Flow Between Clearfield® Rice and Red Rice, Crop Protection, vol. 26, pp. 349-356, 2007.

Somers, D.A., "Aryloxyphenoxypropionate and Cyclohexanedione-Resistant Crops," In: Duke SO (Editor), Herbicide-Resistant Crops Agricultural, Environmental, Economic, Regulatory and Technical Aspects, CRC Press, New York, pp. 175-187, 1996.

Tong et al., Systematic Genetic Analysis with Ordered Arrays of Yeast Deletion Mutants, Science, vol. 294, No. 5550, pp. 2364-2368, 2001.

Tong, A.H.Y. and Boone, C., "Synthetic Genetic Array Analysis in *Saccharomyces cerevisiae*," Methods Mol Biol, vol. 313, pp. 171-192, 2006.

Varanasi, A.V., "Assessment of Acetyl-CoA Carboxylase Mutations Using Partial Gene Replacement in Yeast," Proquest Dissertations and Theses: The Science and Engineering Collection, 2008.

International Search Report and Written Opinion for application No. PCT/US2012/064831, filed Nov. 13, 2012.

International Preliminary Report on Patentability for application No. PCT/US2012/064831, filed Nov. 13, 2012.

* cited by examiner

Figure 2C

```
ctagtttctagagcgcggccggccgaccggcggtgagctgagctcagttttgttcctcagtttagtgagggttaattgcgcgcttggcgtaatcatggtcatagctgtttcctgtgtgaaattgttatcgctcacaattccacacaacatagaagccggaagcataaa
gtgtaaagcctggggtgcctaatgagtgagctaactcacattaattgcgttgcgctcactgcccgctttccagtcgggaaacctgtcgtgccagctgcattaatgaatcggccaacgcgcggggagaggcggtttgcgtattgggcgctcttccgcttcct
cgctcactgactcgctgcgctcggtcgttcggctgcggcgagcggtatcagctcactcaaaggcggtaatacggttatccacagaatcaggggataacgcaggaaagaacatgtgagcaaaaggccagcaaaaggccaggaaccgtaaaaaggcc
gcgttgctggcgtttttccataggctccgcccccctgacgagcatcacaaaaatcgacgctcaagtcagaggtggcgaaacccgacaggactataaagataccaggcgtttccccctggaagctccctcgtgcgctctcctgttccgaccctgccgcttac
cggatacctgtccgcctttctcccttcgggaagcgtggcgctttctcatagctcacgctgtaggtatctcagttcggtgtaggtcgttcgctccaagctgggctgtgtgcacgaaccccccgttcagcccgaccgctgcgccttatccggtaactatcgtcttg
agtccaacccggtaagacacgacttatcgccactggcagcagccactggtaacaggattagcagagcgaggtatgtaggcggtgctacagagttcttgaagtggtggcctaactacggctacactagaagaacagtatttggtatctgcgctctgctga
agccagttaccttcggaaaaagagttggtagctcttgatccggcaaacaaaccaccgctggtagcggtggtttttttgtttgcaagcagcagattacgcgcagaaaaaaaggatctcaagaagatcctttgatcttttctacggggtctgacgctcagtg
gaacgaaaactcacgttaagggattttggtcatgagattatcaaaaaggatcttcacctagatccttttaaattaaaaatgaagttttaaatcaatctaaagtatatatgagtaaacttggtctgacagttaccaatgcttaatcagtgaggcacctatctc
agcgatctgtctatttcgttcatccatagttgcctgactccccgtcgtgtagataactacgatacgggagggcttaccatctggccccagtgctgcaatgataccgcgagacccacgctcaccggctccagatttatcagcaataaaccagccagccgga
agggcgagcgcagaagtggtcctgcaactttatccgcctccatccagtctattaattgttgccgggaagctagagtaagtagttcgccagttaatagtttgcgcaacgttgttgccattgctacaggcatcgtggtgtcacgctcgtcgtttggtatggctt
cattcagctccggttcccaacgatcaaggcgagttacatgatcccccatgttgtgcaaaaaagcggttagctccttcggtcctccgatcgttgtcagaagtaagttggccgcagtgttatcactcatggttatggcagcactgcataattctcttactgtcat
gccatccgtaagatgcttttctgtgactggtgagtactcaaccaagtcattctgagaatagtgtatgcggcgaccgagttgctcttgcccggcgtcaatacgggataataccgcgccacatagcagaactttaaaagtgctcatcattggaaaacgttctt
cggggcgaaaactctcaaggatcttaccgctgttgagatccagttcgatgtaacccactcgtgcacccaactgatcttcagcatcttttactttcaccagcgtttctgggtgagcaaaaacaggaaggcaaaatgccgcaaaaaagggaataagggcga
cacggaaatgttgaatactcatactcttcctttttcaatattattgaagcatttatcagggttattgtctcatgagcggatacatatttgaatgtatttagaaaaataaacaaataggggttccgcgcacatttccccgaaaagtgccacctgacgtctttca
tcagttctataaaaataattaatttaattttaatattttaatataaattaaattaaattaatttaatttaatatgttaatcattaaatataaattaaatctgtagagtacctttattcatattttaatataatataaatactaatttcatttaataaatatataatataaattaaatactgacaagttttgatgagc
ttcctctcaggtattgtaatgccgaattgttctcattcgtcgtaactccttttaccttcaggtatattatttgaagcatttatcagggttattgtctcatgagcggatacatattttcgagaatcttgaatcaatataaaaatctgtagagtacggccctttaccta
atttttaaccttttgtttatatttttttcttcttttcagctttttgatacaatctttaaattataatttcatcagtacaatttaaattaaaattaaacataaaaattaaactgatcttcatactacgtgtattcatgccagccaacctcaatctttctcttcaaatttgattcttgattaag
gagcagacaaagccccgtcaggcgcgcagcggtgttgccaacagaaggaagcaaagcgaagggtgctggtgccatcagcagctgtaacatcatgccatcagctgcatcagaaaagcggtcaccatcaatcatacactcagcagaaaccgctcctctctctctctctctctctccctctcccatttcgttcttttagtgcacctcgttacacaagattactctgtacccactccttaaccactaccacgcatcaggacatattaagaacgttcacctcacacactccagcgaaaagacaaacgcggggaaggaaggaatcgcatcggcgtttcaagctccagatcccatggccctccaacaatgacccatcagttcagaaggaacaacatggcctcatgcactgaggcactgcttgcacgaaagcagacaaacatctgccaccagctgcaacaggtacctatttgtcaaagtcgccgatggccctgcggccccctgcacacatattccagtcctaggtcattcagccatcgagaaacgcgggcccgatgccccggcgaccatacagacaactcccatagacttaatgattggctgcgtgtggcccaactggagacccaagttggaacaagactactcataggttgac
acgttctaccgcggcccgctccctcgactcaaaaatcatgctcctgattaattaccccagaaataaggctacaaaaactaatgcattattcccaccattataccagggatccaagttctcagtgcgcagtgacattaccaatgattgtattggcccactataggg
cgaattgggtaccgggccccccctcgaggtcgacggtatcgataagcttgatatcgaattcctgcagcccgggggatccactagttctagagcggccgccaccgcggtggagctccagcttttgttccctttagtgagggttaattgcgcgcttggcg
tactccagcttttgttccctttagtgagggttaattgcgcgcttggcgtaatcatggtcatagctgtttcctgtgtgaaattgttatccgctcacaattccacacaacatacgagccggaagcataaagtgtaaagcctggggtgcctaatgagtgagctaac
tcacattaattgcgttgcgctcactgcccgctttccagtcgggaaacctgtcgtgccagctgcattaatgaatcggccaacgcgcggggagaggcggtttgcgtattgggcgctcttccgcttcctcgctcactgactcgctgcgctcggtcgttcggctg
cggcgagcggtatcagctcactcaaaggcggtaatacggttatccacagaatcaggggataacgcaggaaagaacatgtgagcaaaaggccagcaaaaggccaggaaccgtaaaaaggccgcgttgctggcgtttttccataggctccgcccccc
tgacgagcatcacaaaaatcgacgctcaagtcagaggtggcgaaacccgacaggactataaagataccaggcgtttccccctggaagctccctcgtgcgctctcctgttccgaccctgccgcttaccggatacctgtccgcctttctcccttcgggaa
gcgtggcgctttctcatagctcacgctgtaggtatctcagttcggtgtaggtcgttcgctccaagctgggctgtgtgcacgaaccccccgttcagcccgaccgctgcgccttatccggtaactatcgtcttgagtccaacccggtaagacacgacttat
cgccactggcagcagccactggtaacaggattagcagagcgaggtatgtaggcggtgctacagagttcttgaagtggtggcctaactacggctacactagaagaacagtatttggtatctgcgctctgctgaagccagttaccttcggaaaaagagttg
gtagctcttgatccggcaaacaaaccaccgctggtagcggtggtttttttgtttgcaagcagcagattacgcgcagaaaaaaaggatctcaagaagatcctttgatcttttctacggggtctgacgctcagtggaacgaaaactcacgttaagggatttt
ggtcatgagattatcaaaaaggatcttcacctagatccttttaaattaaaaatgaagttttaaatcaatctaaagtatatatgagtaaacttggtctgacagttaccaatgcttaatcagtgaggcacctatctcagcgatctgtctatttcgttcatccat
agttgcctgactccccgtcgtgtagataactacgatacgggagggcttaccatctggccccagtgctgcaatgataccgcgagacccacgctcaccggctccagatttatcagcaataaaccagccagccggaagggccgagcgcagaagtggtcctg
caactttatccgcctccatccagtctattaattgttgccgggaagctagagtaagtagttcgccagttaatagtttgcgcaacgttgttgccattgctacaggcatcgtggtgtcacgctcgtcgtttggtatggcttcattcagctccggttcccaacgatca
aggcgagttacatgatcccccatgttgtgcaaaaaagcggttagctccttcggtcctccgatcgttgtcagaagtaagttggccgcagtgttatcactcatggttatggcagcactgcataattctcttactgtcatgccatccgtaagatgcttttctgtga
ctggtgagtactcaaccaagtcattctgagaatagtgtatgcggcgaccgagttgctcttgcccggcgtcaatacgggataataccgcgccacatagcagaactttaaaagtgctcatcattggaaaacgttcttcggggcgaaaactctcaaggatct
taccgctgttgagatccagttcgatgtaacccactcgtgcacccaactgatcttcagcatcttttactttcaccagcgtttctgggtgagcaaaaacaggaaggcaaaatgccgcaaaaaagggaataagggcgacacggaaatgttgaatactcatac
tcttcctttttcaatattattgaagcatttatcagggttattgtctcatgagcggatacatatttgaatgtatttagaaaaataaacaaataggggttccgcgcacatttccccgaaaagtgccacctgacgtctaagaaaccattattatcatgacattaacc
tataaaaataggcgtatcacgaggccctttcgtcttcaagaa
```

Figure 2C-Continued cacttggaagttcaactgttgtgcgataagcatgttgctgtctttgcattctagagattgctgctgttgttcgttccatcttgagactgttgctccatctgaacaagctgtagaag
attggctaagtgcgttcattacgtttggtcgctgcatattggtgctactgttgactactggctgtctcatggaaactggtagtactacttcctgagttgaaccaagattgcaagttgaacatccagttactactttcctgaatggattgctgagattaattgccagctgctcaagttgttg
ttggtatggagttccttatacaatattccgagatcgtggttccaacaaccatgagttgctgatgtgagtggaggttacgatcagaagattccgagttggcaacaagttgcagtgcaaccaagttcgatttggataagctcaatctgtttaagcctaaggtcattgcgttgctgt
tagagtgacttcgaagatctgatgtggtttccaagcctactctgtagagtgaggttgaattcagttcagtcgagtgaggaaatccaaatgttgggctactctcgttaaatcggtggtctattcacgagttctcgactcacaattcggtcatgtttcgttt
cggtgaattctagatctctggctattgccaatatggtcttggttgaaggaaatccaatcaggacaaatgttgattacactggattgtctgtttggtggtgttgttttgaatcgtgaatgctgaatcggagaaacaagattcaccactggtggttgattctagg
attgcaatgagagttagacagaagaccaccatgttactgtcttggttgtggtttgttacgaagttcctagttcactgattactctttgagaatgaagctgaaattcactctttgagaatgaccacctaagcacatccttttggtcaattctgact
gtcactctgaatatcgaaggttcagtacactatcgaaactgttgaatgaacgttcactactttgagaatgaagctgaaattcactctttgagatgatgcaattggttgatgaagaattccagttatt
acgctgaaactgaagctgctggaactagattgctgattaatgttgactaagaacttcctgttgctgtatcctcaagttgttgtgtatctccatgcagttcttcgtgatgttctcattgatgctgataccatacgc
agaagttgaggttatgaagatgtgatgccacttggttcattgttgcagctctggttatccattcgtctgttcaatctgctagatgcagatcgcagattgcatataatggttgcagactggtcagaacttccagtaagttgtgcagactggtcaagaacttcctgaattgccattctt
ctttccaaagttggtccacactggttttggtaaagttcaccaaaagttcgctgctgctgctcactgatttcgtctcactatatattaatgaagttgctcaaggaaacaagattccagctaagttgttgagaggtattatcgaagccaattt
gcaatggcaagaattgatgagttgtttgccaactagatgtcaagtagatcaagaataggaggagtagaatccatcatgctggttagtagcttacgaaggaggatgagaatccatcatgctggttagtaatactttctgacaa
ggcttactgctcgaaaaggatagagttactaatgaaagatggttgaccattgatgtcctggttacgattgttacgttttctcatcaaggtttgcctgttaccatactctgcttacgacaa
tatccaatcgatgtttattgagaagattgagactcaacatgctaaggacttgaacaatgttgtttacattgtttctctcatcaagttgctgagaaagttgttccaaatccatcgcttacagagat
caattgattcgttttctgttttgaataatactgttttactcgaacttgttgattgctcttttgggagttcctgagagttcctacacaaggctgttgctcccttggctgtagagaaactttcaaggatctacttcacttcgtggaacacagtttgaaacttactacagaaagttgtacactggt
aagggttccgttagaatcaaggcatagatcagaaggatgagaggtcatgttgcagagtgctttgaaggaaactctccactactgaaggatctaaagatctataccactgaatactaactccataacagttgtactgcagttcactcagaagtgatatccaaatatggaaacttactagcgattatatagctgaagaatatggaaacttactagcgatgatcagaggatcaaggaaagatgatctaccactcctatatgttggggtactcca
ccaatgctcgttgacaagatctactacgaagaagatccaatgttgagactgttcttgagacgattgtgagatcttcatcgagagttgattctctgaagtccaaagtgcagaggttgctcgatgttgaaattgactgagtgtcgctaggaataat
tgattaagaacaagaagagaacaaagatctaatgaatcaatgactcagaagactgtcttcctaccgattaaccagtttattagcaacaggttgttagaggttgcttacttttgctacacttcttgctaaggcaaagtgttctgggtactcca
tccttgatgcgtcgttggaagaaatgctatgaagattcacgaattggttgctagaagactgtggttgcgatagatctacctttgtctttcatcattgttcctgagagttcatcgagagttcagctctgagaaatgctgagaggttgcatcaaagtgaacaactgtcctctatactt
atgctttgcttaagaaatggctatgaagattcacgaattggttgctagagactgtgctagaaatgttgttaccatccaccaaccttgagttcagttgcctgagaggttattattcctgagacgtcactaccattgtgcagagaatgttgttgcagtagcagtggagaattgtacctcctcatact
gcacttgatatttacagagaaatggagaaatgagaaggatctgttgaaactgcttgagaaacgtgctgttagaaaaatcagtgcttgtgcaagatcgttagtctgttgcaaatgcagtaagaatcaggattccacacttgtgaatacccatccacacatgcgagtattactgaagatgctcaggaataat
aggactactactgctacgatttcccattggcttgaacgatatcggatggtttgaagcatagcagaattgttgccagaatcgttatcagagtttggaaaatgttgtcgttccagttcctcaaggtctacgtttacgctgcttcctttgtgatatggttgtgaaaggaggatgagaatgaagaggcagttgtgaagggatgctcttcta
ttagttcaaatgaacagcagccagctgtttgaacgataatcggattttcactgtggctgcacaaatctggtcaagaatcggttattgctgatgaagttgcatacactgtaagctacgttaagctagacgctgttaaggtcctttgctataagcatggtttctcggtccaagagagatctcttctt
cgagctgtcactaatttgcttgcaaggaagttgcatcggtgctgtgctacttggctcaaggtgtcaactggtgcagaaatcgttgctgatgttcaatttggtcaagatcgttattcgtgtgaaggagtggtttgcgtatgatcgcggttgaatgagaaagatgatgtgctccaagagatgattcgagagagatgtctttctt
tgagaagactacgctagaattgactccctgttattgctacttgtagaactgtagaactgttacggtgctttacagcatctaggtccaatactatccgaagacatccactgtagaccaagaagctgttcagaatgttgatcagaattcaatgctgagtaggtcaaatattcatgtttctgcttactcgag
aggctacaaggaacgttcacttgacttcgttactgtagaacttgctcttgtactggtgagaactgtggcaacaatgtgttgtcaacctctgtctttcgatgatatcttggttatacaaagagctattttggagggtgtcaagtcttatcctttgaggtcttcgtcagttctgtggttggtagagtttactc
gtctcataggcaatttggtgtgaccaaagattgtcaacatcaagccgtttgatacttggacttgaacacaagtgttgagctgttgccttcaacttgatcagagtgtctcaatatccagatagttcgtcagttcaaggaagttgtgtccttcagttcactctccgattcaagcttactcaaaccaggttggaagaagttactc
gtatagaccagttgcttacatccgttcagattacttctgcgatccaagaagctaggttgatgatgacagtatccaaggaaggcttaagaggttggtgcattcgattccgttgagcatgttcgataggagttcgtgatgatctgatcagagcgctagaaatgcatgttgatgtgattcaagagaagactctagaggaaactttccttgtacaagttgtggcaattttccaatgtcttgtagatcagctggctcgcagttttccaagattcttgctattccagagcctttccattccagaacctcttagagcgttgttccagattcgaggcttcagttgaaaacttggtcatctcagcatagcaaaatccaggcgcttgctttcatcaggcgaccaccactcctttcaatctggcgctcctgctaaagctctcctggagaccctttccatggccgcagtgatcaaccagccaccaccagcgatcccaagccttcacagccaatcagttctgttcaagatccgcttctagaagccagctcagcactgcctcaggcttttgccaatctcgcgttcgagttcggcttttcagatctcgtgtagtagtcccttgatactcctaatctccatcgtccaatgcgagtttttggactgacaaagactctgttggcatacggacgctagcaccgcaaatcagactgcggcgaggtagacactcaagaggtgctca
aaaataagtgtatacaatttaaagtgactccttagttttaaacgaaaattcttattcttgagtaactccttttcctgtaggtcaggttcttctcagtatagcatgaggtcgctca

Figure 3B

Figure 3B-Continued cacccgctcgatccgccggataggccggtgcctacatcccgagaactcttgcgaccggagggccgcgagggcgtggacgactccaggcaagtgctcggtggcatggcctttgtgagacattcgagggctgg
ccaagaccgtggtgaccggcaggctaaacttgccggtcgtgatccgggtggagacacagacccatgatgcagatcagaccatcccgggtcagctcagtcgatagccgcgagtcgtgccaagacgcaggacaagtggt
tccggactccgccaaccaagacagcccaggccctctgacttcaatcgcaggactcccgcgttcatctcgagggactggagggcagagagatcttcgaggcatcctccaggcgggctccaccatcgtgagaacct
ccgcacctacaaccagccggccttcgtctgtcatcccaatggccgctgaactgagaggccggcgctcatcccaatggccgctgaactgagaggccggcgctggactgcacagaagatcaaccgacccatcgagtgtctacgcggagcgtacggcgaagggcaacgtgcgagccgcaggg
ccttcatcgagatcaagttccgtctcaccagaactcaggactgcatgtcccgctgatccgacccctcatcgatttaaagccaagtgtgacacctcccgacaccaagctccgcaccaagtccccagagagaacatcgaggccagaaca
aagcaactcatgccgctctacaccagatccgccatccgcttcgcggagctgacagacaccctccctccgcatggccccaagggcgtgatcaagaaggtcgtgattgggaggagtccgctgttcttctacagaggactgcgcagacgcatctc
gaggacgtgctcgccaaggagatcaggccgtccgggacgcgagcagttctcccatcaacagcaatgacgtatcaagaagtgtactccgcctccctccgccagtgggacgacgcttcgtggcctgatggacaacccgaga
actacaaggactacatccagtacctcaaggcccagcgcgtgtccagtccctcagcgccgaccttccatgcctgtcctggcagcagcagcagcagcagcagcagcagcagcagcagcagcagcagcaga
gatccgcaaggtcctcggctgagcgccgcttaattaa

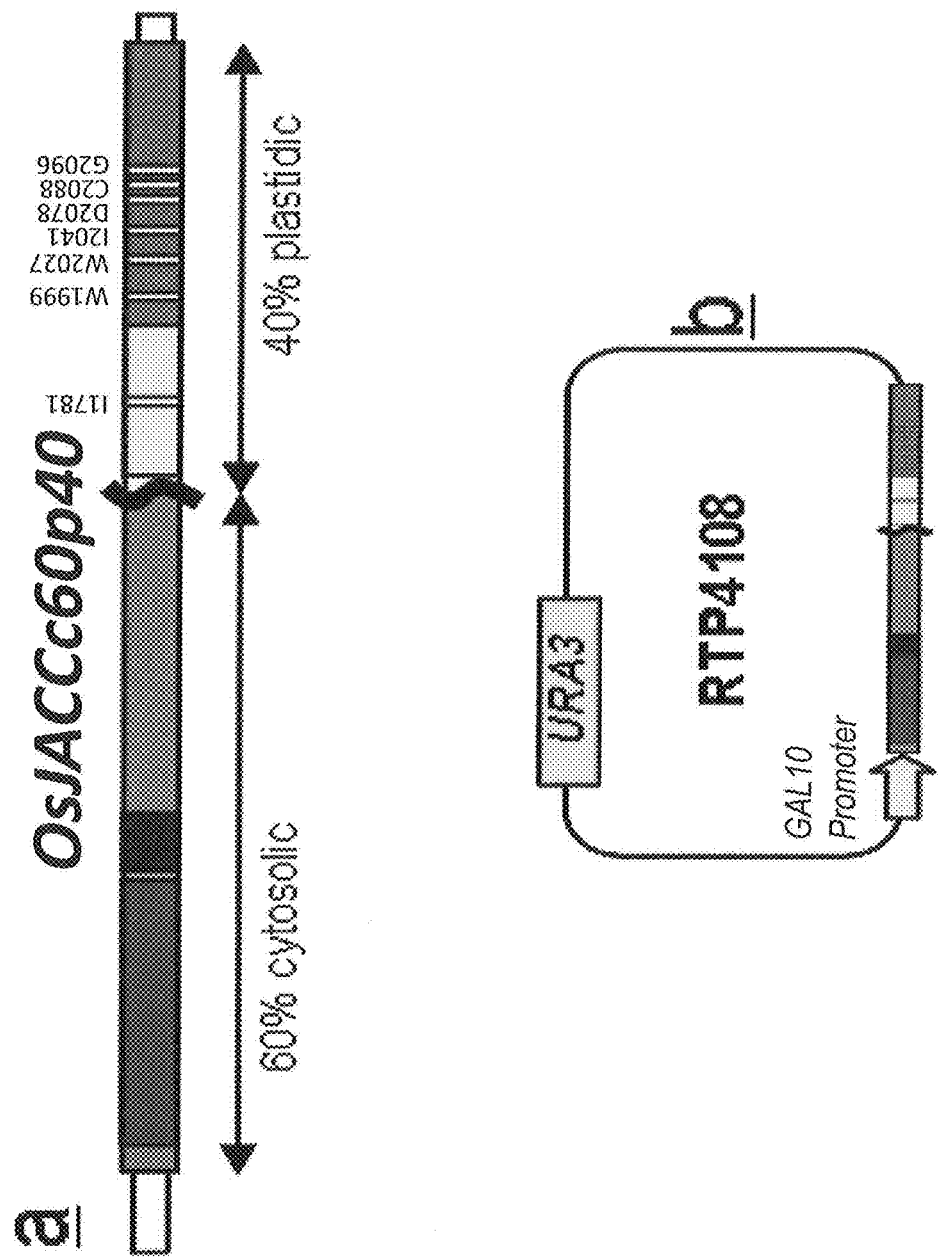
Figure 5-Continued

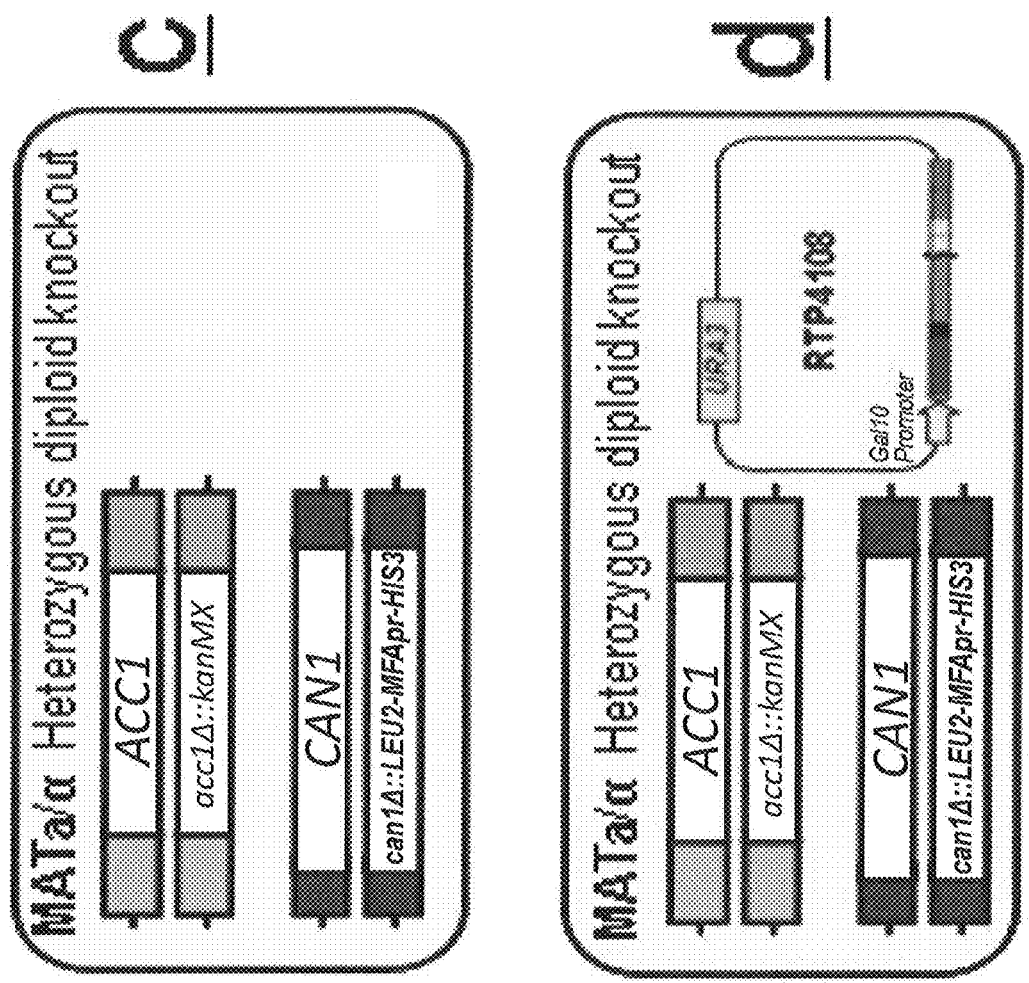
Figure 5-Continued

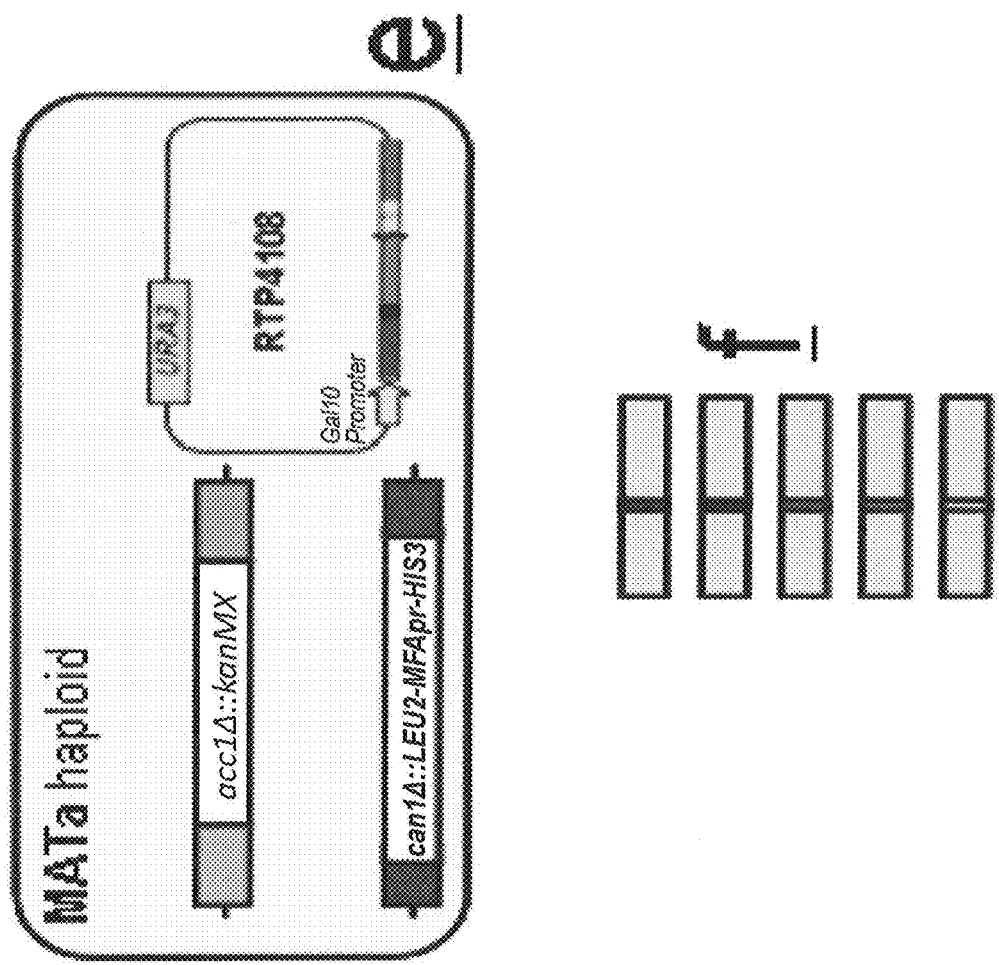
Figure 5-Continued

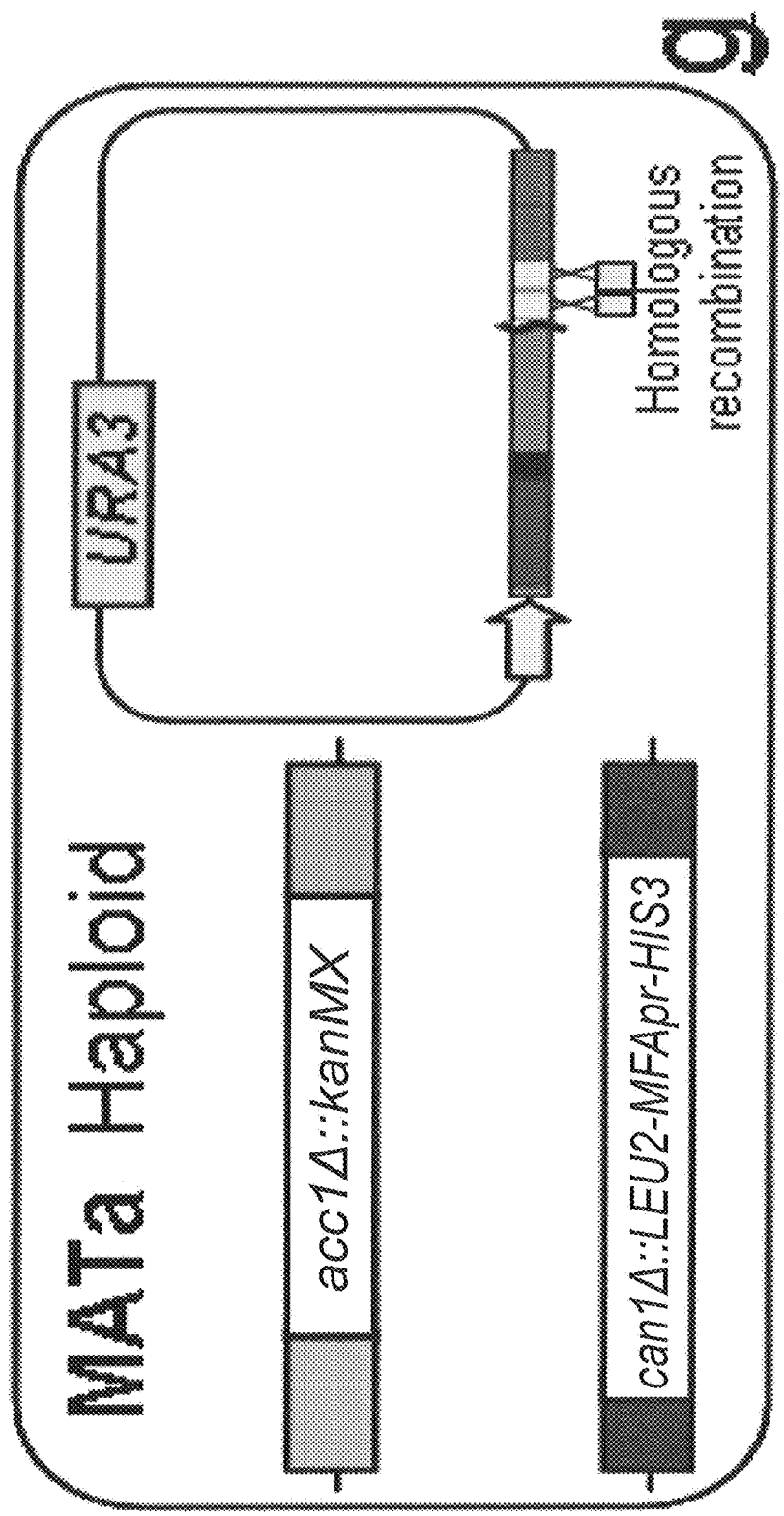
Figure 5-Continued

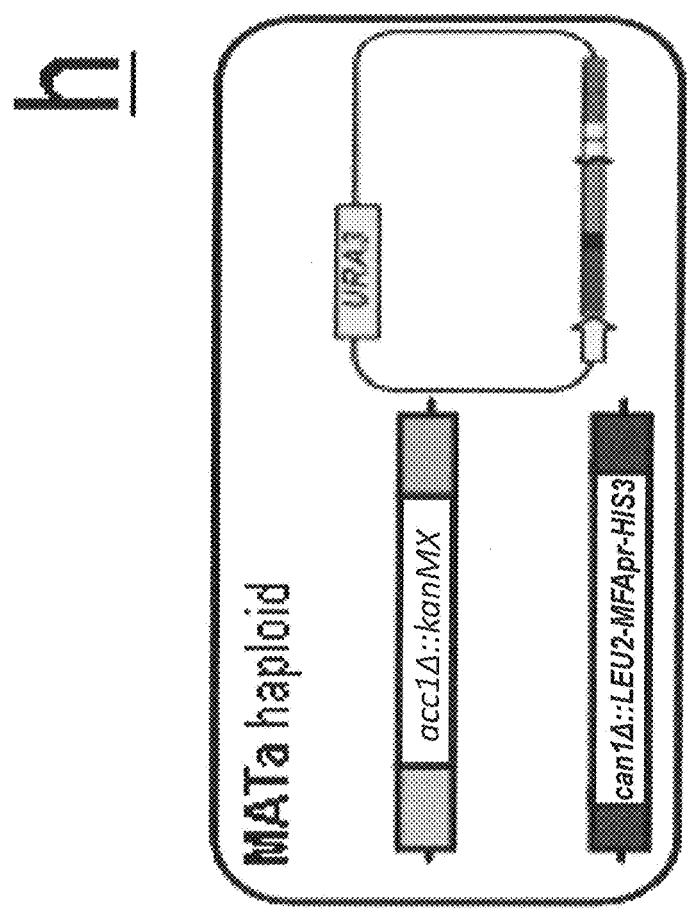
Figure 5-Continued

FIGURE 7
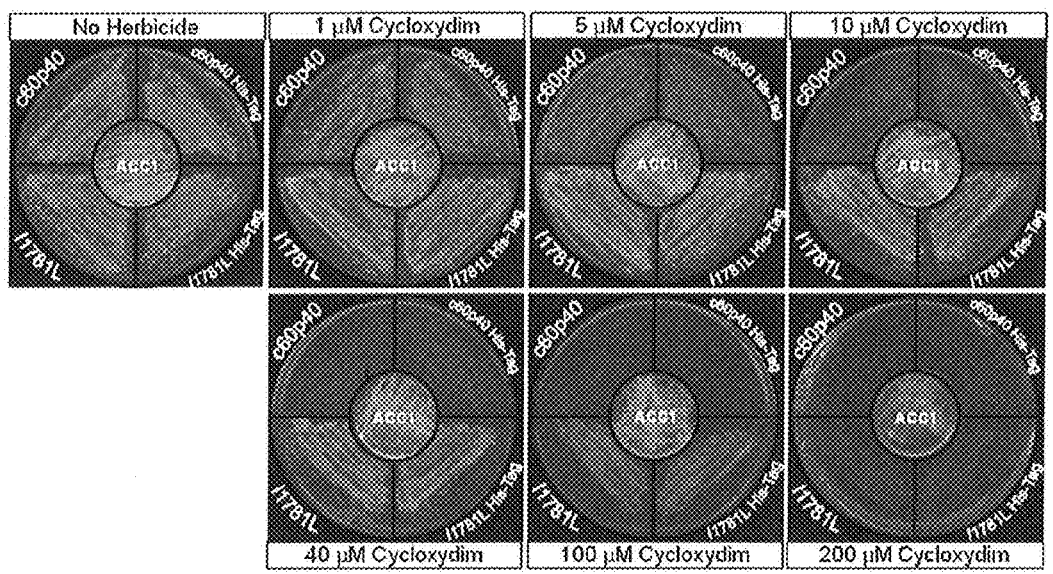
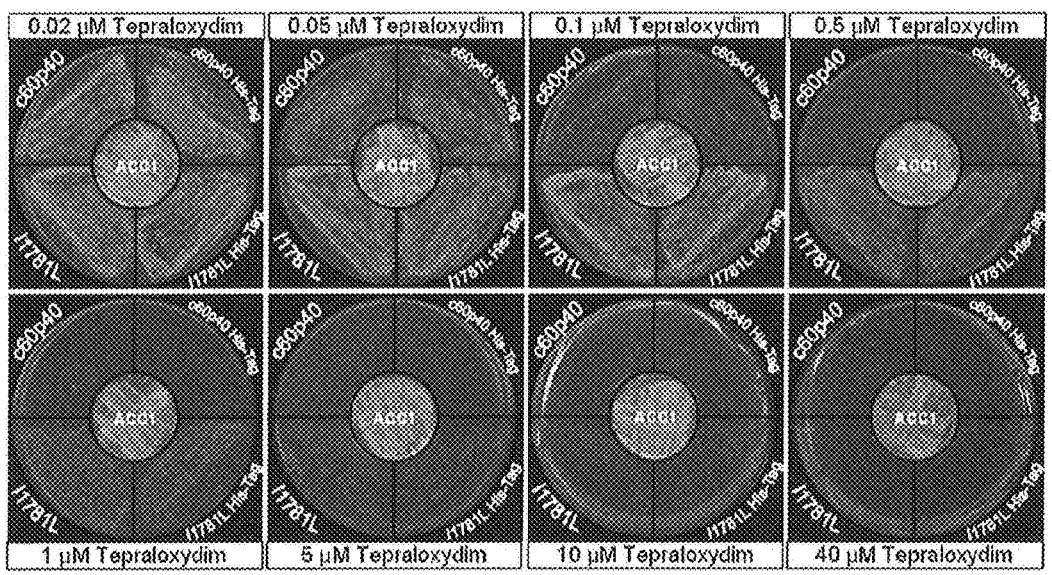

FIGURE 8

| Observed mutation ↓ / Intended mutation + selection (= transformation) → | Wt control C100 | Wt control T1 | I1781X C100 | I1781X T1 | W1999X C100 | W1999X T1 | V2049X C100 | V2049X T1 | V2075X C100 | V2075X T1 | D2078X C100 | D2078X T1 | V2098X C100 | V2098X T1 |
|---|---|---|---|---|---|---|---|---|---|---|---|---|---|---|
| V2098C + C2088W | | | | | | | | | | | | | | 1 |
| V2098S | | | | | | | | | | | | | 2 | 7 |
| V2098P | | | | | | | | | | | | | 2 | 3 |
| V2098H | | | | | | | | | | | | | 1 | 2 |
| V2098G + C2088V | | | | | | | | | | | | | 2 | 2 |
| V2098G + C2088T | | | | | | | | | | | | | 1 | 1 |
| V2098G + C2088S | | | | | | | | | | | | | 1 | 1 |
| V2098G + C2088L | | | | | | | | | | | | | 1 | 1 |
| V2098G + C2088H | | | | | | | | | | | | | | 1 |
| V2098G + C2088G | | | | | | | | | | | | | 1 | 1 |
| V2098G | 2 | 2 | 3 | 4 | 2 | 2 | 3 | 3 | 3 | 2 | 2 | 2 | 25 | 52 |
| V2098A + C2088T | | | | | | | | | | | | | 1 | 1 |
| V2098A + C2088L | | | | | | | | | | | | | 1 | 1 |
| V2098A + C2088K | | | | | | | | | | | | | 1 | |
| V2098A + C2088H | | | | | | | | | | | | | 1 | |
| V2098A + C2088F | | | | | | | | | | | | | | 1 |
| V2098A | | 1 | 3 | 5 | | 1 | 3 | 5 | 1 | | 4 | | 2 | 8 |
| G2096S | 1 | | 2 | | | | 1 | | 2 | | 1 | | | |
| G2096A | 2 | 1 | 6 | 5 | 8 | 2 | 10 | 1 | 4 | | 9 | 1 | 7 | 1 |
| C2088W | | | | | | | 1 | | | | | | | |
| C2088R | 2 | | 1 | 1 | | 1 | | 2 | 2 | 3 | 1 | | 1 | 1 |
| ΔK2080 ΔI2081 | | | | | | | | | | 1 | | | | |
| D2078G + I2041V | | | | | | | | | | | 1 | 1 | | |
| D2078G + C2088G | | | | | | | | | | | 1 | 1 | | |
| D2078G + A2059V | | | | | | | | | | | 1 | 1 | | |
| D2078G + S2079P | | | | 1 | | | | | | | 1 | | | |
| D2078G + E2039G | | | | | | | | | | | 1 | | | |
| D2078T | | | | | | | | | | | 2 | 1 | | |
| D2078G | 4 | 2 | 5 | 2 | 9 | 2 | 18 | 17 | 8 | 1 | 72 | 75 | 6 | 3 |
| V2075M + K2095E | | | | | | | | | | 1 | | | | |
| V2075M + K2080E | | | | | | | | | | 1 | | | | |
| V2075M | | | | | | | | | | 1 | | | | |
| V2075I | 1 | 1 | | | | 1 | | | 1 | | | | | |
| V2075L | | 2 | | 10 | | 9 | | 1 | | 20 | | 8 | | 4 |
| V2049L + V2098A | | | | | | | 1 | 1 | | | | | | |
| V2049T + D2078G | | | | | | | | 4 | 1 | | | | | |
| V2049S + D2078G | | | | | | | 1 | 1 | | | | | | |
| V2049C + M2065T + D2078G | | | | | | | | 1 | | | | | | |
| V2049C + D2078G | | | | | | | | 1 | | | | | | |
| V2049A + D2078G | | | | | | 1 | 1 | 1 | | | | | | |
| V2049F | | | | 1 | | 1 | 1 | 1 | | 2 | | | | |
| W1999G | 2 | 1 | 2 | 2 | 25 | 5 | 4 | 4 | 3 | 2 | 4 | 3 | | 1 |
| I1811N | | | | | | | | | | 1 | | 1 | | |
| A1786P | | | | | | | | | | 1 | | | | |
| A1785G | | | | | | | | | | | | 1 | | |
| I1781L + N1780D | | | | 1 | | | | | | | | | | |
| I1781T | | | | | 1 | | | | | | | | | |
| I1781V | 5 | | 2 | 2 | 1 | | 6 | 1 | 5 | 3 | 1 | 2 | 1 | |
| I1781L | 1 | | 8 | | | | | | 1 | 1 | | | | |

FIGURE 9

| Observed mutation / Intended mutation + selection (= transformation) | I2041X C100 | I2041X T1 | W2027X C100 | W2027X T1 |
|---|---|---|---|---|
| V2098G | 8 | 5 | 1 | 4 |
| V2098A | 4 | 3 |  | 6 |
| G2096S | 1 |  | 1 |  |
| G2096A | 15 | 1 | 8 | 1 |
| C2088W |  |  | 1 |  |
| C2088R | 1 | 1 |  |  |
| ΔK2080 ΔI2081 |  |  | 1 |  |
| D2078G | 8 | 3 | 3 |  |
| V2075I |  | 3 |  | 1 |
| V2075L |  | 11 |  | 13 |
| V2049F |  | 1 |  | 1 |
| W1999G | 2 | 8 | 1 | 5 |
| I1811N |  |  | 1 |  |
| A1785G | 1 |  |  |  |
| I1781T | 1 |  |  |  |
| I1781V | 3 | 3 | 4 | 1 |

FIGURE 11

| Single mutants plated \ Second mutation gained → | +I1781L | +I1781V | +S1792L | +A1837V | +V1864F | +W1999C | +W1999L | +V2049F | +V2049I | +V2075L | +duplV2075 | +D2078G | +D2078G +C2088W | +C2088F | +V2098A | +V2098G |
|---|---|---|---|---|---|---|---|---|---|---|---|---|---|---|---|---|
| I1781L | ■ |  |  |  | 1 |  |  | 10 | 17 | 14 |  |  |  |  | 1 | 1 |
| I1781T |  | ■ |  |  |  |  |  |  |  |  |  |  |  |  |  |  |
| A1785G |  |  |  |  |  |  |  |  |  |  |  | 3 | 1 |  | 2 | 5 |
| A1786P |  |  |  |  |  |  |  |  |  |  |  |  |  |  |  |  |
| W1999G |  |  |  |  | 1 | ■ |  | 4 | 2 |  |  | 14 |  |  |  |  |
| V2049F | 3 | 4 | 1 |  |  |  | 1 | ■ |  |  |  |  |  | 28 |  |  |
| W2074L |  |  |  |  |  |  |  |  |  |  |  |  |  |  |  |  |
| V2075I |  |  |  | 4 | 1 |  |  |  |  | ■ |  |  |  |  |  |  |
| V2075L |  |  |  |  |  |  |  |  |  | ■ |  |  |  |  |  |  |
| V2075M |  |  |  |  |  |  |  |  |  | ■ |  |  |  |  |  |  |
| D2078G |  |  |  |  |  |  |  |  |  |  |  | ■ |  |  |  |  |
| D2078T |  |  |  |  |  |  |  |  |  |  |  | ■ |  |  |  |  |
| ΔK2080I2081 |  |  |  |  |  |  |  |  |  |  |  |  |  |  |  |  |
| C2088R |  |  |  |  |  |  |  |  |  |  |  |  | ■ |  |  |  |
| C2088W |  |  |  |  |  |  |  |  |  |  | 1 | 16 | ■ |  |  |  |
| V2098A |  |  |  |  |  |  |  |  |  |  |  |  |  |  | ■ |  |
| V2098G |  |  |  |  |  |  |  |  |  |  |  |  |  |  |  | ■ |
| V2098H |  |  |  |  |  |  |  |  |  |  |  |  |  |  |  | ■ |
| V2049P |  |  |  |  |  |  |  |  |  |  |  |  |  |  |  | ■ |
| V2098S |  |  |  |  |  |  |  |  |  |  |  |  |  |  |  | ■ |

SEQUENCE LISTING

```
<160> NUMBER OF SEQ ID NOS: 33

<210> SEQ ID NO 1
<211> LENGTH: 630
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
ggatccaact ttgattgact tgaaggctaa gttggaagtt gccaacaaga atggatctgc      60
tgatacgaag tctttgcaag aaaatattga agctagaact aagcaactga tgccattata     120
cacccaaatt gctatcagat tcgctgaatt gcatgatacc tctttgagaa tggctgctaa     180
gggtgttatc aagaaggttg ttgattggga agaatccaga tctttcttct acaagagatt     240
gagaaggaga atttccgaag atgttttggc taaggaaatt agagctgttg ctggtgaaca     300
attctctcat caaccagcta ttgaactgat taagaagtgg tactctgctt ctcatgctgc     360
agaatgggat gatgatgatg ctttcgttgc ttggatggat aacccagaaa actacaagga     420
ctacattcaa tacctgaaag ctcaaagagt gtctcaatct ttgtcctctt tgtctgattc     480
ctcttctgat ctacaagctc taccacaagg tttgtctatg ttgttggata agatggaccc     540
atctagaaga gctcaattgg ttgaagaaat cagaaaggtt ttgggtcatc atcatcatca     600
tcatcatcat catcattgat aagcggccgc                                      630

<210> SEQ ID NO 2
<211> LENGTH: 1169
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: modified_base
<222> LOCATION: (101)..(103)
<223> OTHER INFORMATION: a, c, t, g, unknown or other
<220> FEATURE:
<221> NAME/KEY: modified_base
<222> LOCATION: (755)..(757)
<223> OTHER INFORMATION: a, c, t, g, unknown or other
<220> FEATURE:
<221> NAME/KEY: modified_base
<222> LOCATION: (839)..(841)
<223> OTHER INFORMATION: a, c, t, g, unknown or other
<220> FEATURE:
<221> NAME/KEY: modified_base
```

```
<222> LOCATION: (881)..(883)
<223> OTHER INFORMATION: a, c, t, g, unknown or other
<220> FEATURE:
<221> NAME/KEY: modified_base
<222> LOCATION: (992)..(994)
<223> OTHER INFORMATION: a, c, t, g, unknown or other
<220> FEATURE:
<221> NAME/KEY: modified_base
<222> LOCATION: (1022)..(1024)
<223> OTHER INFORMATION: a, c, t, g, unknown or other
<220> FEATURE:
<221> NAME/KEY: modified_base
<222> LOCATION: (1067)..(1069)
<223> OTHER INFORMATION: a, c, t, g, unknown or other

<400> SEQUENCE: 2
tacctctgtt attgctcaca agatgcaact tgattctggt gaaattagat gggtcattga      60
ttccgttgtt ggtaaggaag atggtttggg agttgaaaat nnncatggtt ctgctgcaat     120
tgcttctgct tactcgagag cttacaagga aacgttcact ttgactttcg ttactggtag     180
aactgttggt attggtgctt acttggctag attgggtatc agatgcatcc aaagacttga     240
tcagcctatt atcttgactg gttactctgc tttgaataag ttgttgggta gagaagttta     300
ctcgtctcat atgcaattgg gtggaccaaa gattatggca acaaatggtg ttgtacactt     360
gactgtttct gatgacttgg aaggtgtctc taatatcctg agatggttgt cttacgttcc     420
agcttacatt ggtggtcctt tgccagttac tactccattg gacccacctg atagaccagt     480
tgcttacata cctgaaaact cttgcgatcc aagagctgca attagaggtg ttgatgactc     540
tcaaggtaag tggcttggtg gcatgttcga taaggattcc ttcgttgaaa ctttcgaagg     600
ttgggctaag actgttgtta ctggtagagc taagctagga ggtattccag ttggtgttat     660
tgcagttgaa acgcaaacta tgatgcaaac tattccagct gacccaggtc aattggattc     720
tagagaacaa agtgttccta gagctggtca agttnnnttc ccagattctg ctacaaagac     780
tgctcaagct tgttggact tcaatcgcga aggtttgcca ttgttcatct ggcaaatnn       840
nagaggtttc tccggaggtc aaagagattt gttcgaaggt nnnttgcaag ctggttctac     900
tatcgtcgaa aacttgagaa cctacaatca accagctttc gtttacattc ctatggctgc     960
tgaattgaga ggtggcgcct gggttgttgt tnnntctaag attaacccgg accgtatcga    1020
annntacgct gaacgtacgg ctaagggtaa tgttttggaa ccacaannnt tgattgaaat    1080
caagttcaga agtgaagaat tgcaagattg catgagtaga ttggatccaa ctttgattga    1140
cttgaaggct aagttggaag ttgccaaca                                     1169

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
ttctcacgtc aagattccac c                                               21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic primer"

<400> SEQUENCE: 4
tactcaccag tttccataga g                                             21

<210> SEQ ID NO 5
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
gtgttgacac cgttcacgtg g                                             21

<210> SEQ ID NO 6
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
caccggagac catttccgtt g                                             21

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
gtttggctcc agaagtacat c                                             21

<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
tcatggtcgc ttctgatctt t                                             21

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tacctctgtt attgctcaca a                                             21

<210> SEQ ID NO 10
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
taaacttctc tacccaacaa c                                              21

<210> SEQ ID NO 11
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ccgttctcta gaactattga c                                              21

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 12
cgacctcatg ctatacctga g                                              21

<210> SEQ ID NO 13
<211> LENGTH: 12335
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
ctagttctag agcggccggc cgccaccgcg gtggagctcc agcttttgtt ccctttagtg      60
agggttaatt gcgcgcttgg cgtaatcatg gtcatagctg tttcctgtgt gaaattgtta    120
tccgctcaca attccacaca acataggagc cggaagcata agtgtaaag cctggggtgc    180 ctaatgagtg aggtaactca cattaattgc gttgcgctca ctgcccgctt tccagtcggg    240
aaacctgtcg tgccagctgc attaatgaat cggccaacgc gcggggagag gcggtttgcg    300
tattgggcgc tcttccgctt cctcgctcac tgactcgctg cgctcggtcg ttcggctgcg    360
gcgagcggta tcagctcact caaaggcggt aatacggtta ccacagaat caggggataa    420 cgcaggaaag aacatgtgag caaaaggcca gcaaaggcc aggaaccgta aaaaggccgc    480
gttgctggcg ttttccata ggctccgccc ccctgacgag catcacaaaa atcgacgctc    540
aagtcagagg tggcgaaacc cgacaggact ataaagatac caggcgtttc ccctggaag    600 ctccctcgtg cgctctcctg ttccgaccct gccgcttacc ggatacctgt ccgcctttct    660
cccttcggga agcgtggcgc tttctcatag ctcacgctgt aggtatctca gttcggtgta    720
ggtcgttcgc tccaagctgg gctgtgtgca cgaacccccc gttcagcccg accgctgcgc    780
cttatccggt aactatcgtc ttgagtccaa cccggtaaga cacgacttat cgccactggc    840
```

```
agcagccact ggtaacagga ttagcagagc gaggtatgta ggcggtgcta cagagttctt    900
gaagtggtgg cctaactacg gctacactag aaggacagta tttggtatct gcgctctgct    960
gaagccagtt accttcggaa aaagagttgg tagctcttga tccggcaaac aaaccaccgc   1020
tggtagcggt ggtttttttg tttgcaagca gcagattacg cgcagaaaaa aaggatctca   1080
agaagatcct ttgatctttt ctacggggtc tgacgctcag tggaacgaaa actcacgtta   1140
agggattttg gtcatgagat tatcaaaaag gatcttcacc tagatccttt taaattaaaa   1200
atgaagtttt aaatcaatct aaagtatata tgagtaaact tggtctgaca gttaccaatg   1260
cttaatcagt gaggcaccta tctcagcgat ctgtctattt cgttcatcca tagttgcctg   1320
actccccgtc gtgtagataa ctacgatacg ggagggctta ccatctggcc ccagtgctgc   1380
aatgataccg cgagacccac gctcaccggc tccagattta tcagcaataa accagccagc   1440
cggaagggcc gagcgcagaa gtggtcctgc aactttatcc gcctccatcc agtctattaa   1500
ttgttgccgg gaagctagag taagtagttc gccagttaat agtttgcgca acgttgttgc   1560
cattgctaca ggcatcgtgg tgtcacgctc gtcgtttggt atggcttcat tcagctccgg   1620
ttcccaacga tcaaggcgag ttacatgatc ccccatgttg tgcaaaaaag cggttagctc   1680
cttcggtcct ccgatcgttg tcagaagtaa gttggccgca gtgttatcac tcatggttat   1740
ggcagcactg cataattctc ttactgtcat gccatccgta agatgctttt ctgtgactgg   1800
tgagtactca accaagtcat tctgagaata gtgtatgcgg cgaccgagtt gctcttgccc   1860
ggcgtcaata cgggataata ccgcgccaca tagcagaact ttaaaagtgc tcatcattgg   1920
aaaacgttct cggggcgaaa actctcaag gatcttaccg ctgttgagat ccagttcgat   1980
gtaacccact cgtgcaccca actgatcttc agcatctttt actttcacca gcgtttctgg   2040
gtgagcaaaa acaggaaggc aaaatgccgc aaaaaaggga ataagggcga cacggaaatg   2100
ttgaatactc atactcttcc tttttcaata ttattgaagc atttatcagg gttattgtct   2160
catgagcgga tacatatttg aatgtattta gaaaaataaa caaatagggg ttccgcgcac   2220
atttccccga aaagtgccac ctgggtcctt ttcatcacgt gctataaaaa taattataat   2280
ttaaattttt taatataaat atataaatta aaaatagaaa gtaaaaaaag aaattaaaga   2340
aaaaatagtt tttgttttcc gaagatgtaa aagactctag ggggatcgcc aacaaatact   2400 acctttatc ttgctcttcc tgctctcagg tattaatgcc gaattgtttc atcttgtctg   2460
tgtagaagac cacacacgaa aatcctgtga ttttacattt tacttatcgt taatcgaatg   2520
tatatctatt taatctgctt ttcttgtcta ataaatatat atgtaaagta cgcttttgt   2580 tgaaattttt taaacctttg tttatttttt tttcttcatt ccgtaactct tctaccttct   2640
ttatttactt tctaaaatcc aaatacaaaa cataaaaata aataaacaca gagtaaattc   2700
ccaaattatt ccatcattaa aagatacgag gcgcgtgtaa gttacaggca agcgatccgt   2760
cctaagaaac cattattatc atgacattaa cctataaaaa taggcgtatc acgaggccct   2820
ttcgtctcgc gcgtttcggt gatgacggtg aaaacctctg acacatgcag ctcccggaga   2880
cggtcacagc ttgtctgtaa gcggatgccg ggagcagaca agcccgtcag ggcgcgtcag   2940
cgggtgttgg cgggtgtcgg ggctggctta actatgcggc atcagagcag attgtactga   3000
gagtgcacca taccacagct tttcaattca attcatcatt ttttttttat tcttttttt   3060 gatttcggtt tctttgaaat ttttttgatt cggtaatctc cgaacagaag gaagaacgaa   3120
ggaaggagca cagacttaga ttggtatata tacgcatatg tagtgttgaa gaaacatgaa   3180
attgcccagt attcttaacc caactgcaca gaacaaaaac ctgcaggaaa cgaagataaa   3240
```

```
tcatgtcgaa agctacatat aaggaacgtg ctgctactca tcctagtcct gttgctgcca    3300
agctatttaa tatcatgcac gaaaagcaaa caaacttgtg tgcttcattg gatgttcgta    3360
ccaccaagga attactggag ttagttgaag cattaggtcc caaaatttgt ttactaaaaa    3420
cacatgtgga tatcttgact gatttttcca tggagggcac agttaagccg ctaaaggcat    3480
tatccgccaa gtacaatttt ttactcttcg aagacagaaa atttgctgac attggtaata    3540
cagtcaaatt gcagtactct gcgggtgtat acagaatagc agaatgggca gacattacga    3600
atgcacacgg tgtggtgggc ccaggtattg ttagcggttt gaagcaggcg gcagaagaag    3660
taacaaagga acctagaggc cttttgatgt tagcagaatt gtcatgcaag ggctccctat    3720
ctactggaga atatactaag ggtactgttg acattgcgaa gagcgacaaa gatttttgtta   3780 tcggctttat tgctcaaaga gacatggggt gaagagatga aggttacgat tggttgatta    3840
tgacacccgg tgtgggttta gatgacaagg gagacgcatt gggtcaacag tatagaaccg    3900
tggatgatgt ggtctctaca ggatctgaca ttattattgt tggaagagga ctatttgcaa    3960
agggaaggga tgctaaggta gagggtgaac gttacagaaa agcaggctgg gaagcatatt    4020
tgagaagatg cggccagcaa aactaaaaaa ctgtattata agtaaatgca tgtatactaa    4080
actcacaaat tagagcttca atttaattat atcagttatt accctatgcg gtgtgaaata    4140
ccgcacagat gcgtaaggag aaaataccgc atcaggaaat tgtaaacgtt aatattttgt    4200
taaaattcgc gttaaatttt tgttaaatca gctcattttt taaccaatag gccgaaatcg    4260
gcaaaatccc ttataaatca aaagaataga ccgagatagg gttgagtgtt gttccagttt    4320
ggaacaagag tccactatta aagaacgtgg actccaacgt caaagggcga aaaccgtct     4380 atcagggcga tggcccacta cgtgaaccat caccctaatc aagttttttg gggtcgaggt    4440
gccgtaaagc actaaatcgg aaccctaaag ggagccccg atttagagct tgacggggaa     4500
agccggcgaa cgtggcgaga aaggaaggga agaaagcgaa aggagcgggc gctagggcgc    4560
tggcaagtgt agcggtcacg ctgcgcgtaa ccaccacacc cgccgcgctt aatgcgccgc    4620
tacagggcgc gtcgcgccat tcgccattca ggctgcgcaa ctgttgggaa gggcgatcgg    4680
tgcgggcctc ttcgctatta cgccagctgg cgaaggggg atgtgctgca aggcgattaa    4740
gttgggtaac gccagggttt tcccagtcac gacgttgtaa aacgacggcc agtgagcgcg    4800
cgtaatacga ctcactatag ggcgaattgg gtacgtaccg gccccccct cgactcaaaa     4860 atcatcgctt cgctgattaa ttaccccaga aataaggcta aaaaactaat cgcattatca    4920
tcctatggtt gttaatttga ttcgttcatt tgaaggtttg tggggccagg ttactgccaa    4980
tttttcctct tcataaccat aaaagctagt attgtagaat ctttattgtt cggagcagtg    5040
cggcgcgagg cacatctgcg tttcaggaac gcgaccggtg aagacgagga cgcacggagg    5100
agagtcttcc ttcggagggc tgtcacccgc tcggcggctt ctaatccgta cttcaatata    5160
gcaatgagca gttaagcgta ttactgaaag ttccaaagag aaggtttttt taggctaaga    5220
taatggggct ctttacattt ccacaacata aagtaagat tagatatgga tatgtatatg    5280
gatatgtata tggtggtaat gccatgtaat atgattatta aacttctttg cgtccatcca    5340
aaaaaaaagt aagaattttt gaaggcgcg ccaccatgga aggatcttac caaatgaacg     5400
ggattttgaa cggcatgtca aactctagac atccatcttc tccatcagaa gttgatgagt    5460
tctgtaaggc tttgggtggt gattctccga ttcattctgt tttggtcgct aataatggta    5520
tggctgctgt taagttcatg agatctatca gaacttgggc tttggaaact ttcggtactg    5580
```

```
aaaaggctat cttgttggtt gcaatggcta ctccagaaga cttgaagatt aatgctgaac     5640
acattaggat tgctgatcaa ttcgttgagg ttccaggagg tacaaacaat aacaactacg     5700
ctaatgtcca attgattgtg gagattgctg aaagaaccca tgtttctgct gtttggccag     5760
gatggggaca tgcttctgaa aatccagaac ttccagatgc tttgaaggaa aaggggatta     5820
tcttcttggg tccaccatct gctgctatgg ctgctttggg agataagata ggatcttcct     5880
tgattgctca agctgctgga gttcctactc taccatggtc tggttctcac gtcaagattc     5940
caccagaaag ctgcaattct atcccagaag aaatgtatag atctgcttgc gtttctacaa     6000
ctgaagaagc tgttgcttct tgccaagttg tcggttaccc agctatgatc aaagcttctt     6060
ggggaggtgg tggtaagggt attagaaagg tgcacaatga tgatgaagtt agagctttgt     6120
ttaaacaagt tcaaggagaa gttccaggtt ctccaatttt catcatgaag gttgcttcac     6180
aatctagaca cttggaagtt caactgttgt gcgataagca tggtaatgtt gctgctttgc     6240
attctagaga ttgctctgtt caaagaaggc atcaaaagat aatcgaagaa ggtcctatta     6300
ctgttgctcc atctgagact gttaaggagt tggaacaagc tgctagaaga ttggctaagt     6360
gcgttcatta cgttggtgct gctacttgtt agtacttgta ctctatggaa actggtgagt     6420
actacttcct tgagttgaac ccaagattgc aagttgaaca tccagttact gaatggattg     6480
ctgagattaa tttgccagct gctcaagttg ttgttggtat gggagttcct ttatacaata     6540
ttcctgagat cagaagattc tacgtatgg aacatggtgg aggttacgat gcttggagaa     6600
agatttctgc agttgcaacc aagttcgatt tggataacgc tcaatctgtt aagcctaagg     6660
gtcattgcgt tgctgttaga gtgacttctg aagatcctga tgatggtttc aagcctactt     6720
ctggtagagt ggaagagttg aatttcaagt ctaagccaaa tgtttgggcg tacttctctg     6780
ttaaatctgg tggtgctatt cacgagttct ctgactcaca attcggtcat gttttcgctt     6840
tcggtgaatc tagatccttg gctattgcca atatggtctt gggtttgaag gaaatccaaa     6900
tcagaggtga aatcaggaca aatgtggatt acactgtcga tttgttgaat gctgctgaat     6960
acagagaaaa caagattcac actggttggt tggattctag gattgcaatg agagttagag     7020
cagaaagacc accatggtac ttgtctgttg ttggtggtgc tttgtacgaa gcttcttcta     7080
gatcttcttc tgttgtcact gattacgttg gttacttgtc taagggtcaa ataccaccta     7140
agcacatctc tttggttaat ctgactgtca ctctgaatat cgaaggttct aagtacacta     7200
tcgaaactgt tagaagaggt cctagatctt acactttgag aatgaacggt tctgaaatcg     7260
aagctgaaat tcactctttg agagatggtg gtttgttgat gcaattggat ggaaattctc     7320 acgttatttta cgctgaaact gaagctgctg gaactagatt gctgattaat ggtagaactt     7380
gcttgttgca aaaggaacat gatccatcta agttgttggc tgatactcca tgcaagttgc     7440
tgagattctt ggttgctgat ggttctcatg ttgatgctga taccatac gcagaagttg     7500 aggttatgaa gatgtgtatg ccattgttgt tgccagcttc tggtgttatc catttcgtta     7560
tgccagaagg tcaagctatg caagctgcag atctgattgc tagattggat ttggatgatc     7620
catcttctgt tagaagagct gaaccatttc atggtacttt cccaaagttg ggtccaccaa     7680
ctgctgtttc tggtaaggtt caccaaaagt tcgctgcttc tgtcaattct gctcacatga     7740
ttttggctgg atacgagcat aatattaatg aagttgtgca agacttgctg aattgcttgg     7800
attctcctga attgccattc ttgcaatggc aagaattgat gagtgttttg gcaactagat     7860
tgcctaagga cttgagaaac gaattggatg gaaagtacaa ggaatacgag ttgaattctg     7920
acttcaggaa gaacaaggat ttcccagcta agttgttgag aggtattatc gaagccaatt     7980
```

```
tggcttactg ctctgaaaag gatagagtta ctaatgaaag attggttgaa ccattgatgt    8040
ccttggttaa gtcttacgaa ggaggtagag aatctcatgc tagagtggtt gttaagtcct    8100
tgttcgaaga gtacttgtct gttgaagaac tattctctga caatatccaa tctgatgtta    8160
ttgagagatt gagacttcaa catgctaagg acttggaaaa ggttgtttac attgttttct    8220
ctcatcaagg tgttaggact aagaacaagc tgatcttgag attgatggaa gctttggttt    8280
acccaaatcc atctgcttac agagatcaat tgattcgttt ctctggtttg aataatactg    8340
tttactctga acttgctttg aaagcttctc aattgttgga acacactaag ttgtctgagt    8400
tgagaacttc aatcgctaga tctttgtctg aattggaaat gttcactgaa gaaggtgaaa    8460
gagtgtctac tccaagaaga aagatggcta ttaatgagag aatggaggat ttggttggtg    8520
ctcctttggc tgttgaagat gctttggttg ctttgttcga tcattctgat ccaactttgc    8580
aaagaagagt tgtcgaaact tacatcagaa ggttgtacca accatacttg gttaagggtt    8640
cggttagaat gcaatggcat agatctggtt tgattgcttt gtgggagttc tctgaggaac    8700
atatcaagca gagaaatgga caagatgcta tgtccttgaa gcaacaagtt gaagatcctg    8760
aggaaaagag atggggagtt atggttgtta ttaagtcctt gcagtacttg tcttctgcta    8820
ttgatgctgc tttgaaggaa acttctcact acaaggctgg tgctggtaac gtttccaatg    8880
gtaactcagc ttcttcgtct catgggaata tgctacatat cgctttggtt gggattaata    8940
accaaatgtc tacgttgcaa gattctggag atgaagatca agctcaggaa aggatcaaca    9000
agatctcaaa gatcttgaag gattctactg tcacttctca cttgaatggt gctggtgtta    9060
gagttgtctc ttgcattatt caaagagatg aaggtagacc acctatgaga cattccttcc    9120
aatggtctgt tgacaagatc tactacgaag aagatccaat gttgagacat gttgaaccac    9180
cattgtctac cttcttggaa ctgaataagg ttaatttgga tggttacaac gaagttaagt    9240
acactccatc tagagataga caatggcaca tttacaccct tgattaagaac aagaaggatc    9300
aaagatctaa tgatcagaga ctgttcttga gaacgattgt tagacaacca ggtgttacta    9360
atggtttctt gtctggtaat gtcgataatg aggttggtag agctcaagct tcttcctctt    9420
acacctcttc ttctatttg agatccttga tggctgcttt ggaggaaatt gaacttcatg    9480
ctcacaatga gactgttaga tcttcttact ctcacatgta cctttgcatc ttgagagttc    9540
agcaactgtt cgatttgatt ccgttctcta gaactattga caacgttgga caagatgaag    9600
caactgcatg ctctttgctt aaggaaatgg ctatgaagat tcacgaattg gttggtgcta    9660
gaatgcatca tttgtctgtt tgccaatggg aagttaagct gaagttggat tgcgatggtc    9720
cagcttctgg aacttggaga attgttacca cgaatgttac ctctcatact gcactgttg     9780
atatttacag agaaatggaa gataaggaaa gcagaaagtt ggtttaccat ccagctactc    9840
cagctgctgg tcctttgcat ggtgttgcgt tgaataaccc ataccaacct tgagtgttaa    9900
ttgacttgaa gagatgctct gctaggaata taggactac  ttactgctac gatttcccat    9960
tggctttcga aactgctgtt agaaagtctt ggagttcttc tacttctgga gcttctaagg    10020
gtgttgaaaa tgctcaatgc tacgttaagg ctactgaatt ggttttttgct gataagcatg    10080
gttcttgggg tactccatta gttcaaatgg acagaccagc tggtttgaac gatatcggta    10140
tggttgcttg gactttgaag atgtctacac ctgagttccc ttctggtaga gaaataattg    10200
tcgttgcgaa tgatattact ttcagagctg gttcttcgg tccaagagaa gatgcttct     10260
tcgaagctgt cactaatttg gcttgcgaaa agaagttgcc attgatttac ttggctgcaa    10320
```

```
attctggtgc aagaatcggt attgctgatg aagttaagtc ttgcttcaga gttggttggt    10380
ctgatgatgg ttctcctgaa agaggtttcc aatacatcta cctttctgaa gaagactacg    10440
ctagaattgg tacctctgtt attgctcaca agatgcaact tgattctggt gaaattagat    10500
gggtcattga ttccgttgtt ggtaaggaag atggtttggg agttgaaaat attcatggtt    10560
ctgctgcaat tgcttctgct tactcgagag cttacaagga aacgttcact ttgactttcg    10620
ttactggtag aactgttggt attggtgctt acttggctag attgggtatc agatgcatcc    10680
aaagacttga tcagcctatt atcttgactg ttactctgc tttgaataag ttgttgggta    10740
gagaagttta ctcgtctcat atgcaattgg gtggaccaaa gattatggca acaaatggtg    10800
ttgtacactt gactgtttct gatgacttgg aaggtgtctc taatatcctg agatggttgt    10860
cttacgttcc agcttacatt ggtggtcctt tgccagttac tactccattg acccacctg    10920 atagaccagt tgcttacata cctgaaaact cttgcgatcc aagagctgca attagaggtg    10980
ttgatgactc tcaaggtaag tggcttggtg gcatgttcga taaggattcc ttcgttgaaa    11040
ctttcgaagg ttgggctaag actgttgtta ctggtagagc taagctagga ggtattccag    11100
ttggtgttat tgcagttgaa acgcaaacta tgatgcaaac tattccagct gacccaggtc    11160
aattggattc tagagaacaa agtgttccta gagctggtca agtttggttc ccagattctg    11220
ctacaaagac tgctcaagct ttgttggact tcaatcgcga aggtttgcca ttgttcatct    11280
tggcaaattg gagaggtttc tccggaggtc aaagagattt gttcgaaggt attttgcaag    11340
ctggttctac tatcgtcgaa aacttgagaa cctacaatca accagctttc gtttacattc    11400
ctatggctgc tgaattgaga ggtggcgcct gggttgttgt tgactctaag attaacccgg    11460
accgtatcga atgctacgct gaacgtacgg ctaagggtaa tgttttggaa ccacaaggtt    11520
tgattgaaat caagttcaga agtgaagaat tgcaagattg catgagtaga ttggatccaa    11580
ctttgattga cttgaaggct aagttggaag ttgccaacaa gaatggatct gctgatacga    11640
agtctttgca agaaaatatt gaagctagaa ctaagcaact gatgccatta tacacccaaa    11700
ttgctatcag attcgctgaa ttgcatgata cctctttgag aatggctgct aagggtgtta    11760
tcaagaaggt tgttgattgg gaagaatcca gatctttctt ctacaagaga ttgagaagga    11820
gaatttccga agatgttttg gctaaggaaa ttagagctgt tgctggtgaa caattctctc    11880
atcaaccagc tattgaactg attaagaagt ggtactctgc ttctcatgct gcagaatggg    11940
atgatgatga tgctttcgtt gcttggatgg ataacccaga aaactacaag gactacattc    12000
aatacctgaa agctcaaaga gtgtctcaat ctttgtcctc tttgtctgat tcctcttctg    12060
atctacaagc tctaccacaa ggtttgtcta tgttgttgga taagatggac ccatctagaa    12120
gagctcaatt ggttgaagaa atcagaaagg ttttgggtta ggcggccgcc gaatttctta    12180
tgatttatga ttttttattat taaataagtt ataaaaaaaa taagtgtata caaatttttaa    12240 agtgactctt aggttttaaa acgaaaattc ttattcttga gtaactcttt cctgtaggtc    12300
aggttgcttt ctcaggtata gcatgaggtc gctca                               12335
```

<210> SEQ ID NO 14
<211> LENGTH: 7011
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14

```
ggcgcgccac catgacctcc acccacgtcg ccacactcgg agtcggcgcg caggccccac     60
cacgccacca gaagaagtcc gccggcaccg ccttcgtgtc ctccggctcc tccaggccgt    120
cctaccgcaa gaacggccag aggacccgct ctctccgcga ggagtccaac ggcggcgtgt    180
ccgactccaa gaagctcaac cactccatcc gccaggcct cgccggcatc atcgacctcc     240
cgaacgacgc cgcctccgag gtggacatct cccacggctc cgaggaccca aggggcccaa    300
ccgtgccggg ctcctaccag atgaacggca tcatcaacga cacacacaac ggacggcacg    360
cctctgtctc taaggtggtg gagttctgca cagccctggg ggggaaaaacc ccgatccact    420
ccgtgctcgt ggccaacaac ggcatggctg ctgccaagtt catgcgctct gtgcgcacct    480
gggccaacga caccttkgga tctgagaagg ccatccagct cattgccatg ccaccccgg     540
aggacctccg catcaacgcc gagcacatca ggatcgccga ccagttcgtg gaggtgccag    600
gcggcaccaa caacaacaac tacgccaacg tccagctcat cgtggagatc gccgagagga    660
ccggcgtgtc tgctgtctgg ccaggctggg gccatgcctc cgagaacccc gagctgccgg    720
atgccctcac cgccaagggc atcgtgttcc tcggcccacc ggcctcttct atgcacgcgc    780
tcggcgacaa agtgggctcc gccctcattg cccaggctgc cggcgtgcca acactcgcgt    840
ggagcggctc ccatgtggag gtgccgctgg agtgctgcct cgactccatc ccggacgaga    900
tgtaccgcaa ggcctgcgtg accaccacag aggaggccgt ggcttcttgc caggttgtgg    960
gctacccggc catgatcaag gcctcttggg gcggaggggg aaagggcatc cgcaaggtgc   1020
acaacgacga cgaagtgcgc accctcttca gcaggtcca gggcgaggtc ccaggctccc    1080
cgatcttcat catgcgcctc gccgcccagt ctaggcacct ggaggtccag ctcctctgcg   1140
accagtacgg caacgtggcc gccctccact ccagggactg ctccgtccaa agacggcatc   1200
agaagatcat cgaggagggc ccggtcacag tcgccccacg cgagacagtg aaggagctgg   1260
agcaggccgc tagacggctg gccaaggctg tgggctatgt gggcgctgcc accgtggagt   1320
acctctactc catggagaca ggcgagtact acttcctgga gctgaacccg cgcctccagg   1380
tggagcaccc ggtgaccgag tggatcgccg aggtgaacct cccagccgcc caagtggcag   1440
tgggcatggg catcccgctc tggcagatcc agagatccg ccgcttctac ggcatgaacc   1500
atggaggagg ctacgatctc tggcgcaaga cagccgccct cgccacccc gttcaacttcg   1560
acgaggtgga ctccaagtgg ccgaagggcc actgcgtggc tgtgcgcatc accagcgagg   1620
acccggacga cggcttcaag ccgaccggcg gcaaggtcaa ggaaatctcc ttcaagtcca   1680
agccgaatgt ctgggcctac ttctccgtga agtctggagg cggcatccac gagttcgccg   1740
actcccagtt cggccatgtg ttcgcctacg gcaccacacg ctccgccgcc atcaccacaa   1800
tggccctcgc cctcaaggag gtccagatcc ggggcgagat ccactccaac gtggactaca   1860
ccgtggacct gctcaacgcc tccgacttcc gcgagaacaa gatccacacc ggctggctcg   1920
acaccaggat cgccatgcgc gtccaggccg agaggccgcc gtggtacatc tctgttgtgg   1980
gcggagccct ctacaagacc gtgaccgcca acaccgccac cgtgtccgac tatgtgggct   2040
acctcaccaa gggccagatc ccgccgaagc acatctccct cgtctacacc accgtggccc   2100
tcaacatcga cggcaagaag tacaccatcg acacagtgcg ctccggccat ggctcttacc   2160
gcctccgcat gaacggctct accgtggatg ctaacgtcca gatcctgtgc gacggaggac   2220
tcctcatgca gctcgacggc aactcccacg tcatctacgc cgaggaggag gcctctggca   2280
cccggctcct catcgatggc aagacctgta tgctccagaa cgaccacgac ccgtccaagc   2340
```

```
tcctcgccga gacaccgtgc aagctcctcc gcttcctcgt ggccgatggc gcgcatgtcg    2400
atgctgacgt gccctacgcc gaggtcgagg tgatgaagat gtgtatgccg ctcctcagcc    2460
cagcctccgg cgtgatccac gtcgtgatgt ccgagggcca agccatgcag gctggcgacc    2520
tgatcgctag gctcgacctc gacgaccccga gcgccgtgaa gagggccgag cccttcgagg    2580
acaccttccc gcagatgggc ctcccaatcg ccgcctctgg ccaggtgcac aagctctgcg    2640
ccgcctccct caatgcctgc cgcatgatcc tcgccggcta cgagcacgac atcgacaagg    2700
tggtgcccga gctggtgtac tgcctcgaca ccccagagct gccgttcctc cagtgggagg    2760
agctgatgtc cgtgctcgcc accaggctcc cgcgcaacct caagtccgag ctggagggca    2820
agtacgagga gtacaaggtg aagttcgact ccggcatcat taacgacttc ccggccaaca    2880
tgctccgcgt gatcattgag gagaacctcg cctgcggcag cgagaaggag aaggccacca    2940
acgagcgcct cgtggagccg ctcatgtccc tgctcaagtc ctacgagggc ggcagggagt    3000
cccacgccca cttcgtggtg aagtcccgtg tcgaggagta cctgtacgtg gaggagctgt    3060
tctccgacgg catccagtcc gacgtgattg agagactgcg cctccagcac tccaaggacc    3120
tccagaaggt ggtcgatatt gtcctcagcc accagtctgt gcgcaacaag accaagctca    3180
tcctcaagct catggagtcc ctcgtgtacc cgaacccagc cgcctaccgc gaccagctca    3240
tccgcttctc cagcctcaac cacaaggcct actacaagct cgcgctcaag gcctccgagc    3300
tgctggagca gaccaagctc tccgagctgc gcgccaggat tgcccgctcc ctcagcgagc    3360
tggagatgtt caccgaggag agcaagggcc tctccatgca caagcgcgag atcgccatca    3420
aagaatccat ggaggacctc gtgaccgcc cactcccagt ggaggacgcc ctcatctccc    3480
tcttcgactg ctccgacacc accgttcagc aacgggtgat cgagacttac attgcccgcc    3540
tctaccagcc gcacctcgtg aaggactcca tcaagatgaa gtggatcgag agcggcgtga    3600
tcgctctctg ggagttccct gagggccact cgatgccag gaacggcgga gccgtcctcg    3660
gcgataagag atgggcgcg atggtgatcg tcaagtccct ggagtccctc tccatggcca    3720
tccgcttcgc cctgaaggag acatcccact acacctccag cgagggcaat atgatgcata    3780
tcgctctttt gggcgctgac aacaagatgc acatcatcca ggagtccggc gacgacgccg    3840
acaggatcgc caagctcccg ctcatcctga aggacaacgt gaccgacctc cacgcctccg    3900
gcgtcaagac catctccttc atcgtccagc gcgacgaggc ccgcatgacc atgccccgca    3960
cgttcctctg gagcgacgag aagctctcct acgaggaaga gccgattctc agacatgtgg    4020
agccgccact ctccgccctg ctggagctgg acaagctcaa ggtgaagggc tacaacgaga    4080
tgaagtacac cccgtcccgc gacaggcagt ggcacatcta caccctccgc aacaccgaga    4140
acccgaagat gctccaccgc gtgttcttcc gcacccttgt gaggcagccg tccgtgtcca    4200
acaagttctc cagcggccag atcggcgaca tggaagtggg cagcgccgag gagccactct    4260
ccttcacctc cacctccatc ctgagatctc tcatgaccgc catcgaggag cttgagctgc    4320
acgccatcag gaccggccac tcccacatgt atctccacgt tctcaaggag cagaagctcc    4380
tcgacctcgt cccggtgtcc ggcaacaccg tgctcgatgt gggccaggat gaggccaccg    4440
cctactccct gcttaaggaa atggccatga agatccacga gcttgtcggc gcgaggatgc    4500
accacctctc agtgtgccag tgggaggtga agctcaagct cgactgcgac ggcccagcct    4560
ctggcacatg gcgcatcgtg accaccaacg tgacctccca cacctgcacc gtggacatct    4620
accgcgagat ggaggacaag gagtcccgca agctcgtcta ccaccggcc acaccagccg    4680
ctggcccact ccatggcgtc gccctcaaca acccgtacca gccgctctcc gtgatcgacc    4740
```

```
tcaagcggtg ctccgcccgc aacaaccgca ccacctactg ctacgacttc ccgctcgcct    4800
tcgagactgc tgtgcgcaag tcctggtcct cttccacctc tggcgcgtct aagggcgtgg    4860
agaacgccca gtgctacgtg aaggccacag agctggtgtt cgccgacaag cacggctctt    4920
ggggcactcc tctcgtccag atggatcggc ctgccgggct caacgatatc ggcatggtgg    4980
cctggaccct caagatgtcc accccgagt tcccatctgg ccgcgagatc atcgtggtgg     5040
ccaacgacat caccttcagg gccggcagct tcggcccacg cgaggatgcg ttcttcgagg    5100
ccgtgaccaa cctggcctgc gagaagaagc tcccgctgat ctacctcgcc gccaactccg    5160
gcgcgaggat cggcattgcc gacgaggtga agtcctgctt cagagtgggc tggagcgacg    5220
atggctcccc agagcgcggc ttccagtaca tctacctctc cgaggaggac tacgcccgca    5280
tcggtacctc tgtcatcgct cacaagatgc agctcgattc cggcgagatc cgctgggtga    5340
tcgactccgt tgtgggcaag gaggatggcc tcggcgtcga aacctccat ggcagcgccg     5400 ccattgcctc tgcctactcg agggcctaca aggagacatt caccctcacc ttcgtgaccg    5460
gccgcacagt gggcattggc gcgtacctcg ccaggctggg catccgctgc atccagcgcc    5520
tcgaccagcc gatcatcctc accggctact ccgcgctcaa caagctcctc ggccgcgagg    5580
tgtactcctc ccatatgcag ctcggcggac caaagatcat ggccaccaac ggcgttgtac    5640
acctcacggt gtccgacgac ctggagggcg tgtccaacat cctccgctgg ctgtcctacg    5700
tgccggccta cattggcgga cctcttccgg tgaccacccc gctcgatccg ccggataggc    5760
cggtggccta catccccgag aactcttgcg acccgagggc cgccattagg ggcgtggacg    5820
actcccaggg caagtggctc ggtggcatgt ttgataagga cagctttgtc gagacattcg    5880
agggctgggc caagaccgtg gtgaccggca gggctaaact tggcgggatt ccagtgggcg    5940
tgatcgcggt ggagacacag accatgatgc agaccatccc ggccgacccg ggtcagctcg    6000
atagccgcga gcagtccgtg ccaagagcag acaagtgtg gttcccggac tccgccacca    6060
agacagccca ggccctcctc gacttcaatc gcgagggact cccgctgttc atcctcgcca    6120
actggcgcgg cttttccgga ggccagagag atctcttcga gggcatcctc caggcgggct    6180
ccaccatcgt ggagaacctc cgcacctaca accagccggc cttcgtctac atcccaatgg    6240
ccgctgaact gagaggcggc gcctgggtgg tggtggacag caagatcaac ccggaccgca    6300
tcgagtgcta cgcggagcgt acggcgaagg caacgtgct ggagccgcag ggcctcatcg     6360
agatcaagtt ccgctccgag gaactccagg actgcatgtc ccgcctggat ccgaccctca    6420
tcgatcttaa agccaagctg gaggtggcca acaagaacgg ctccgccgac accaagtccc    6480
tccaggagaa catcgaggcc agaacaaagc aactcatgcc gctctacacc cagatcgcca    6540
tccgcttcgc ggagctgcac gacacctccc tccgcatggc cgccaagggc gtgatcaaga    6600
aggtcgtcga ttgggaggag tcccgctcgt tcttctacaa gagactgcgc agacgcatct    6660
ccgaggacgt gctcgccaag gagatcaggg ccgtcgcggg cgagcagttc tcccatcaac    6720
cagcaatcga gctgatcaag aagtggtact ccgcctccca tgccgccgag tgggacgacg    6780
acgacgcctt cgtggcctgg atggacaacc ccgagaacta caaggactac atccagtacc    6840
tcaaggccca gcgcgtgtcc cagtccctca gcagcctctc cgactcctcc agcgaccttc    6900
aggctcttcc tcagggcctg tccatgctcc tcgacaagat ggaccttct cgcagagcac     6960 agctcgtgga ggagatccgc aaggtcctcg gctgagcggc cgcttaatta a              7011
```

<210> SEQ ID NO 15

```
<211> LENGTH: 318
<212> TYPE: PRT
<213> ORGANISM: Alopecurus myosuroides

<400> SEQUENCE: 15

Ile His Gly Ser Ala Ala Ile Ala Ser Ala Tyr Ser Arg Ala Tyr Glu
1               5                   10                  15

Glu Thr Phe Thr Leu Thr Phe Val Thr Gly Arg Thr Val Gly Ile Gly
                20                  25                  30

Ala Tyr Leu Ala Arg Leu Gly Ile Arg Cys Ile Gln Arg Ile Asp Gln
            35                  40                  45

Pro Ile Ile Leu Thr Gly Phe Ser Ala Leu Asn Lys Leu Leu Gly Arg
    50                  55                  60

Glu Val Tyr Ser Ser His Met Gln Leu Gly Gly Pro Lys Ile Met Ala
65                  70                  75                  80

Thr Asn Gly Val Val His Leu Thr Val Pro Asp Asp Leu Glu Gly Val
                85                  90                  95

Ser Asn Ile Leu Arg Trp Leu Ser Tyr Val Pro Ala Asn Ile Gly Gly
            100                 105                 110

Pro Leu Pro Ile Thr Lys Ser Leu Asp Pro Ile Asp Arg Pro Val Ala
    115                 120                 125

Tyr Ile Pro Glu Asn Thr Cys Asp Pro Arg Ala Ala Ile Ser Gly Ile
130                 135                 140

Asp Asp Ser Gln Gly Lys Trp Leu Gly Gly Met Phe Asp Lys Asp Ser
145                 150                 155                 160

Phe Val Glu Thr Phe Glu Gly Trp Ala Lys Thr Val Val Thr Gly Arg
                165                 170                 175

Ala Lys Leu Gly Gly Ile Pro Val Gly Val Ile Ala Val Glu Thr Gln
            180                 185                 190

Thr Met Met Gln Leu Val Pro Ala Asp Pro Gly Gln Pro Asp Ser His
    195                 200                 205

Glu Arg Ser Val Pro Arg Ala Gly Gln Val Trp Phe Pro Asp Ser Ala
210                 215                 220

Thr Lys Thr Ala Gln Ala Met Leu Asp Phe Asn Arg Glu Gly Leu Pro
225                 230                 235                 240

Leu Phe Ile Leu Ala Asn Trp Arg Gly Phe Ser Gly Gly Gln Arg Asp
                245                 250                 255

Leu Phe Glu Gly Ile Leu Gln Ala Gly Ser Thr Ile Val Glu Asn Leu
            260                 265                 270

Arg Thr Tyr Asn Gln Pro Ala Phe Val Tyr Ile Pro Lys Ala Ala Glu
    275                 280                 285

Leu Arg Gly Gly Ala Trp Val Val Ile Asp Ser Lys Ile Asn Pro Asp
290                 295                 300

Arg Ile Glu Cys Tyr Ala Glu Arg Thr Ala Lys Gly Asn Val
305                 310                 315

<210> SEQ ID NO 16
<211> LENGTH: 318
<212> TYPE: PRT
<213> ORGANISM: Oryza sativa

<400> SEQUENCE: 16

Ile His Gly Ser Ala Ala Ile Ala Ser Ala Tyr Ser Arg Ala Tyr Lys
1               5                   10                  15

Glu Thr Phe Thr Leu Thr Phe Val Thr Gly Arg Thr Val Gly Ile Gly
                20                  25                  30
```

```
Ala Tyr Leu Ala Arg Leu Gly Ile Arg Cys Ile Gln Arg Leu Asp Gln
            35                  40                  45

Pro Ile Ile Leu Thr Gly Tyr Ser Ala Leu Asn Lys Leu Leu Gly Arg
 50                  55                  60

Glu Val Tyr Ser Ser His Met Gln Leu Gly Gly Pro Lys Ile Met Ala
 65                  70                  75                  80

Thr Asn Gly Val Val His Leu Thr Val Ser Asp Asp Leu Glu Gly Val
                 85                  90                  95

Ser Asn Ile Leu Arg Trp Leu Ser Tyr Val Pro Ala Tyr Ile Gly Gly
                100                 105                 110

Pro Leu Pro Val Thr Thr Pro Leu Asp Pro Pro Asp Arg Pro Val Ala
            115                 120                 125

Tyr Ile Pro Glu Asn Ser Cys Asp Pro Arg Ala Ala Ile Arg Gly Val
130                 135                 140

Asp Asp Ser Gln Gly Lys Trp Leu Gly Gly Met Phe Asp Lys Asp Ser
145                 150                 155                 160

Phe Val Glu Thr Phe Glu Gly Trp Ala Lys Thr Val Val Thr Gly Arg
                165                 170                 175

Ala Lys Leu Gly Gly Ile Pro Val Gly Val Ile Ala Val Glu Thr Gln
            180                 185                 190

Thr Met Met Gln Thr Ile Pro Ala Asp Pro Gly Gln Leu Asp Ser Arg
            195                 200                 205

Glu Gln Ser Val Pro Arg Ala Gly Gln Val Trp Phe Pro Asp Ser Ala
        210                 215                 220

Thr Lys Thr Ala Gln Ala Leu Leu Asp Phe Asn Arg Glu Gly Leu Pro
225                 230                 235                 240

Leu Phe Ile Leu Ala Asn Trp Arg Gly Phe Ser Gly Gly Gln Arg Asp
                245                 250                 255

Leu Phe Glu Gly Ile Leu Gln Ala Gly Ser Thr Ile Val Glu Asn Leu
            260                 265                 270

Arg Thr Tyr Asn Gln Pro Ala Phe Val Tyr Ile Pro Met Ala Ala Glu
        275                 280                 285

Leu Arg Gly Gly Ala Trp Val Val Val Asp Ser Lys Ile Asn Pro Asp
    290                 295                 300

Arg Ile Glu Cys Tyr Ala Glu Arg Thr Ala Lys Gly Asn Val
305                 310                 315

<210> SEQ ID NO 17
<211> LENGTH: 318
<212> TYPE: PRT
<213> ORGANISM: Echinochloa crus-galli

<400> SEQUENCE: 17

Ile His Gly Ser Ala Ala Ile Ala Ser Ala Tyr Ser Arg Ala Tyr Glu
1               5                   10                  15

Glu Thr Phe Thr Leu Thr Phe Val Thr Gly Arg Thr Val Gly Ile Gly
            20                  25                  30

Ala Tyr Leu Ala Arg Leu Gly Ile Arg Cys Ile Gln Arg Leu Asp Gln
            35                  40                  45

Pro Ile Ile Leu Thr Gly Phe Ser Ala Leu Asn Lys Leu Leu Gly Arg
 50                  55                  60

Glu Val Tyr Ser Ser His Met Gln Leu Gly Gly Pro Lys Ile Met Ala
 65                  70                  75                  80

Thr Asn Gly Val Val His Leu Thr Val Ser Asp Asp Leu Glu Gly Val
                 85                  90                  95
```

```
                     85                  90                  95
Ser Asn Ile Leu Arg Trp Leu Ser Tyr Val Pro Ala Asn Ile Gly Gly
                100                 105                 110

His Leu Pro Ile Thr Lys Pro Leu Asp Pro Asp Arg Pro Val Ala
                115                 120                 125

Tyr Ile Pro Glu Asn Thr Cys Asp Pro Arg Ala Ala Ile Arg Gly Val
        130                 135                 140

Asp Asp Ser Gln Gly Lys Trp Leu Gly Gly Met Phe Asp Lys Asp Ser
145                 150                 155                 160

Phe Val Glu Thr Phe Glu Gly Trp Ala Lys Thr Val Val Thr Gly Arg
                165                 170                 175

Ala Lys Leu Gly Gly Ile Pro Val Gly Val Ile Ala Val Glu Thr Gln
                180                 185                 190

Thr Met Met Gln Leu Ile Pro Ala Asp Pro Gly Gln Leu Asp Ser His
                195                 200                 205

Glu Arg Ser Val Pro Arg Ala Gly Gln Val Trp Phe Pro Asp Ser Ala
                210                 215                 220

Thr Lys Thr Ala Gln Ala Leu Leu Asp Phe Asn Arg Glu Gly Leu Pro
225                 230                 235                 240

Leu Phe Ile Leu Ala Asn Trp Arg Gly Phe Ser Gly Gly Gln Arg Asp
                245                 250                 255

Leu Phe Glu Gly Ile Leu Gln Ala Gly Ser Thr Ile Val Glu Asn Leu
                260                 265                 270

Arg Thr Tyr Asn Gln Pro Ala Phe Val Tyr Ile Pro Met Ala Gly Glu
                275                 280                 285

Leu Arg Gly Gly Ala Trp Val Val Val Asp Ser Lys Ile Asn Pro Asp
                290                 295                 300

Arg Ile Glu Cys Tyr Ala Glu Arg Thr Ala Lys Gly Asn Val
305                 310                 315

<210> SEQ ID NO 18
<211> LENGTH: 318
<212> TYPE: PRT
<213> ORGANISM: Setaria italica

<400> SEQUENCE: 18

Ile His Gly Ser Ala Ile Ala Ser Ala Tyr Ser Arg Ala Tyr Glu
1               5                   10                  15

Glu Thr Phe Thr Leu Thr Phe Val Thr Gly Arg Thr Val Gly Ile Gly
                20                  25                  30

Ala Tyr Leu Ala Arg Leu Gly Ile Arg Cys Ile Gln Arg Leu Asp Gln
                35                  40                  45

Pro Ile Ile Leu Thr Gly Phe Ser Ala Leu Asn Lys Leu Leu Gly Arg
            50                  55                  60

Glu Val Tyr Ser Ser His Met Gln Leu Gly Gly Pro Lys Ile Met Ala
65                  70                  75                  80

Thr Asn Gly Val Val His Leu Thr Val Ser Asp Leu Glu Gly Val
                85                  90                  95

Ser Asn Ile Leu Arg Trp Leu Ser Tyr Val Pro Ala Asn Ile Gly Gly
                100                 105                 110

Pro Leu Pro Ile Thr Lys Pro Leu Asp Pro Asp Arg Pro Val Ala
                115                 120                 125

Tyr Ile Pro Glu Asn Thr Cys Asp Pro Arg Ala Ala Ile Arg Gly Val
        130                 135                 140
```

```
Asp Asp Ser Gln Gly Lys Trp Leu Gly Gly Met Phe Asp Lys Asp Ser
145                 150                 155                 160

Phe Val Glu Thr Phe Glu Gly Trp Ala Lys Thr Val Val Thr Gly Arg
            165                 170                 175

Ala Lys Leu Gly Gly Ile Pro Val Gly Val Ile Ala Val Glu Thr Gln
        180                 185                 190

Thr Met Met Gln Leu Ile Pro Ala Asp Pro Gly Gln Leu Asp Ser His
    195                 200                 205

Glu Arg Ser Val Pro Arg Ala Gly Gln Val Trp Phe Pro Asp Ser Ala
    210                 215                 220

Thr Lys Thr Ala Gln Ala Leu Leu Asp Phe Asn Arg Glu Gly Leu Pro
225                 230                 235                 240

Leu Phe Ile Leu Ala Asn Trp Arg Gly Phe Ser Gly Gly Gln Arg Asp
            245                 250                 255

Leu Phe Glu Gly Ile Leu Gln Ala Gly Ser Thr Ile Val Glu Asn Leu
        260                 265                 270

Arg Thr Tyr Asn Gln Pro Ala Phe Val Tyr Ile Pro Met Ala Gly Glu
    275                 280                 285

Leu Arg Gly Gly Ala Trp Val Val Val Asp Ser Lys Ile Asn Pro Asp
    290                 295                 300

Arg Ile Glu Cys Tyr Ala Glu Arg Thr Ala Lys Gly Asn Val
305                 310                 315

<210> SEQ ID NO 19
<211> LENGTH: 318
<212> TYPE: PRT
<213> ORGANISM: Sorghum bicolor

<400> SEQUENCE: 19

Ile His Gly Ser Ala Ala Ile Ala Ser Ala Tyr Ser Arg Ala Tyr Glu
1               5                   10                  15

Glu Thr Phe Thr Leu Thr Phe Val Thr Gly Arg Thr Val Gly Ile Gly
            20                  25                  30

Ala Tyr Leu Ala Arg Leu Gly Ile Arg Cys Ile Gln Arg Leu Asp Gln
        35                  40                  45

Pro Ile Ile Leu Thr Gly Phe Ser Ala Leu Asn Lys Leu Leu Gly Arg
    50                  55                  60

Glu Val Tyr Ser Ser His Met Gln Leu Gly Gly Pro Lys Ile Met Ala
65              70                  75                  80

Thr Asn Gly Val Val His Leu Thr Val Pro Asp Asp Leu Glu Gly Val
            85                  90                  95

Ser Asn Ile Leu Arg Trp Leu Ser Tyr Val Pro Ala Asn Ile Gly Gly
        100                 105                 110

Pro Leu Pro Ile Thr Lys Pro Leu Asp Pro Pro Asp Arg Pro Val Ala
    115                 120                 125

Tyr Ile Pro Glu Asn Thr Cys Asp Pro Arg Ala Ala Ile Arg Gly Val
    130                 135                 140

Asp Asp Ser Gln Gly Lys Trp Leu Gly Gly Met Phe Asp Lys Asp Ser
145                 150                 155                 160

Phe Val Glu Thr Phe Glu Gly Trp Ala Lys Thr Val Val Thr Gly Arg
            165                 170                 175

Ala Lys Leu Gly Gly Ile Pro Val Gly Val Ile Ala Val Glu Thr Gln
        180                 185                 190

Thr Met Met Gln Leu Val Pro Ala Asp Pro Gly Gln Leu Asp Ser His
    195                 200                 205
```

```
Glu Arg Ser Val Pro Arg Ala Gly Gln Val Trp Phe Pro Asp Ser Ala
            210                 215                 220

Thr Lys Thr Ala Gln Ala Leu Leu Asp Phe Asn Arg Glu Gly Leu Pro
225                 230                 235                 240

Leu Phe Ile Leu Ala Asn Trp Arg Gly Phe Ser Gly Gly Gln Arg Asp
                245                 250                 255

Leu Phe Glu Gly Ile Leu Gln Ala Gly Ser Thr Ile Val Glu Asn Leu
            260                 265                 270

Arg Thr Tyr Asn Gln Pro Ala Phe Val Tyr Ile Pro Met Ala Gly Glu
            275                 280                 285

Leu Arg Gly Gly Ala Trp Val Val Val Asp Ser Lys Ile Asn Pro Asp
            290                 295                 300

Arg Ile Glu Cys Tyr Ala Glu Arg Thr Ala Lys Gly Asn Val
305                 310                 315

<210> SEQ ID NO 20
<211> LENGTH: 318
<212> TYPE: PRT
<213> ORGANISM: Triticum aestivum

<400> SEQUENCE: 20

Ile His Gly Ser Ala Ala Ile Ala Ser Ala Tyr Ser Arg Ala Tyr Glu
1               5                   10                  15

Glu Thr Phe Thr Leu Thr Phe Val Thr Gly Arg Thr Val Gly Ile Gly
            20                  25                  30

Ala Tyr Leu Ala Arg Leu Gly Ile Arg Cys Ile Gln Arg Thr Asp Gln
            35                  40                  45

Pro Ile Ile Leu Thr Gly Phe Ser Ala Leu Asn Lys Leu Leu Gly Arg
50                  55                  60

Glu Val Tyr Ser Ser His Met Gln Leu Gly Gly Pro Lys Ile Met Ala
65              70                  75                  80

Thr Asn Gly Val Val His Leu Thr Val Ser Asp Leu Glu Gly Val
            85                  90                  95

Ser Asn Ile Leu Arg Trp Leu Ser Tyr Val Pro Ala Asn Ile Gly Gly
            100                 105                 110

Pro Leu Pro Ile Thr Lys Ser Leu Asp Pro Pro Asp Arg Pro Val Ala
            115                 120                 125

Tyr Ile Pro Glu Asn Thr Cys Asp Pro Arg Ala Ala Ile Ser Gly Ile
            130                 135                 140

Asp Asp Ser Gln Gly Lys Trp Leu Gly Gly Met Phe Asp Lys Asp Ser
145                 150                 155                 160

Phe Val Glu Thr Phe Glu Gly Trp Ala Lys Ser Val Val Thr Gly Arg
                165                 170                 175

Ala Lys Leu Gly Gly Ile Pro Val Gly Val Ile Ala Val Glu Thr Gln
            180                 185                 190

Thr Met Met Gln Leu Ile Pro Ala Asp Pro Gly Gln Leu Asp Ser His
            195                 200                 205

Glu Arg Ser Val Pro Arg Ala Gly Gln Val Trp Phe Pro Asp Ser Ala
            210                 215                 220

Thr Lys Thr Ala Gln Ala Met Leu Asp Phe Asn Arg Glu Gly Leu Pro
225                 230                 235                 240

Leu Phe Ile Leu Ala Asn Trp Arg Gly Phe Ser Gly Gly Gln Arg Asp
                245                 250                 255

Leu Phe Glu Gly Ile Leu Gln Ala Gly Ser Thr Ile Val Glu Asn Leu
```

```
                    260                 265                 270
Arg Thr Tyr Asn Gln Pro Ala Phe Val Tyr Ile Pro Lys Ala Ala Glu
                275                 280                 285
Leu Arg Gly Gly Ala Trp Val Val Ile Asp Ser Lys Ile Asn Pro Asp
            290                 295                 300
Arg Ile Glu Phe Tyr Ala Glu Arg Thr Ala Lys Gly Asn Val
305                 310                 315

<210> SEQ ID NO 21
<211> LENGTH: 318
<212> TYPE: PRT
<213> ORGANISM: Zea mays

<400> SEQUENCE: 21

Ile His Gly Ser Ala Ala Ile Ala Ser Ala Tyr Ser Arg Ala Tyr Glu
1               5                   10                  15
Glu Thr Phe Thr Leu Thr Phe Val Thr Gly Arg Thr Val Gly Ile Gly
                20                  25                  30
Ala Tyr Leu Ala Arg Leu Gly Ile Arg Cys Ile Gln Arg Leu Asp Gln
                35                  40                  45
Pro Ile Ile Leu Thr Gly Phe Ser Ala Leu Asn Lys Leu Leu Gly Arg
    50                  55                  60
Glu Val Tyr Ser Ser His Met Gln Leu Gly Gly Pro Lys Ile Met Ala
65                  70                  75                  80
Thr Asn Gly Val Val His Leu Thr Val Pro Asp Asp Leu Glu Gly Val
                85                  90                  95
Ser Asn Ile Leu Arg Trp Leu Ser Tyr Val Pro Ala Asn Ile Gly Gly
                100                 105                 110
Pro Leu Pro Ile Thr Lys Pro Leu Asp Pro Pro Asp Arg Pro Val Ala
            115                 120                 125
Tyr Ile Pro Glu Asn Thr Cys Asp Pro Arg Ala Ala Ile Cys Gly Val
130                 135                 140
Asp Asp Ser Gln Gly Lys Trp Leu Gly Gly Met Phe Asp Lys Asp Ser
145                 150                 155                 160
Phe Val Glu Thr Phe Glu Gly Trp Ala Lys Thr Val Thr Gly Arg
                165                 170                 175
Ala Lys Leu Gly Gly Ile Pro Val Gly Val Ile Ala Val Glu Thr Gln
                180                 185                 190
Thr Met Met Gln Ile Ile Pro Ala Asp Pro Gly Gln Leu Asp Ser His
                195                 200                 205
Glu Arg Ser Val Pro Arg Ala Gly Gln Val Trp Phe Pro Asp Ser Ala
            210                 215                 220
Thr Lys Thr Ala Gln Ala Leu Leu Asp Phe Asn Arg Glu Gly Leu Pro
225                 230                 235                 240
Leu Phe Ile Leu Ala Asn Trp Arg Gly Phe Ser Gly Gly Gln Arg Asp
                245                 250                 255
Leu Phe Glu Gly Ile Leu Gln Ala Gly Ser Thr Ile Val Glu Asn Leu
                260                 265                 270
Arg Thr Tyr Asn Gln Pro Ala Phe Val Tyr Ile Pro Met Ala Gly Glu
                275                 280                 285
Leu Arg Gly Gly Ala Trp Val Val Asp Ser Lys Ile Asn Pro Asp
            290                 295                 300
Arg Ile Glu Cys Tyr Ala Glu Arg Thr Ala Lys Gly Asn Val
305                 310                 315
```

```
<210> SEQ ID NO 22
<211> LENGTH: 26
<212> TYPE: PRT
<213> ORGANISM: Alopecurus myosuroides

<400> SEQUENCE: 22

His Lys Ala Ser Tyr Gln Met Asn Gly Ile Leu Asn Glu Ser His Asn
1               5                   10                  15

Gly Arg His Ala Ser Leu Ser Lys Val Tyr
            20                  25

<210> SEQ ID NO 23
<211> LENGTH: 26
<212> TYPE: PRT
<213> ORGANISM: Oryza sativa

<400> SEQUENCE: 23

Val Pro Gly Ser Tyr Gln Met Asn Gly Ile Ile Asn Glu Thr His Asn
1               5                   10                  15

Gly Arg His Ala Ser Val Ser Lys Val Val
            20                  25

<210> SEQ ID NO 24
<211> LENGTH: 27
<212> TYPE: PRT
<213> ORGANISM: Oryza sativa

<400> SEQUENCE: 24

Met Glu Gly Ser Tyr Gln Met Asn Gly Ile Leu Asn Gly Met Ser Asn
1               5                   10                  15

Ser Arg His Pro Ser Ser Pro Ser Glu Val Asp
            20                  25

<210> SEQ ID NO 25
<211> LENGTH: 27
<212> TYPE: PRT
<213> ORGANISM: Oryza sativa

<400> SEQUENCE: 25

Met Glu Gly Ser Tyr Gln Met Asn Gly Ile Leu Asn Gly Met Ser Asn
1               5                   10                  15

Ser Arg His Pro Ser Ser Pro Ser Glu Val Asp
            20                  25

<210> SEQ ID NO 26
<211> LENGTH: 15
<212> TYPE: PRT
<213> ORGANISM: Triticum aestivum

<400> SEQUENCE: 26

Met Val Glu Ser Asp Gln Ile Asn Gly Arg Met Ser Ser Val Asp
1               5                   10                  15

<210> SEQ ID NO 27
<211> LENGTH: 15
<212> TYPE: PRT
<213> ORGANISM: Triticum aestivum

<400> SEQUENCE: 27

Met Val Glu Ser Asp Gln Ile Asn Gly Arg Met Ser Ser Val Asp
1               5                   10                  15
```

<210> SEQ ID NO 28
<211> LENGTH: 18
<212> TYPE: PRT
<213> ORGANISM: Triticum aestivum

<400> SEQUENCE: 28

Met Val Glu Ser Asp Gln Ile Asn Gly Thr Pro Asn Arg Met Ser Ser
1               5                   10                  15

Val Asp

<210> SEQ ID NO 29
<211> LENGTH: 15
<212> TYPE: PRT
<213> ORGANISM: Saccharomyces cerevisiae

<400> SEQUENCE: 29

Met Ser Glu Glu Ser Leu Phe Glu Ser Ser Pro Gln Lys Met Glu
1               5                   10                  15

<210> SEQ ID NO 30
<211> LENGTH: 56
<212> TYPE: PRT
<213> ORGANISM: Alopecurus myosuroides

<400> SEQUENCE: 30

Ala Gly Ile Ile Asp Leu Pro Lys Glu Gly Ala Ser Ala Pro Asp Val
1               5                   10                  15

Asp Ile Ser His Ile Asp Leu Pro Lys Glu Gly Ala Ser Ala Pro Asp
                20                  25                  30

Val Asp Ile Ser His Gly Ser Glu Asp His Lys Ala Ser Tyr Gln Met
        35                  40                  45

Asn Gly Ile Leu Asn Glu Ser His
    50                  55

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 10xHis tag"

<400> SEQUENCE: 31

His His His His His His His His His His
1               5                   10

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
ctggtgcaag aatcggtatt                                              20

<210> SEQ ID NO 33
<211> LENGTH: 21
<212> TYPE: DNA
<213> ORGANISM: Artificial Sequence
<220> FEATURE:
<221> NAME/KEY: source -continued

```
<223> OTHER INFORMATION: /note="Description of Artificial Sequence:
      Synthetic primer"

<400> SEQUENCE: 33
tgggtgtata atggcatcag t                                         21
```

METHODS AND COMPOSITIONS FOR ISOLATING, IDENTIFYING AND CHARACTERIZING MONOCOT PLASTIDIC ACCASE HERBICIDE TOLERANT MUTATIONS USING A MODEL SYSTEM

RELATED APPLICATIONS

This application is a national stage application under 35 U.S.C. §371 of PCT/US2012/064831, filed Nov. 13, 2012, which claims benefit of U.S. provisional application No. 61/559,618, filed Nov. 14, 2011.

SUBMISSION OF SEQUENCE LISTING

The Sequence Listing associated with this application is filed in electronic format via EFS-Web and hereby incorporated by reference into the specification in its entirety. The name of the text file containing the Sequence Listing is PF70236_SeqList. The size of the text file is 54 KB, and the text file was created on May 8, 2014.

FIELD OF THE INVENTION

The present invention relates compositions and methods for identifying and isolating herbicide tolerant mutations in plant acetyl-CoA carboxylases.

BACKGROUND OF THE INVENTION

Aryloxyphenoxypropionate (FOP) and cyclohexanedione (DIM) herbicides are used post-emergence in dicot crops to control gramineous weeds. Because these herbicides effectively kill most monocotyledonous species at low concentrations, there is low toxicity to non-target organisms. Great potential exists for developing cereal varieties that can be treated post-emergence to control weedy grasses that escape other pre-emergent herbicides treatments (Somers, 1996). Furthermore, these herbicides have low persistence in soil and provide growers with increased flexibility for weed control and crop rotation. For example, red rice is the most pervasive and expensive pest in U.S. rice production (USDA-ARS Dale Bumpers National Rice Research Center 2006 Annual Report) and can serve as a host for rice diseases. CLEARFIELD® Rice is the premier tool for managing red rice in infested areas; however, gene flow between red rice and CLEARFIELD® Rice can result in ~170 FI hybrids/ha (Shivrain et al., 2007). Thus, stewardship guidelines limit CLEARFIELD® Rice market penetration to two out of any four years on any given field. Therefore, the generation of cultivated rice with tolerance to different herbicides will provide farmers CLEARFIELD® with a rotation partner to help manage red rice weed populations.

FOPs and DIMs target the enzyme Acetyl-CoA Carboxylase (EC 6.4.1.2), which catalyzes the first committed step in fatty acid (FA) biosynthesis. ACCase is a biotinylated enzyme that converts acetyl-CoA to malonyl-CoA in a 2-step reversible reaction. The enzyme first carboxylates the biotin group and then the intrinsic carboxytranferase activity transfers the carboxyl group from carboxybiotin to acetyl-CoA (Nikolau et al., 2003). ACCase activity is necessary in the plastid which is the primary site for FA biosynthesis for membrane biogenesis. ACCase activity is also present in the cytosol, where it is involved in the synthesis of very long chain FA and flavonoids (Chugh and Eudes, 2008). The multidomain, cytoplasmic monocot and dicot ACCases are not sensitive to the FOP and DIM herbicides. It is the plastidic form of ACCase that confers the selectivity to this class of herbicides. Dicot plastidic ACCases are naturally insensitive while monocot plastidic ACCases are herbicide-sensitive. The plastidic ACCases are highly expressed in meristematic tissue to feed the high demand for membrane biogenesis in rapidly growing, young seedlings (Podkowinski et al., 2003). This essential role for growth explains the effectiveness of targeting ACCase inhibition in post-emergent weeds.

Since the inception of FOP and DIM use for controlling weeds in world agriculture in the 1980s, there has been an emergence of tolerance amid various weed species. Among these, the most extensively studied are *Alopecurus myosuroides* (blackgrass) and *Avena sterilis* (wild oat). Comprehensive studies of natural blackgrass and wild oat mutants have revealed six residues within the carboxyltransferase domain of the plastidic isoform that confer tolerance to FOPs and/or DIMs (Delye et al., 2003; Delye et al., 2005; Liu et al., 2007) and these are I1781L, W2027C, I2041N, G2096A, D2078G and C2088R (designation according to standard blackgrass ACCase reference sequence). Interestingly, I1781L and D2078G confer tolerance to both FOPs and DIMs while the other four mutations confer tolerance only to FOPs, suggesting that the binding sites of the two classes of herbicides is overlapping, yet distinct.

Two approaches to develop DIM tolerant rice that have been tried include the following. In the first approach, previously identified mutations in natural blackgrass and wild oat are introduced by means of molecular biological techniques in rice plastidic ACCase. The effects of the mutations are studied in rice after *Agrobacterium*-mediated transformation of the modified ACCase genes. Ultimately, the same mutations can be engineered at the endogenous locus through oligonucleotide gene targeting (Beetham et al., 1999). In the second approach rice callus is propagated in medium with gradually increasing DIM concentrations. This procedure can enrich the callus for cells in which plastidic ACCase has mutated to become more tolerant to the herbicide. Plants can be regenerated from the callus when a satisfactory tolerance level has been reached. However, both approaches are limited in the number of mutations that can be generated and/or tested.

Yeast is an excellent model organism for screening and testing large numbers of mutated rice ACCase genes for increased herbicide tolerance. However, yeast contains a single, endogenous ACCase gene (ACC1), which encodes a multidomain protein that is highly tolerant to herbicides. Haploid yeast in which ACC1 is disrupted is not viable (Hasslacher et al., 1993). Joachimiak et al. (1997) introduced wheat cytoplasmic ACCase into a diploid strain heterozygous for ACC1. Standard tetrad analysis demonstrated that the ACC1 mutation was complemented by the plant ACCase. A similar experiment with the herbicide-sensitive wheat plastidic ACCase gene showed that this gene was not able to take over the function of ACC1 (Nikolskaya et al., 1999). A series of chimeric constructs consisting of the N-terminus of wheat cytoplasmic ACCase and the C-terminus of wheat plastidic ACCase was tested for complementation and herbicide sensitivity. Wheat c60p40 ACCase, which is comprised of the first 60% of cytoplasmic ACCase and last 40% of plastidic ACCase, complemented an ACCase deletion mutant, Δacc1, while showing the highest sensitivity towards haloxyfop, clodinafop, quizalofop, cethoxydim and sethoxydim of all constructs tested. The c60p40 chimeric ACCase is a suitable target for mutagenesis, as all herbicide-conferring mutations known have been mapped to the last 40% of plastidic ACCase. Yet, the Joachimiak approach is limited in its efficiency in that each new mutant plastid ACCase construct is separately introduced into yeast cells to create a new yeast knockout complement.

DIMs and FOPs are important herbicides and there is a need for methods and compositions to isolate, identify and characterize herbicide tolerant ACCase variants. The methods and compositions described herein are suitable for isolating, identifying, and characterizing such herbicide tolerant ACCase variants. Citation or discussion of a reference herein shall not be construed as an admission that such is prior art to the present invention.

SUMMARY OF THE INVENTION

In some embodiments, the present invention provides methods of producing an acetyl-CoA carboxylase (ACCase) enzyme that is tolerant to at least one herbicide. Typically, the methods of the invention are high throughput methods. Such methods will typically comprise providing an ACCase-deficient yeast that comprises a nucleic acid encoding a chimeric ACCase. Any nucleic acid molecule known in the art may be used for this purpose. Suitable examples include, but are not limited to, plasmids, for example single copy plasmids. The chimeric ACCase encoded by the nucleic acid will comprise two or more regions. In some embodiments, the nucleic acid will comprise an N-terminal region and a C-terminal region, wherein the C-terminal region comprises an herbicide sensitivity region (HSR). The ACCase-deficient yeast comprising the nucleic acid will be contacted with at least one mutagenic oligonucleotide under conditions that permit site-directed mutagenesis of at least one codon of the nucleic acid encoding the chimeric ACCase. The mutagenized yeast can then be grown thereby forming a library of mutagenized yeast colonies. The library of mutagenized yeast colonies can be cultured in the presence of at least one ACCase-inhibiting herbicide to form treated colonies; and at least one of said treated colonies isolated so as to identify at least one mutagenized yeast that grows in the presence of the herbicide, wherein the mutagenized yeast that grows in the presence of the herbicide comprises a mutagenized ACCase that has a tolerance to the herbicide that is greater than that exhibited by the chimeric ACCase prior to mutagenesis. As indicated above, typically these methods are high throughput, for example, in an embodiment of the present method, one trained worker can generate and screen at least 500 different HSR-variant ACCases, each from its own cell colony, in 1 month, more preferably at least or about 1000, 2000, or 4000, and preferably up to or about 5000, 8000, or 10000 per month; as compared to the Nikolskaya yeast method (tetrad dissection) in which one worker could accomplish 10 to less than about 50. In some embodiments of the invention, the present methods are capable of producing at least about 100, 200, 300, 400, 500, 1,000, 2,500, 5,000, or 10,000 different HSR-variant ACCases per month per trained worker. Preferably methods of the invention are capable of producing at least about 500, 1,000, 2,500, 5,000, or 10,000 different HSR-variant ACCases per month per trained worker. This assumes that the trained worker in either case begins with all needed supplies of competent cells and vectors useful to transform those cells either with mutagenic oligos according to a present embodiment or with the ACCase variant according to the Nikolskaya method; and that no cell colonies are split to form multiplicates for assaying, after the clonal colonies are established.

The present invention relates to methods of producing, isolating, identifying and characterizing herbicide tolerant ACCase variants. In one embodiment, the invention encompasses a method of screening for an acetyl-CoA carboxylase (ACCase) enzyme which is tolerant to at least one herbicide, comprising: a) providing an ACCase-deficient yeast with a chimeric ACCase, said chimeric ACCase comprising: at least two regions wherein said regions further comprise; i) an N-terminal region, said N-terminal region derived from yeast, fungi or monocot cytoplasmic ACCases, preferably a yeast ACCase; ii) a C-terminal region, said C-terminal region derived from monocot plastidic ACCases and comprising an HSR; and iii) said N-terminal region comprises about 50% to about 60% of the chimeric ACCase; b) isolating herbicide tolerant yeast cells after culturing in the presence of at least one herbicide; and c) further comprising identifying the mutation(s) not present in chimeric ACCase prior to culturing, which confers tolerance to at least one herbicide.

In other embodiments, the present invention relates to a yeast cell tolerant to at least one herbicide wherein the cell is produced by: a) complementing an ACCase-deficient yeast with a chimeric ACCase, said chimeric ACCase comprising at least two regions wherein said regions further comprise; i) an N-terminal region, said N-terminal region derived from yeast, fungi or monocot ACCases; ii) a C-terminal region, said C-terminal region derived from one or more monocot-species plastidic ACCases and comprising an HSR; and iii) said N-terminal region comprises about 50% to about 60% of the chimeric ACCase; and b) isolating herbicide tolerant yeast cells after culturing in the presence of at least one herbicide.

In yet other embodiments, the present invention relates to an isolated yeast cell comprising: a) no active genomic ACCase; b) a nucleic acid encoding a chimeric ACCase, said chimeric ACCase comprising at least two regions wherein said regions further comprise; i) an N-terminal region, said N-terminal region derived from yeast, fungi or monocot ACCases; ii) a C-terminal region, said C-terminal region derived from monocot-species plastidic ACCase and comprising an HSR; and iii) said N-terminal region comprises about 50% to about 60% of the chimeric ACCase; and c) at least one oligonucleotide that is mutagenic for the non-yeast ACCase.

In yet other embodiments, the present invention relates to a mutant ACCase which is tolerant to at least on herbicide wherein the ACCase is identified by: a) providing an ACCase-deficient yeast with a chimeric ACCase, said chimeric ACCase comprising at least two regions wherein said regions comprise; i) an N-terminal region, said N-terminal region derived from yeast, fungi or monocot ACCases; ii) a C-terminal region, said C-terminal region derived from monocot-species plastidic ACCases and comprising an HSR; and iii) said N-terminal region comprises about 50% to about 60% of the chimeric ACCase; b) isolating herbicide tolerant yeast cells after culturing in the presence of at least one herbicide; c) further comprising identifying the mutation(s) not present in chimeric ACCase prior to culturing, which confers tolerance to at least one herbicide; and d) recapitulating said mutation in a full-length monocot plastidic ACCase gene.

In yet other embodiments, the present invention relates to an isolated DNA molecule encoding a chimeric ACCase which is tolerant to at least one herbicide, said chimeric ACCase comprising at least two regions wherein said regions comprise; a) an N-terminal region, said N-terminal region derived from yeast, fungi or monocot cytoplasmic ACCases; b) a C-terminal region, said C-terminal region derived from monocot plastidic ACCases and comprising an HSR, wherein said C-terminal region further comprises at least one mutation that confers tolerance to the herbicide; and c) said N-terminal region comprises about 50% to about 60% of the chimeric ACCase.

In yet other embodiments, the present invention relates to an isolated chimeric ACCase which is tolerant to at least one herbicide, said chimeric ACCase comprising at least two regions wherein said regions comprise: a) an N-terminal region, said N-terminal region derived from yeast, fungi or monocot cytoplasmic ACCases; b) a C-terminal region, said C-terminal region derived from monocot plastidic ACCases and comprising an HSR; and c) said N-terminal region comprises about 50% to about 60% of the chimeric ACCase.

In other embodiments, methods and compositions of the invention encompass ACCase-deficient yeast due to a mutation of the genomic yeast ACCase gene which can include a single point mutation, multiple point mutations, a partial deletion, a partial knockout, a complete deletion and a complete knockout.

In other embodiments, methods and compositions of the invention encompass an chimeric or mutant ACCase, wherein said N-terminal region is derived from a yeast or fungi genus selected from the group consisting of *Saccharomyces, Schizosaccharomyces, Candida, Ascomycetes Neurospora, Kluyveromyces, Pichia Cryptococcus, Chrysosporium, Yarrowia, Arxula,* and *Hansenula*.

In other embodiments, methods and compositions of the invention encompass a chimeric or mutant ACCase, wherein said N-terminal region or C-terminal region is derived from a monocot genus selected from the group consisting of *Saccharum, Poa, Agrostis, Lolium, Festuca, Zoysia, Cynodon, Stenotaphrum, Paspalum, Eremochloa, Axonopus, Bouteloua, Arundinaria, Bambusa, Chusquea, Guadua, Shibataea, Erharta, Leersia, Microlaena, Oryza, Zizania, Triticeae, Aveneae, Hordeum, Lolium, Digitaria, Cyperus, Kyllinga, Erigeron, Hydrocotyle, Kummerowia, Euphorbia,* and *Viola, Zea, Sorghum, Pennisetum, Panicum, Setaria, Eleusine, Ananas,* and *Musa*.

In a specific embodiments, methods and compositions of the invention encompass a chimeric ACCase, wherein said N-terminal region is derived from a cytoplasmic ACCase from an *Oryza* species.

In yet other specific embodiments, in other embodiments, methods and compositions of the invention encompass a chimeric ACCase, wherein said C-terminal region is derived from a plastidic ACCase from an *Oryza* species.

In other embodiments, methods and compositions of the invention encompass at least one herbicide that is an aryloxyphenoxypropionate (FOP) or cyclohexanedione (DIM) herbicide. In other embodiments, methods and compositions of the invention encompass a FOP herbicide selected from the group consisting of haloxyfop, cyhalofop, quizalofop, diclofop, clodinafop, fluazifop, metamifop, propaquizafop, and fenoxyprop. In other embodiments, methods and compositions of the invention encompass a DIM herbicide selected from the group consisting of alloxydim, butroxydim, clethodim, cycloxydim, tepraloxydim, sethoxydim, tralkoxydim, and profoxydim. In yet further embodiments, methods and compositions of the invention encompass at least one herbicide present at a concentration from about 0.02 µM to about 200 µM.

In other embodiments, methods and compositions of the invention encompass mutagenesis of the chimeric ACCase. In further embodiments, methods and compositions of the invention encompass mutagenesis induced by chemical agents, ultraviolet radiation, or a library of DNA oligos provided to the yeast cell.

In other embodiments, methods and compositions of the invention encompass a chimeric ACCase were C-terminal region comprises about 50% to about 60% of the chimeric ACCase.

In other embodiments, methods and compositions of the invention encompass yeast cells cultured at a temperature of about 23° C. to about 30° C. In other embodiments, methods and compositions of the invention encompass yeast cells are cultured in liquid or on solid media.

In other embodiments, methods and compositions of the invention encompass a chimeric or mutant ACCase wherein said C-terminal region comprises a sequence which encodes for at least one mutation selected from the group consisting of I1781L, W1999G, I1781T, V2049F, V2075L, V2075I, D2078G, and V2098A.

BRIEF DESCRIPTION OF THE FIGURES

For the purpose of illustrating the invention, there are depicted in the drawings certain embodiments on the invention. However, the invention is not limited to the precise arrangements and instrumentalities of the embodiments depicted in the drawings.

FIG. 2C provides the DNA sequence of RTP4108 (SEQ ID NO:13).

FIG. 3B provides the DNA sequence of the rice plastidic ACCase portion of plasmid RTP3378 (SEQ ID NO:14).

FIG. 4 discloses the "10×His tag" as SEQ ID NO:31.

FIG. 8 is a table showing frequency of mutations observed (columns) after transformation with different fragments and plating on different DIMs (rows). I1781X C100=transformation carried out with fragments with degeneracy in the triplet corresponding to I1781 and plating on 100 µM cycloxydim. I1781X T1=same transformation plated on 1 µM tepraloxydim, etc. Wt control=a fragment corresponding to the I1781X fragment, but with the "Wt" isoleucine-encoding triplet only. Shaded squares represent mutants that obtained the intended mutation (of which a fraction may be spontaneous as they only differed in one nucleotide from the "Wt" sequence).

FIG. 9 is a table showing frequency of mutations observed (columns) after transformation with I2041X and W2027X fragments and plating on different DIMs (rows).

FIG. 11 is a table showing double mutations identified by plating single mutants and waiting for spontaneous second mutations.

TERMINOLOGY

Figure 1A:
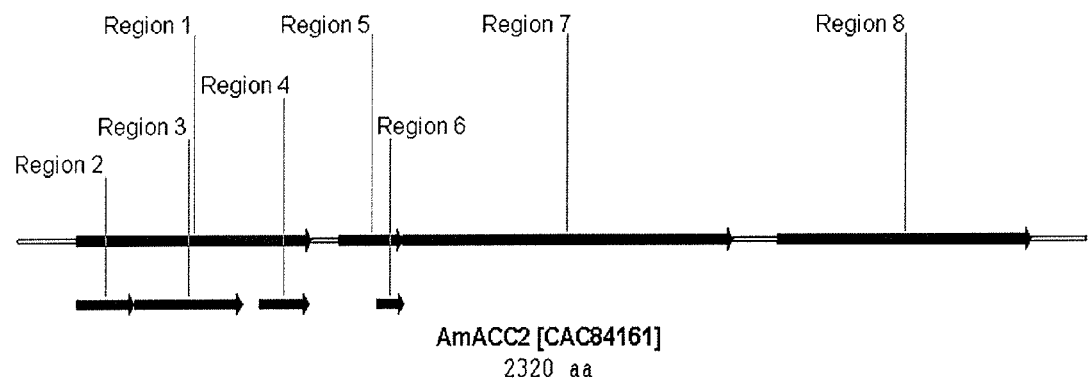
FIG. 1A provides a schematic view of the domain structure of a monocot plastidic ACCase.

As used herein, "tolerant" or "herbicide-tolerant" indicates a yeast cell or strain; a plant; or a plant cell capable of growing in the presence of an amount of herbicide that normally causes growth inhibition in a non-tolerant (e.g., a wild-type) yeast cell or strain; a plant; or a plant cell.

As used herein, an ACCase is "sensitive" to a particular herbicide if the enzymatic activity of the ACCase is reduced in the presence of the herbicide when compared to the activity of the ACCase under identical conditions in the absence of the herbicide. Examples of herbicides to which an ACCase might be sensitive are set forth in Table 1.

TABLE 1

List of Herbicides

| ACCase Inhibitor | Class | Company | Example Trade Names | Maximum Rate [g ai/ha] | Use |
| --- | --- | --- | --- | --- | --- |
| alloxydim | DIM | BASF | Fervin, Kusagard, NP-48Na, BAS 9021H | 1000 | POST |
| butroxydim | DIM | Syngenta | Falcon, ICI-A0500 | 75 | POST |
| clethodim | DIM | Valent | Select, Prism, RE-45601 | 280 | POST |
| clodinafop-propargyl | FOP | Syngenta | Discover, Topik, CGA 184 927 | 80 | POST |
| cycloxydim | DIM | BASF | Focus, Laser, Stratos, BAS 517H | 448 | POST |
| cyhalofop-butyl | FOP | Dow | Clincher, XDE 537, DEH 112 | 310 | POST |
| diclofop-methyl | FOP | Bayer | Hoegrass, Hoelon, Illoxan, HOE 23408 | 1120 | POST |
| fenoxaprop-P-ethyl | FOP | Bayer | Super Whip, Option Super, Exel Super, HOE-46360, Aclaim, Puma S | 111 | POST |

TABLE 1-continued

List of Herbicides

| ACCase Inhibitor | Class | Company | Example Trade Names | Maximum Rate [g ai/ha] | Use |
|---|---|---|---|---|---|
| fluazifop-P-butyl | FOP | Syngenta | Fusilade, Fusilade 2000, Fusilade DX, ICI-A 0009, ICI-A 0005, SL-236, IH-773B, TF-1169 | 210 | POST |
| haloxyfop-etotyl | FOP | Dow | Gallant, DOWCO 453EE | 600 | POST |
| haloxyfop-methyl | FOP | Dow | Verdict, DOWCO 453ME | 600 | POST |
| haloxyfop-P-methyl | FOP | Dow | Edge, DE 535 | 600 | POST |
| metamifop | FOP | Dongbu | NA | 201 | POST |
| pinoxaden | DEN | Syngenta | Axial | 60 | POST |
| profoxydim | DIM | BASF | Aura, Tetris, BAS 625H | 212 | POST |
| propaquizafop | FOP | Syngenta | Agil, Shogun, Ro 17-3664 | 150 | POST |
| quizalofop-P-ethyl | FOP | DuPont | Assure, Assure II, DPX-Y6202-3, Targa Super, NC-302 | 112 | POST |
| quizalofop-P-tefuryl | FOP | Uniroyal | Pantera, UBI C4874 | 112 | POST |
| sethoxydim | DIM | BASF | Poast, Poast Plus, NABU, Fervinal, NP-55, Sertin, BAS 562H | 560 | POST |
| tepraloxydim | DIM | BASF | BAS 620H, Aramo | 60 | POST |
| tralkoxydim | DIM | Syngenta | Achieve, Splendor, ICI-A0604 | 3400 | POST |

As used herein, "chimeric" refers to a non-naturally occurring polypeptide composed of two or more regions derived from different sources. Examples of a chimeric polypeptide include, but are not limited to, polypeptides having ACCase activity wherein the polypeptides have an N-terminal region derived from one source and a C-terminal region derived from another source. Examples of chimeric ACCases include, but are not limited to, a chimeric ACCase comprising an N-terminal region derived from a monocot cytosolic ACCase and a C-terminal region derived from a monocot plastidic ACCase, and a chimeric ACCase comprising an N-terminal region derived from a yeast ACCase and a C-terminal region derived from a monocot plastidic ACCase, e.g., a rice plastidic ACCase.

As used herein, an "ACCase-deficient yeast" is a yeast cell or strain that does not express a functional ACCase activity other than that of the chimeric ACCase of the invention. An ACCase-deficient yeast cell will typically comprise an exogenous source of ACCase activity, for example, an extra-genomic nucleic acid, e.g., a plasmid, encoding a chimeric ACCase of the invention.

As used herein, "recombinant" refers to an organism having genetic material from different sources.

As used herein, "mutagenized" refers to a segment of DNA that has been modified to contain one or more nucleotides that vary from the original DNA sequence. Any method known in the art may be used to induce mutations. Methods of inducing mutations may induce mutations in random positions in the genetic material or may induce mutations in specific locations in the genetic material (i.e., may be directed mutagenesis techniques).

As used herein, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Similarly, the terms "tolerant" and "resistant" are used interchangeably and are intended to have an equivalent meaning and an equivalent scope.

As used herein, the amino acid numbering, and the associated DNA sequence numbering are based on the numbering of the ACCase in *Alopecurus myosuroides* (blackgrass) (Genbank CAC84161.1) and denoted with an (Am). The reference positions cited within are intended to correspond to the actual recited positional equivalent in the ACCase of *Alopecurus myosuroides*.

As used herein, and "herbicide sensitivity region" (HSR) is an amino acid sequence present in the carboxyl transferase domain of a monocot plastidic ACCase that: (1) when present in the ACCase in its wild-type amino acid sequence, permits the ACCase to be sensitive to inhibition by at least one DIM, FOP or DEN herbicide, and (2) is capable of being mutagenized to contain at least one amino acid substitution that provides to the ACCase tolerance toward at least one DIM, FOP or DEN herbicide. Minimally, the wild type HSR comprises a monocot plastidic ACCase amino acid sequence of or corresponding to residues 1781(Am)-2098(Am).

As used herein, "high throughput" means capable of producing at least about 100, 200, 300, 400, 500, 1,000, 2,500, 5,000, or 10,000 different HSR-variant ACCases per month per trained worker. Preferably methods of the invention are capable of producing at least about 500, 1,000, 2,500, 5,000, or 10,000 different HSR-variant ACCases per month per trained worker

DETAILED DESCRIPTION

The invention encompasses methods and compositions useful for isolating, identifying and characterizing mutations in ACCase that confer tolerance to at least one herbicide. For this purpose, a yeast model system was employed. The yeast model system included an ACCase-deficient yeast cell with a chimeric ACCase which comprises and HSR. The chimeric ACCase complements the ACCase-deficiency of the yeast.

The methods and compositions encompassed by the invention relate to making and using such a system to isolate, identify and characterize mutations in ACCase which confer tolerance to an herbicide by screening or selection on media with herbicide present. Such isolated mutants in the ACCase that confer tolerance to the herbicide are not present prior to the screening or culturing in the presence of herbicide.

Prior art screening systems, for example that reported by Nikolskaya, were limited in the number of mutations that could be generated and screened. The present invention has overcome these limitations by expressing the chimeric ACCase of the invention from a single copy plasmid. Any mutation, either spontaneous or introduced through transformation will be identified far more efficiently. Prior art systems made use of high copy number plasmids (like pRS426 with 20 copies/haploid cell). In theory, a single plasmid with a herbicide resistance-conferring mutation could be formed in the presence of 19 or so wild-type plasmids in a cell. In subsequent rounds of cell division, daughter cells should start containing the mutated plasmid only, if the selection pressure is kept throughout. However, this does not happen, because the expression from the initial, single, mutated plasmid among the 19 wild-type plasmids is not robust enough to make it through the early stages of herbicide selection pressure. An additional difficulty of the prior art method is the failure of the prior art construct to complement efficiently in yeast at 30 degrees. It only complements efficiently at 23 degrees. The chimeric ACCases described herein are more efficient and complement at 30 degrees.

In some embodiments, the invention encompasses a method of screening for an acetyl-CoA carboxylase (ACCase) enzyme that is tolerant to at least one herbicide. Typically, such methods may include providing a yeast cell deficient in ACCase activity, i.e., an ACCase-deficient yeast cell. Also, such methods can include providing an ACCase-deficient yeast with a chimeric ACCase. The chimeric ACCase may comprise at least two or more regions. The chimeric ACCase may comprise an N-terminal region. The N-terminal region may be derived from a yeast, fungi or monocot cytoplasmic ACCase. The N-terminal region may comprise from about 10% to about 75% of the chimeric ACCase. The chimeric ACCase also comprises a C-terminal region. Typically, the C-terminal region may comprise from about 90% to about 25% of the chimeric ACCase. The C-terminal region comprises an HSR and may be derived from a monocot plastidic ACCase sensitive to at least one herbicide. Percentages herein are calculated relative to amino acids 98-2320 of a mature Am ACCase.

In other embodiments, the invention encompasses methods of isolating herbicide tolerant yeast cells expressing a chimeric ACCase after culturing in the presence of at least one herbicide. Typically, the chimeric ACCase in such herbicide tolerant yeast cells may harbor at least one mutation that confers the tolerance to the herbicide the yeast cell is cultured in. Also, the mutation(s) conferring tolerance to the ACCase and the yeast cell may be further identified using the yeast cells.

In other embodiments, the invention encompasses a yeast cell tolerant to at least one herbicide. Such a yeast cell may be produced by complementing an ACCase-deficient yeast with a chimeric ACCase. Typically, the chimeric ACCase may comprise at least two or more regions. The chimeric ACCase may comprise an N-terminal region. The N-terminal region may be derived from a yeast, fungi, dicot, or monocot cytoplasmic ACCase. The N-terminal region may comprise from about 10% to about 75% of the chimeric ACCase. The chimeric ACCase also comprises a C-terminal region. Typically, the C-terminal region may comprise from about 90% to about 25% of the chimeric ACCase. The C-terminal region comprises an HSR and may be derived from a monocot plastidic ACCase sensitive to at least one herbicide. Generally, the yeast cell may be cultured in the presence of at least one or more herbicides.

In still other embodiments, the invention encompasses an isolated DINA molecule encoding a chimeric ACCase which is tolerant to at least one herbicide. In some embodiments, the DNA molecule encodes a chimeric ACCase which comprises at least two or more regions. Typically, the DNA molecule encodes a chimeric ACCase that may comprise at least one ore more N-terminal regions. Generally, the DNA molecule encodes an ACCase N-terminal region that may be derived from yeast, fungi, dicot or monocot cytoplasmic ACCases. The N-terminal region may comprise from about 10% to about 75% of the chimeric ACCase. The chimeric ACCase encoded by the DNA molecule also comprises at least one C-terminal region. The C-terminal region that may comprise from about 90% to about 25% of the chimeric ACCase. The C-terminal region will comprise an HSR and may be derived from a monocot plastidic ACCase sensitive to at least one herbicide.

In other embodiments, the invention encompasses an isolated chimeric ACCase which is tolerant to at least one herbicide. The chimeric ACCase may comprise an N-terminal region. The N-terminal region may be derived from a yeast, fungi, dicot or monocot cytoplasmic ACCase. The N-terminal region may comprise from about 10% to about 75% of the chimeric ACCase. The chimeric ACCase also comprises a C-terminal region. Typically, the C-terminal region may comprise from about 90% to about 25% of the chimeric ACCase. The C-terminal region comprises an HSR and may be derived from a monocot plastidic ACCase sensitive to at least one herbicide.

In yet other embodiments, the invention encompasses a mutant ACCase which is tolerate to at least one herbicide. Typically, the mutant ACCase is generated by inducing one or more mutations in the HSR of a chimeric ACCase. The chimeric ACCase may comprise an N-terminal region. The N-terminal region may be derived from a yeast, fungi, dicot or monocot cytoplasmic ACCase. The N-terminal region may comprise from about 10% to about 75% of the chimeric ACCase. The chimeric ACCase also comprises a C-terminal region. Typically, the C-terminal region may comprise from about 90% to about 25% of the chimeric ACCase. The C-terminal region comprises an HSR and may be derived from a monocot plastidic ACCase sensitive to at least one herbicide. Once induced, the mutation(s) in the chimeric ACCase that result in tolerance to herbicides in the yeast cell may be identified by, for example, sequencing the DNA molecule encoding the chimeric ACCase. Further, the method may comprise introducing the herbicide tolerant mutation(s) identified from the chimeric ACCase into a full-length, or other ACCase.

ACCase-Deficient Yeast and Complementation with Chimeric ACCase

Yeast contain a single, endogenous ACCase gene (ACC1), which encodes a multidomain protein that is highly tolerant to herbicides. Haploid yeast in which ACC1 is disrupted is not viable (Hasslacher et al., 1993).

In some embodiments, methods of the invention comprise ACCase-deficient yeast. An ACCase-deficient yeast may lack endogenous ACCase activity due to one or more mutations of the genomic yeast ACCase gene which may include a single point mutation, multiple point mutations, a partial deletion, a partial knockout, a complete deletion and a complete knockout. Typically, genomic yeast ACCase activity may be reduced or ablated using other molecular biology techniques such as RNAi, siRNA or antisense RNA. Such molecular biology techniques are well known in the art.

In some embodiments, the invention comprises introducing a nucleic acid molecule encoding a chimeric ACCase into a diploid yeast strain heterozygous for a functional genomic ACC1 gene. Typically, the method includes verifying incorporation of the nucleic acid encoding the chimeric ACCase into a heterozygous strain. Generally, the method also may include inducing sporulation and isolation of haploid yeast cells containing an inactive yeast ACC1 gene and a chimeric ACCase gene. Accordingly, the method may include verifying incorporation of the chimeric ACCase into a haploid strain with an inactivated genomic ACC1 gene.

In an alternative embodiment, the invention comprises incorporation of a nucleic acid molecule encoding a chimeric ACCase into a homozygous strain followed by inactivation of one or both copies of the yeast ACC1 gene. Typically, the method includes verifying incorporation of the chimeric ACCase gene into a homozygous strain. In yet further embodiments, the invention comprises inducing sporulation and isolation of haploid yeast cells containing an inactive yeast ACC1 gene and a chimeric ACCase gene.

In other embodiments, the invention comprises a chimeric ACCase gene that complements a deficiency in the yeast ACC1 gene. In other embodiments, complementation of the yeast ACC1 gene deficiency occurs when yeast cells containing the chimeric ACCase are cultured at a temperature of about 23° C. to about 30° C. In other embodiments, complementation of the yeast ACC1 gene occurs when yeast cells containing the chimeric ACCase are cultured at a temperature of about 23° C., about 24° C., about 25° C., about 26° C., 27° C., about 28° C., about 29° C., or about 30° C. In yet other embodiments, complementation may occur at a permissive temperature, but not a restrictive temperature. Such permissive temperatures may range from about 23° C. to about 30° C. In other embodiments, such permissive temperatures may be about 23° C., about 24° C., about 25° C., about 26° C., 27° C., about 28° C., about 29° C., or about 30° C. In other embodiments, restrictive temperatures include but are not limited to a range from about 23° C. to about 30° C. In other embodiments, such permissive temperatures may be about 23° C., about 24° C., about 25° C., about 26° C., 27° C., about 28° C., about 29° C., or about 30° C.

Chimeric ACCases

In one embodiment, the present invention encompasses chimeric ACCases and nucleic acid molecules encoding the same. Generally, at least a portion of the chimeric ACCase will comprise an amino acid sequence that is the same as, or corresponds to, that found in a monocot plastidic ACCase, for example, in *Alopecurus myosuroides* multi-functional ACCase 2 (Genbank CAC84161).

Monocot plastidic ACCases share a similar structure characterized by the occurrence and arrangement of 8 functional regions as shown in FIG. 1A. The (Am) residue numbers for these regions are as follows (bullet points show regions falling within Region 1 or Region 5).

| AmACCase Part | Start | Stop |
|---|---|---|
| AmACCase | 1 | 2320 |
| Region 1 | 135 | 643 |
| ● Region 2 | 135 | 257 |
| ● Region 3 | 259 | 492 |
| ● Region 4 | 530 | 637 |
| Region 5 | 703 | 841 |
| ● Region 6 | 787 | 841 |
| Region 7 | 842 | 1556 |
| Region 8 | 1654 | 2204 |

The official COG designations from the "Clusters of Orthologous Groups" database administered by the US NIH National Center for Biotechnology Information, in Bethesda, Md., US and/or the pfam designations from the "Pfam Protein Families" database administered by the Wellcome Trust Sanger Institute, in Hinxton, Cambridge, UK of each of these regions is as follows.

Region 1: COG0439 (Biotin carboxylase [Lipid metabolism])

Region 1 containing Regions 2, 3, 4:

Region 2: pfam00289 (CPSase_L_chain) Carbamoyl-phosphate synthase L chain, N-terminal domain;

Region 3: pfam02786 (CPSase_L_D2) Carbamoyl-phosphate synthase L chain, ATP binding domain;

Region 4: pfam02785 (Biotin_carb_C) Biotin carboxylase C-terminal domain.

Region 5: COG0511 (Biotin carboxyl carrier protein [Lipid metabolism])

Region 5 containing Region 6

Region 6: pfam00364 (Biotin_lipoyl) Biotin-requiring enzyme.

Region 7: pfam08326 (ACC_central) Acetyl-CoA carboxylase, central region.

Region 8: pfam01039 (Carboxyl_trans) Carboxyl transferase domain (of biotin-dependent carboxylases).

The carboxyl transferase domain catalyzes the transcarboxylation from biotin to an acceptor molecule. All ACCases useful as sources of sequences for constructing chimeric ACCase enzymes for the practice of the present invention contain a set of these 8 regions, arranged in the same relative order. Thus, standardized residue numbering for all monocot plastidic ACCases, as well as for all dicot, yeast, and animal cytosolic/etc. multifunctional ACCases listed herein relies on the Am ACCase standard, to which they are all homologous.

Region 8 comprises the carboxyl transferase domain of the ACCase enzyme of the invention. Herbicide sensitivity has been mapped to a region termed the Herbicide Sensitivity Region (HSR) located in region 8 of monocot plastidic ACCases. All or a part of region 8 of a monocot plastidic ACCase may be used as an HSR. For example, a chimeric ACCase of the invention may comprise an HSR that starts anywhere from 1654(Am) to 1781(Am), and could end, e.g., anywhere from 2098(Am) to 2204(Am). Thus, an HSR of the invention may comprise amino acids corresponding to 1654(Am) to 2204(Am), 1654(Am) to 2130(Am), 1654(Am) to 2098(Am), 1750(Am) to 2204(Am), 1750(Am) to 2130(Am), 1750(Am) to 2098(Am), 1781(Am) to 2204(Am), 1781(Am) to 2130(Am), or 1781(Am) to 2098(Am). Examples of suitable HSR regions for use in the practice of the present invention include, but are not limited to, those in the following table.

Table of HSR sequences

```
A. myosuroides  ihgsaaiasa ysrayeetft ltfvtgrtvg igaylarlgi rciqrldqpi
O. sativa       ihgsaaiasa ysrayeetft ltfvtgrtvg igaylarlgi rciqrldqpi
E. crus-galli   ihgsaaiasa ysrayeetft ltfvtgrtvg igaylarlgi rciqrldqpi
Set. italica    ihgsaaiasa ysrayeetft ltfvtgrtvg igaylarlgi rciqrldqpi
Sor. bicolor    ihgsaaiasa ysrayeetft ltfvtgrtvg igaylarlgi rciqrldqpi
T. aestivum     ihgsaaiasa ysrayeetft ltfvtgrtvg igaylarlgi rciqrtdqpi
Z. mays         ihgsaaiasa ysrayeetft ltfvtgrtvg igaylarlgi rciqrldqpi A. myosuroides  iltgfsalnk llgrevyssh mqlggpkima tngvvhltvp ddlegvsnil
O. sativa       iltgfsalnk llgrevyssh mqlggpkima tngvvhltvp ddlegvsnil
E. crus-galli   iltgfsalnk llgrevyssh mqlggpkima tngvvhltvp ddlegvsnil
Set. italica    iltgfsalnk llgrevyssh mqlggpkima tngvvhltvp ddlegvsnil
Sor. bicolor    iltgfsalnk llgrevyssh mqlggpkima tngvvhltvp ddlegvsnil
T. aestivum     iltgfsalnk llgrevyssh mqlggpkima tngvvhltvp ddlegvsnil
Z. mays         iltgfsalnk llgrevyssh mqlggpkima tngvvhltvp ddlegvsnil A. myosuroides  rwlsyvpani ggplpitksl dpidrpvayi pentcdpraa isgiddsqgk
O. sativa       rwlsyvpayi ggplpvttpl dppdrpvayi penscdpraa irgvddsqgk
E. crus-galli   rwlsyvpani gghlpitkpl dppdrpvayi pentcdpraa irgvddsqgk
Set. italica    rwlsyvpani ggplpitkpl dppdrpvayi pentcdpraa irgvddsqgk
Sor. bicolor    rwlsyvpani ggplpitkpl dppdrpvayi pentcdpraa irgvddsqgk
T. aestivum     rwlsyvpani ggplpitksl dppdrpvayi pentcdpraa isgiddsqgk
Z. mays         rwlsyvpani ggplpitkpl dppdrpvayi pentcdpraa icgvddsqgk A. myosuroides  wlggmfdkds fvetfegwak tvvtgraklg gipvgviave tqtmmqlvpa
O. sativa       wlggmfdkds fvetfegwak tvvtgraklg gipvgviave tqtmmqtipa
E. crus-galli   wlggmfdkds fvetfegwak tvvtgraklg gipvgviave tqtmmqlipa
Set. italica    wlggmfdkds fvetfegwak tvvtgraklg gipvgviave tqtmmqlipa
Sor. bicolor    wlggmfdkds fvetfegwak tvvtgraklg gipvgviave tqtmmqlvpa
T. aestivum     wlggmfdkds fvetfegwak svvtgraklg gipvgviave tqtmmqlipa
Z. mays         wlggmfdkds fvetfegwak tvvtgraklg gipvgviave tqtmmqiipa A. myosuroides  dpgqpdsher svpragqvwf pdsatktaqa mldfnreglp lfilanwrgf
O. sativa       dpgqldsreq svpragqvwf pdsatktaqa lldfnreglp lfilanwrgf
E. crus-galli   dpgqldsher svpragqvwf pdsatktaqa lldfnreglp lfilanwrgf
Set. italica    dpgqldsher svpragqvwf pdsatktaqa lldfnreglp lfilanwrgf
Sor. bicolor    dpgqldsher svpragqvwf pdsatktaqa lldfnreglp lfilanwrgf
T. aestivum     dpgqldsher svpragqvwf pdsatktaqa mldfnreglp lfilanwrgf
Z. mays         dpgqldsher svpragqvwf pdsatktaqa lldfnreglp lfilanwrgf A. myosuroides  sggqrdlfeg ilqagstive nlrtynqpaf vyipkaaelr ggawvvidsk
O. sativa       sggqrdlfeg ilqagstive nlrtynqpaf vyipmaaelr ggawvvvdsk
E. crus-galli   sggqrdlfeg ilqagstive nlrtynqpaf vyipmagelr ggawvvvdsk
Set. italica    sggqrdlfeg ilqagstive nlrtynqpaf vyipmagelr ggawvvvdsk
Sor. bicolor    sggqrdlfeg ilqagstive nlrtynqpaf vyipmagelr ggawvvvdsk
T. aestivum     sggqrdlfeg ilqagstive nlrtynqpaf vyipkaaelr ggawvvidsk
Z. mays         sggqrdlfeg ilqagstive nlrtynqpaf vyipmagelr ggawvvvdsk A. myosuroides  inpdriecya ertakgnv (SEQ ID NO: 15)
O. sativa       inpdriecya ertakgnv (SEQ ID NO: 16)
E. crus-galli   inpdriecya ertakgnv (SEQ ID NO: 17)
Set. italica    inpdriecya ertakgnv (SEQ ID NO: 18)
Sor. bicolor    inpdriecya ertakgnv (SEQ ID NO: 19)
T. aestivum     inpdriefya ertakgnv (SEQ ID NO: 20)
Z. mays         inpdriecya ertakgnv (SEQ ID NO: 21)
```

These sequences are *Alopecurus myosuroides* 1781-2098 (GenBank accession number CAC84161) (SEQ ID NO:15); *Oryza sativa* 1792-2109 (GenBank accession number AAM18728) (SEQ ID NO:16); *Echinochloa crus-galli* 1775-2092 (GenBank accession number ADR32358) (SEQ ID NO:17); *Setaria italica* 1780-2097 (GenBank accession number AAO062902) (SEQ ID NO:18); *Sorghum bicolor* 1785-2102 (GenBank accession number EES10506) (SEQ ID NO:19); *Triticum aestivum* 1769-2086 (GenBank accession number AAC49275) (SEQ ID NO:20); *Zea mays* 1783-2100 (GenBank accession number AAP78896) (SEQ ID NO:21).

Chimeric ACCases of the invention typically comprise at least two regions, an N-terminal region and a C-terminal region. Typically, the present invention may encompass full-length chimeric ACCases. Alternatively, the present invention may encompass chimeric ACCases with truncated N-terminal and/or C-terminal ends that retain acetyl-CoA carboxylase activity. Additionally, chimeric ACCases may include N-terminal and/or C-terminal regions that include sequences that are derived from the same sources as the remainder of the N-terminal and/or C-terminal regions. Such sequences may be incorporated for purposes of identification of mutants, purification of the ACCase, or other such functions.

N-Terminal Regions of Chimeric ACCases

In some embodiments, the present invention comprises a chimeric ACCase with an N-terminal region derived from a yeast, fungi, dicot or monocot-cytoplasmic ACCase. In a specific embodiment, the N-terminal region of the chimeric ACCase may be derived from a rice cytoplasmic ACCase. Alternatively, the N-terminal region may be derived from *Saccharomyces*. In addition, although monocot cytoplasmic ACCases are preferred sources of N-terminal regions, other sources of N-terminal region include dicot, yeast, and ani mal cytoplasmic and other (e.g., endoplasmic reticulum) ACCases, examples of which are provided herein. Any ACCase that is multifunctional, homologous to/hybridizable with and within the same general size range—e.g., 2000-2500 amino acids, or more preferably 2200-2400 amino acids, may be used as a source of the N-terminal region of a chimeric ACCase of the invention.

Typically, the N-terminal region comprises from about 10% to about 75% of the total length of the chimeric ACCase. More specifically, the N-terminal region may comprise about 10%, about 20%, about 30%, about 40%, about 50%, about 60%, about 70%, or about 75% of the total length of the chimeric ACCase.

When the N-terminal region comprises about 10% of the chimeric ACCase, the 3'-most amino acid residue of the N-terminal region may correspond to an amino acid in the vicinity of 319(Am). When the N-terminal region comprises about 20% of the chimeric ACCase, the 3'-most amino acid residue of the N-terminal region may correspond to an amino acid in the vicinity of 542(Am). When the N-terminal region comprises about 30% of the chimeric ACCase, the 3'-most amino acid residue of the N-terminal region may correspond to an amino acid in the vicinity of 764(Am). In some embodiments, the N-terminal region comprises about 62% of the chimeric ACCase and the 3'-most amino acid residue of the N-terminal region may correspond to an amino acid in the vicinity of 1472(Am). In some embodiments, the N-terminal region comprises about 39% of the chimeric ACCase and the 3'-most amino acid residue of the N-terminal region may correspond to an amino acid in the vicinity of 969(Am). In some embodiments, the N-terminal region comprises about 33.5% of the chimeric ACCase and the 3'-most amino acid residue of the N-terminal region may correspond to an amino acid in the vicinity of 841 (Am). In some embodiments, the N-terminal region comprises about 76% of the chimeric ACCase and the 3'-most amino acid residue of the N-terminal region may correspond to an amino acid in the vicinity of 1781(Am).

In some preferred embodiments, the N-terminal region comprises about 35% to about 76% of the length of the chimeric ACCase assuming that the total length of the chimeric ACCase is about the same as amino acids 98-2320 of a mature Am ACCase.

In some embodiments, the N-terminal region may comprise regions 1 to 7, 1 to 6, or 1-5 of an ACCase derived from a yeast, fungi, dicot or monocot-cytoplasmic ACCase.

In some embodiments, the N-terminal regions of the invention begin at the cytoplasmic methionine whose position corresponds to Am ACCase (plastidic) H98. In other embodiments, N-terminal regions may begin at other native methionines, e.g., the cytoplasmic methionine corresponding to Am ACCase M104 or S111. The following alignment shows the positions of other methionine residues in cytosolic ACCases that may be used as the first amino acid of the N-terminal region of the chimeric ACCases of the invention (see arrows below). In the alignment, cytosolic sequences are shown with numbering starting at their native Met-1 residues, whereas the plastidic sequences are shown without their leader peptides/chloroplast transit peptides (ctps).

```
                  100       110       120
                   |         |         |
       HKASYQMNGILNESHNGRHAS-LSKVY (SEQ ID NO: 22) AmACCase plastidic (w/o leader/ctp)
       VPGSYQMNGIINETHNGRHAS-VSKVV (SEQ ID NO: 23) Rice ACCase Plastidic (w/o leader/ctp)
       MEGSYQMNGILNGMSNSRHPSSPSEVD (SEQ ID NO: 24) Rice Cytosolic (Genbank AAM18728)
       MEGSYQMNGILNGMSNSRHPSSPSEVD (SEQ ID NO: 25) Rice Cytosolic
       MVESDQING---RMSS---------VD (SEQ ID NO: 26) Wheat Cytosolic
       mvesdqing---rmss---------vd (SEQ ID NO: 27) Wheat Cytosolic (Genbank AAA19970)
       mvesdqingtpnrmss---------vd (SEQ ID NO: 28) Wheat Cytosolic (Genbank 2208491A)
       ↑        ↑    ↑
```

These are examples of preferred options for constructs utilizing a native Met position as the initiator. In other embodiments, an N-terminal region containing a plant ACCase leader peptide included upstream from the start of the cytoplasmic ACCase segment, i.e. added upstream of the position at which a cytoplasmic ACCase's native Met-1 occurs, may be used and the native Met-1 of the added leader peptide can serve as a native-type initiator Met.

In some embodiments, a construct encoding a synthetic Met site can be used to initiate the chimeric ACCase. The synthetic Met site could be situated anywhere upstream from the beginning of Region 1 of the ACCase, e.g., up to about 100 or 150 amino acids upstream therefrom, though preferably from about 10 or 15 to about 50 or 60 amino acids residues upstream of Region 1.

The presence of peptide sequence upstream from such a preferred start site is optional, e.g., leader peptides, ctp's, etc., but can be included, provided that it is other than a mitochondrial, plastidic, nuclear, endoplasmic reticulum, secretion, or other targeting peptide operative in the yeast host cell. Preferably, N-terminal leader peptides, particularly N-terminal targeting peptides, are absent from chimeric ACCases of the invention.

A yeast cytoplasmic ACCase can be used as an alternative source of an N-terminal sequence for the chimeric ACCase of the invention. As in the case of the monocot cytoplasmic ACCases, any native or synthetic Met site upstream of Region 1 of the yeast ACCase can be used as a native initiator Met for the construct; preferably native Met-1 of the yeast polypeptide is used in one embodiment. For example, *Saccharomyces cerevisiae* ACC1 (Genbank AAA20073) includes two native Met sites in its N-terminal region: Met-1 and Met-14, i.e. as numbered according to the *S. cerevisiae* sequence: MSEESLFESSPQKME. The numbering of these positions relative to the Am ACCase standard can vary, based on the alignment chosen, as being aligned with either H98(Am) and S111(Am), or A57(Am) and P70(Am), respectively. Yet, in any event, these two residues fall adjacent to I77(Am) and D90(Am) when the yeast cytoplasmic and Am plastidic ACCase enzyme domains, i.e. Regions 1-8, are optimally aligned without also computationally aligning their upstream peptide sequences. See the exemplary alignments below, with numbering according to the Am standard above, and *S. cerevisiae* numbering below.

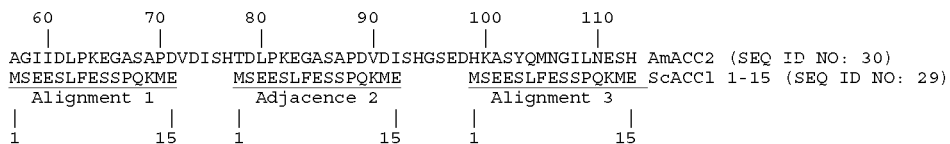

Monocot cytoplasmic and plastidic ACCases, and the yeast cytoplasmic ACCases, even though they all are single-chain (multi-functional) enzymes, do not necessarily correspond with each other or with Am ACCase in every position occupied by an amino acid. Alignment of these shows the presence of some gaps, insertions, etc. In addition to these differences, there is absent from the cytoplasmic forms a ctp-containing N-terminal leader peptide that is present in plastidic forms. Yet, commonly these monocot and yeast multifunctional forms are about 2000-2500 amino acids in length, typically about 2200-2400 amino acids in length, and all share the same 8-Region structural pattern.

The following table presents useful examples of cytosolic and other (e.g., endoplasmic reticulum) multi-functional ACCase sources for N-terminal regions in a chimeric ACCases of the invention. The table also shows key start and stop sites in native herbicide sensitive ACCases that correspond to those of the Am standard.

| Source Type | Source Organism | Genbank Accession | Length

| Source Organism | Genbank Accession | Length (aa) | Reg. 1 Start | Reg. 7 Start | Reg. 7 Stop | Reg. 8 Start | Reg. 8 Stop | 'HSR' From | 'HSR' To |
|---|---|---|---|---|---|---|---|---|---|
| *Alopecurus myosuroides* | CAC84161 | 2320 | 135 | 842 | 1556 | 1654 | 2204 | 1781 | 2098 |
| *Oryza sativa* | EAY97401 | 2327 | 135 | 842 | 1561 | 1665 | 2216 | 1792 | 2109 |
| *Echinochloa crus-galli* | ADR32358 | 2316 | 132 | 839 | 1549 | 1648 | 2201 | 1775 | 2092 |
| *Setaria italica* | AAO62902 | 2321 | 132 | 839 | 1549 | 1653 | 2206 | 1780 | 2097 |
| *Sorghum bicolor* | EES10506 | 2326 | 132 | 839 | 1554 | 1658 | 2211 | 1785 | 2102 |
| *Zea mays* | AAP78896 | 2324 | 132 | 839 | 1552 | 1656 | 2219 | 1783 | 2100 |

The HSR ("Herbicide Sensitivity Region") in the above ACCases is the segment corresponding to that spanning the set of all ACCase herbicide tolerance mutations known to date, which comprises the sequence from and to the positions indicated above in the final two columns. Note that the complete HSR may include some amount of sequence further upstream and/or further downstream from the above-indicated sequence of the HSR, e.g., from about 10, 20, or 30 residues upstream and/or to about 10, 20, or 30 residues downstream of the indicated sequence, or from about 1750 (Am), 1760(Am), 1770(Am), or 1780(Am) to about 2100 (Am), 2110(Am), 2120(Am), or 2130(Am).

Because the HSR has now been defined to be a finite portion of Region 8 of such multi-functional ACCases, this also now make possible yeast system embodiments that employ a chimeric ACCase that comprises three regions, an N-terminal region derived from a cytoplasmic ACCase, an HSR containing region derived from a monocot plastidic ACCase and an additional region 3' to the HSR derived from a cytoplasmic ACCase. Thus, the above-described HSR segment, or the larger Region 8 segment, or the entirety of the Region 8 can be used.

In other embodiments, the C-terminal region comprises about 50% to about 60% of the total length of the chimeric ACCase. In specific embodiments, the C-terminal region comprises about 50%, about 51%, about 52%, about 53%, about 54%, about 55%, about 56%, about 57%, about 58%, about 59%, or about 60% of the total length of the chimeric ACCase.

The native monocot ACCase HSR has been found, in the present work, to include the ACCase segment from 1781 (Am) to 2098(Am). In some embodiments, a larger portion of Region 8 of an herbicide-sensitive, monocot ACCase can be used, e.g., a region starting at about 1750(Am), 1760 (Am), 1770(Am), or 1780(Am), and extending to about 2100(Am), 2110(Am), 2120(Am), or 2130(Am). In some embodiments, such a later portion of an herbicide-susceptible, monocot plastidic ACCase Region 8 can comprise: the entirety of the herbicide susceptible, monocot ACCase's sequence corresponding to the segment from about 1750 (Am) to about 2130(Am); or a complete herbicide-susceptible, monocot plastidic ACCase's Region 8 sequence, i.e. the sequence corresponding to the segment from about 1654(Am) to 2204(Am).

Herbicide sensitive residue positions include the following, listed with exemplary, native-type herbicide-sensitive amino acid residues: I1781(Am), A1785(Am), A1786(Am), I1811(Am), Q1824(Am), V1864(Am), W1999(Am), W2027(Am), E2039(Am), I2041(Am), V2049(Am), A2059 (Am), W2074(Am), V2075(Am), D2078(Am), S2079(Am), K2080(Am), I2081(Am), C2088(Am), K2095(Am), G2096 (Am), and V2098(Am). In some embodiments, one or more of these positions may be mutated to an herbicide tolerant residue and the resulting HSR included in a chimeric ACCase of the invention. Such a chimeric ACCase can be used to generate additional mutations in the chimeric ACCase that may allow for a greater herbicide tolerance than that exhibited by the chimeric ACCase having only a single herbicide tolerance mutation.

The following table provides some examples of mutations and expected herbicide tolerance characteristics of and ACCase having the indicated mutation:

| Mutation | Cycloxydim Tolerance | Tepraloxydim Tolerance | Haloxyfop Tolerance |
|---|---|---|---|
| I1781L | High | Low | High |
| I1781T | Medium | None | Low |
| I1781V | Medium | Low | Medium |
| G1783C | Low | None | Low |
| A1785G | Low | None | Low |
| A1786P | Low | None | Medium |
| I1811N | Low | None | None |
| A1837V* | Higher | Higher | Higher |
| V1864F* | Lower | Higher | None |
| W1999C* | Higher | Higher | Higher |
| W1999G | High | Medium | Very High |
| I2041V* | Higher | Higher | Higher |
| V2049C* | Higher | Higher | None |
| V2049F | Low | Medium | None |
| V2049I* | Same | Higher | Same |
| V2049T* | Lower | Higher | Hone |
| W2074L | Low | None | None |
| V2075G | Low | None | Medium |
| V2075I | None | Low | None |
| V2075L | Low | High | Low |
| V2075M | None | Very High | Medium |
| 2xV2075* | Same | Higher | Same |
| D2078G | High | High | High |
| D2078T | High | High | High |
| K2080E* | None | Higher | Higher |
| ΔK2080ΔI2081 | None | Low | Low |
| C2088G* | Lower | Higher | Higher |
| C2088H* | Higher | Higher | Higher |
| C2088K* | Higher | Same | Same |
| C2088L* | Higher | Higher | Higher |
| C2088R | High | Medium | Very High |
| C2088T | Lower | Higher | None |
| C2088V* | Lower | Higher | Higher |
| C2088W | Low | None | None |
| K2095E* | None | Higher | Same |
| G2096A | High | Medium | High |
| G2096S | Medium | Low | Medium |
| V2098A | High | High | Medium |
| V2098C* | Lower | Higher | None |
| V2098G | High | High | Low |
| V2098H | Medium | Medium | Low |
| V2098P | Medium | High | Medium |
| V2098S | Medium | High | Low |

*indicates identified in double mutants

Yeast/Fungi Sources of Cytoplasmic ACCase

In one embodiment, the present invention encompasses cytoplasmic ACCases or portions thereof from Yeast or Fungi. Members of the Yeast/Fungi group include, but are not limited to genus members of *Saccharomyces, Schizosac-*

*charomyces, Candida, Ascomycetes Neurospora, Kluyveromyces, Picha, Cryptococcus, Chrysosporium, Yarrowia, Arxula,* and *Hansenula.*

In other embodiments, the invention encompasses chimeric ACCases that have at least 90%, at least 91%, at least 92%, at least 93%, at least 94%, at least 95%, at least 96%, at least 97%, at least 98%, or at least 99% identity to a particular amino acid sequence for a cytoplasmic ACCases from Yeast or Fungi referenced herein.

Monocot Sources of ACCase

In some embodiments, the invention encompasses cytoplasmic and/or plastidic ACCases or portions thereof from the monocot family of plants.

In another embodiment, the present invention encompasses cytoplasmic and/or plastidic ACCases of the Ehrhartoideae subfamily. Examples of the subfamily Ehrhartoideae include, but are not limited to, those of the genera *Erharta, Leersia, Microlaena, Oryza,* and *Zizania.*

In yet another embodiment, the present invention encompasses cytoplasmic and/or plastidic ACCases of rice plants or portions thereof. Two species of rice are most frequently cultivated, *Oryza sativa* and *Oryza glaberrima.* Numerous subspecies of *Oryza sativa* are commercially important including, but not limited to *Oryza sativa* subsp. *indica, Oryza sativa* subsp. *japonica, Oryza sativa* subsp. *javanica, Oryza sativa* subsp. *glutinosa* (glutinous rice), *Oryza sativa* Aromatica group (basmati), and *Oryza sativa* Floating rice group.

In one embodiment, the present invention encompasses cytoplasmic and/or plastidic ACCases of the grass family Poaceae or portions thereof. The family Poaceae may be divided into two major clades, the clade containing the subfamilies Bambusoideae, Ehrhartoideae, and Pooideae (the BEP clade) and the clade containing the subfamilies Panicoideae, Arundinoideae, Chloridoideae, Centothecoideae, Micrairoideae, Aristidoideae, and Danthonioideae (the PACCMAD clade).

In another embodiment, the present invention encompasses cytoplasmic and/or plastidic ACCases of the commercially important monocots or portions thereof, including, but not limited to Sugarcane (*Saccharum* spp.), as well as Turfgrasses, e.g., *Poa pratensis* (Bluegrass), *Agrostis* spp. (Bentgrass), *Lolium* spp. (Ryegrasses), *Festuca* spp. (Fescues), *Zoysia* spp. (*Zoysia* grass), *Cynodon* spp. (Bermudagrass), *Stenotaphrum secundatum* (St. Augustine grass), *Paspalum* spp. (Bahiagrass), *Eremochloa ophiuroides* (Centipedegrass), *Axonopus* spp. (Carpetgrass), *Bouteloua dactyloides* (Buffalograss), and *Bouteloua* var. spp. (Grama grass).

In another embodiment, the present invention encompasses cytoplasmic and/or plastidic ACCases of the Bambusoideae subfamily or portions thereof. Examples of the subfamily Bambusoideae include, but are not limited to, those of the genera *Arundinaria, Bambusa, Chusquea, Guadua,* and *Shibataea.*

In another embodiment, the present invention encompasses cytoplasmic and/or plastidic ACCases of the Pooideae subfamily or portions thereof. Examples of the subfamily Ehrhartoideae include, but are not limited to, those of the genera *Triticeae, Aveneae,* and *Poeae.*

In yet another embodiment, the present invention encompasses cytoplasmic and/or plastidic ACCases of wheat plants or portions thereof. Two species of wheat are most frequently cultivated, *Triticum aestivum,* and *Triticum turgidum.* Numerous other species are commercially important including, but not limited to, *Triticum timopheevii, Triticum monococcum, Triticum zhukovskyi* and *Triticum urartu* and hybrids thereof. Examples of *T. aestivum* subspecies included within the present invention are *aestivum* (common wheat), *compactum* (club wheat), *macha* (macha wheat), *vavilovi* (vavilovi wheat), *spelta* and sphaecrococcum (shot wheat). Examples of *T. turgidum* subspecies included within the present invention are *turgidum, carthlicum, dicoccon, durum, paleocolchicuna, polonicum, turanicum* and *dicoccoides.* Examples of *T. monococcum* subspecies included within the present invention are *monococcum* (einkon) and *aegilopoides.*

In another embodiment, the present invention encompasses cytoplasmic and/or plastidic ACCases of barley plants or portions thereof. Two species of barley are most frequently cultivated, *Hordeum vulgare* and *Hordeum arizonicum.* Numerous other species are commercially important including, but not limited, *Hordeum bogdanii, Hordeum brachyantherum, Hordeum brevisubulatum, Hordeum bulbosum, Hordeum comosum, Hordeum depressum, Hordeum intercedens, Hordeum jubalum, Hordeum marinum, Hordeum marinurm, Hordeum parodii, Hordeum pusillum, Hordeum secalinum, Hordeum spontaneum.*

In another embodiment, the present invention encompasses cytoplasmic and/or plastidic ACCases of rye plants or portions thereof. Two species of rye are most frequently cultivated, *Lolium canariense* and *Lolium edwardi.* Numerous other species are commercially important including, but not limited to, *Lolium multiflorum, Lolium perenne, Lolium pericum, Lolium remotrum, Lolium rigidum,* and *Lolium temulentum.*

In another embodiment, the present invention encompasses cytoplasmic and/or plastidic ACCases of turfgrass or portions thereof. A turfgrass, as used herein, is a monocot, preferably a member of the Poaceae, that exhibits a growth habit as a ground-cover; such a growth habit is in many cases the result of a spreading or stoloniferous propagation pattern of the plant. Examples of genera to which turgrass species and varieties belong include: *Agropyron, Agrostis, Alopecurus, Ammophila, Andropogon, Arrhenatherum, Axonopus, Bouteloua, Bromus, Buchloe, Calamovilfa, Cenchrus, Chloris, Cynodon, Dactylis, Digitaria, Echinochloa, Ehrharta, Elymus, Eragrostis, Eremochloa, Festuca, Hilaria, Lolium, Muhlenbergia, Oryzopsis, Panicum, Paspalum, Pennisetum, Phalaris, Phleum, Poa, Setaria, Sorghastrum, Sorghum, Sporobolus, Stenotaphrum, Stipa, Trichachne, Tripsacum* and *Zoysia.* Numerous commercially important species of Turf grass include *Zoysia japonica, Agrostris palustris, Poa pratensis, Poa annua, Digitaria sanguinalis, Cyperus rotundus, Kyllinga brevifolia, Cyperus amuricus, Erigeron canadensis, Hydrocotyle sibthorpioides, Kummerowia striata, Euphorbia humifusa,* and *Viola arvensis.*

In yet other embodiments, the invention encompasses cytoplasmic and/or plastidic ACCases from monocot plants selected from *Zea* (for example *Zea mays*), *Sorghum* (for example *Sorghum bicolor, Sorghum vulgare*), millet (e.g. pearl millet (*Pennisetum glaucum*), proso millet (*Panicum miliaceum*), foxtail millet (*Setaria italica*), finger millet (*Eleusine coracana*)), pineapple (*Ananas comosus*), and banana species (*Musa* spp.) or portions thereof.

In other embodiments, the invention encompasses chimeric ACCases that have at least 90%, at least 91%, at least 92%, at least 93%, at least 94%, at least 95%, at least 96%, at least 97%, at least 98%, or at least 99% identity to a particular amino acid sequence for a monocot cytoplasmic and/or plastidic ACCase referenced herein.

In a specific embodiment, the invention encompasses a chimeric ACCase comprising an N-terminal region derived from a cytoplasmic ACCase from *Oryza sativa*.

In a specific embodiment, the invention encompasses a chimeric ACCase comprising a C-terminal region derived from a plastidic ACCase from *Oryza sativa*.

Methods of Screening/Growing/Isolating Yeast Cells Comprising a Chimeric ACCase

Methods of culturing yeast cells are well known in the art. However, in some embodiments, the invention encompasses culturing yeast cells deficient in yeast ACC1 while having a chimeric ACCase as described herein in an effort to induce, screen, grow, and/or isolate mutant ACCases comprising mutations that confer herbicide tolerance to the yeast cells.

In some embodiments, methods of the invention encompass culturing yeast cells in the presence of at least one herbicide in liquid or on solid media. In other embodiments, yeast cells are cultured in rich media prior to being exposed to at least one herbicide. In some embodiments, rich media may be supplemented with fatty acids, (including, but not limited to palmitic acid or steric acid) or biotin, alone or in combination. In some embodiments, yeast cells are cultured in media containing an increasing concentration of herbicide over time. In further embodiments, yeast cells are exposed to a stepwise increase of herbicide concentration over time.

In some embodiments, the methods of the invention encompass culturing yeast cells deficient in yeast ACC1 while having a chimeric ACCase in the presence of at least one herbicide. In such embodiments, herbicides include, but are not limited to an aryloxyphenoxypropionate (FOP) or cyclohexanedione (DIM) herbicide. In some embodiments, FOP herbicides include, but are not limited to, of cyhalofop, quizalofop, diclofop, clodinafop, fluazifop, metamifop, propaquizafop, and fenoxyprop. In other embodiments, DIM herbicides include, but are not limited to, alloxydim, butroxydim, clethodim, cycloxydim, tepraloxydim, sethoxydim, tralkoxydim, and profoxydim. In yet other embodiments, the herbicide includes, but is not limited to, any herbicide listed in Table 1 herein.

In some embodiments, yeast cells are exposed to at least one herbicide present at a concentration from about 0.02 µM to about 200 µM. In other embodiments, yeast cells are exposed to at least one herbicide present at a concentration of about 0.02 µM, about 0.05 µM, about 0.1 µM, about 0.5 µM, about 0.1 µM, about 5 µM, about 10 µM, about 40 µM, about 100 µM, or about 200 µM. In specific embodiments, yeast cells are exposed to cycloxidim at a concentration of about 1 µM, about 10 µM, about 40 µM, about 100 µM, or about 200 µM. In another specific embodiment, yeast cells are exposed to tepraloxydim at a concentration of about 1 µM, about 10 µM, about 40 µM, about 100 µM, or about 200 µM.

In some embodiments, yeast cells are exposed 1, 2, 3, 4, 5, 6, 7, 8, or more herbicides in one selection event. In other embodiments, yeast cells are exposed to at least 1, at least 2, at least 3, at least 4, at least 5, at least 6, at least 7, at least 8, or more herbicides in one selection event. Typically, a selection event represents one round of selection conditions whereby a collection of cells are screened for, in this case, herbicide tolerance. In other embodiments comprising at least 2 or more herbicides, said herbicides may be present at a concentration that is not inhibitory to the chimeric ACCase when used in isolation from other herbicides. In yet other embodiments, 2 or more herbicides may be used concurrently or sequentially.

Methods of Generating Mutant Chimeric ACCases

In some embodiments the invention encompasses mutant chimeric ACCases tolerant to at least one herbicide that arise due to mutations (for example, spontaneous or induced) of the chimeric ACCase present and selection in the presence of the at least one herbicide. In a specific embodiment, yeast cells are cultured in rich media prior to exposure to herbicide. In some embodiments, spontaneous mutagenesis may lead to at least one, at least two, at least three, at least four, at least five, at least six or more mutations that confer tolerance to the herbicide. In some embodiments, individual spontaneous mutations are sufficient to elicit tolerance to the herbicide used for selection. In other embodiments, mutations at multiple sites are required to provide tolerance to the herbicide tested. In yet other embodiments, the invention comprises using an ACCase with at least one known mutation that confers herbicide tolerance in a method to isolate or identify additional spontaneous mutations that increase or augment herbicide tolerance of the known mutation.

In a specific embodiment, the invention encompasses spontaneous mutation rates of about 1 tolerant mutation in every $5 \times 10^9$ cells.

In other embodiments, the invention encompasses a mutagenesis step to introduce mutations of the chimeric ACCase that will result in herbicide tolerance when yeast containing the mutated chimeric ACCase are cultured in the presence of the herbicide. In some embodiments, the mutagenesis step involves random mutagenesis of the nucleic acid encoding the chimeric ACCase.

In some embodiments, the chemical mutagenesis is performed by incubation of the yeast cell comprising the chimeric ACCase with a base analog mutagen. Base analog mutagens are chemicals that are structurally similar to normal bases and as such fool the DNA replication system. Their essential property is that they base-pair with two different bases thus making mutations because of their lack of consistency in base-pairing. To be mutagens they must be incorporated into the DNA and therefore they need be present during active DNA synthesis. One example is 5-bromo-deoxyuridine (5-BU), which can exist in two tautomeric forms: typically it exists in a keto form (T mimic) that pairs with A, but it can also exist in an enol form (C mimic) that pairs with G.

In other embodiments, the chemical mutagenesis is performed by incubation of the yeast cell comprising the chimeric ACCase with a base alkylating agent. Base alkylating agents react directly with certain bases and thus do not require active DNA synthesis in order to act but still do require DNA synthesis in order to be "fixed". They are very commonly used because they are powerful mutagens in nearly every biological system. Examples of alkylators include ethyl methane sulfonate (EMS), methyl methane sulfonate (MMS), diethylsulfate (DES), and nitrosoguanidine (NTG, NG, MNNG). These mutagens tend to prefer G-rich regions, reacting to form a variety of modified G residues, the result often being depurination. Some of these modified G residues have the property of inducing error-prone repair although mispairing of the altered base might also be possible. This stimulation of error-prone repair allows all sorts of mutation types to occur as a result of these mutagens, though base substitutions are by far the most frequent. It also appears that alkylated bases can mispair during replication.

In other embodiments, random mutagenesis is performed with UV radiation. In such methods, yeast cells comprising the chimeric ACCase sensitive to an herbicide is exposed to a UV source for a period of time sufficient to develop lesions in the DNA. Further protocols relating to UV induced mutagenesis can be found throughout the art including: Rose, M. D., Winston, F., and Hieter, P. 1990. Laboratory Course Manual for Methods in Yeast Genetics. Cold Spring Harbor Laboratory, Cold Spring Harbor, N.Y. which is hereby incorporated by reference for all purposes.

In other embodiments, the invention encompasses directed mutagenesis towards at least one or more amino acids. In some embodiments, directed mutagenesis may target 1, 2, 3, 4, 5, 6, 7, 8, or more amino acids in one event. In other embodiments, directed mutagenesis may be to randomize the selection of an amino acid substitution for at least one or more amino acid present in the ACCase. In other embodiments, the directed mutagenesis is a restrictive substitution of at least one amino acid present in the ACCase. In other words, directed mutagenesis may be developed to include particular amino acids, or classes of amino acids while excluding others.

In one embodiment, the directed mutagenesis is performed by providing a library of oligonucleotides which hybridize to the nucleic acid encoding the chimeric ACCase, but are mutagenic for at least one amino acid position. The randomized library will hybridize to the chimeric ACCase gene and trigger recombination, thereby incorporating the randomization of at least one amino acid position in the chimeric ACCase gene. In some embodiments, the randomized library is a complete randomization for nucleotide base inclusion into the codon. In other embodiments, the randomized library is a restricted diversity library where the inclusion of nucleotides into the codon is not completely random, for example, the restriction of the first position being adenine with result in codons that code for amino acids that all begin with adenine. The resultant mutagenized chimeric ACCase gene can then be expressed and selected for herbicide tolerance as described herein.

Other suitable mutations that may be encoded in an oligonucleotide and used to construct an ACCases to be used in the present invention include those in the following table.

| Wild type amino acid and position | possible mutations |
|---|---|
| I1781 | L, V, T, A |
| G1783 | C |
| A1785 | G |
| A1786 | P |
| I1811 | N |
| Q1824 | P |
| A1837 | V |
| V1864 | F |
| W1999 | C, G |
| W2027 | C, R |
| E2039 | G |
| I2041 | N, V |
| V2049 | F, I, L, C, T |
| A2059 | V |
| W2074 | L |
| V2075 | M, L, I, GVV(double valine) |
| D2078 | K, G, T |
| S2079 | F |
| K2080 | E, deleted |
| I2081 | deleted |
| C2088 | R, W, F, G, H, K, S, T, L, V |
| K2095 | E |
| G2096 | A, S |
| V2098 | A, G, P, H, S, C |

In other embodiments, the invention encompasses mutant and chimeric ACCase wherein the at least one or more of the following specific substitutions is not present: I1781L, W2027C, I2041N, G2096A, D2078G and C2088R.

In a specific embodiment, the invention encompasses a yeast cell which comprises no active genomic ACCase gene, a nucleotide sequence encoding a chimeric ACCase as described herein, and at least one oligonucleotide that is mutagenic for at least one amino acid position in the chimeric ACCase.

In a specific embodiment, the invention encompasses compositions and methods where a chimeric ACCase is randomized at the amino acid corresponding to position 1781(Am) of the plastidic ACCase of *Oryza sativa*. In other embodiments, the invention encompasses compositions and methods in which a chimeric ACCase is randomized at the amino acid corresponding to a position selected from 1781 (Am), 1999(Am), 2049(Am), 2075(Am), 2075(Am), 2078 (Am), 2098(Am), 2027(Am), 2041(Am), 2096(Am), and 2088(Am) of the plastidic ACCase of *Oryza sativa* (which are positions referenced to *Alopecurus myosuroides*).

Products

In some embodiments, the invention encompasses mutant ACCases which are tolerant to at least one herbicide. Typically, mutant ACCases are constructed providing an ACCase-deficient yeast with a chimeric ACCase. Generally, the chimeric ACCase comprising at least two regions, an N-terminal and a C-terminal region. In some embodiments the N-terminal region is derived from yeast, fungi or monocot cytoplasmic ACCases while the C-terminal region is derived from monocot plastidic ACCases and comprises an HSR. Once yeast cells complemented with the chimeric ACCase gene are cultured in the presence of herbicide, tolerant cells may be isolated. These tolerant cells may be studied to identify the mutation(s) not present in chimeric ACCase prior to culturing, which confers tolerance to at least one herbicide. Once the mutations conferring tolerance to the chimeric ACCase are known, they may be introduced into a full-length monocot plastidic ACCase gene.

Methods for introducing the herbicide tolerant mutation in a full-length monocot plastidic ACCase gene include general molecular biology techniques known in the art. In some instances, the mutation can be excised from the chimeric ACCase gene via restriction endonucleases and 'spliced' into the full length monocot plastidic ACCase gene. Alternatively, the mutation can be engineered into the full length gene through PCR. Additionally, an oligo encoding the mutation may be generated and delivered to a host cell containing the full-length gene and, through homologous recombination, the mutation can be incorporated.

Full length monocot plastic ACCase genes containing the desired mutations can then be introduced into plants and/or plant cells using any method known to those skilled in the art. Typically the gene will included nucleotide sequences that direct expression of the gene in the desired plant cells and organelles. Such sequences include, but are not limited to, promoter sequences, leader sequences, targeting sequences (for example, chloroplast targeting sequences), terminator sequences and the like. The genes may be introduced using any methods known to those skilled in the art including, but not limited to, by using tumor-inducing (Ti) plasmid vectors, plant transformation vectors, PEG mediated protoplast transformation, electroporation, microinjections, and biolistics or microprojectile bombardment. Plant cells comprising the mutated ACCase gene may then be regenerated into plants using known techniques. The regenerated plants will comprise the mutated ACCase gene. Typically, the mutated gene will render the plant herbicide resistant. In some embodiments, the ACCase gene comprising one or more substitutions will be introduced into the wild type locus of the ACCase gene.

Methods for Determining Herbicide Sensitivity

In some embodiments of the invention, chimeric ACCases invention comprise an HSR derived from a monocot plastidic ACCase, rendering the chimeric ACCase herbicide sensitive. To determine if a monocot plastidic ACCase is suitable for use in constructing an herbicide-sensitive chimeric ACCase, the sensitivity of the monocot plastidic ACCase to inhibition by an ACCase-inhibiting herbicide may be determined using any assay method known to those skilled in the art.

The assay can be, e.g., either (1) a whole-plant assay, e.g., a visual injury rating scale, scored following contact with a 1× rate of ACCase-inhibitor selected from among the DIMs, FOPs, and DENs, according to manufacturer's instructions; or (2) a cell-based assay (e.g., plant cell-based or microbial cell-based) wherein the cells are exposed to equivalent concentrations of ACCase inhibitor as are delivered to in planta cells in the plant-based assay, taking into account the increase in delivery of herbicide active ingredient(s) to the cells of an in vitro cell-based assay. In either the whole-plant or cell-based assay, the ACCase whose herbicide susceptibility is being determined can be native to the plant or cell or can be exogenous thereto. The degree of herbicide-induced injury to the plant or cell/cell culture provides an indication of whether or not the monocot plastidic ACCase therein is to be considered "susceptible" to the herbicide.

Whole Plant (PVHI) Assay Example

For example, in a whole-plant assay to determine herbicide susceptibility, a visual injury rating scale of 0 to 10 can be used, wherein 0 indicates no visually detectable injury symptoms, and 10 indicates death of the plant. Use of such a scale to score plant "injury" can take into account symptoms including, e.g., chlorosis or other discoloration, necrosis, wilting, stunting and other plant deformity. In one exemplary 0- to 10 plant injury rating, plants rated from 0 to 3=tolerant, with 0 to 1=highly tolerant; plants rated 4 to 10=susceptible, with 8 to 10=highly susceptible.

In an exemplary embodiment, an herbicide sprayer calibrated to deliver a spray volume of typically about 100-500 L/ha (usually about 250 L/ha) can be used and, following treatment, the injury determination can be made at least once within 4 weeks after treatment. An example of such a visual injury rating scale is as follows:

0 no visible symptoms
1 slight symptoms
2 minor symptoms
3 mild symptoms, with agronomically-acceptable appearance maintained
4 evident symptoms, with no reduction in biomass
5 obvious symptoms, with likely reduction in biomass
6 substantial symptoms, with definite reduction in biomass
7 25-50% of plant tissue exhibits necrosis
8 50-75% of plant tissue exhibits necrosis
9 >75% of plant tissue exhibits necrosis
10 total plant death Such an assay can be referred to herein as a Plant Visual Herbicide Injury (PVHI) assay.

Cell-Based (CBHI) Assay Example

In the case of cell-based assay to determine herbicide susceptibility, a post-herbicide-treatment rating scale can be used that ranges, e.g., from 0 to 6, with 0 indicating no symptoms and 6 indicating death of all cells, wherein a score of 0-2 indicates tolerant, with 0-1 being highly tolerant; and 3-6 indicating susceptible, with 5-6 being highly susceptible. In scoring "injury" for cells, symptoms to be noted include, e.g., temporary decrease in rate of cell multiplication, decrease in production of normal metabolites (e.g., fatty acids, phospholipids), increase in production of stress-related metabolites (e.g., abscisic acid, ethylene, GABA), sustained decrease in rate of cell multiplication, decrease in plant cell chloroplast population, plant cell senescence, chloroplast localization in the plant cell vacuole, cell membrane deformation or disruption, cell leakage, and cell lysis. In an exemplary embodiment, the scoring can be performed at least once within 10 days following exposure to the herbicide. In the case of such a cell-based assay, the visual scoring can be done by eye alone, or with the aid of a microscope, metabolic screen, dye or contrast agent, or other analytical equipment or supplemental agent.

Such an assay can be referred to herein as a Cell-Based Herbicide Injury (CBHI) assay.

EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

Example 1

Construction of Yeast ACCase Screening Cell Line

Summary: For the invention described here, we constructed a rice (Oryza sativa) chimeric ACCase gene (OsJACCc60p40) corresponding to the N-terminal 60% of the rice cytoplasmic ACCase gene fused to the C-terminal 40% of the rice plastidic ACCase gene. A low copy number CEN plasmid with OsJACCc60p40 (where c60=cytoplasmic 60% and p40=plastidic 40%) was introduced into the yeast heterozygous diploid YNR016C BY4743 (acc1::kanMX/ACC1), which was equipped with the SGA reporter for plasmid-chromosome shuffling (Tong et al., 2001). After sporulation and germination on selective medium, MATa haploid cells relying solely on rice OsJACCc60p40 for fatty acid biosynthesis were obtained. These cells can be used to isolate mutations by plating cells directly on medium containing herbicide. These cells were made competent for LiAc/PEG-based transformation (Gietz et al., 1992) of DNA fragment mixtures that could create mutant chimeric ACCase genes through homologous recombination. We demonstrated that directed and spontaneous mutagenesis leads to herbicide tolerant chimeric ACCases.

Yeast Strains and Growth Conditions

The heterozygous diploid YNR016C BY4743 (MATa/α his3Δ1/his3Δ1 leu2Δ0/leu2Δ0 lys2Δ0/LYS met15Δ0/MET15 ura3Δ0/ura3Δ0 can1Δ::LEU2-MFApr-HIS3/CAN1 acc1::kanMX/ACC1 [Chromosome: 14]) was ordered from Open Biosystems (catalogue number YSC4034-97040689, clone ID 25391). YNR016C BY4743 was grown in YPG (20 g/L yeast extract, 40 g/L bacto tryptone, 2% filter-sterilized galactose, pH 6.5) with 200 mg/l G418 (Invitrogen, Carlsbad, Calif.) at 30° C. and 200 rpm. Haploid strains, which depend on plasmid-borne plant ACCase for fatty acid biosynthesis, were grown in 1 g/L monosodium L-glutamic acid, 1.7 g/L yeast nitrogen base without amino acids and without ammonium sulfate (BD, Franklin Lakes, N.J.), 1.57 g/L SC-Arg-His-Leu-Ura (Sunrise Science, San Diego, Calif.), 2% galactose, 200 mg/L G418 and 50 mg/L L-Canavanine (Sigma-Aldrich, St. Louis, Mo.) at 30° C. and 200 rpm. The control haploid strain which depends on yeast ACC1 for fatty acid biosynthesis was grown in 1 g/L mono sodium L-glutamic acid, 1.7 g/L yeast nitrogen base without amino acids and without ammonium sulfate, 1.57 g/L SC-Arg-His-Leu-Ura, 2% galactose, 50 mg/L L-Canavanine and 0.02 g/L Ura at 30° C. and 200 rpm. For growth on plates, all media were supplemented with 20 g/L Difco Agar Noble 214230. For all media, with the exception of YP, agar was autoclaved separate from the other solutions as suggested by Tong and Boone (2006). Cycloxydim was kept as a 614 mM stock solution in naphtha or a 100 mM stock solution dissolved in methanol. Both haloxyfop and tepraloxydim were kept as 100 mM solutions in DMSO.

Plasmid Construction

A fusion construct of the GAL10 promoter, OsJACCc60p40 and the ADH1 terminator (FIGS. 1B and 2C) was synthesized by GENEART (Regensburg, Germany). The nucleotide sequence of OsJACCc60p40 was optimized for expression in yeast with Leto 3.0 software (Entelechon, Regensburg, Germany). Restriction sites for mutagenesis and subcloning were introduced at key points (FIG. 1B) and homology with yeast ACC1 was kept to a minimum to avoid gene conversion. The construct was delivered as purified plasmid in the pMK vector (RTP3240, FIG. 2A). The yeast expression vector pRS416 (Mumberg et al., 1995) was modified prior to cloning of the 7468 bp SalI-SpeI fragment of RTP3240 containing GAL10pr-OsJACCc60p40-tADH1. The NotI and Acc651 site in the multiple cloning site of pRS416 were sequentially eliminated by digestion with the corresponding enzymes, 'blunting' with T4 DNA polymerase (Promega, Madison, Wis.) and re-ligation. The adapted pRS416ΔNotIΔAcc651 plasmid was digested with XhoI and SpeI and RTP4108 was constructed by ligation of the 7468 bp SalI-SpeI fragment of RTP3240 (FIGS. 2B and 2C).

Figure 3A:
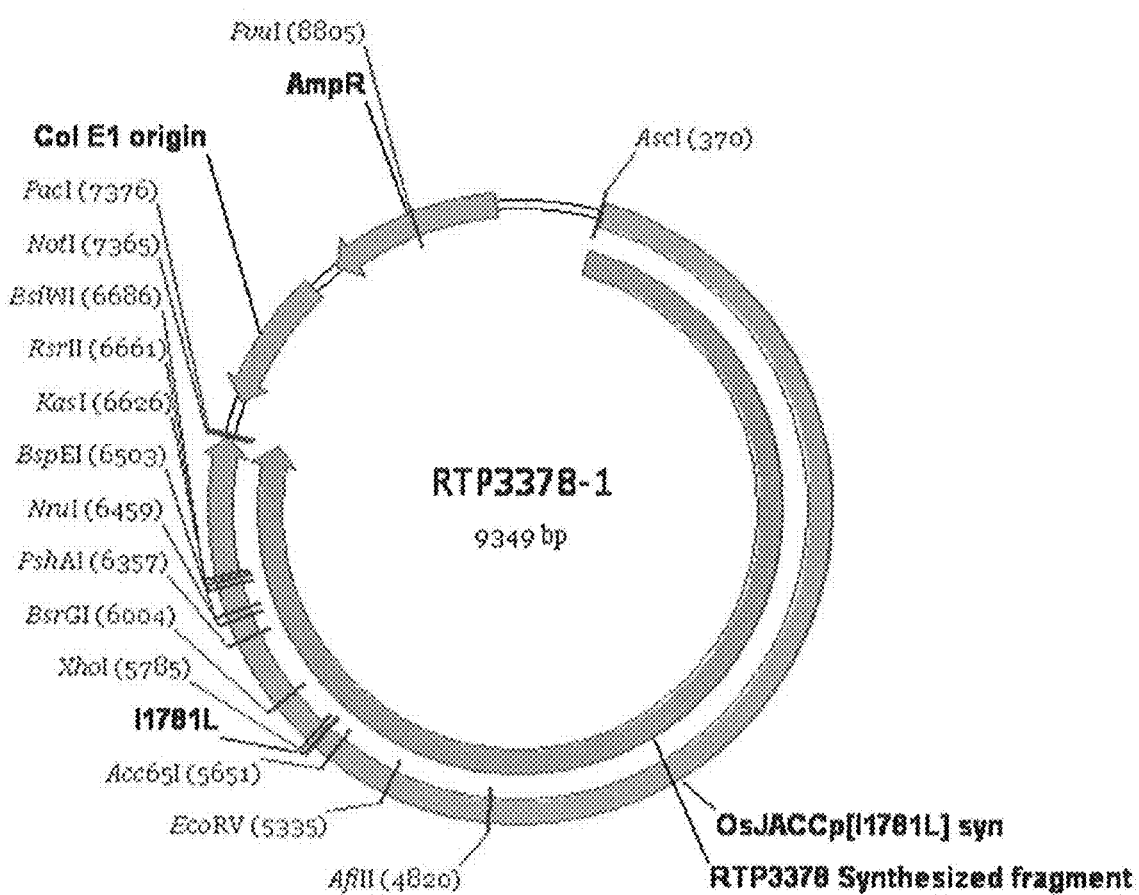
FIG. 3A provides an overview of plasmid RTP3378.

The complete rice plastidic ACCase coding sequence was also synthesized by GENEART and delivered as RTP3378 (FIG. 3A). This ACCase sequence (FIG. 3B) was optimized for expression in rice and most of the restriction sites present in RTP4108 were included in corresponding positions to allow exchange of subfragments. The triplet at relative position 1781 in RTP3378 was synthesized to encode leucine rather than the 'wild type' amino acid isoleucine (I1781L). A 134 bp Acc65I-XhoI fragment of RTP3378 with the I1781L mutation was exchanged with the corresponding fragment in RTP4108 to produce the control plasmid RLW001. C-terminal 10×His tags (SEQ ID NO: 31) were added to both RLW001 and RTP4108 for plasmids RTP4106 and RTP4107, respectively by exchanging the BamHI-NotI fragments at the 3' coding end with the BamHI NotI-digested synthetic sequence:

```
                                        SEQ ID NO: 1
ggatccaactttgattgacttgaaggctaagtggaagttgccaacaagaa tggatctgctgatacgaagtctttgcaagaaaatattgaagctagaacta agcaactgatgccattatacacccaaattgctatcagattcgctgaattg catgatacctctttgagaatggctgctaagggtgttatcaagaaggttgt tgattgggaagaatccagatctttcttctacaagagattgagaaggagaa tttccgaagatgttttggctaaggaaattagagctgttgctggtgaacaa ttctctcatcaaccagctattgaactgattaagaagtggtactctgcttc tcatgctgcagaatgggatgatgatgatgctttcgttgcttggatggata
```

Figure 4:
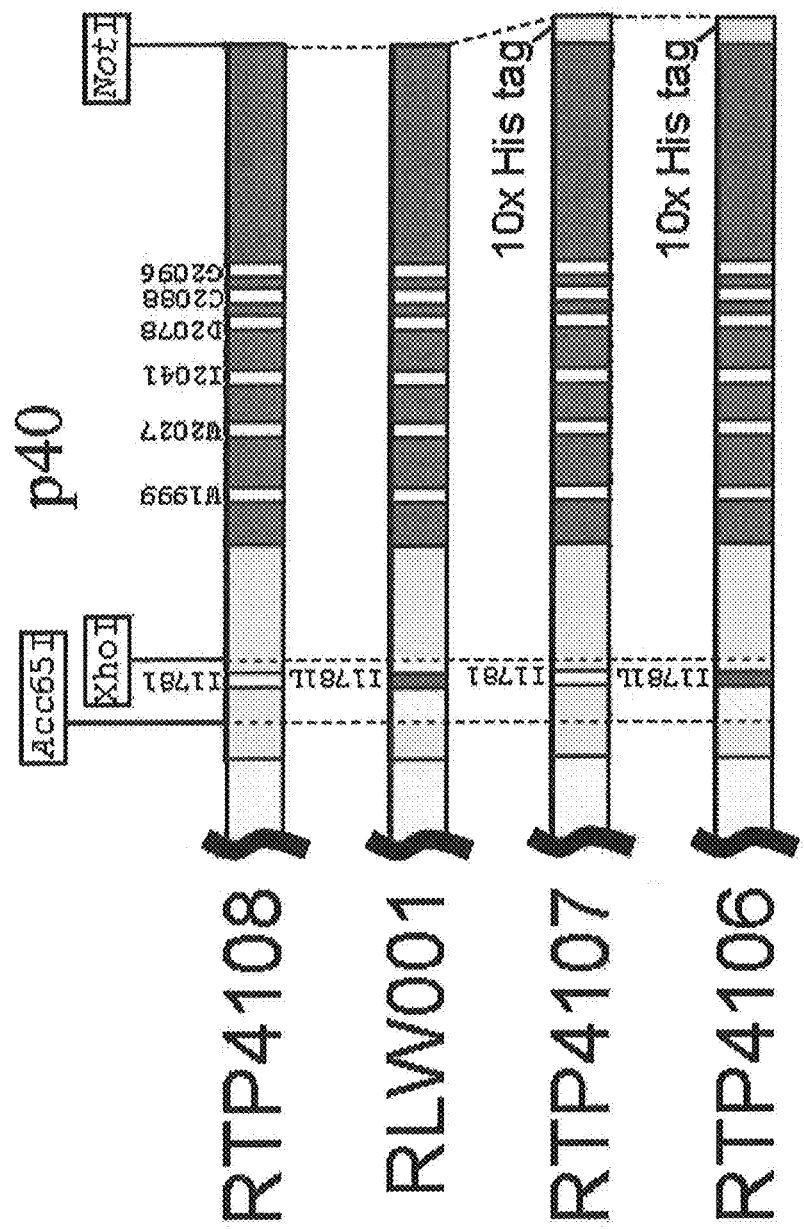
FIG. 4 provides an overview of the p40 (40% plastidic) regions of four yeast vectors used in this work. All plasmids were identical to RTP4108 outside these regions. RLW001 and RTP4106 contain a small stretch that is optimized for expression in rice between Acc65I and XhoI.

```
                                        -continued
acccagaaaactacaaggactacattcaatacctgaaagctcaaagagtg tctcaatctttgtcctctttgtctgattcctcttctgatctacaagctct accacaaggtttgtctatgttgttggataagatggacccatctagaagag ctcaattggttgaagaaatcagaaaggttttgggtcatcatcatcatcat catcatcatcatcattgataagcggccgc
(RTP3889, 10x His (SEQ ID NO: 31) codons underlined,
FIG. 4).
```

Transformation of Plasmids Harboring Rice Chimeric ACCase Gene Constructs

Transformation was carried out with the Yeastmaker™ Yeast Transformation System 2 kit (Clontech, Mountain View, Calif.) as described in Clontech's manual with 200 ng plasmid. Cells were plated on 20 g/l Difco Agar Noble 214230, 1 g/L monosodium L-glutamic acid, 1.7 g/L yeast nitrogen base without amino acids and without ammonium sulfate, 1.57 g/L SC-Arg-His-Leu-Ura, 2% galactose, 200 mg/L G418 and 0.02 g/L His.

Sporulation and Plasmid-Chromosome Shuffling

Single colonies of the heterozygous diploid YNR016C BY4743 harboring a plasmid with rice chimeric ACCase were grown in 10 mL 1 g/L monosodium L-glutamic acid, 1.7 g/L yeast nitrogen base without amino acids and without ammonium sulfate, 1.57 g/L SC-Arg-His-Leu-Ura, 2% galactose, 200 mg/L G418 and 0.02 g/L His at 30° C. and 200 rpm until the OD600 nm reached 0.400. Cell cultures were transferred to 50 mL tubes, centrifuged (700×g, 5 minutes) and washed in 40 ml H₂O. The wash step was repeated and cells were resuspended in 2 ml sporulation medium (1% KAc, 0.005% ZnAc, 0.3 mM His). Tubes were shaken horizontally at 25° C., 200 rpm for 5 days. Cells were collected through centrifugation, washed with 40 ml H₂O and resuspended in 10 mL H₂O after the final centrifugation step. 50 μL and 50 μL of 10× and 100× dilutions were plated on 20 g/L Difco Agar Noble 214230, 1 g/L monosodium L-glutamic acid, 1.7 g/L yeast nitrogen base without amino acids and without ammonium sulfate, 1.57 g/L SC-Arg-His-Leu-Ura, 2% galactose, 200 mg/L G418 and 50 mg/L L-Canavanine and incubated at 30° C. for 5 days. To obtain the control haploid strain which depends on yeast ACC1 for fatty acid biosynthesis the same procedure was used with the following changes: Initial growth took place in YPG with 200 mg/mL G418 and plates for selection of haploids did not contain G418, but were supplemented with 0.02 g/L Ura.

Confirmation of Genotype

Cells from 1 mL of culture were washed twice with 1 mL TE buffer. Following the last centrifugation step, excess liquid was aspirated and the cells were resuspended and disrupted by freeze-thawing. Subsequently, samples were heated at 95° C. for 5 min with occasional shaking. Cell debris was removed by centrifugation for 5 min and 2 μL of the denatured genomic DNA sample was used to confirm the genotype by PCR amplification with rice chimeric ACCase-specific primers (c60p40-5924FW: ttctcacgtcaagattccacc [SEQ ID NO:3] and c60p40-6421RV: tactcaccagtttccatagag [SEQ ID NO:4]) and ACC1-specific primers (ACC1aFW: gtgttgacaccgttcacgtgg [SEQ ID NO:5] and ACC1aRV: caccggagaccatttccgttg [SEQ ID NO:6]; ACC1bFW: gtttggctcagaagtacatc [SEQ ID NO:7] and ACC1bRV: tcatggtcgct-tctgatcttt [SEQ ID NO:8]). PCR was performed with the Expand High Fidelity PCR system (Roche, Mannheim, Germany) according to the manufacturer's instructions.

Mutagenesis with DNA Fragments Containing Degenerate Nucleotides

Fragment mixtures with degenerate nucleotides in selected positions were ordered from Epoch Biolabs (Sugar Land, Tex.). A fragment designated LN1-mut spanned 1169 bp of the 3' coding end of OsJACCc60p40 and had the following composition:

SEQ ID NO: 2
```
tacctctgttattgctcacaagatgcaacttgattctggtgaaattagat
gggtcattgattccgttgttggtaaggaagatggtttgggagttgaaaat
nnncatggttctgcgcaattgcttctgcttactcgagagcttacaaggaa
acgttcactttgactttcgttactggtagaactgttggtattggtgctta
cttggctagattgggtatcagatgcatccaaagacttgatcagcctatta
tcttgactggttactctgctttgaataagttgttgggtagagaagtttac
tcgtctcatatgcaatgggtggaccaaagattatggcaacaaatggtgt
tgtacacttgactgtttctgatgacttggaaggtgtctctaatatcctga
gatggttgtcttacgttccagcttacattggtggtcctttgccagttact
actccattggacccacctgatagaccagtgcttacatacctgaaaactct
tgcgatccaagagctgcaattagaggtgttgatgactctcaaggtaagtg
gcttggtggcatcttcgataaggattccttcgttgaaactttcgaaggtt
gggctaagactgttgttactggtagagctaagctaggaggtattccagtt
ggtgttattgcagttgaaacgcaaactatgatgcaaactattccagctga
ccaggtcaattggattctagagaacaaagtgttcctagagctggtcaagt
tnnnttcccagattctgctacaaagactgctcaagctttgttggacttca
atcgcgaaggttgccattgttcatcttggcaaatnnnagaggtttctccg
gaggtcaaagagatttgttcgaaggtnnnttgcaagctggttctactatc
gtcgaaaacttgagaacctacaatcaaccagctttcgtttacattcctat
ggctgctgaattgagaggtggcgcctgggttgttgttnnntctaagatta
acccggaccgtatcgaannnntacgctgaacgtacggctaagggtaatgtt
ttggaaccacaannnttgattgaaatcaagttcagaagtgaagaattgca
agattgcatgagtagattggatccaactttgattgacttgaaggctaagt
tggaagttgccaaca
```

In one study only degeneracy in the triplet that corresponds to isoleucine at relative position 1781 was tested (nucleotides underlined). A 299 bp fragment mixture was amplified with the Expand High Fidelity PCR system using LN1-mut as template and c60p40-10451FW (tacctctgttattgctcacaa [SEQ ID NO:9]) and c60p40-10750RV (taaacttctctacccaacaac [SEQ ID NO: 10]) as primers.

In other experiments, each degenerate triplet was flanked by 150 bp OsJACCc60p40 DNA to allow incorporation through homologous recombination except the triplet corresponding to I1781. PCR was performed with the Expand High Fidelity PCR system using primers that match the outer 21 nucleotides of the 303 bp synthetic fragments. For I1781, the degenerate triplet was flanked by 100 bp at the 5' coding end and 197 bp at the 3' coding end in the final PCR product.

Preferably, the mutated triplet is centered in the synthetic fragment. In our first experiments with substitutions for I1781, the first set of synthetic fragment mixtures that was ordered contained large fragments with multiple mutations at multiple positions. That was used as template for the I1781 fragments in a PCR reaction (excluding the other mutations that were present). Later, synthetic, symmetric fragments for each position were used.

After PCR, primers and dNTPs were removed with the Wizard® SV Gel and PCR Clean-Up System (Promega) and the PCR product was checked on gel. Approximately 200 ng was used for transformation. When mixtures of oligonucleotides are being transformed, the scale of the transformation procedure may be increased to ensure each of the components in the mixture will be represented among the transformed colonies. For mixtures we used 6×5 μg in parallel using the Yeastmaker® library scale protocol (per herbicide). When a single mutation is introduced (for example I1781L) by using a purified single fragment, only one transformed colony is required on a plate. Thus the scale can be much lower, e.g 200 ng and the standard transformation protocol may be used.

Cells that rely on RTP4108 for fatty acid biosynthesis (designated RTP4108-8b-2) were pre-grown in YPG G418 or YPG G418 supplemented with 1% Tween, 0.015% palmitic acid, 0.015% stearic acid and/or 0.4 mg/L biotin. Prior to transformation cells were washed 2× with $H_2O$ to remove fatty acids from the medium. Transformation was performed as described in the Yeastmaker™ Yeast Transformation System 2 kit protocol with a 1½ hour recovery step in YPG. For each fragment mixture 6 transformations were plated onto medium with tepraloxydim and 6 onto medium with cycloxydim. Thus, 12 transformations at Yeastmaker's library scale are started simultaneously for each fragment mixture and they are treated the same until it is time to plate them on their respective herbicide plates. Control DNA consisted of the same fragment in which nnn was ATT (encoding isoleucine, therefore creating the original sequence present in RTP4108) and TTG (encoding leucine, therefore creating a positive control for transformation).

DNA Isolation, PCR of the 3' Coding End and Sequencing of Candidate Herbicide Tolerant Genes Single colonies growing on plates with herbicide were transferred to fresh plates and selected once more on medium with the same herbicide to remove any traces of unwanted, untransformed cells. Cells were subsequently grown in 1 mL liquid medium (1 g/L mono sodium L-glutamic acid, 1.7 g/L yeast nitrogen base without amino acids and without ammonium sulfate, 1.57 g/L SC-Arg-His-Leu-Ura, 2% galactose, 200 mg/L G418 and 50 mg/L L-Canavanine) without herbicide until the $OD_{600}$ nm reached 0.400. DNA was isolated with Zymoprep™ II, Yeast Plasmid Miniprep Kit (Zymo Research, Orange, Calif.). PCR was performed with the Expand High Fidelity PCR system and c60p40-9561FW (ccgttctctagaactattgac [SEQ ID NO:11]) and c60p40-12331RV (cgacctcatgctatacctgag [SEQ ID NO:12]) primers. Sequencing of PCR products was performed by DNA Landmarks. For high throughput sequencing cultures were grown in 1 ml medium in 96 deepwell blocks mounted on the shaker for 2 days. 0.4 ml of the fully grown yeast cultures was spun down and the pellets were resuspended in 30 ul zymolyase solution (2.5 mg/ml ICN zymolyase, 1.2 M Sorbitol, 0.1 M Na Phosphate pH 7.4). 10 ul of that suspension was aliquoted in V-shaped bottom 96-well plates and frozen on dry ice before shipping to DNA Landmarks. A stretch of DNA ranging from 227 bp upstream from the codon for I1781 to 194 bp downstream form the codon for V2098 was PCR-amplified (primers CTGGTGCAAGAATCGGTATT (SEQ ID NO:20) and TGGGTGTATAATGGCATCAGT (SEQ ID NO:21)) and sequenced.

High Throughput Production of Growth Curves in the Absence and Presence of Herbicides Single colonies of mutants and controls were grown in 1 g/l mono sodium L-glutamic acid, 1.7 g/l yeast nitrogen base without amino acids and without ammonium sulfate, 1.57 g/l SC-Arg-His-Leu-Ura, 2% galactose, 50 mg/l L-Canavanine and 200 mg/l G418 (rice hybrid ACCase-dependent strains) or 0.02 g/l Ura (ACC1-dependent strain) at 30° C. and 200 rpm for two days. Fully grown cultures were spun down and resuspended in 300-800 μl medium to produce starting strains with roughly comparable densities. 5 μl of starting strain was transferred in triplicate to 96 deepwell blocks with 1.5 ml of the same medium or the same medium supplemented with herbicide. Blocks were mounted on the shaker and 100 μl samples were taken every 24 hours to determine the optical density at 600 nm with the Multiskan Ascent (ThermoLabs) plate reader.

Results and Discussion

Design of OsJACCc60p40 and Construction of RTP4108

Figure 1B:
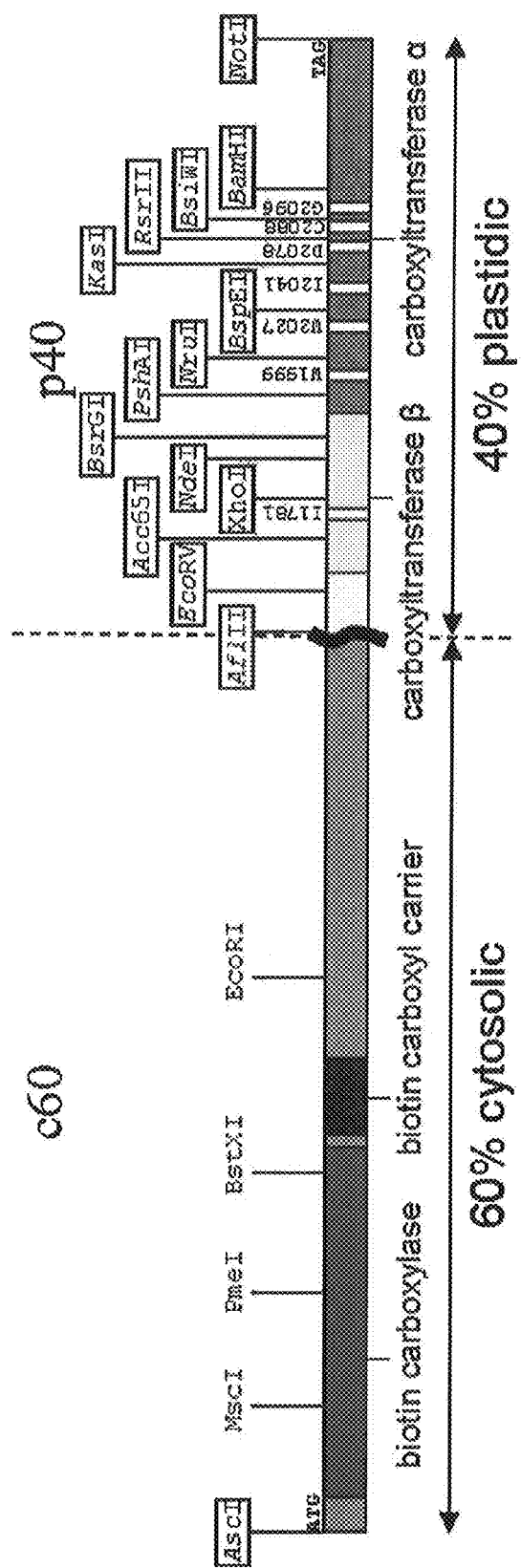
FIG. 1B provides an overview of the OsJACCc60p40 chimeric protein. Unique restriction sites introduced in the corresponding DNA sequence for subcloning are indicated. Amino acids for which substitutions have been found to confer herbicide tolerance are indicated by white rectangles.
Figure 2A:
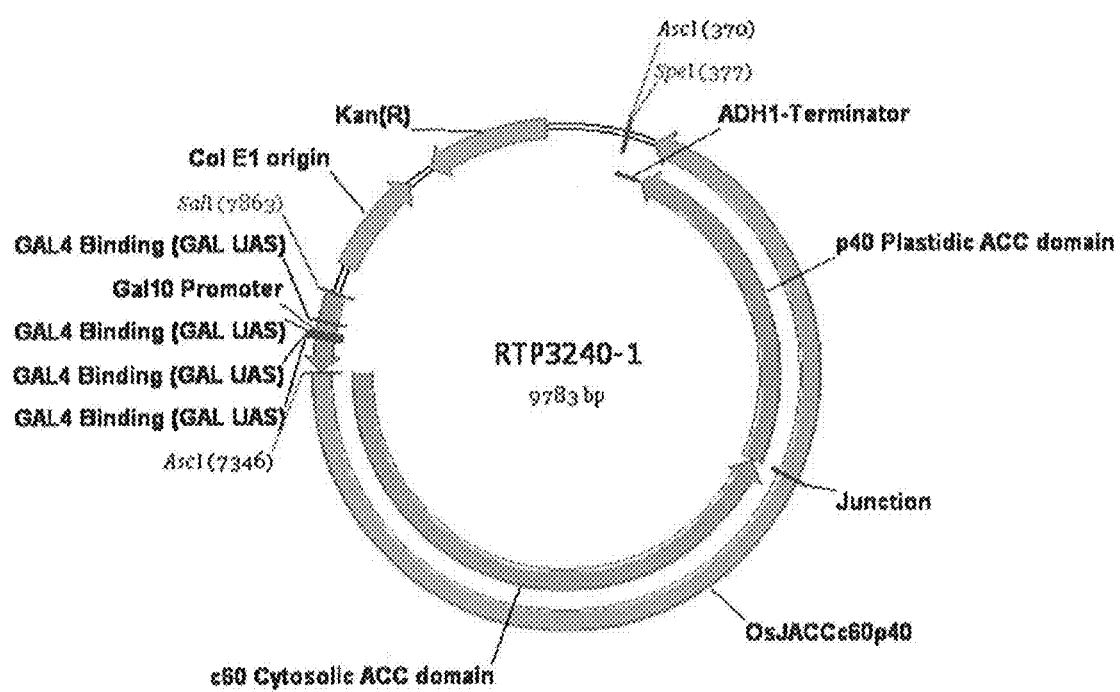
FIG. 2A provides an overview of plasmid RTP3240-1.
Figure 2B:
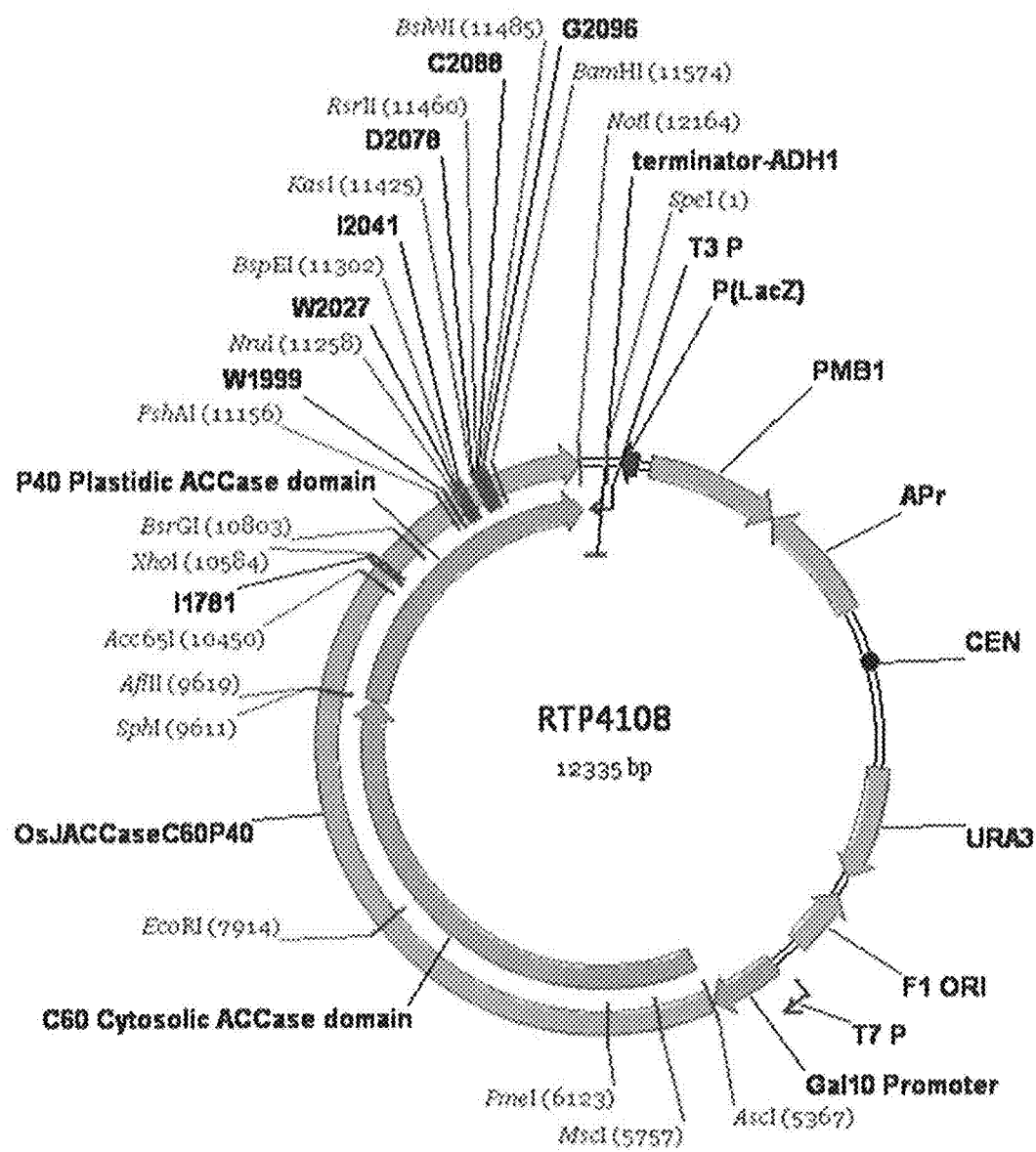
FIG. 2B provides an overview of plasmid RTP4108.

The sequences of the rice (Oryza sativa Japonica group) plastidic and cytoplasmic ACCase genes (Accession numbers EAZ33685 and AAM18728, respectively) were used to design the synthetic, chimeric ACCase gene OsJACCc60p40 (FIGS. 1B and 2C). The protein encoded by OsJACCc60p40 consists of the first 60% of the cytoplasmic ACCase protein and the last 40% of the plastidic ACCase protein. The sequence of the plastidic ACCase protein that was submitted to GenBank (EAZ33685) contained sequence errors, which were corrected with the help of ref|NC_008398.1|. With these corrections the amino acids sequence was found to be identical to that of the plastidic ACCase protein of the Indica group (EAY97401). The GAL10pr-OsJACCc60p40-tADH1 fusion construct was synthesized and cloned into a modified pRS416 shuttle vector (Mumberg et al., 1995) to create RTP4108. RTP4108 and all other plasmids that contain the GAL10pr-OsJACCc60p40 fusion construct or derivatives thereof are highly toxic to E. coli and prolonged growth of bacterial cultures results in gross rearrangements within the plasmid. Therefore, identical E. coli cultures were grown in parallel in five culture tubes in the presence of glucose until early log phase after which samples were checked for rearrangements. All culture tubes in which rearrangements were not apparent on gel after HindIII digestion were pooled and subjected to plasmid isolation. Maintenance of plasmids in E. coli was minimized to this step only. Next to RTP4108 (GAL10pr-OsJACCc60p40), we also constructed RTP4107 (GAL10pr-OsJACCc60p40+10× C-terminal His tag ("10×His tag" disclosed as SEQ ID NO:31)), RLW001 (GAL10pr-OsJACCc60p40 I1781L) and RTP4106 (GAL10pr-OsJACCc60p40 I1781L+10× C-terminal His tag ("10×His tag" disclosed as SEQ ID NO:31)) (FIG. 4).

Transformation of the Heterozygous Diploid YNR016C BY4743 (Acc1::kanMX/ACC1), Plasmid-Chromosome Shuffling and Complementation of ACC1 Deficiency by OsJACCc60p40

Figure 5:
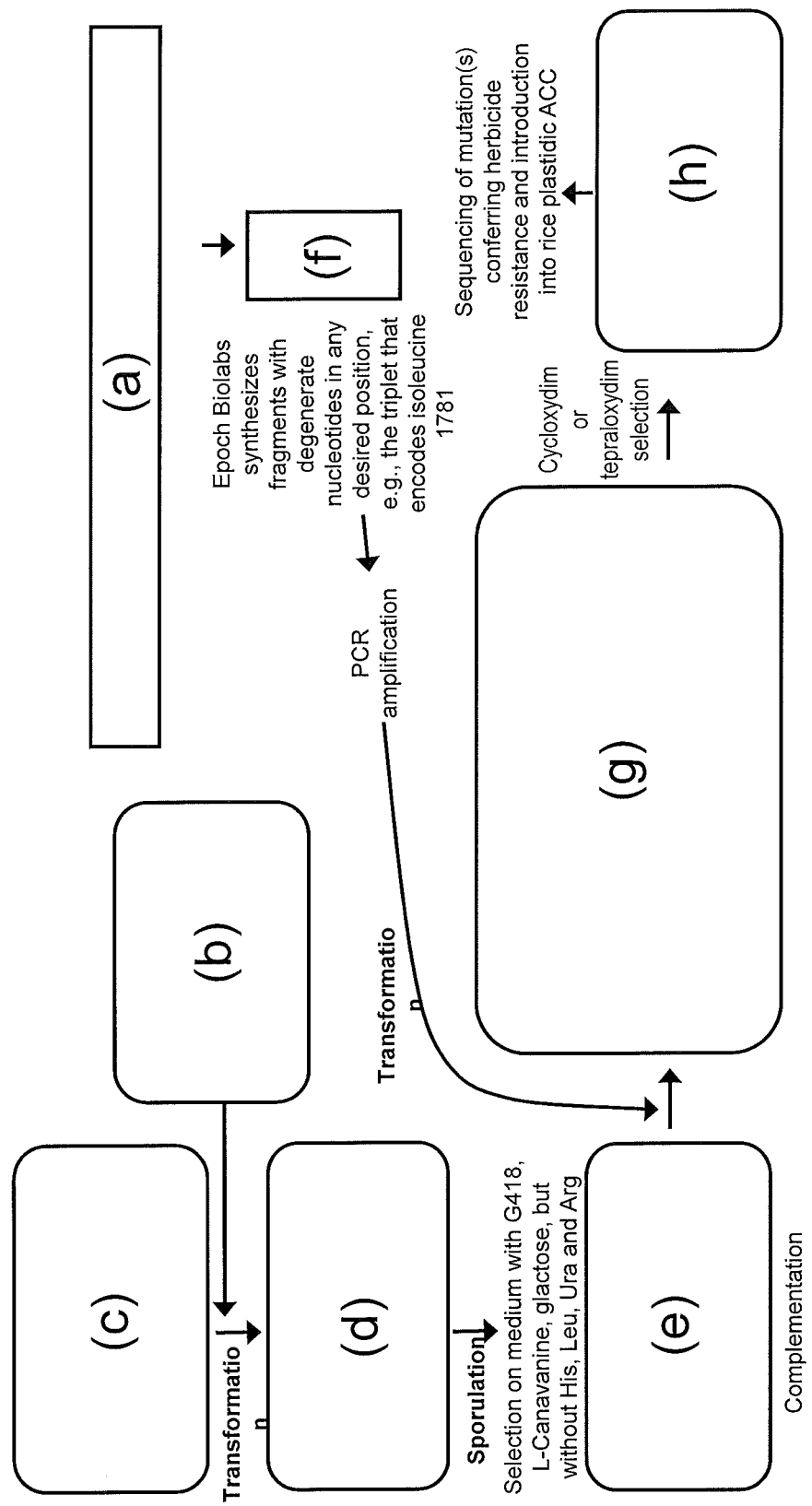
FIG. 5 presents an overview of directed in vitro evolution screening. Depicted in (a) is an overview of the rice chimeric ACCase present on RTP4108. Panels (b) through (e) represent plasmid-chromosome shuffling with the SGA reporter (can1Δ::LEU2-MFApr-HIS3/CAN1). Plasmids RTP4106, RTP4107 and RLW001 were also used for shuffling, (e)-(h). Panel (f) represents a library of synthetic DNA fragments with degenerate nucleotides at a desired position to mutagenize the chimeric ACCase present in the yeast cell. Panel (g) represents homologous recombination events that occur between the library of synthetic DNA fragments with the chimeric ACCase gene in the yeast cell followed by screening for mutations that confer tolerance to FOPs or DIMs along with sequencing of mutations conferring tolerance in panel (h).
Figure 6:
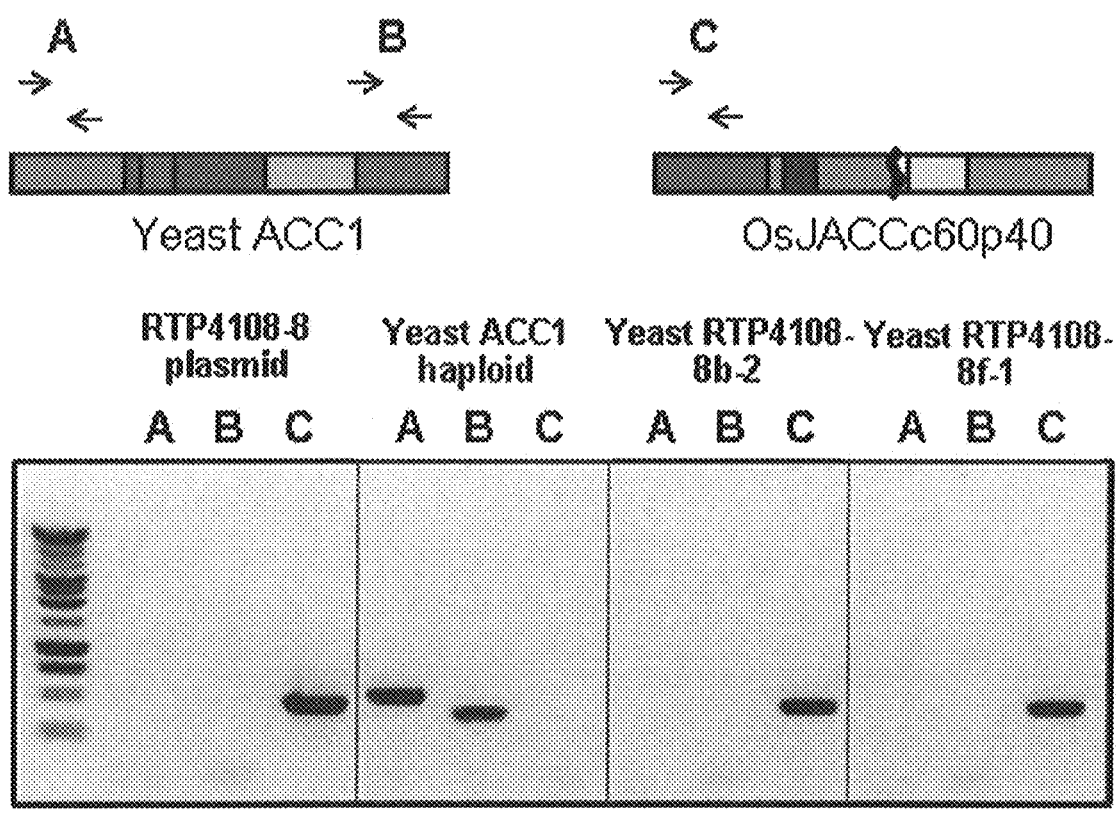
FIG. 6 represents an example of verifying the absence of an intact genomic copy of the Yeast ACC1 gene (primer pairs A and B) along with the presence of the chimeric ACCase gene (primer pair C). Independent haploid colonies relying on RTP4108 for FA biosynthesis were checked by PCR using ACC1-specific primer set A (ACC1aFW and ACC1aRV) and set B (ACC1bFW and ACC1bRV) and OsJACCc60p40-specific primer set C (c60p40-5924FW and c60p40-6421RV). A yeast haploid with ACC1 on chromosome 14 was used as a control.

Yeast mutants in which the endogenous ACC1 gene is deleted are not viable. We used a plasmid-chromosome shuffling method to replace the ACC1 gene with plasmid-borne rice chimeric ACCase (FIG. 5a-5e). The low copy number plasmids RTP4108, RTP4107, RLW001 and RTP4106 were transformed to the heterozygous diploid YNR016C BY4743 and cells were selected for the presence of the URA3 gene on the plasmid (FIG. 5b-5d). Thus, the diploid cells contained both the endogenous ACC1 gene and a rice chimeric ACCase. Shuffling was made possible due to two heterozygous loci: (i) on one of the chromosomes 14, the endogenous ACC1 gene had been replaced by the kanMX cassette, which confers resistance to G418 and (ii) on one of the chromosomes 5 the CAN1 gene had been replaced by the SGA reporter (can1Δ::LEU2-MFA1pr-HIS3/CAN1, Tong et al., 2001). Sporulation was induced in diploid cells which contained both ACCase genes. After sporulation cells were plated on selective medium and grown at 23° C. and 30° C. (FIG. 5d-5e). Haploid cells which inherited the endogenous ACC1 gene were killed by G418. All diploid cells still present in the sporulation mix and all haploid cells which possessed the CAN1 gene were killed by L-Canavanine; a toxic arginine analogue that is imported into the cell by the CAN1 gene product. The SGA reporter consists of the auxotrophic HIS3 selection gene under control of the MATa-specific MFA1 promoter. The absence of histidine in the medium ensured that only MATa haploid cells were able to survive. Haploid cells with RTP4108, RTP4107, RLW001 and RTP4106 were checked for the presence of rice chimeric ACCase and the absence of ACC1 with primer sets specific for both genes. The genotype of multiple independent colonies for each of these haploid cells was confirmed (data shown for RTP4108 in FIG. 6). All four plasmids complemented the acc1 knockout at both 23° C. and 30° C. The wheat ACCc60p40 construct used by Nikolskaya et al. (1999) was not able to complement at 30° C., despite being expressed from a high copy number plasmid. The result obtained here underlined the solid design of the rice chimeric ACCase nucleotide sequence and expression system, although the observed difference in growth at 30° C. could also be caused by specific differences in amino acid sequence between the chimeric ACCases from rice and wheat. Sporulation was also induced with diploid cells that did not contain a plasmid to obtain a haploid strain that relied on ACC1 (designated yeast ACC1, FIG. 6).

'Kill Curves' for Yeast Strains Containing Various ACCase Variants with Cycloxydim and Tepraloxydim Model strains with RTP4108 (RTP4108-8b-2), RTP4107 (RTP4107-5b-1), RLW001 (also referred to as RLW001-1a-1, or YIL-1a-1) and RTP4106 (RTP4106-7a-1) and yeast ACC1 were plated on different concentrations of haloxyfop, cycloxydim and tepraloxydim (FIG. 7) and incubated at 30° C. for 4 days. Growth of strains with I1781 was severely hampered by 100 μM cycloxydim and 1 μM tepraloxydim. The mutation I1781L, which has been known to confer tolerance in plants, increased the tolerance and significant reduction in growth was observed at 200 μM cycloxydim and 10 μM tepraloxydim. This test established that yeast could be used as a model organism to screen for increased cycloxydim and tepraloxydim tolerance. As expected, yeast ACC1 was tolerant to all concentrations tested, although a slight, yet reproducible reduction in growth was observed at 200 μM cycloxydim. Control plates with comparable volumes of DMSO and methanol showed no effect on the growth of any of the strains used here (data not shown). His-tags did not have a detrimental effect. Hence, mutagenesis can also be done starting with RTP4107-5b-1 or RTP4106-7a-1 (the latter for finding double mutations with I1781L) and the presence of the His-tags could be beneficial for subsequent biochemical characterization. The results shown in FIG. 7 were highly reproducible with 3-4 independent haploid lines which contained the same plasmids (data not shown).

Mutagenesis with Fragments Containing Degeneracy at Preselected Sites

RTP4108-8b-2 was chosen for a pilot transformation experiment with a 299 bp fragment corresponding with the sequence of RTP4108 with TTG, encoding I1781L, in the center (Mu13). A similar, 299 bp control fragment contained the original ATA codon for isoleucine at that position (Wt10). RTP4108-8b-2 cells were initially grown in monosodium L-glutamic acid, yeast nitrogen base without amino acids and without ammonium sulfate, SC-Arg-His-Leu-Ura, 2% galactose, 200 mg/l G418 and 50 mg/l L-Canavanine, but the transformation efficiency turned out to be impractically low due to the slow growth rate in this medium (data not shown) and possibly altered membrane composition (Schneiter et al., 1996). Table 2 shows the transformation efficiency after pregrowth in rich medium or rich medium supplemented with FA and/or biotin and plating on medium with 100 µM cycloxydim. Pregrowth in YPG G418+FA and biotin resulted in 11 transformants and this number can be increased to 200-300 colonies by switching from the '200 ng' to the 'library scale' (15 µg) transformation protocol described in Clontech's Yeastmaker™ Yeast Transformation System 2 kit manual (data not shown). Transformation with a 299 bp fragment mixture containing all possible triplets at the site corresponding to I1781 has been carried out.

Table of Transformation Efficiencies after Pre-Growth in Different Media

| Fragment transformed | Pregrowth | Plating on | # colonies |
|---|---|---|---|
| Wt10 | YPGal G418 | 100 µM cycloxydim | 0 |
| Wt10 | YPGal G418 Biotin | 100 µM cycloxydim | 0 |
| Wt10 | YPGal G418 FA | 100 µM cycloxydim | 2 |
| Wt10 | YPGal G418 Biotin FA | 100 µM cycloxydim | 0 |
| Mu13 (I1781L) | YPGal G418 | 100 µM cycloxydim | 5 |
| Mu13 (I1781L) | YPGal G418 Biotin | 100 µM cycloxydim | 7 |
| Mu13 (I1781L) | YPGal G418 FA | 100 µM cycloxydim | 6 |
| Mu13 (I1781L) | YPGal G418 Biotin FA | 100 µM cycloxydim | 11 |

A series of such experiments were performed. In pilot experiments the efficiency was typically only 5-20 transformants/µg DNA (data not shown). The haploid strains RTP4108-8b-2 and RTP4107-5b-1 (as well as RLW001-1a-1 and RTP4106-7a-1) have a doubling time of approximately 4½ hours in liquid YPG G418 biotin FA medium. The slow growth rate and possibly altered membrane composition (Schneiter et al., 1996) are believed to be the primary reasons for the poor transformation efficiencies. The transformation efficiency was ~20% higher when pre-growth of cells took place in YPG medium supplemented with biotin and fatty acids and recovery took place in YPG medium as opposed to Clontech's standard YPD plus transformation recovery medium. Despite the improvements, transformation rates were poor, thus hampering efficient screening of high complexity mutagenized fragment mixtures.

Spontaneous Mutants and Sequence Analysis

The table of transformation efficiencies above showed that transformation with Wt10 resulted in the growth of two colonies when cells were pregrown in YPG G418+fatty acids. In theory, the Wt10 PCR-amplified fragment could contain unintentional mutations, either introduced by Epoch Biolabs during synthesis or by PCR with Expand DNA polymerase, which could incorporate into OsJACCc60p40 through homologous recombination and give rise to herbicide tolerant colonies. However, it was found that direct plating of RTP4108-8b-2 on 200 µM cycloxydim or 10 µM tepraloxydim, resulted in 1 spontaneous mutant for every $\sim 5 \times 10^9$ cells. This phenomenon was fully exploited and RTP4108-8b-2 was plated in large quantities on 200 µM cycloxydim and 10 µM tepraloxydim. Similarly, RLW001-1a-1 was plated on 40 µM tepraloxydim and 100 µM tepraloxydim to obtain double mutants. In addition, all colonies that grew on control plates in earlier experiments aimed at optimizing the transformation procedure were analyzed (data not shown). All herbicide-tolerant colonies were grown on plates with 100 and 200 µM cycloxydim and 1 and 10 µM tepraloxydim and the relative growth rate was estimated. The following table summarizes other colonies of interest for which sequence data was obtained.

Table of mutants obtained in various screens (left column) and tolerance to C100 (100 µM cycloxydim), C200 (200 µM cycloxydim), T1 (1 µM tepraloxydim) and T10 (10 µM tepraloxydim).

| Identifier | Starting heploid cells | Inverted from plate wits | Relative growth on condition after transfer | | | | | Substitution |
| | | | No herb. | C100 | C200 | T1 | T10 | |
|---|---|---|---|---|---|---|---|---|
| RTP4108-8b-2 control | RTP4108-8b-2 | No herbicide | ++++ | − | − | − | − | None |
| RLW001-1a-1 control | RLW001-1a-1 | No herbicide | ++++ | +++ | ++ | ++ | + | I1781L |
| 8 | RTP4108-8b-2 | 100 µM cycloxydim | ++++ | ++ | ++ | +++ | + | W1999G |
| 22 | RTP4108-8b-2 | 100 µM cycloxydim | ++++ | +++ | ++ | − | − | I1781T |
| 29 | RTP4108-8b-2 | 1 µM tepraloxydim | ++++ | + | − | ++ | + | V2049F |
| 30 | RTP4108-8b-2 | 1 µM tepraloxydim | ++++ | + | − | +++ | + | V2049F |
| 32 | RTP4108-8b-2 | 1 µM tepraloxydim | ++++ | + | − | +++ | + | V2049F |
| 33 | RTP4108-8b-2 | 1 µM tepraloxydim | ++++ | + | + | +++ | + | V2049F |
| 18 | RTP4108-8b-2 | 10 µM tepraloxydim | ++++ | + | − | ++++ | +++ | V2075L |
| 24 | RTP4108-8b-2 | 1 µM tepraloxydim | ++++ | ++ | + | +++ | +++ | V2075L |
| 25 | RTP4108-8b-2 | 1 µM tepraloxydim | ++++ | ++ | + | +++ | +++ | V2075L |
| 26 | RTP4108-8b-2 | 1 µM tepraloxydim | ++++ | ++ | + | +++ | +++ | V2075L |
| 27 | RTP4108-8b-2 | 1 µM tepraloxydim | ++++ | ++ | − | +++ | +++ | V2075L |
| 57 | RTP4108-8b-2 | 10 µM tepraloxydim | ++++ | ++ | + | +++ | +++ | V2075L |
| 58 | RTP4108-8b-2 | 10 µM tepraloxydim | ++++ | ++ | + | +++ | +++ | V2075L |
| 34 | RTP4108-8b-2 | 1 µM tepraloxydim | ++++ | ++ | + | ++ | + | V2075I |
| 31 | RTP4108-8b-2 | 100 µM cycloxydim | ++++ | +++ | +++ | +++ | +++ | D2078G |
| 21 | RTP4108-8b-2 | 10 µM tepraloxydim | ++++ | +++ | +++ | +++ | +++ | V2098A |
| 28 | RTP4108-8b-2 | 200 µM cycloxydim | ++++ | +++ | ++ | +++ | ++ | V2098A |
| 78 | RLW001-1a-1 | 40 µM tepraloxydim | ++++ | ++++ | ++++ | ++++ | ++++ | I1781L + V2049F |

Mutant 8 possessed a new mutation, W1999G, which gave tolerance to both cycloxydim and tepraloxydim. The mutation W1999C has been associated with fenoxaprop tolerance, but this mutation did not lead to tolerance for sethoxydim and tralkoxydim (Liu et al., 2007).

I1781T in mutant 22 also represented a new mutation at a known position. Interestingly, this mutation only conferred tolerance to cycloxydim. V2049F led to moderate tolerance to tepraloxydim. This single mutation was found in four independent colonies (29, 30, 32 and 33) and the growth rates on plates with different herbicides was highly reproducible.

Likewise, the mutation V2075L, which led to high tepraloxydim tolerance only, was found multiple times and led to consistent growth rates as shown above. The cycloxydim tolerance-conferring mutation I1781T and tepraloxydim tolerance-conferring mutation V2075L may be used in rotation in rice.

The mutation V2075I was less favorable for DIM tolerance compared to V2075L.

Mutant 31 contained a known mutation: D2078G. This mutation has been known to be associated with a fitness penalty in rice. In yeast, the fitness penalty does not translate itself in a slow growth rate (Liu et al., 2007 and this study). However, reducing GAL10 promoter activity by decreasing the galactose concentration in the medium may reveal suboptimal enzymatic activity of ACCase with D2078G.

V2098A was identified twice and led to high tolerance to both cycloxydim and tepraloxydim.

In one experiment, in which RLW001-1a-1 was plated on 40 μM tepraloxydim, a tolerant double mutant with I1781L was uncovered. The second mutation turned out to be V2049F. The double mutant performed better than each of the two single mutants separately on medium with DIMs.

The isolation of ACCases with the same mutation in multiple independent colonies and the high reproducibility of the growth characteristics on plates with different (concentrations of) herbicides strongly support the fact that these mutations are involved in increased tolerance.

Example 2

Replacing Yeast ACC1 with OsJACCc60p40 Dramatically Reduced Transformation Efficiency, but Allowed Direct Isolation of Spontaneous Mutants that are Resistant to DIMs RTP4107-5b-1 cells can be mutagenized by transformation of fragments carrying degeneracy in selected sites and subsequent plating on cycloxydim or tepraloxydim medium (FIG. 5*e*-5*h*). To determine the transformation efficiency we transformed fragments encoding the mutation I1781L to RTP4107-5b-1 and RTP4108-8b-2. In pilot experiments the efficiency was typically only 5-20 transformants/μg DNA (data not shown). The haploid strains RTP4108-8b-2 and RTP4107-5b-1 (as well as RLW001-1a-1 and RTP4106-7a-1) have a doubling time of approximately 4½ hours in liquid YPG G418 biotin FA medium. The slow growth rate and possibly altered membrane composition (Schneiter et al., 1996) are believed to be the primary reasons for the poor transformation efficiencies. The transformation efficiency was ~20% higher when pre-growth of cells took place in YPG medium supplemented with biotin and fatty acids and recovery took place in YPG medium as opposed to Clontech's standard YPD plus transformation recovery medium. Despite the improvements, transformation rates were poor, thus hampering efficient screening of high complexity mutagenized fragment mixtures.

In control experiments it was noticed that transformation of fragments not carrying any mutation resulted in the appearance of colonies on 100 and 200 μM cycloxydim and 1 and 10 μM tepraloxydim plates. Moreover, direct plating of cells on selective medium yielded resistant colonies at a frequency of 1 in ~1–5×10$^9$ cells. Sequence analysis of these spontaneous mutants revealed that these colonies possessed specific mutations in the C-terminal domain of rice hybrid ACCase. Spontaneous mutations also occurred after transformation of fragments that carried mutations, like for instance I1781L. Thus in some cases the intended mutation, like in this example I1781L, was not observed, but another mutation was found in a different position. The following summarizes all spontaneous mutations obtained deliberately by direct plating of RTP4107-5b-1 or unintentionally as background in transformation experiments described below.

Table of spontaneous mutations conferring DIM resistance and the number of colonies harboring these mutations identified in all experiments. Novel mutations are indicated by *; novel mutations at novel sites by **

| Mutation | Identified | Nucleotide change |
|---|---|---|
| I1781L | 7x | ATT → CTT |
| I1781T* | 5x | ATT → ACT |
| I1781V* | 42x | ATT → GTT |
| G1783C** | 1x | GGT → TGT |
| A1785G** | 2x | GCT → GGT |
| A1786P** | 2x | GCA → CCA |
| I1811N** | 4x | ATT → AAT |
| W1999G* | 57x | TGG → GGG |
| V2049F** | 13x | GTC → TTC |
| W2074L** | 2x | TGG → TTG |
| V2075G | 5x | GTT → GGT |
| V2075I** | 8x | GTT → ATT |
| V2075L** | 99x | GTT → CTT |
| D2078G | 142x | GAC → GGC |
| ΔK2080I2081** | 2x | AAGATT → Δ |
| C2088R | 35x | TGC → CGC |
| C2088W* | 5x | TGC → TGG |
| G2096A | 101x | GGT → GCT |
| G2096S* | 12x | GGT → AGT |
| V2098A** | 62x | GTT → GCT |
| V2098G** | 66x | GTT → GGT |

Among the mutations identified, we found I1781L, D2078G, C2088R and G2096A. These mutations have been known to confer resistance (Powles and Yu, 2010) and validated the yeast model system. I1781V and I1781T are novel mutations in a known site. W1999C has been reported as a mutation that allowed growth in the presence of FOPs, but not DIMs (Powles and Yu, 2010). Interestingly, we identified W1999G as a strong candidate for conferring DIM resistance. The remaining mutations in the preceding table are novel mutations at novel sites, of which I1811, V2049, V2075 and V2098 were later implied to be involved in tepraloxydim binding by studying the protein structure of yeast ACC1 (Xiang et al., 2009).

The yeast model is further validated by the high frequency at which the same, novel mutations were identified (preceding table, second column). All A1785G and V2075G mutants may be dependent as they were isolated in one experiment, but all others appeared independently in two or more experiments, often after starting with the RTP4107-5b-1 and RTP4108-8b-2 strains. In a single experiment, liquid cultures of RTP4107-5b-1 were incubated in the presence of cycloxydim to enrich the culture for cells with mutations that confer resistance to this herbicide. This alternative method for obtaining spontaneous mutants was successful, but was not followed up on because of the increased likeliness that mutants are daughter cells from a single mutation event.

Some of the herbicide resistance-conferring new amino acids in the plastidic domain turned out to correspond to residues already present in ACC1 and cytosolic plant ACCases, suggesting that these residues may partially contribute to the natural resistance of the non-plastidic forms. Isoleucine at position 1781 and alanine at position 1785 in plastidic ACCases are leucine and glycine, respectively in non-plastidic ACCase. Alignments between resistant and susceptible ACCase may be valuable in identifying potential DIM-resistance conferring residues. Apart from I1781L and A1785G we did not obtain more mutations of this type, but it should be noted that the screenings described here were not fully saturated.

Generation of DIM-Resistant Mutants Through Transformation of Fragments Carrying Degeneracy in Selected Codons Although plating of RTP4108-8b-2 and RTP4107-5b-1 is an easy and convenient method to obtain mutants, it has limitations. All mutations listed in the table of spontaneous mutations conferring DIM resistance above were single nucleotide substitutions. The spontaneous introduction of two or three mutations in a single triplet is a rare event. With single nucleotide substitutions approximately ⅔ of the amino acids will never be found at any given position. We used mutagens to increase the frequency of mutations, but such treatments led to an increased number of single nucleotide substitutions in two or more triplets throughout the 3' coding end. Despite the low efficiency, transformation of fragments with complete degeneracy at a chosen position is the best method to test all amino acids at that position. Based on pilot experiments with I1781L fragments and the average frequency of the appearance of spontaneous mutants, it was estimated that transformations had to be performed at a scale that was six times larger than the library scale described in Clontech's Yeastmaker™ Yeast Transformation System 2 kit protocol to obtain 99% certainty that all triplets were transformed.

Sites that were randomized were chosen based on results obtained in the table of spontaneous mutations conferring DIM resistance above (I1781, W1999, V2049, V2075, D2078 and V2098) and literature (W2027 and I2041). Resistant colonies isolated after transformation and plating on cycloxydim and tepraloxydim were partially sequenced FIGS. 8 and 9). Transformations were significantly "contaminated" with spontaneous mutants as anticipated. However, for most transformations we observed enrichment in the number of colonies that have mutations in the triplet that was varied (shaded cells in FIG. 8). Transformations with fragments with degeneracy in W2027 and I2041 yielded only spontaneous mutants (FIG. 9), consistent with the results described above.

We identified novel amino acid mutations that required more than one base pair to be altered in a single triplet. These included V2075M (GTT→ATG), D20781 (GAC→ACG and ACT), V2098H (GTT→CAC), V2098P (GTT→CCG and CCC) and V2098S (GTT→AGC, AGT and TCG). Thus the transformation method described here allowed the isolation of novel mutants which were practically impossible to obtain by relying on spontaneous mutations alone. Other methods by which novel mutants can be identified include: i. changing the codon usage of OsJACCc60p40 in RTP4107-5b-1 to allow alternative amino acid substitutions upon spontaneous nucleotide changes. ii. exploring mutagens that alter consecutive nucleotides. iii. switching the chromosome-plasmid shuffling and mutagenesis step in FIG. 5; the diploid strain with OsJACCc60p40, which still relies on ACC1 for FA biosynthesis, can be made more competent for LiAc/PEG-based transformation of mutagenized fragments prior to sporulation and subsequent selection on DIM plates. Alternatively, linearized plasmids harboring OsJACCc600p40 with small deletions can be co-transformed with mutagenized repair fragments which can be incorporated by homologous recombination repair prior to sporulation and DIM selection. These methods may increase the throughput of mutagenized fragments allowing the discovery of novel mutations in a more efficient way.

In many cases two or three different triplets were found to be mutated in a single colony (FIG. 8). For instance novel V2049 variants (V2049A, V2049C, V2049L, V2049S, V2049T) always had a second D2078G or V2098A mutation. From this experiment we cannot conclude whether the novel V2049 mutations contributed to resistance or represented mutations that could be classified as "neutral" to both herbicide-tolerance and enzymatic function of the protein. The easiest way to test this is to compare growth curves of strains having V2049 mutations in combination with D2078G or V2098A to D2078G and V2098A single mutants in the presence of DIMs (see below). V2098A and V2098G mutations were often accompanied by C2088 mutations. Both the V2098 and C2088 mutations used a wide variety of codons (data not shown); thus both mutations were almost certainly introduced from the synthetic DNA fragments (unlike the double mutants involving V2049, which were always accompanied by "single nucleotide-mutated" D2078G and V2098A residues). Epoch Biolabs confirmed that their synthetic fragment mixtures possessed imperfections due to technical limitations to the production of these fragments. V2098 mutagenesis "enriched" for imperfections at position C2088.

Control experiments with I1781L fragments that were performed in parallel resulted in the appearance of 333 colonies on cycloxydim plates. "Wt control" fragments yielded 33 colonies on the same medium (table 2 only displays the mutants that were sequenced). We calculated the level of saturation as follows:

$$\text{Saturation} = \left(1 - \left(\frac{63}{64}\right)^{(333-33)}\right) \times 100\% = 99.1\%$$

The high level of saturation is initially supported by the appearance of six V2075M mutants (FIG. 8). Methionine is encoded by ATG only and the six transformants were independently obtained as the doubling time of rice ACCase-dependent yeast strains is much longer (4½ h) than the regeneration time used in the transformation procedure (1½ h). However, other statistics suggest a lack of saturation. For instance, the V2075L mutants were encoded by CTG, CTT, TTG and TTA, but never by CTC or CTA and V2075I mutants were never isolated from tepraloxydim plates, even though this mutation should confer resistance to the concentration used. We speculate that Epoch's fragment mixtures do not contain equimolar amounts of all possible variants and that our screening was not completely saturated. Thus, additional mutations in V2075, as well as in all other sites investigated here, that confer DIM resistance may still exist. These putative mutants can be uncovered by increasing the scale of the transformation experiments or by parallel transformations with fragments encoding for single, untested amino acids in selected sites.

Generation of Double Mutants with Increased Tolerance to Herbicides

Figure 10:
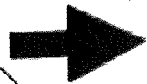
FIG. 10 is a table showing frequency of observed double mutations (columns) after transformation of fragments (donor) to strains that have already one mutation in place (acceptor) and plating on 75 µM tepraloxydim. Shaded squares represent intended double mutants. DuplV2075 means a duplication of V2075.

Double mutants can be made by transforming fragments with a DIM-resistance-conferring mutation to an acceptor strain with another DIM-resistance-conferring mutation and subsequent plating on a high DIM concentration that inhibits growth of untransformed single mutants and allows selection of superior double mutants. FIG. 7 shows that growth of yeast expressing yeast ACC1 was slightly reduced by 200

µM cycloxydim. We confirmed that this effect was not caused by methanol, which was used as a solvent for cycloxydim. Therefore, we chose tepraloxydim at a concentration of 75 µM (~150× the concentration that significantly inhibited OsJACCc60p40-dependent strains and ~8× the concentration that significantly inhibited "I1781L strains") for selection. FIG. 10 shows that I1781L+V2075L, W1999G+V2075L, W1999G+D2078G, W1999G+G2096A and W1999G+V2098A mutants were obtained as intended. However, most intended double mutants were not obtained. Instead, spontaneous second mutations were often found in addition to the mutation already in place in the acceptor strain. The absence of intended double mutants could have had two causes: i. the two single mutations didn't have a synergistic or even additive effect on herbicide tolerance or compromised the function of the enzyme in a general way, ii. the transformation efficiency of rice hybrid ACCase dependent yeast was too low in some cases. All transformations that yielded the intended double mutants (indicated in shaded squares in FIG. 10) were obtained in a single transformation experiment. All other transformations shown in FIG. 10 were attempted four times without success. Some mutations may not work well together, but additional transformations are required to acquire more certainty.

Double mutants involving residues that are close together (e.g. G2096A and V2098A) can be obtained by transforming RTP4107-5b-1 with a fragment carrying both mutations. This strategy was not used here. Instead, we reasoned that those and other double mutants could be obtained much easier by plating single mutants on plates with 75 µM tepraloxydim and waiting for spontaneous second mutations to appear. This method is not only less labor-intensive, it also automatically selects for mutations that perform well together. FIG. 11 shows the single mutants that were plated (between $1.5\times10^9$ and $5\times10^9$ cells), including the mutants that required more than one nucleotide change (V2075M, D2078T, V2098H, V2098P, V2098S), and the additional, spontaneous mutations that were gained. In this table the frequency of the appearance of these mutations is less relevant, because the double mutants could be daughter cells from a single event.

Figure 7C:
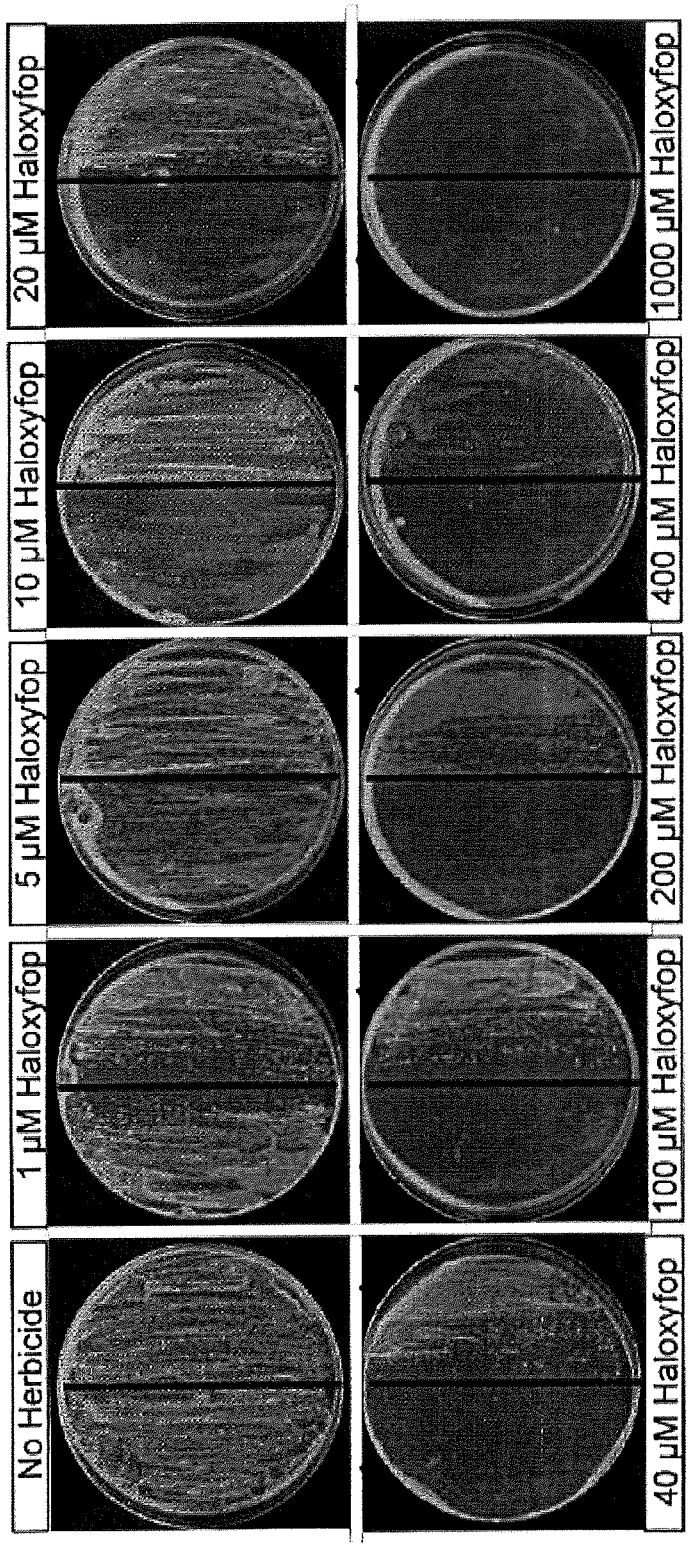
FIG. 7 represents a depiction of 'Kill curves' for RTP4108-8b-2 (indicated by 'c60p40'). RTP4107-5b-1 (indicated by 'c60p40 His-Tag'), RLW001-1a-1 (indicated by 'I1781L'), RTP4106-7a-1 (indicated by 'I1781L His-Tag') and yeast ACC1 (indicated by 'ACC1') with varying concentrations of the herbicides cycloxydim (7A), tepraloxydim (7B), and haloxyfop (7C). Yeast containing a wild-type yeast ACC1 gene were used as a tolerant control, center of each inset.

Growth Curves of Mutants in the Presence of Tepraloxydim, Cycloxydim and Haloxyfop The majority of the single and double mutants isolated here were grown in liquid cultures with and without herbicides to obtain growth curves and compare their relative effectiveness. Next to cycloxydim and tepraloxydim we were interested in the growth characteristics of mutants in the presence of haloxyfop, which belongs to the FOP class of herbicides. We made "kill curves" on solid haloxyfop plates first with RTP4107-5b-1 and DIVE292, a strain that possessed the I1781L mutation (FIG. 7C). The activity of haloxyfop was comparable to that of cycloxydim. All methods described here can also be applied to FOP herbicides.

Figure 12:
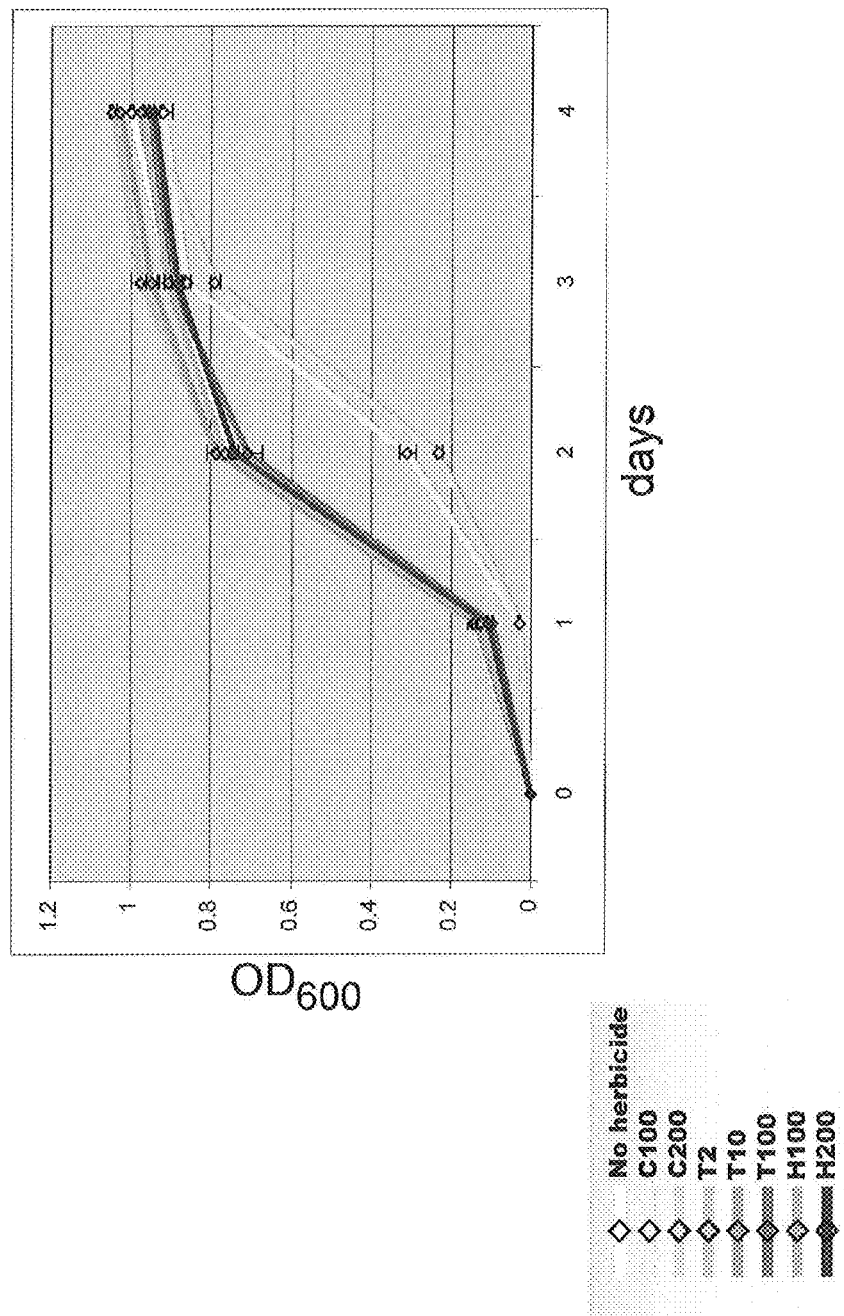
FIG. 12 is line graph showing the growth of yeast expressing a yeast ACC1 gene grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration.

Growth curves were made with 100 and 200 µM cycloxydim, 2, 10 and 100 µM tepraloxydim, 100 and 200 µM haloxyfop and without herbicide (see Figures). In all previous experiments we used cycloxydim from Sigma-Aldrich dissolved in methanol. However, the product got discontinued, so the final growth curves were made with cycloxydim formulation, dissolved in naphta. The formulation has a negative effect on the yeast strain that depends on ACC1 for FA biosynthesis during the first 2 days of growth (FIG. 12). This phenomenon was not observed in earlier experiments with cycloxydim dissolved in methanol. We believe that naphta delays growth, but after evaporation of the solvent growth is quickly restored. The rice hybrid ACCase-dependent strains grow much slower and naphta effects were not clearly visible. Pilot growth curve experiments with cycloxydim dissolved in methanol confirmed this view for all mutants tested as graphs were found to be highly similar to the graphs presented here (data not shown).

Figure 13:
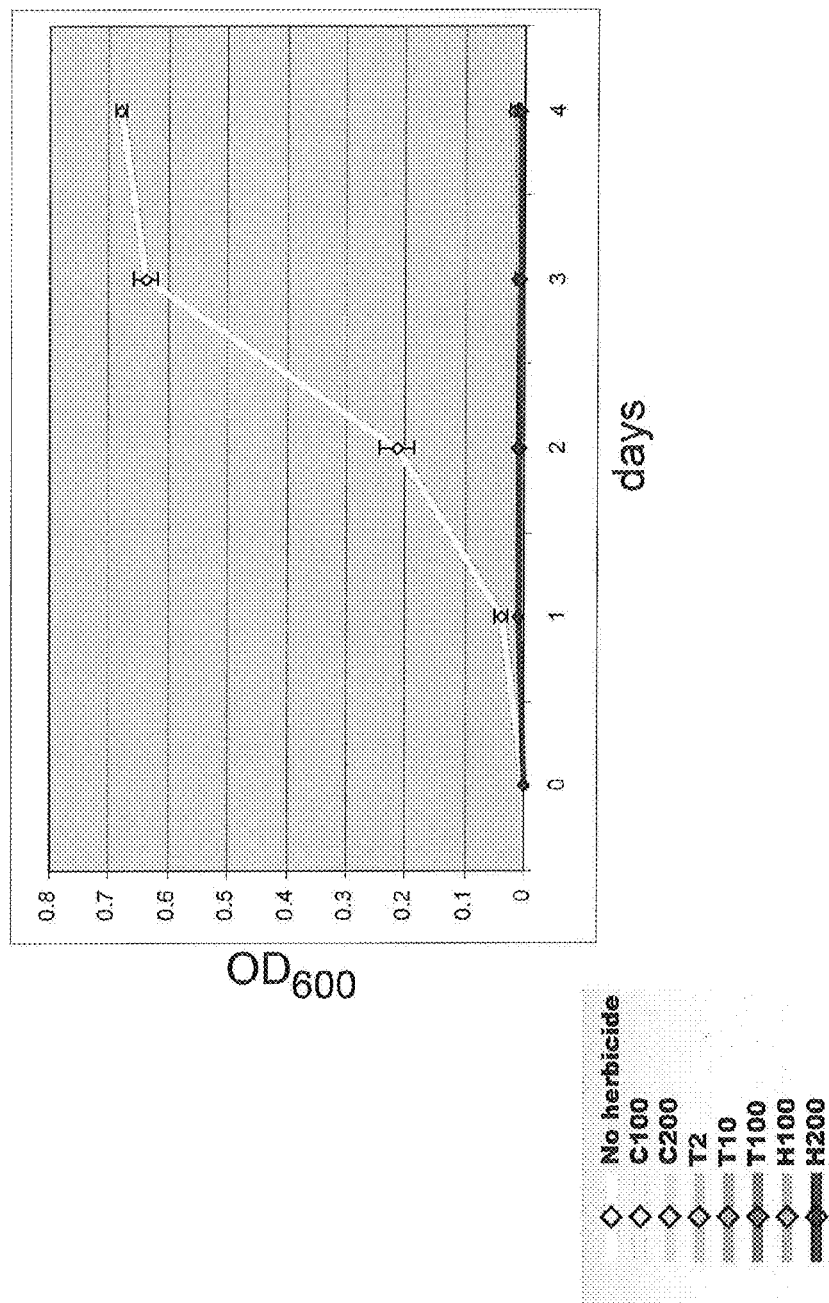
FIG. 13 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration.
Figure 14:
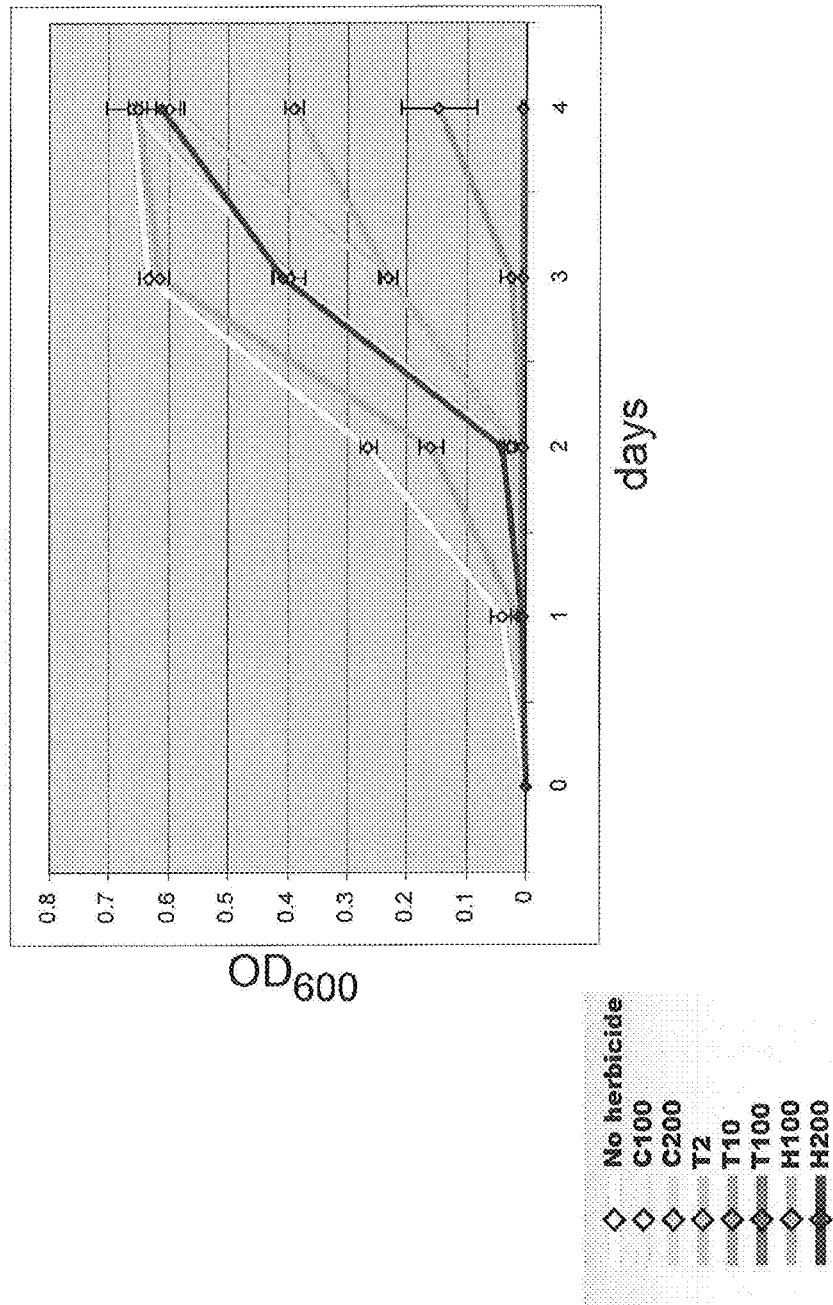
FIG. 14 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 15:
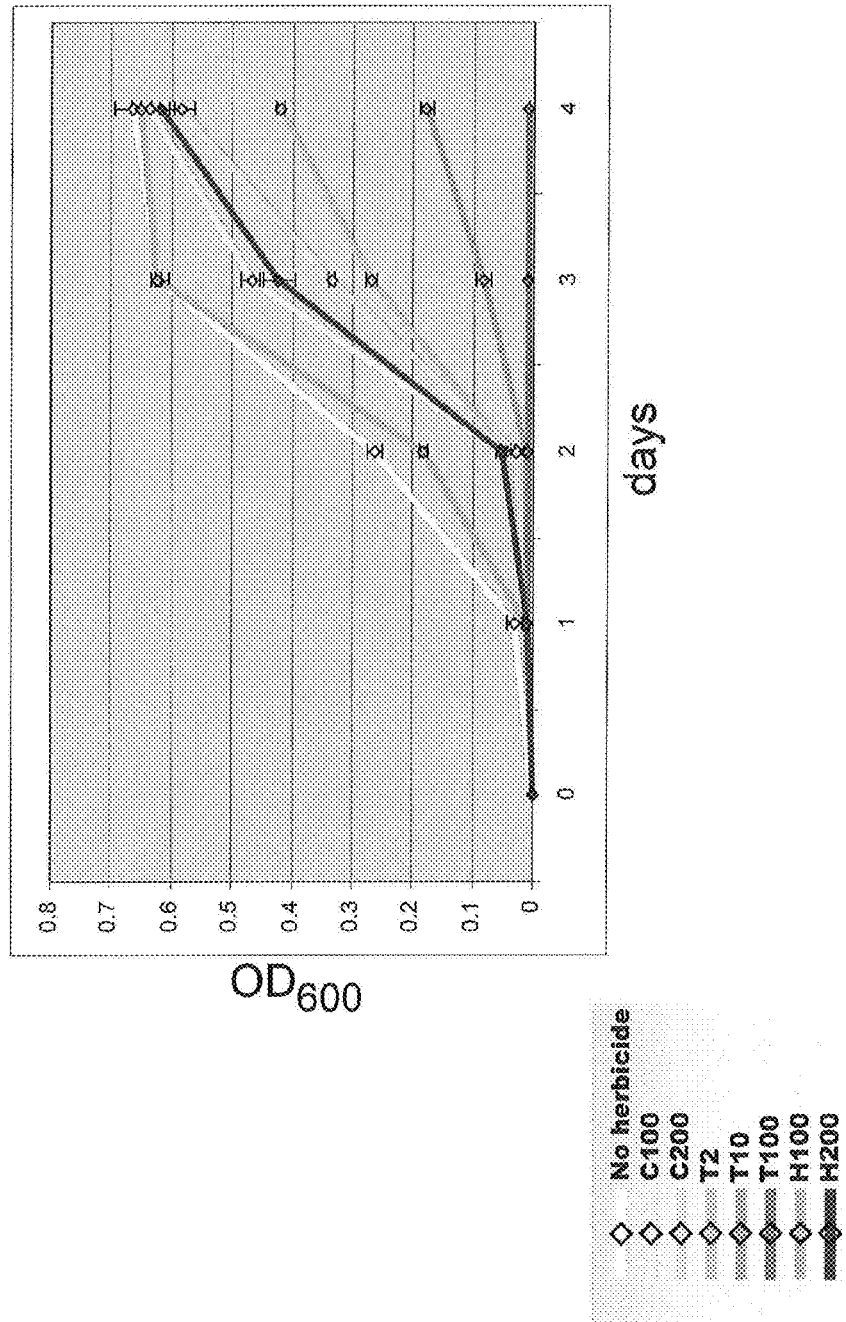
FIG. 15 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 16:
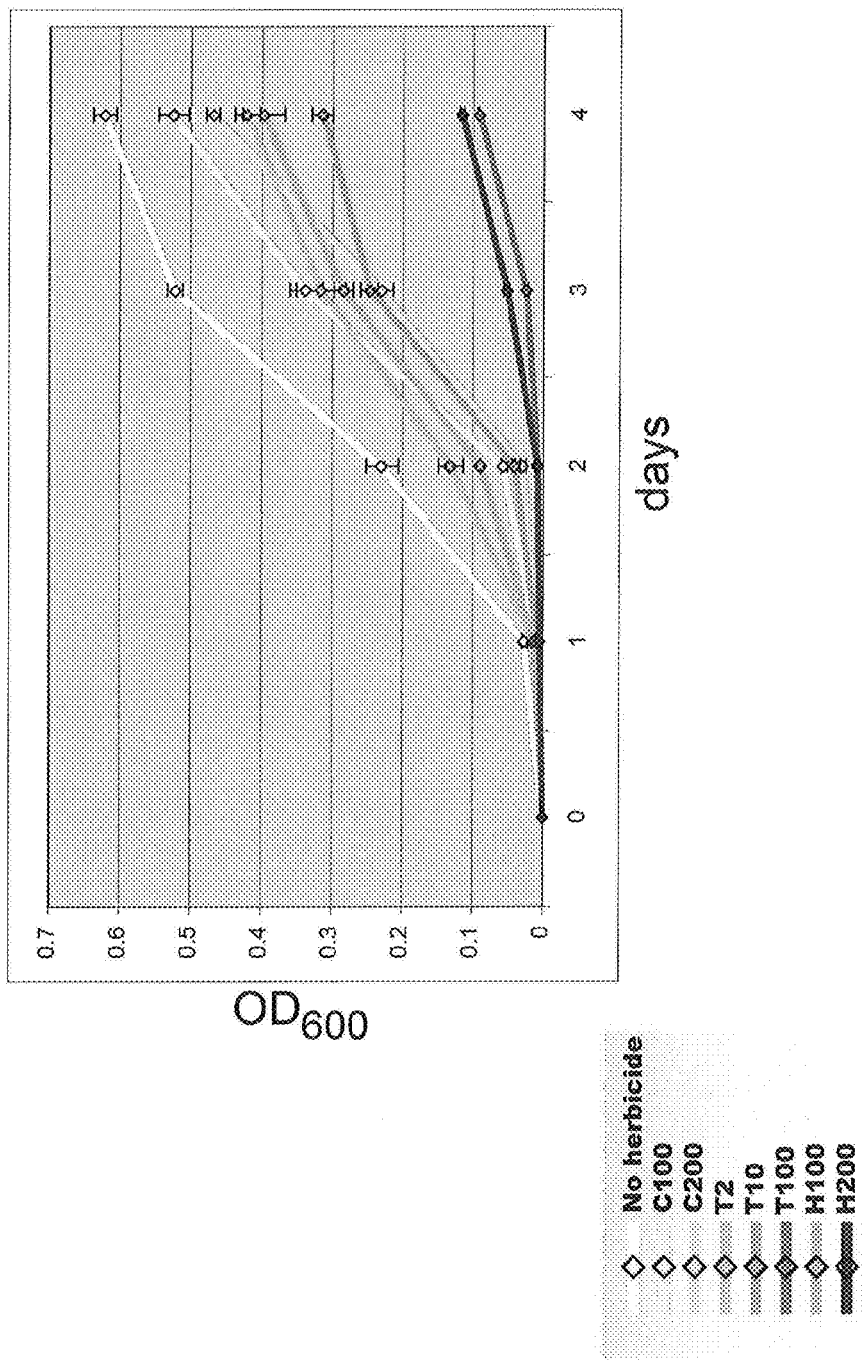
FIG. 16 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 17:
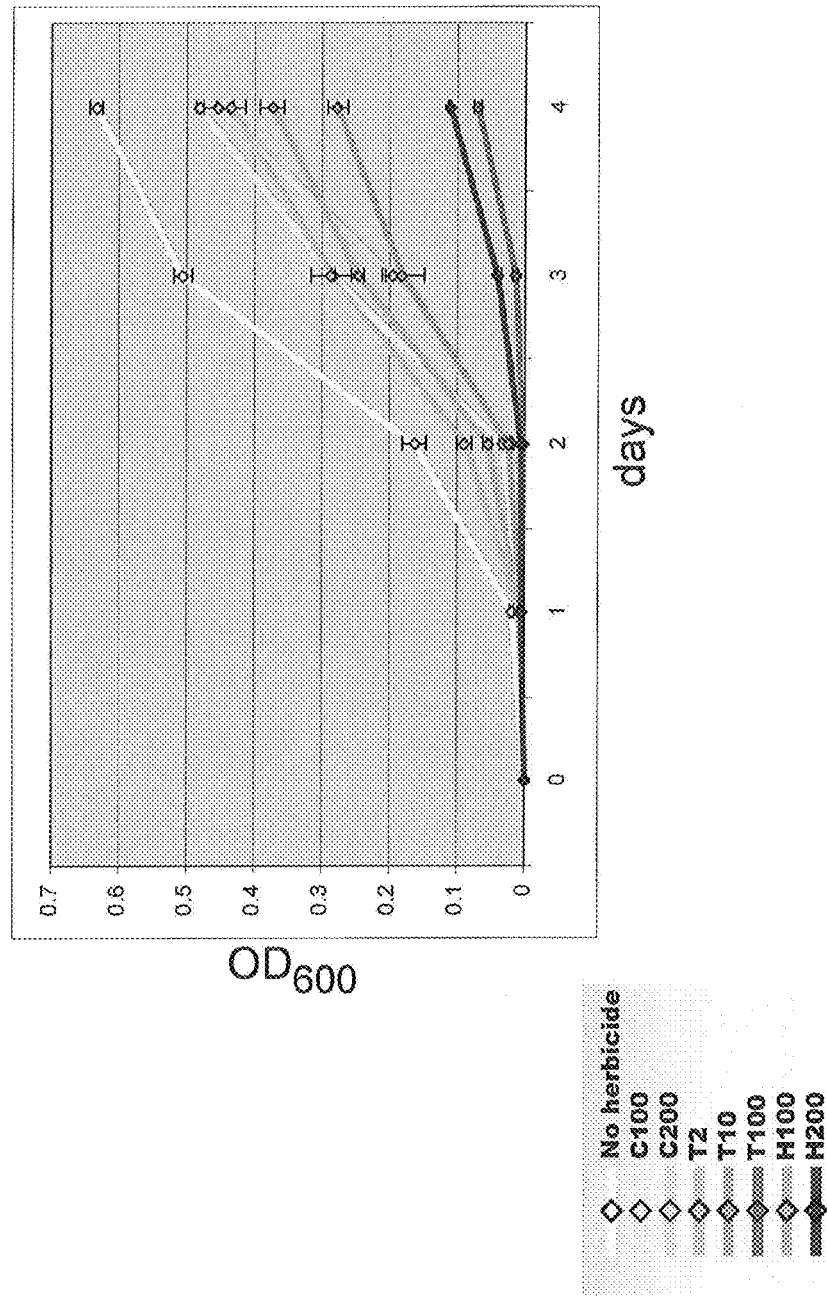
FIG. 17 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 18:
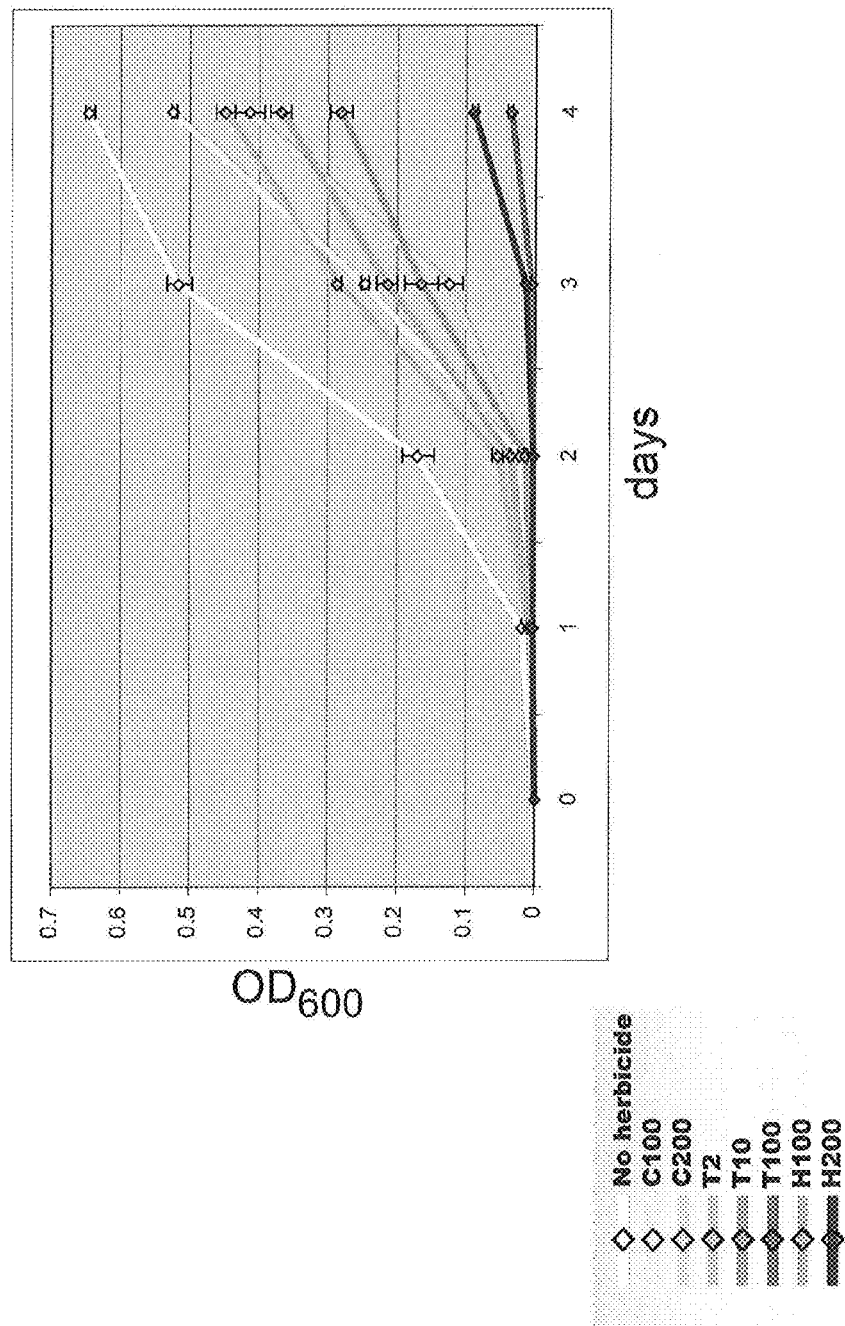
FIG. 18 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 19:
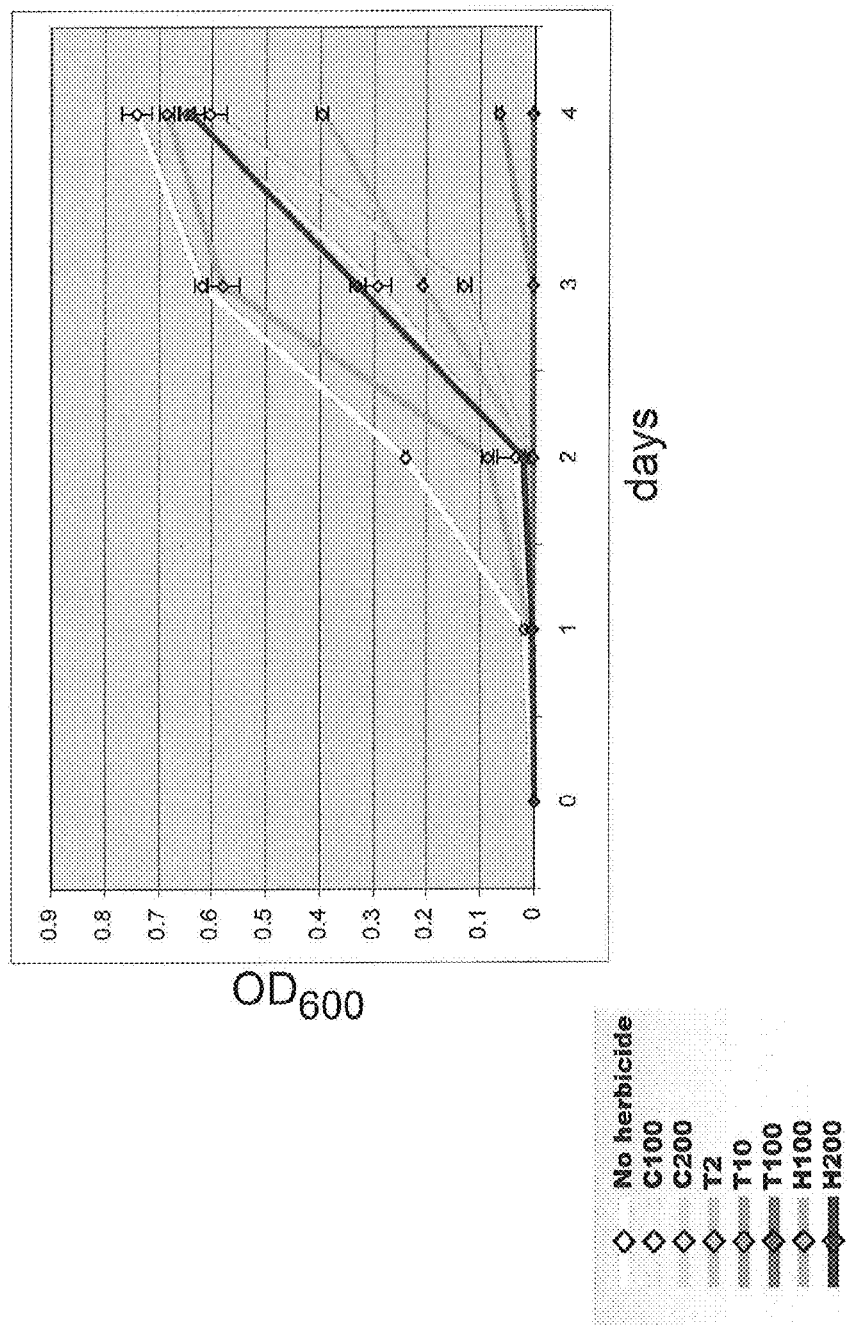
FIG. 19 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 20:
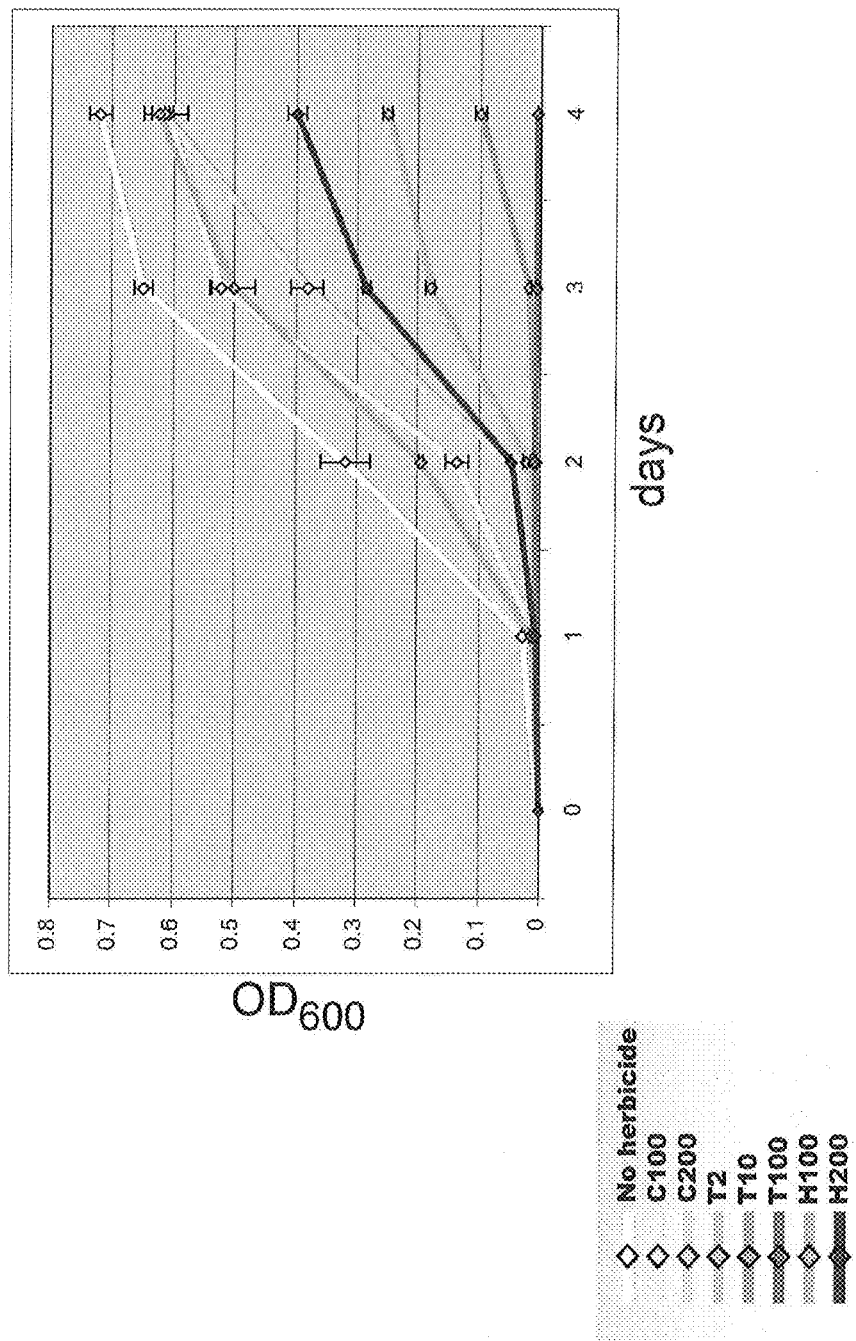
FIG. 20 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 21:
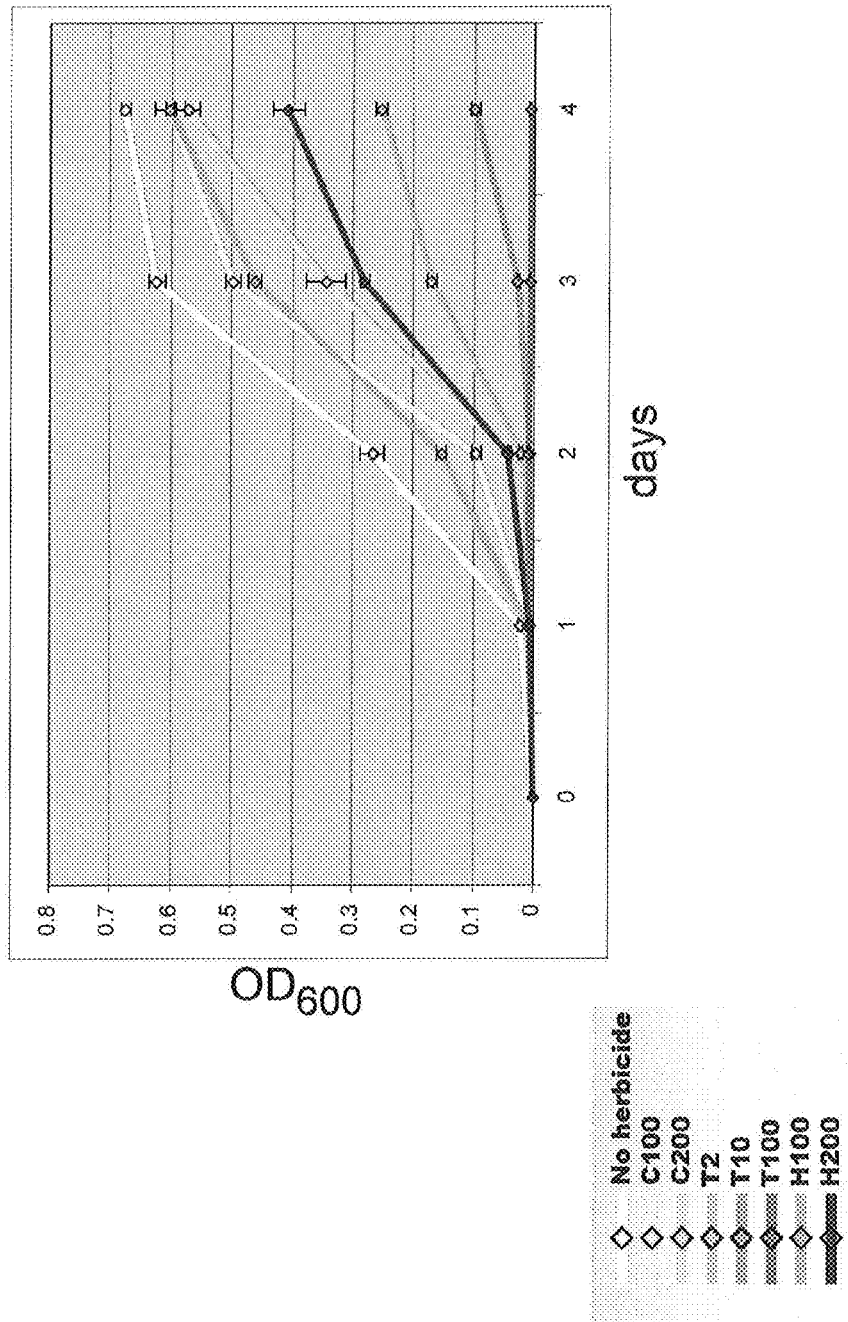
FIG. 21 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 22:
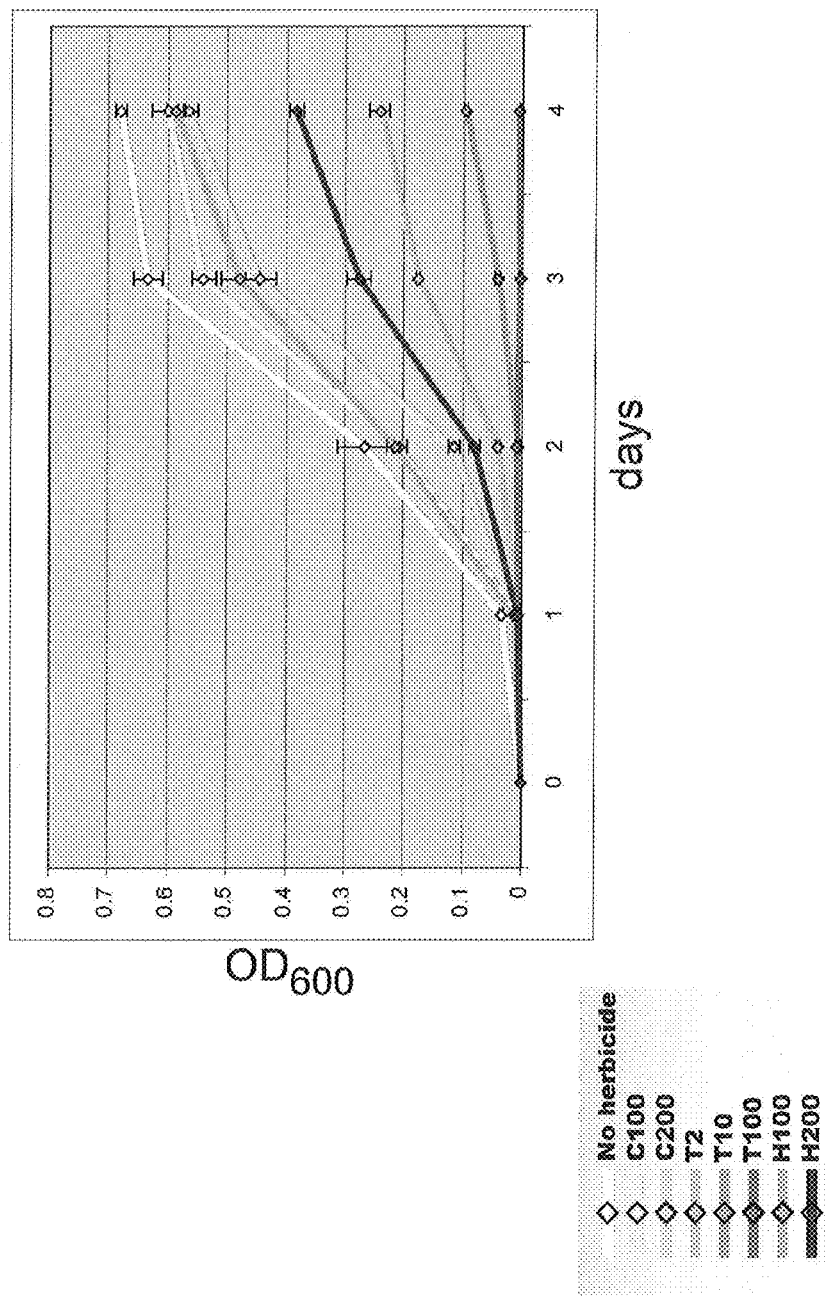
FIG. 22 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 23:
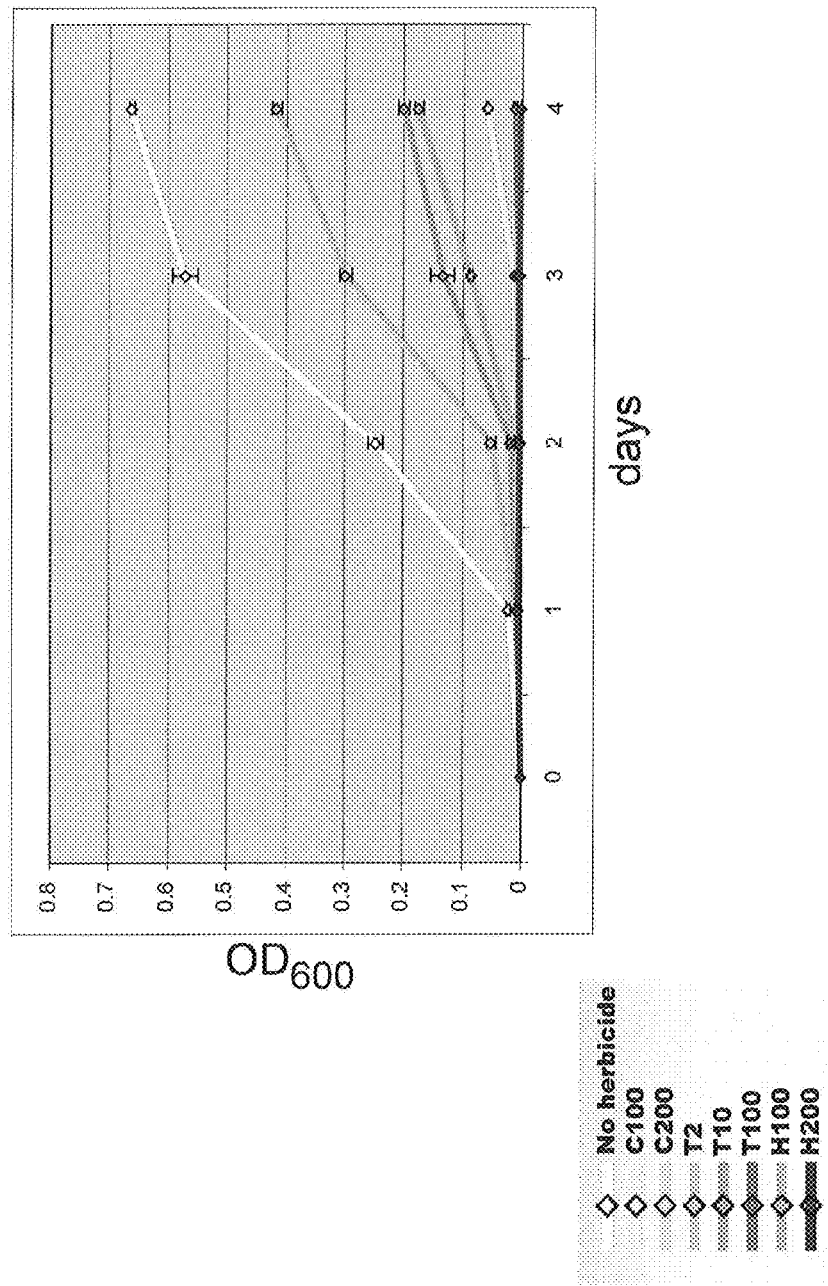
FIG. 23 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 24:
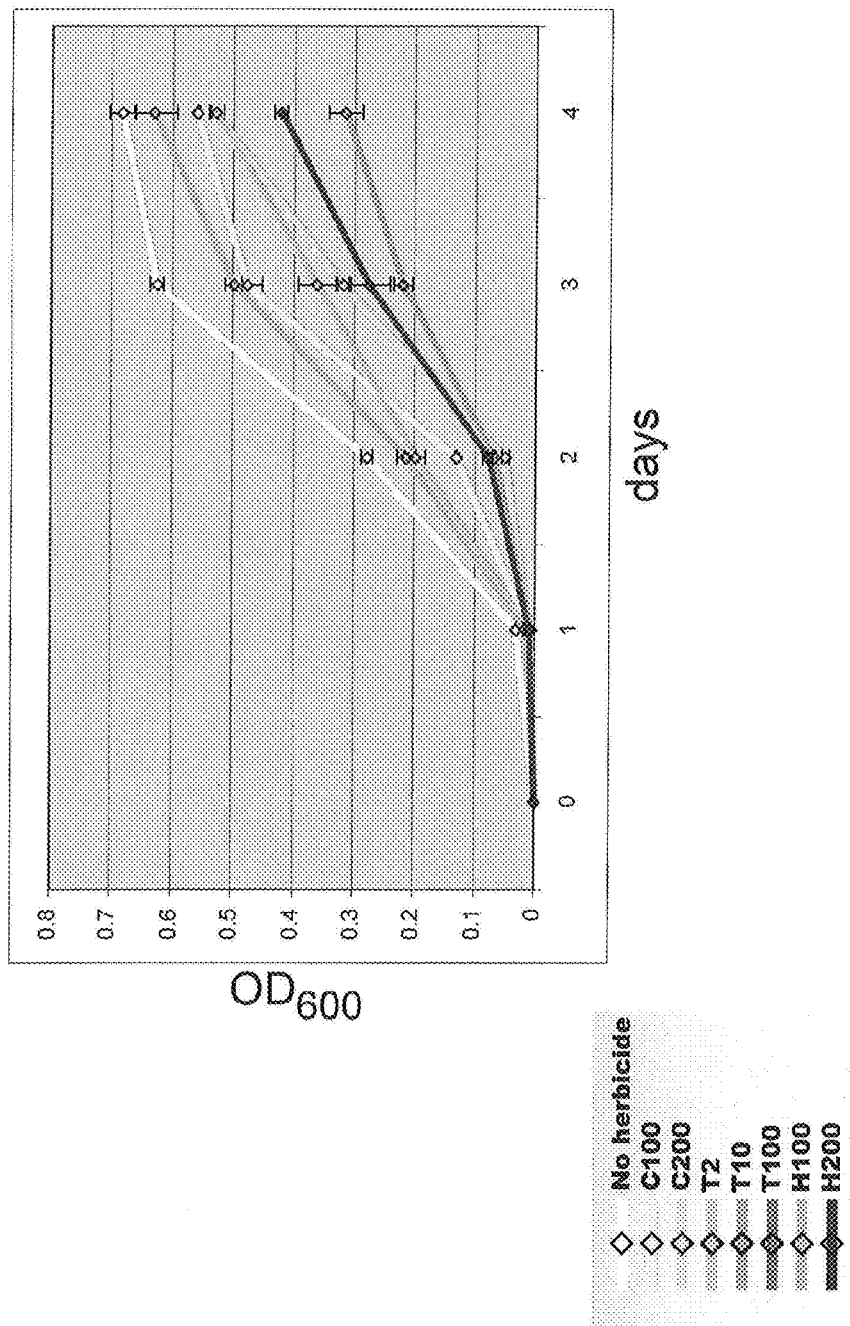
FIG. 24 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 25:
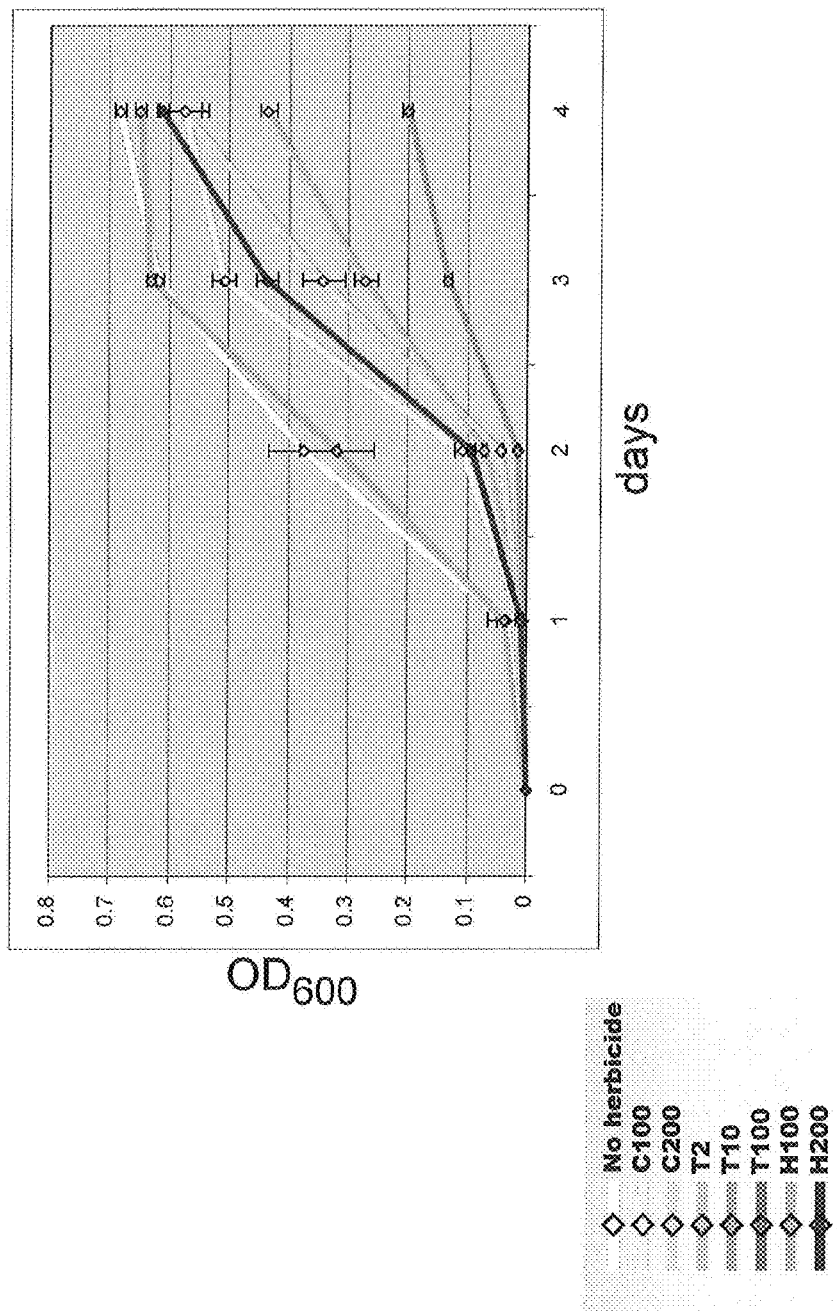
FIG. 25 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 26:
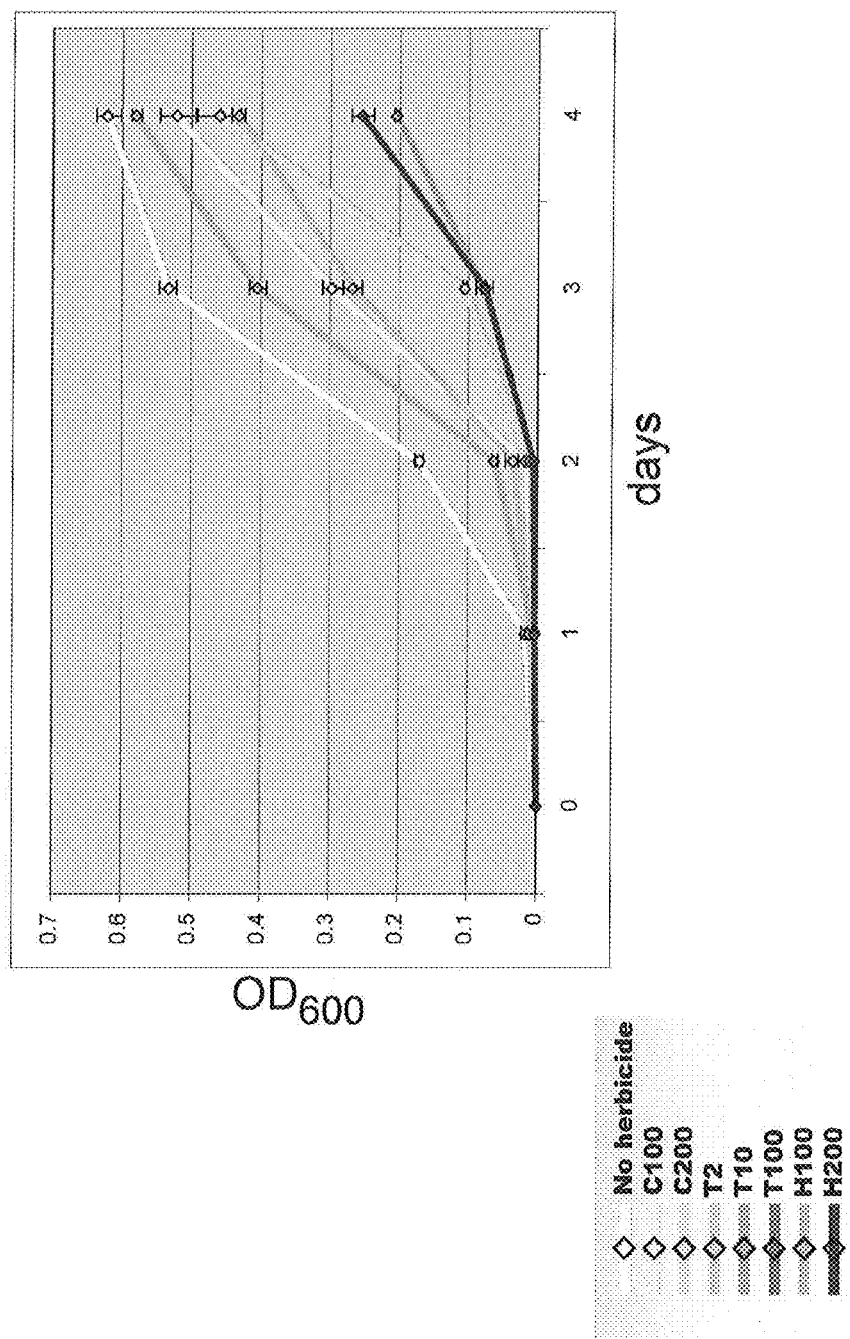
FIG. 26 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 27:
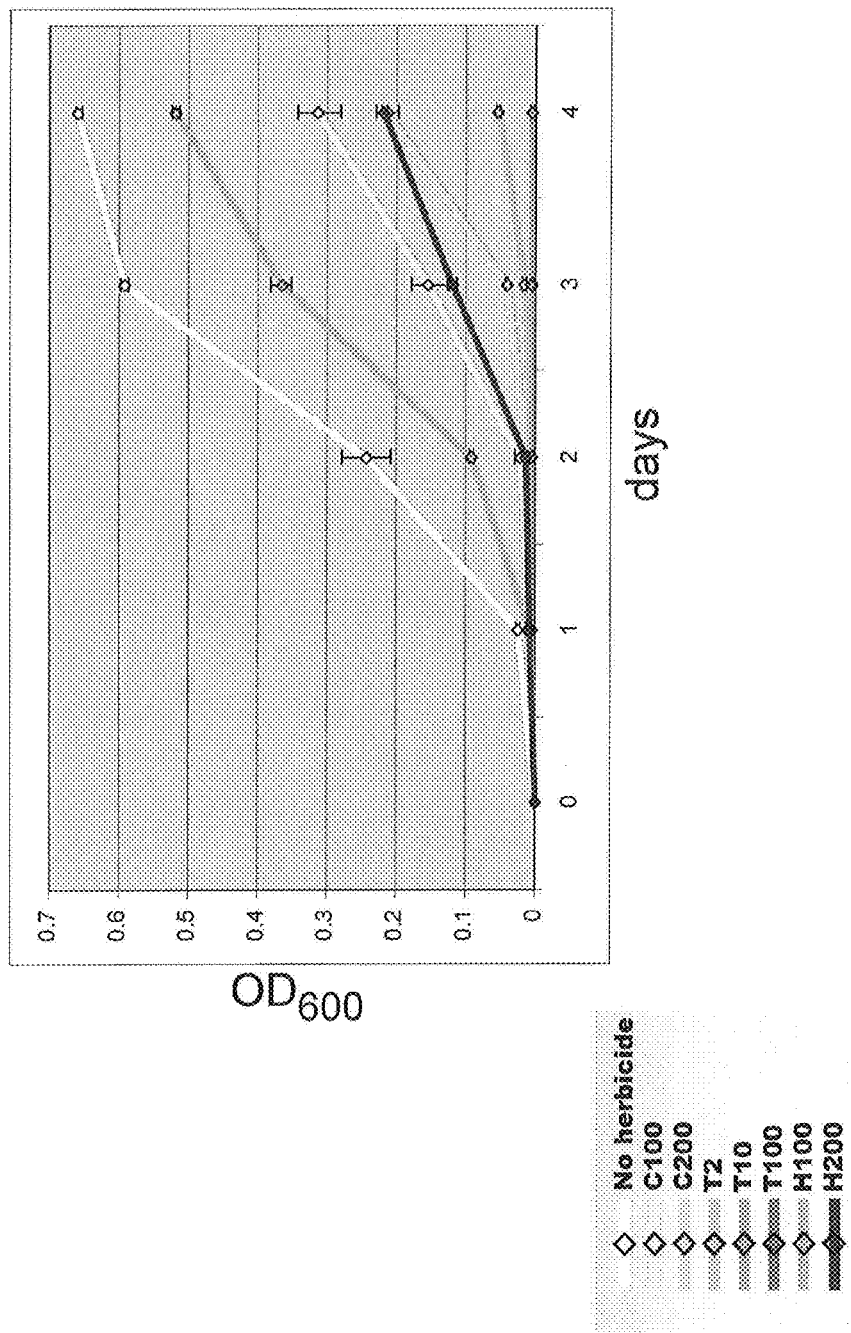
FIG. 27 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 28:
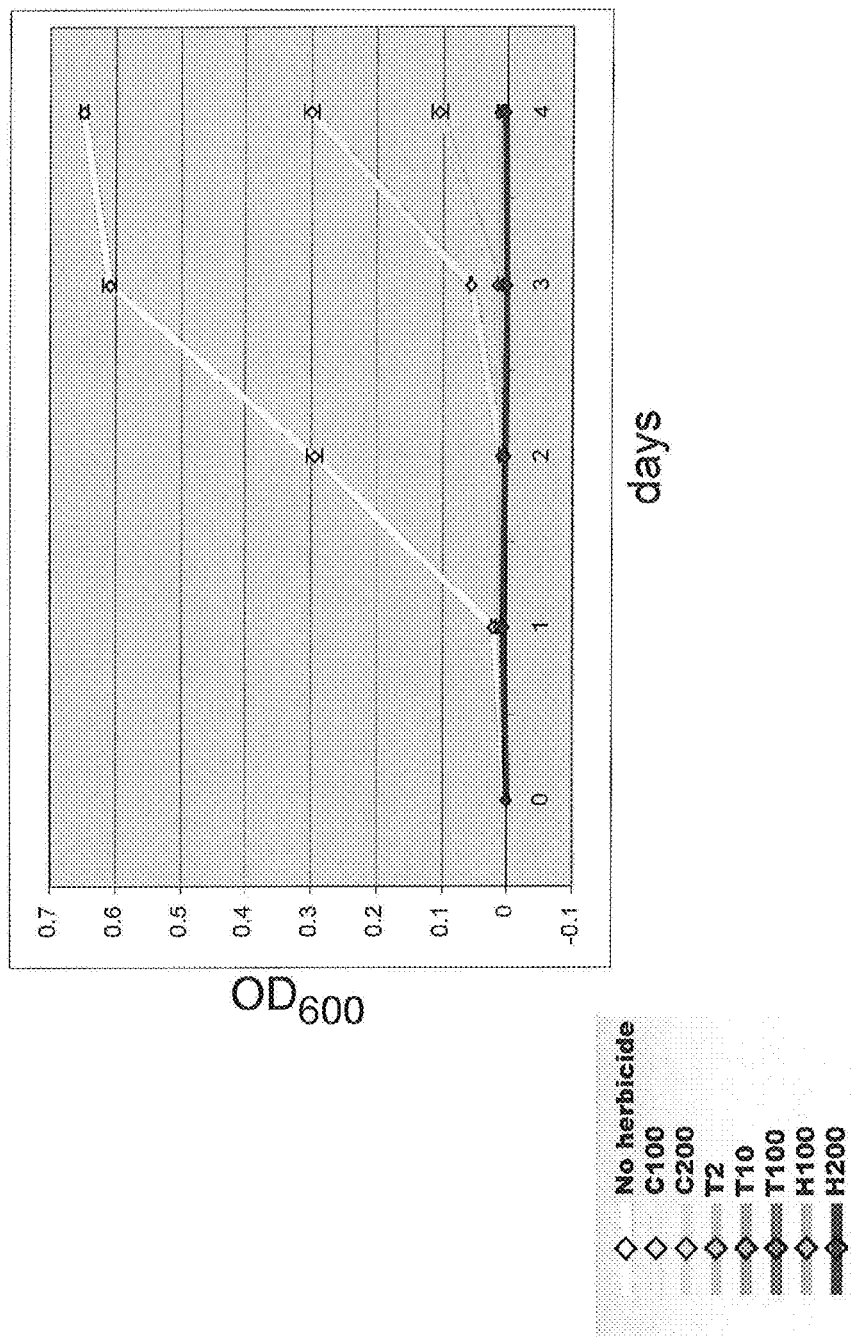
FIG. 28 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 29:
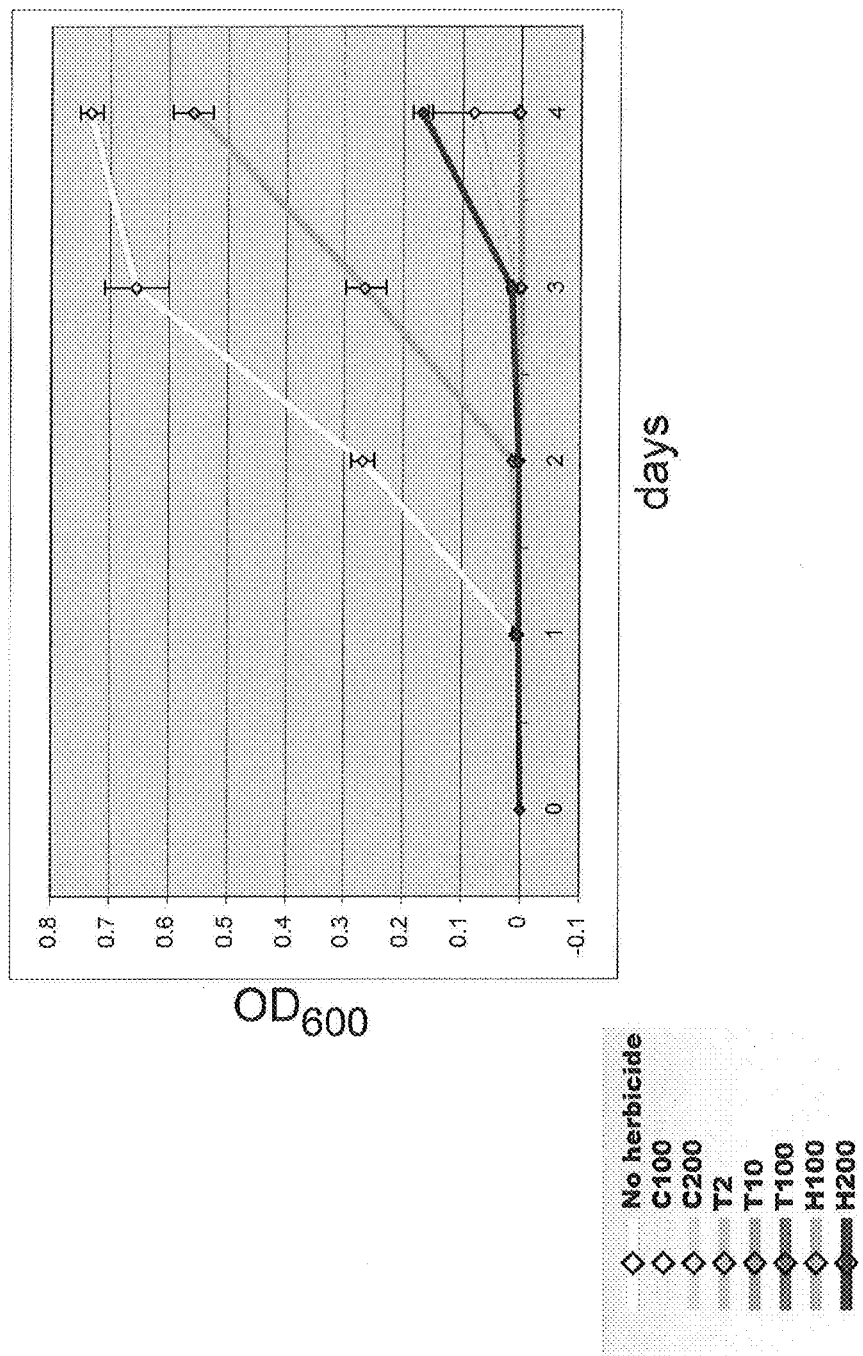
FIG. 29 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 30:
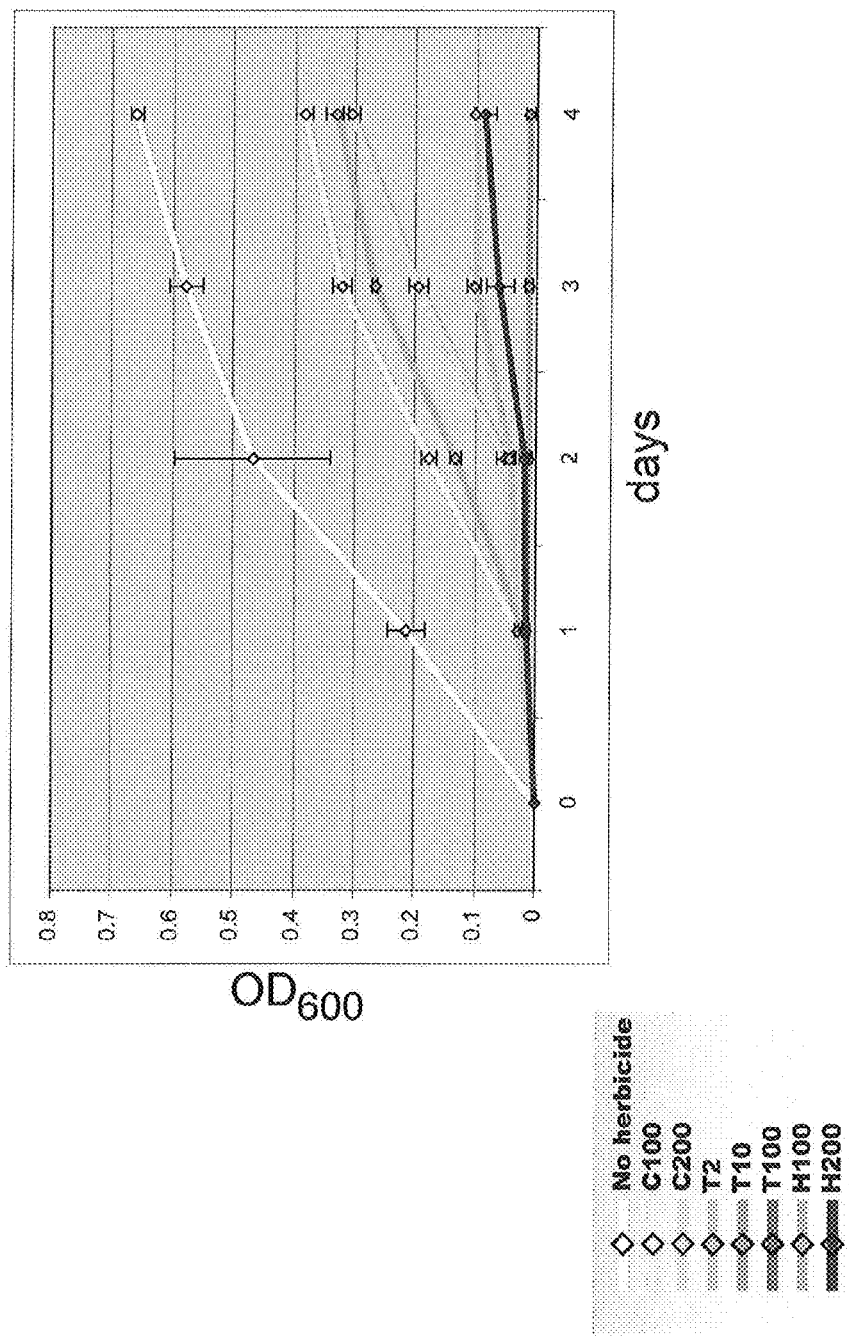
FIG. 30 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 31:
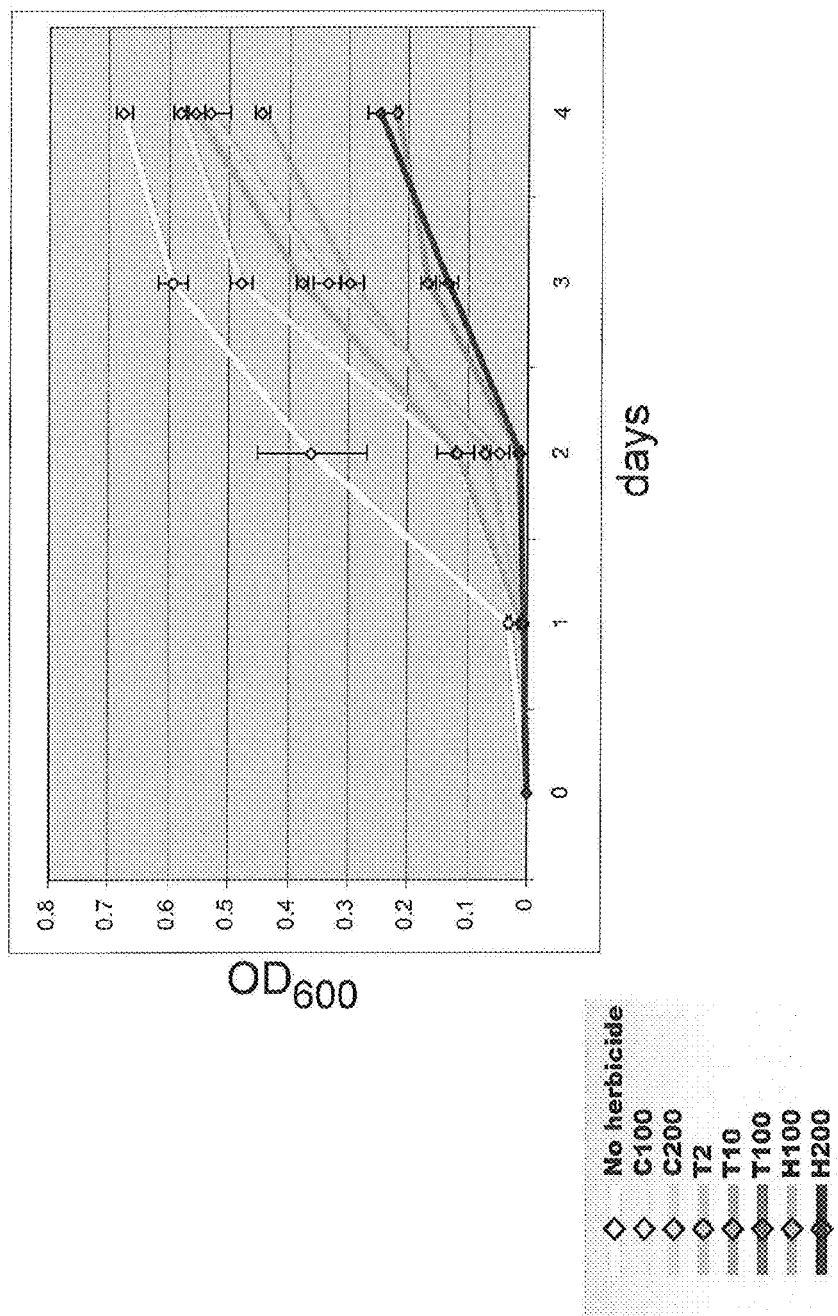
FIG. 31 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 32:
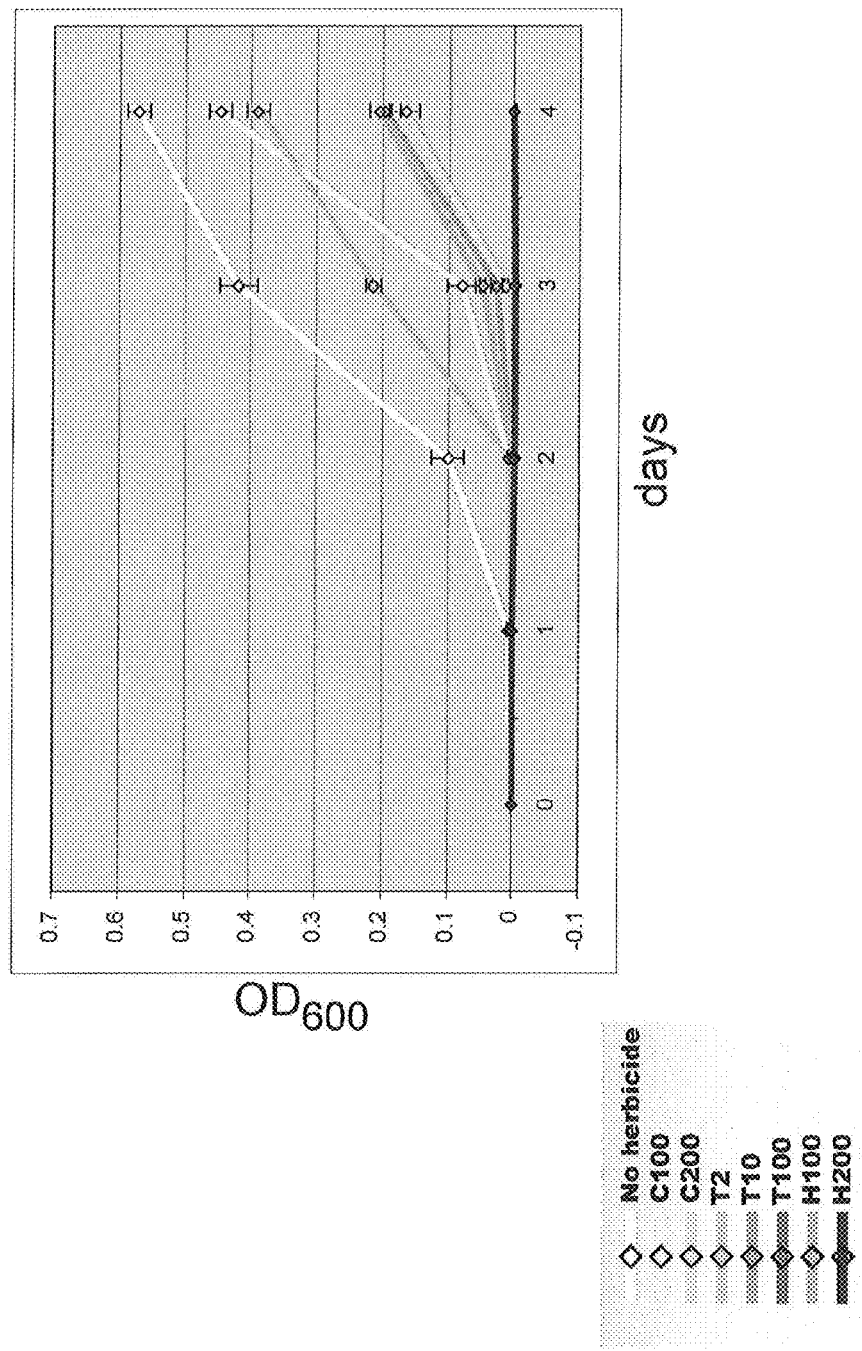
FIG. 32 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 33:
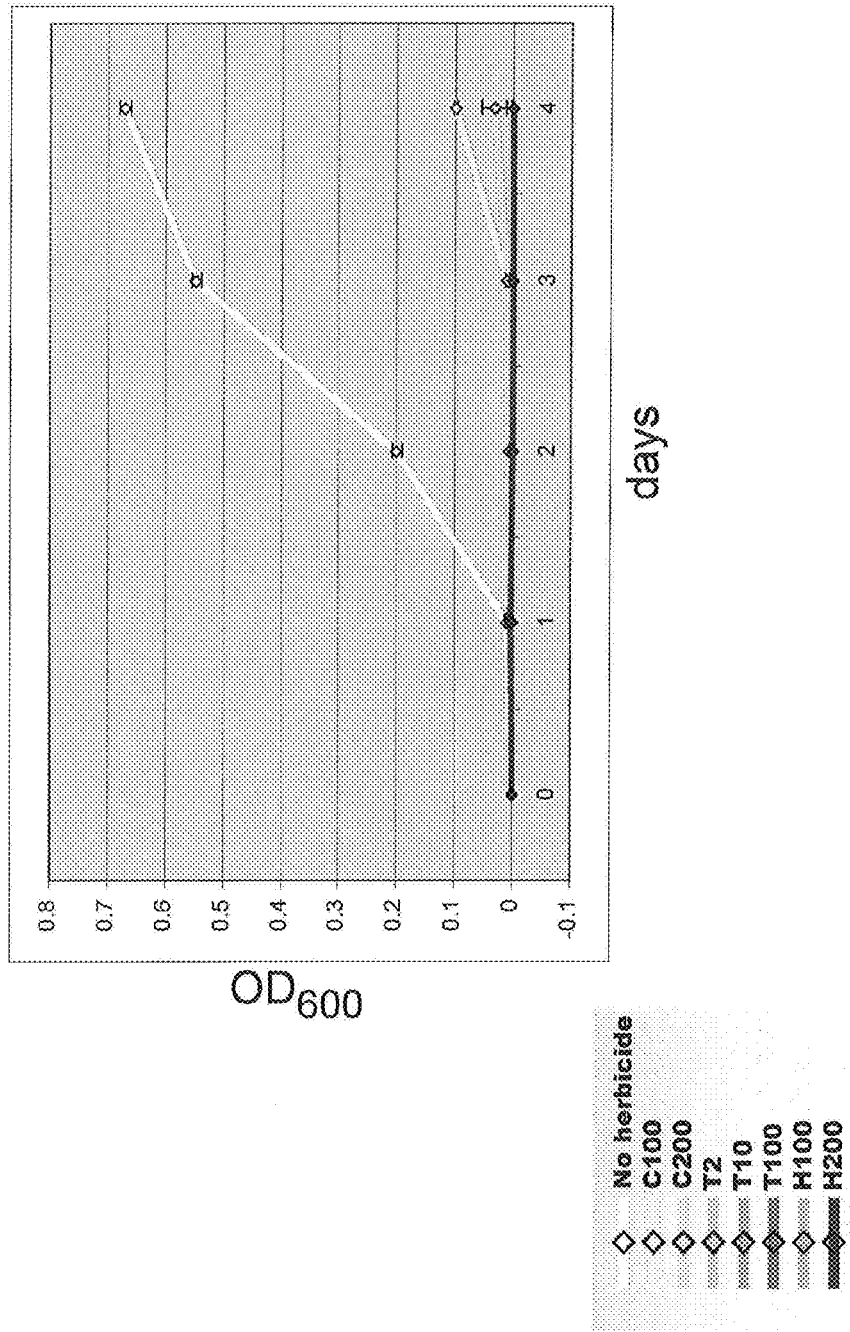
FIG. 33 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 34:
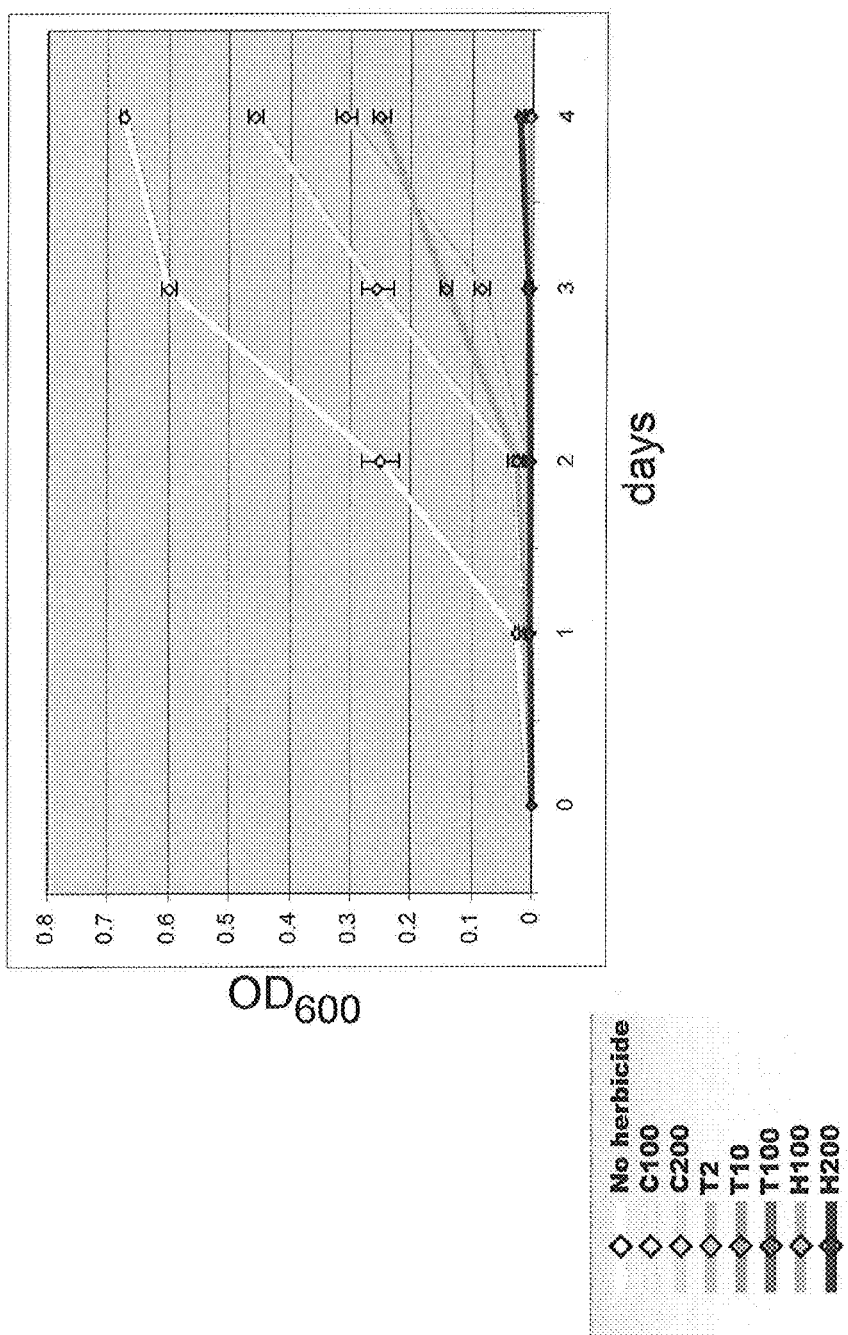
FIG. 34 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 35:
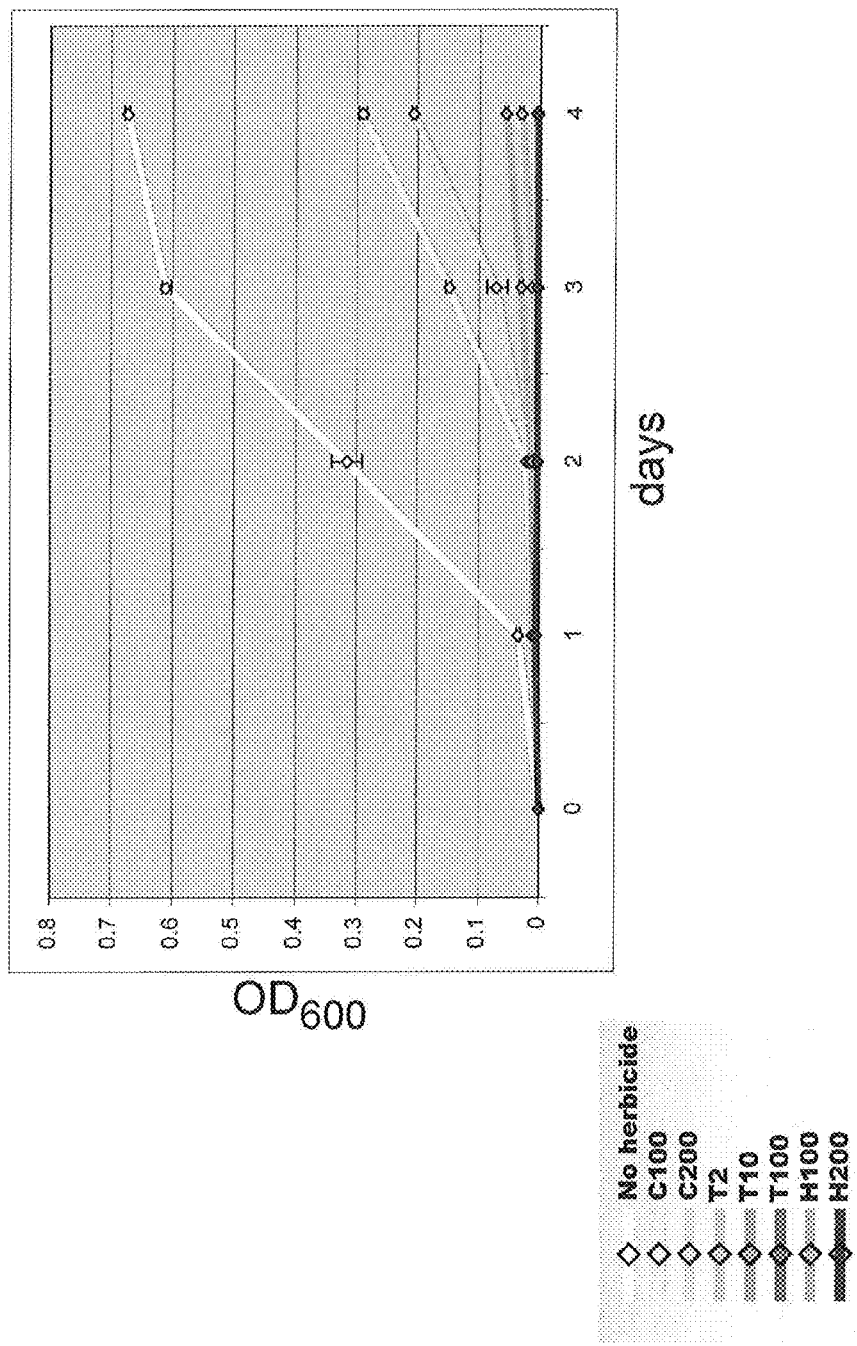
FIG. 35 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 36:
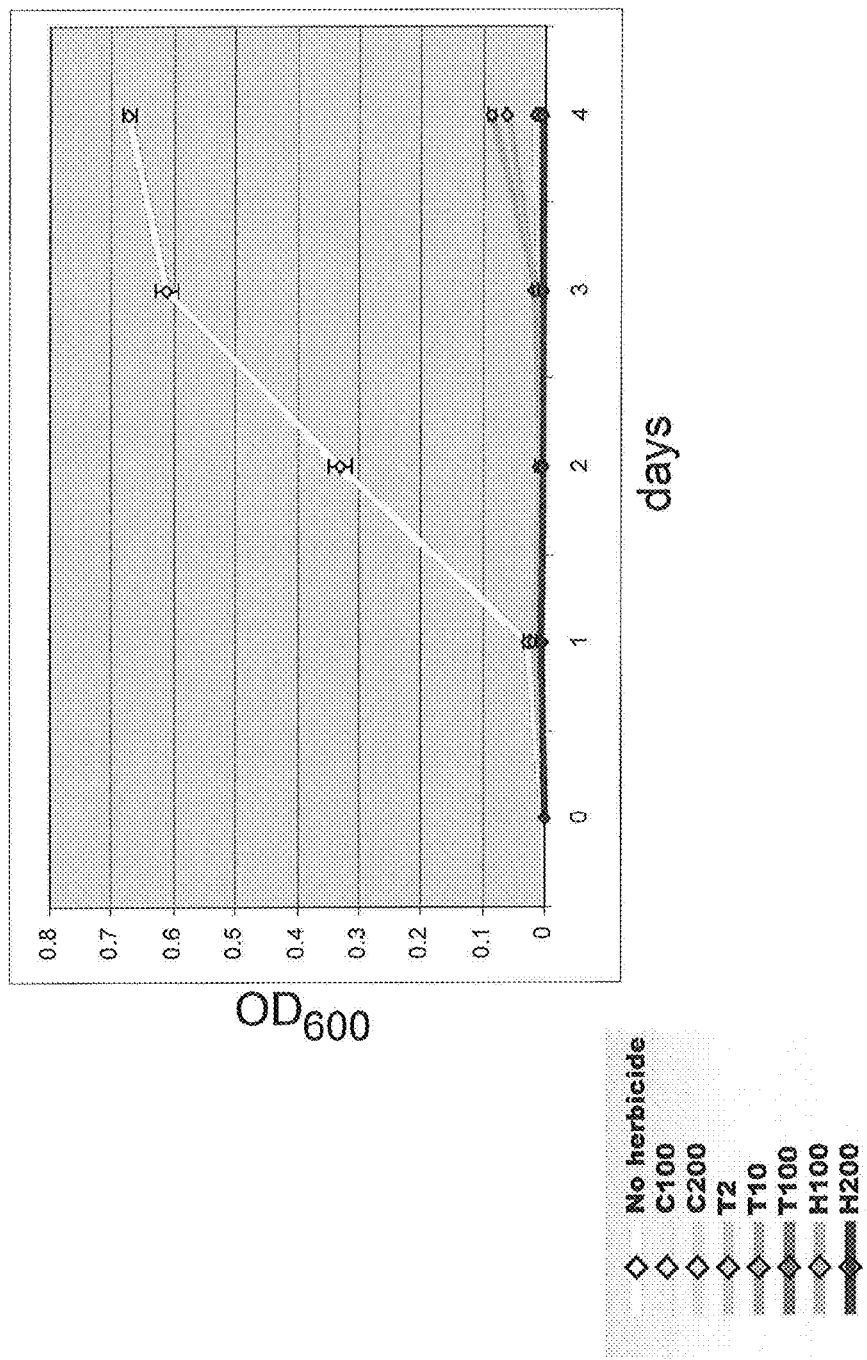
FIG. 36 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 37:
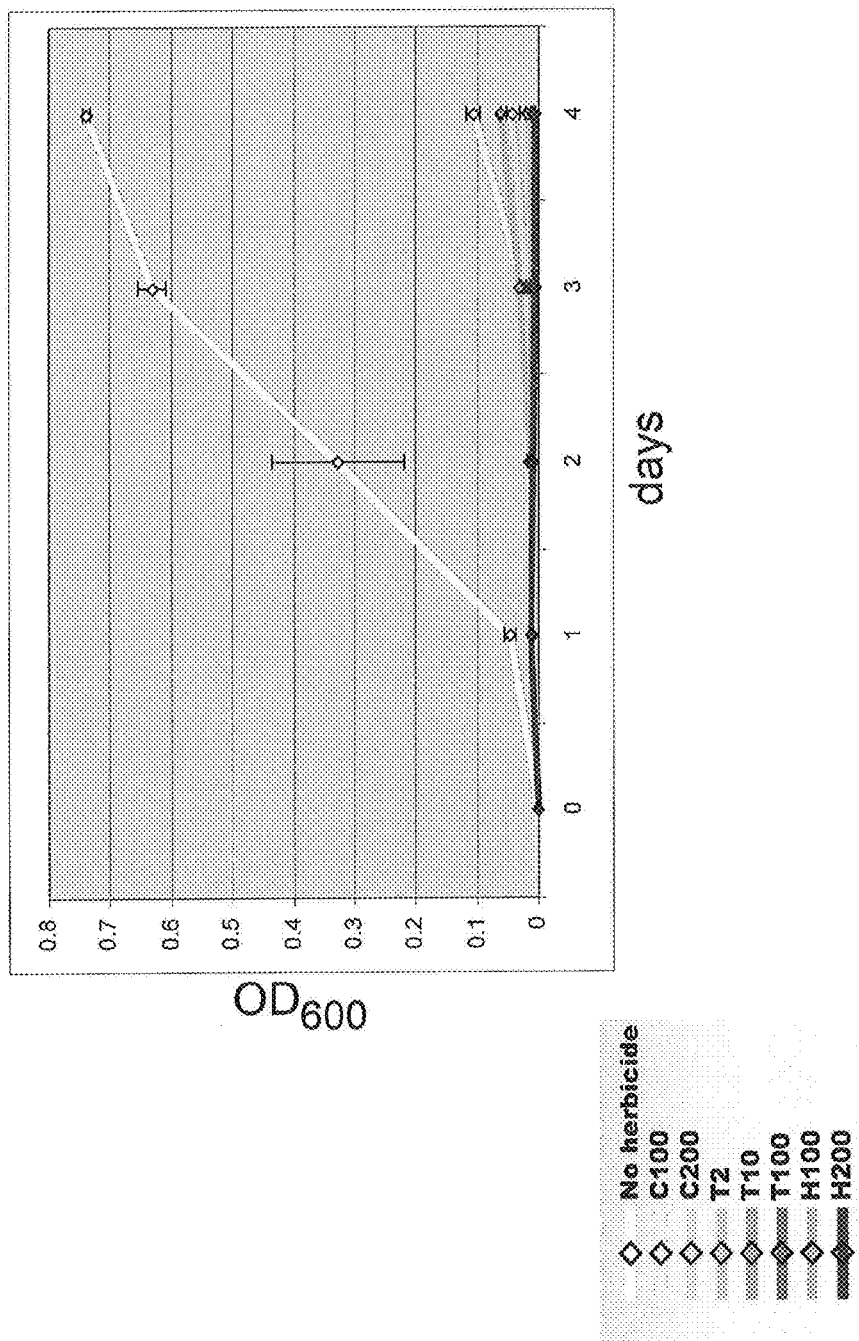
FIG. 37 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 38:
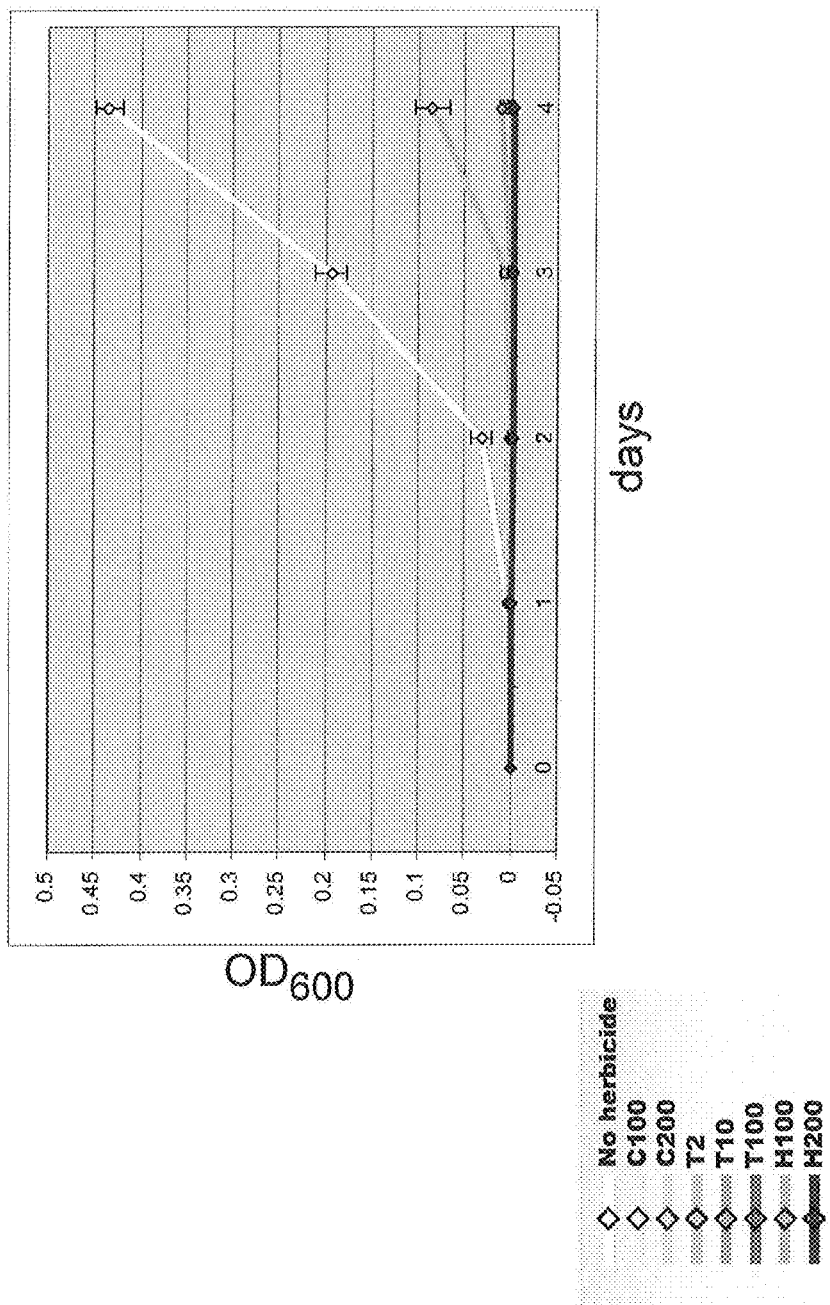
FIG. 38 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 39:
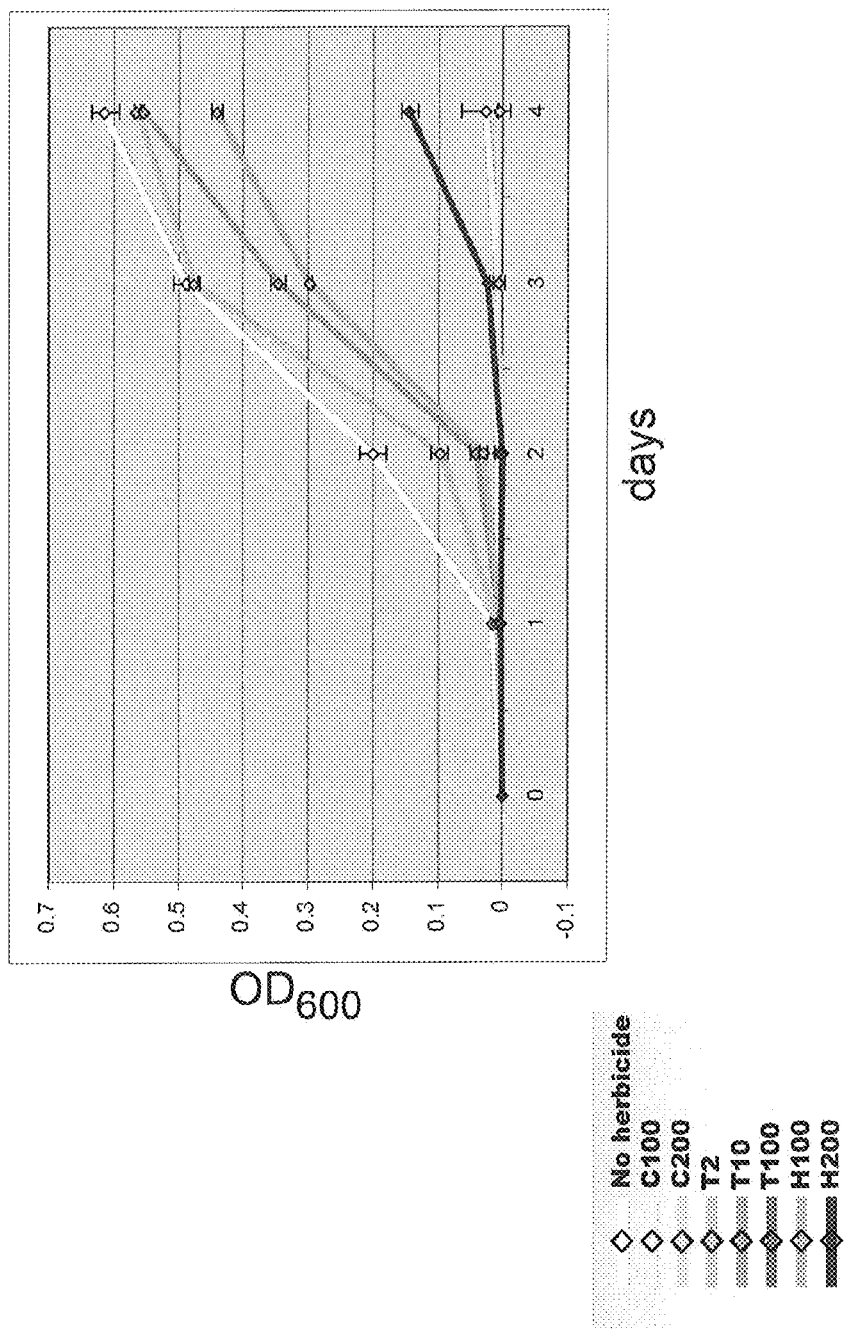
FIG. 39 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 40:
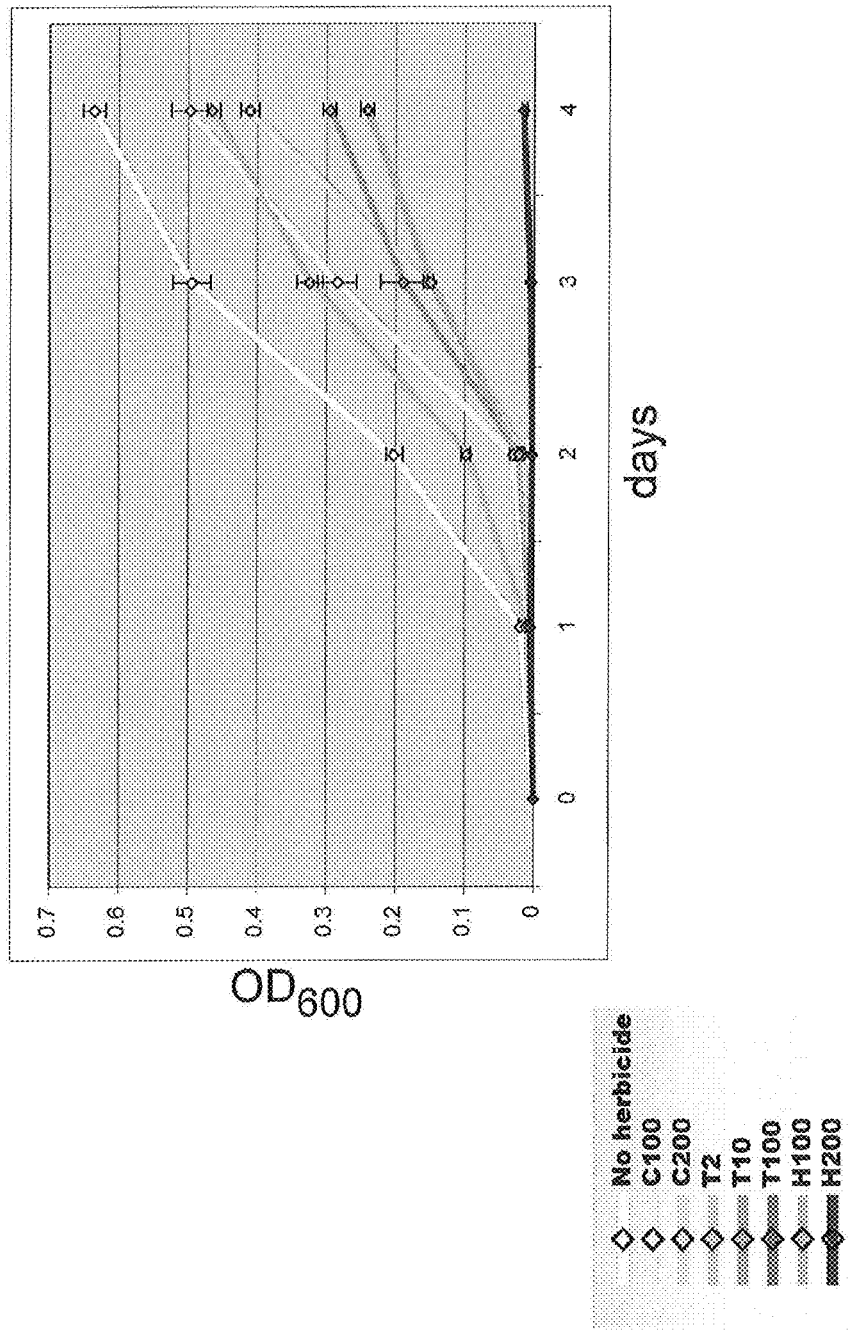
FIG. 40 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 41:
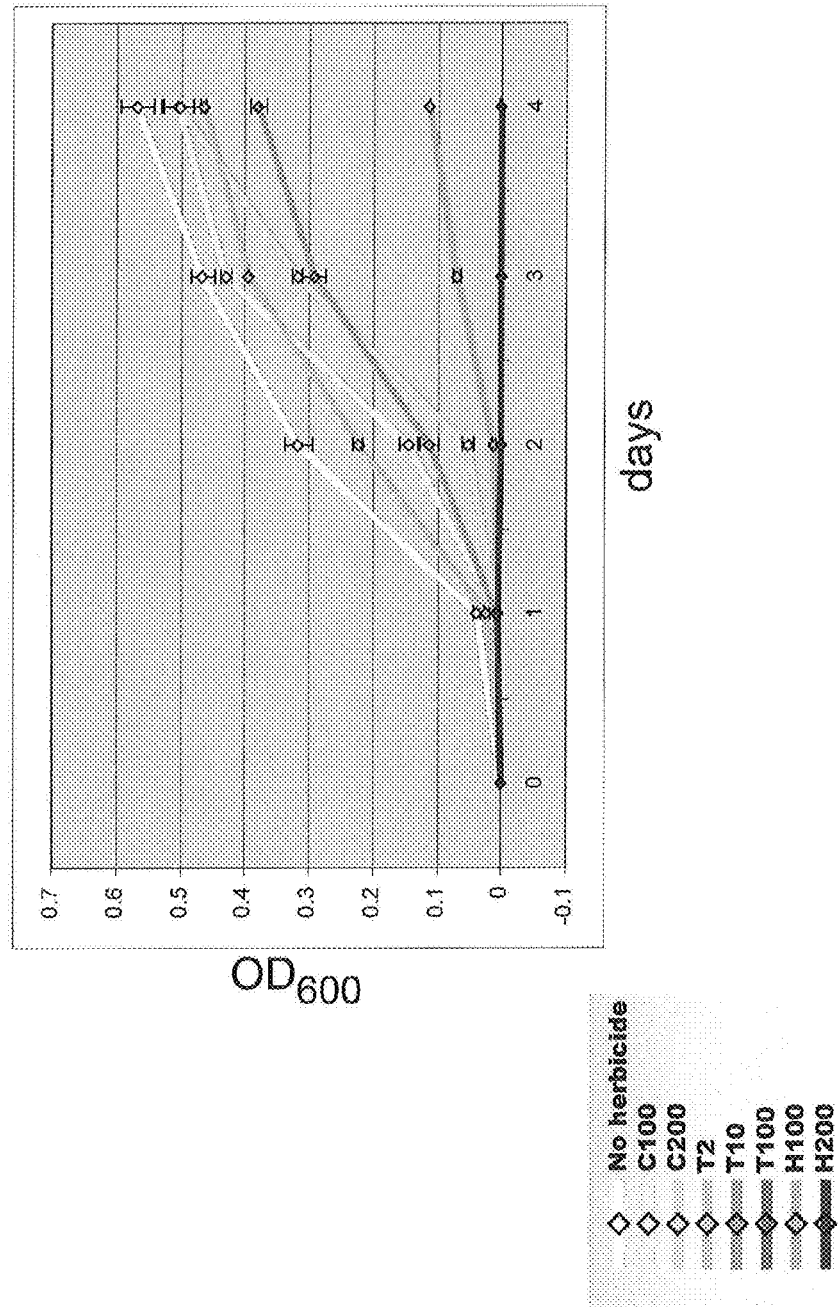
FIG. 41 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 42:
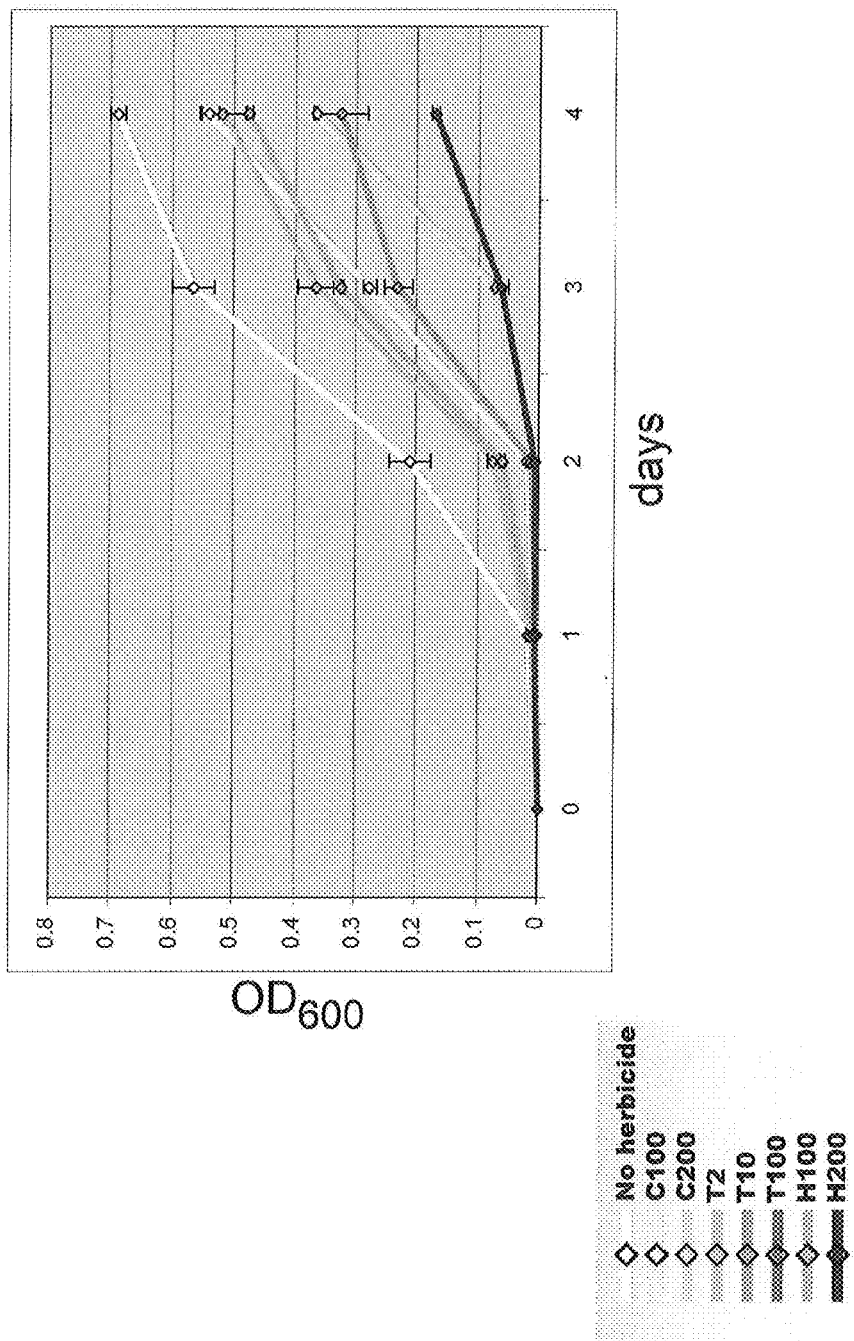
FIG. 42 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 43:
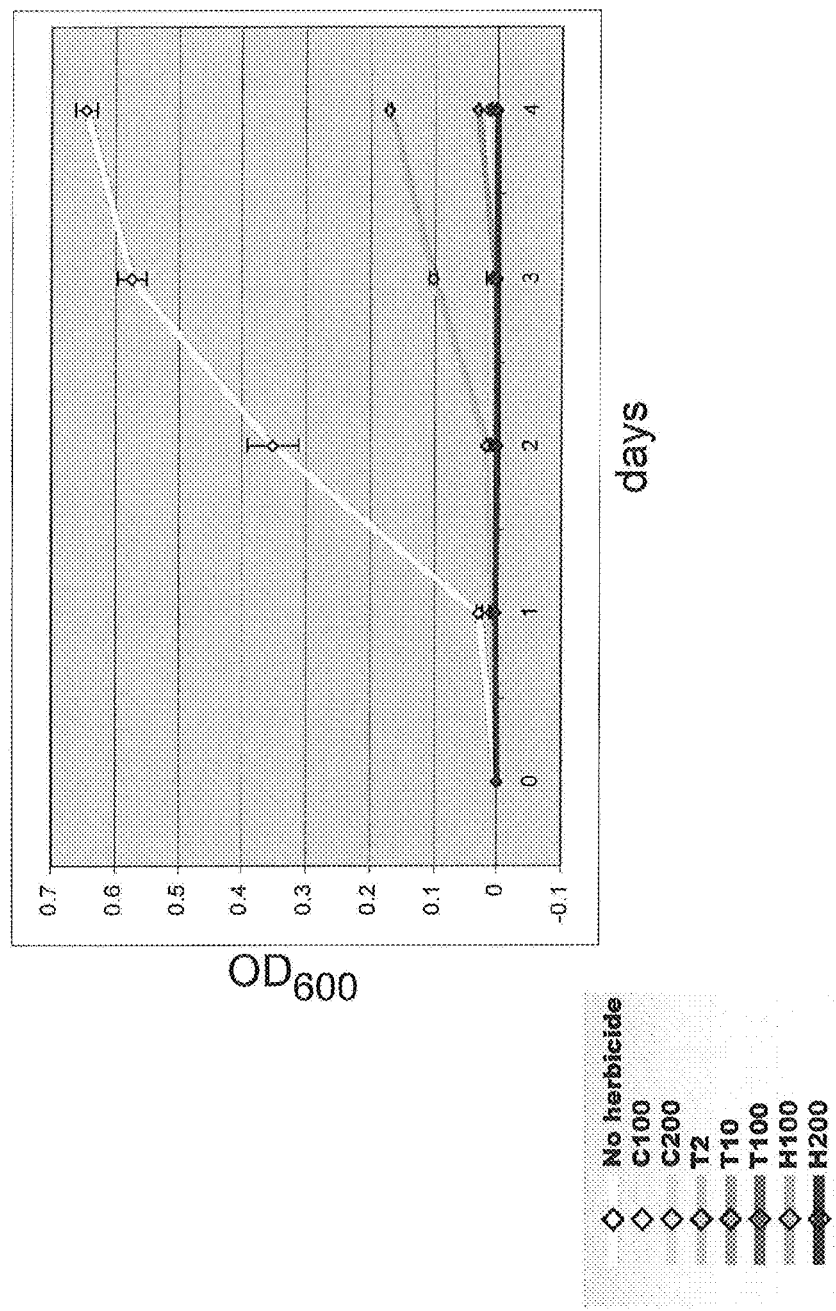
FIG. 43 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 44:
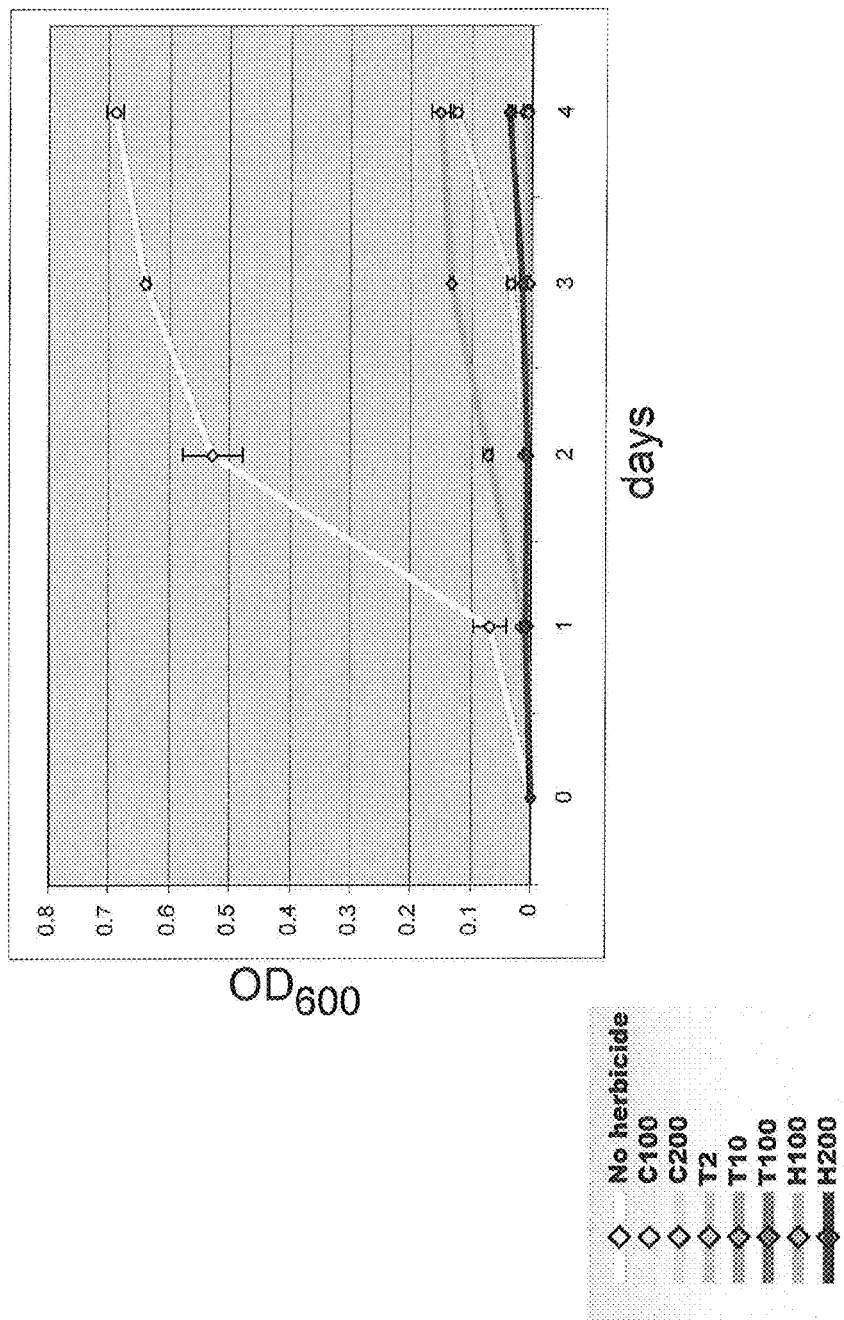
FIG. 44 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 45:
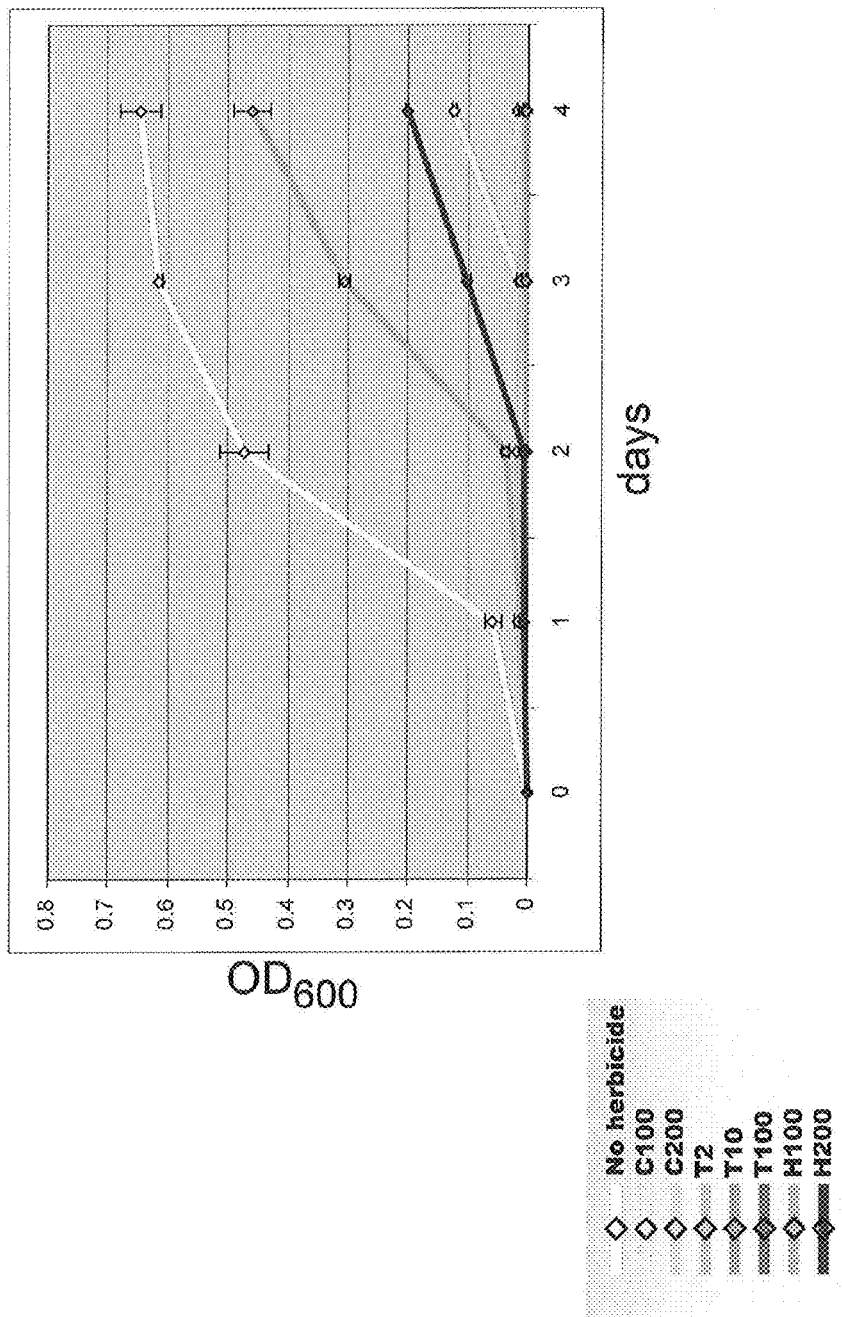
FIG. 45 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 46:
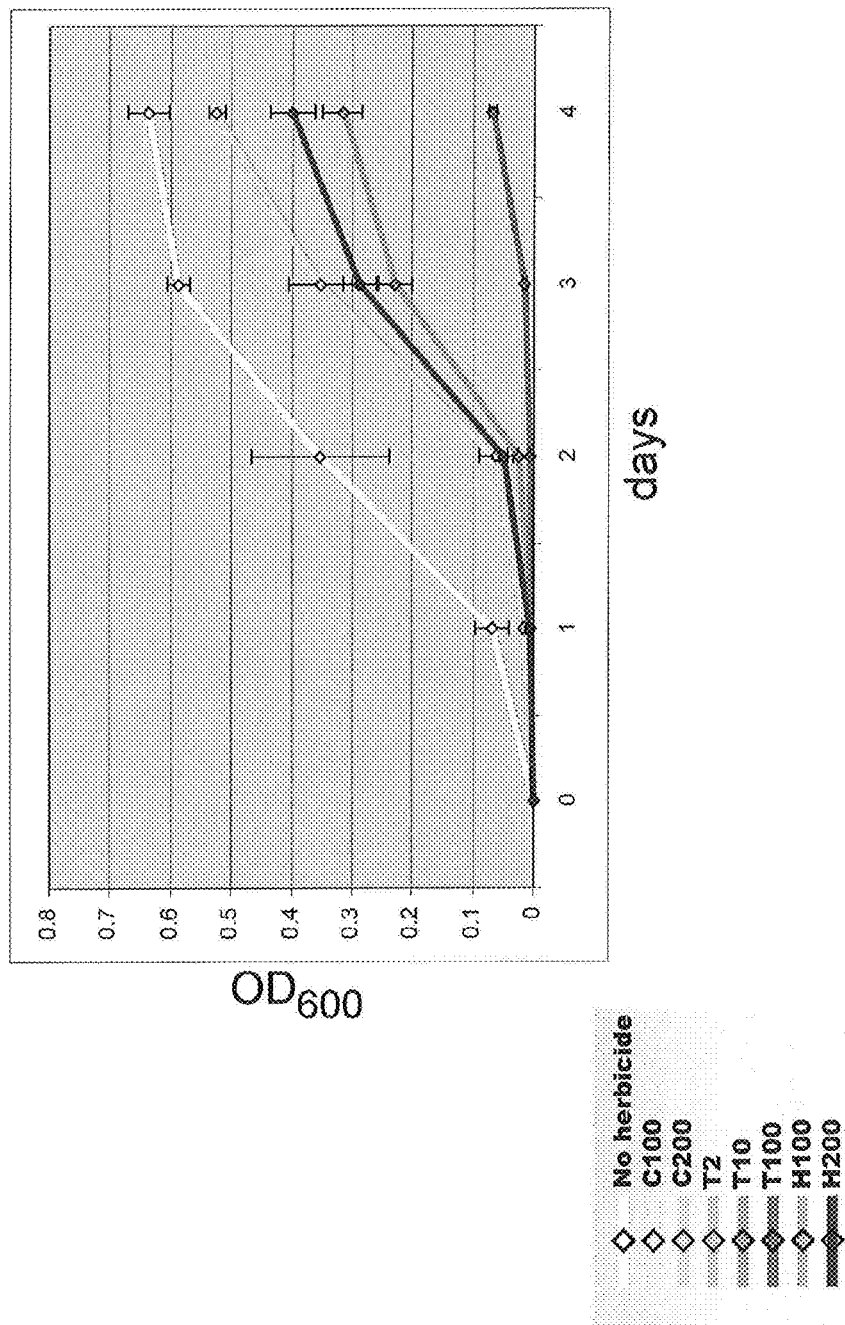
FIG. 46 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 47:
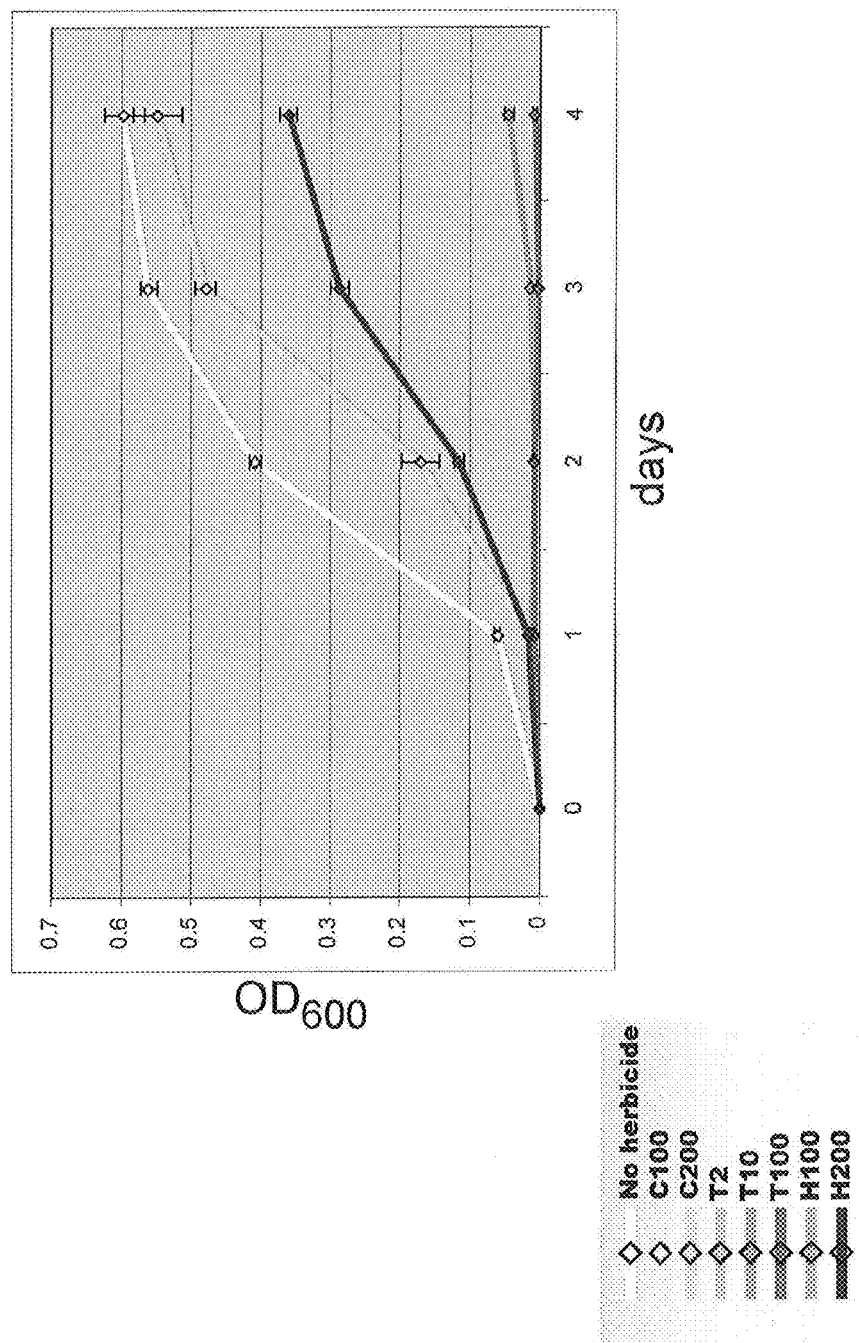
FIG. 47 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 48:
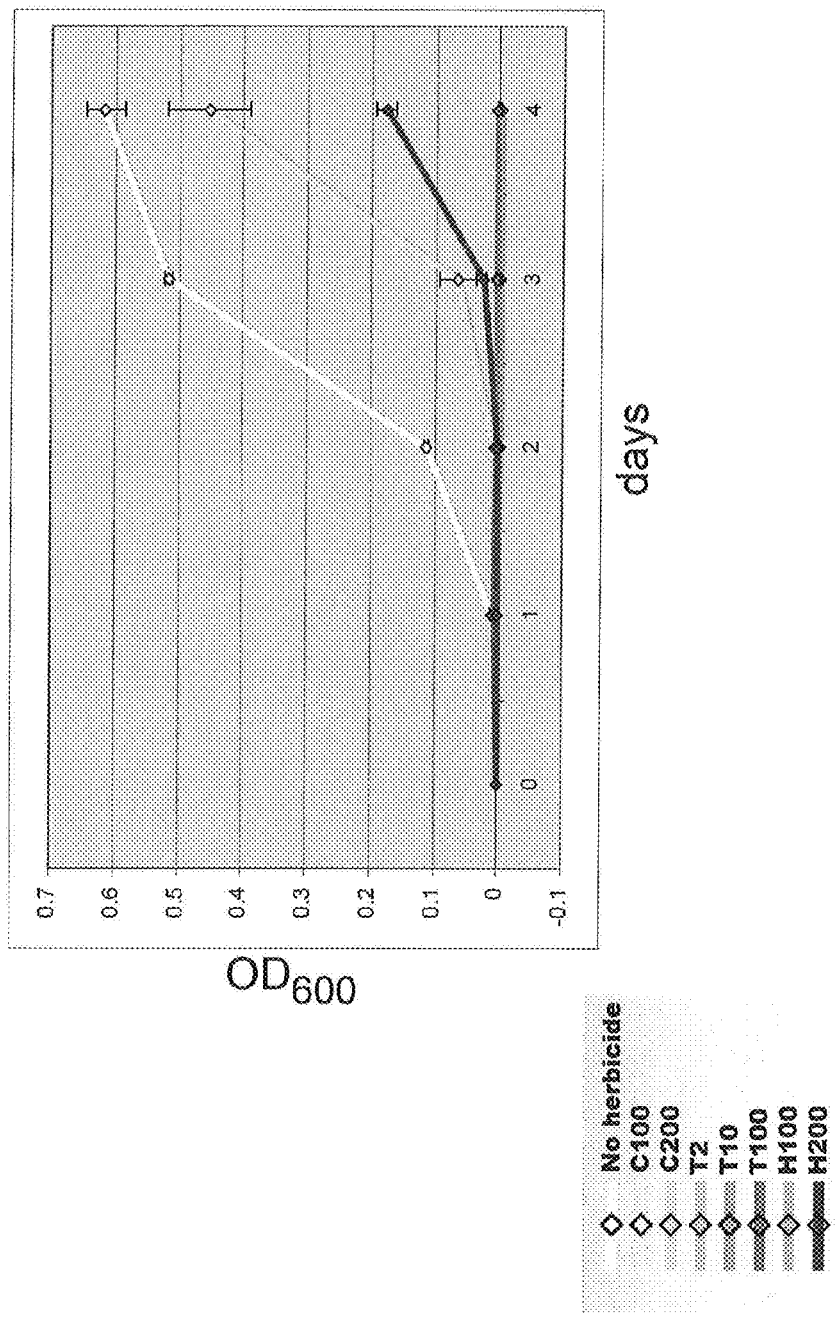
FIG. 48 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 49:
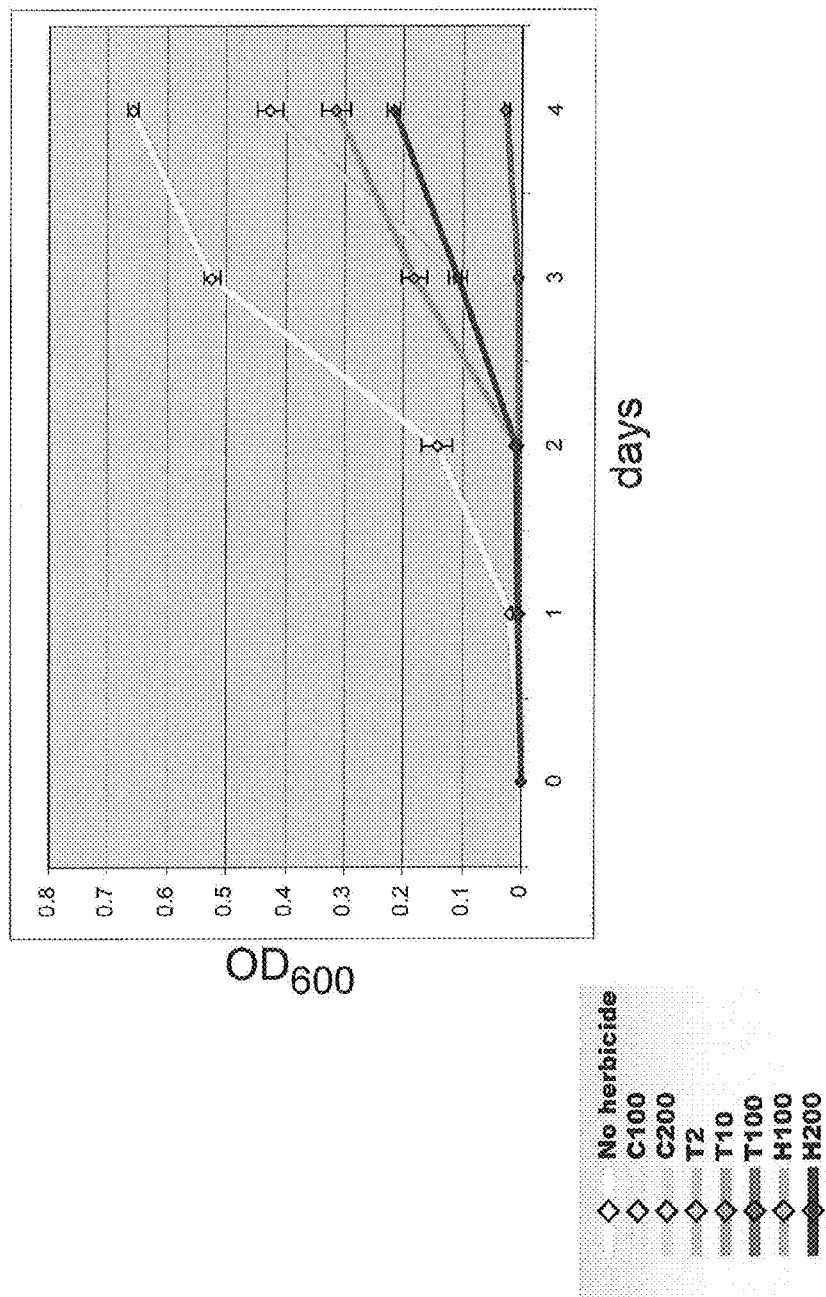
FIG. 49 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 50:
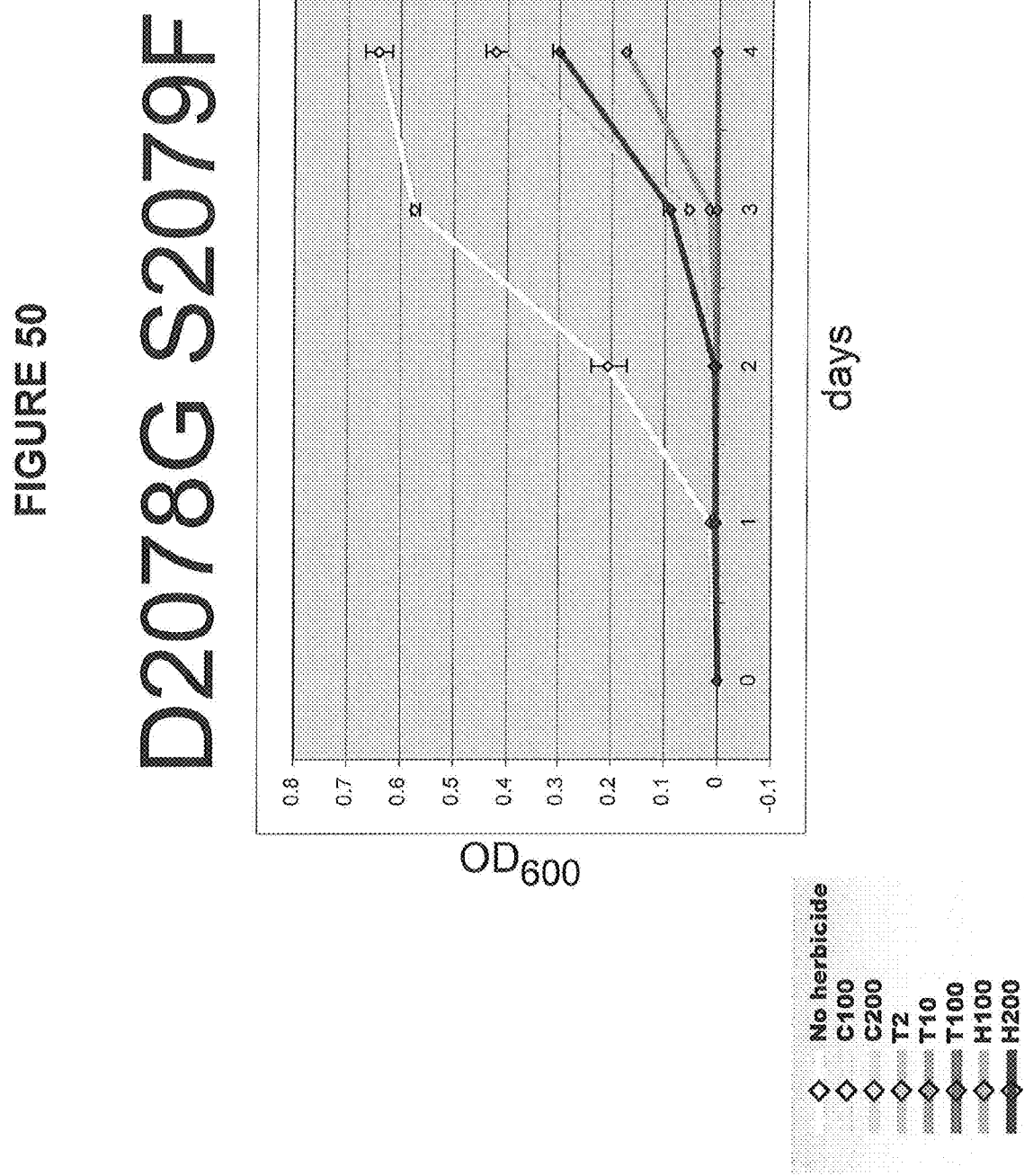
FIG. 50 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 51:
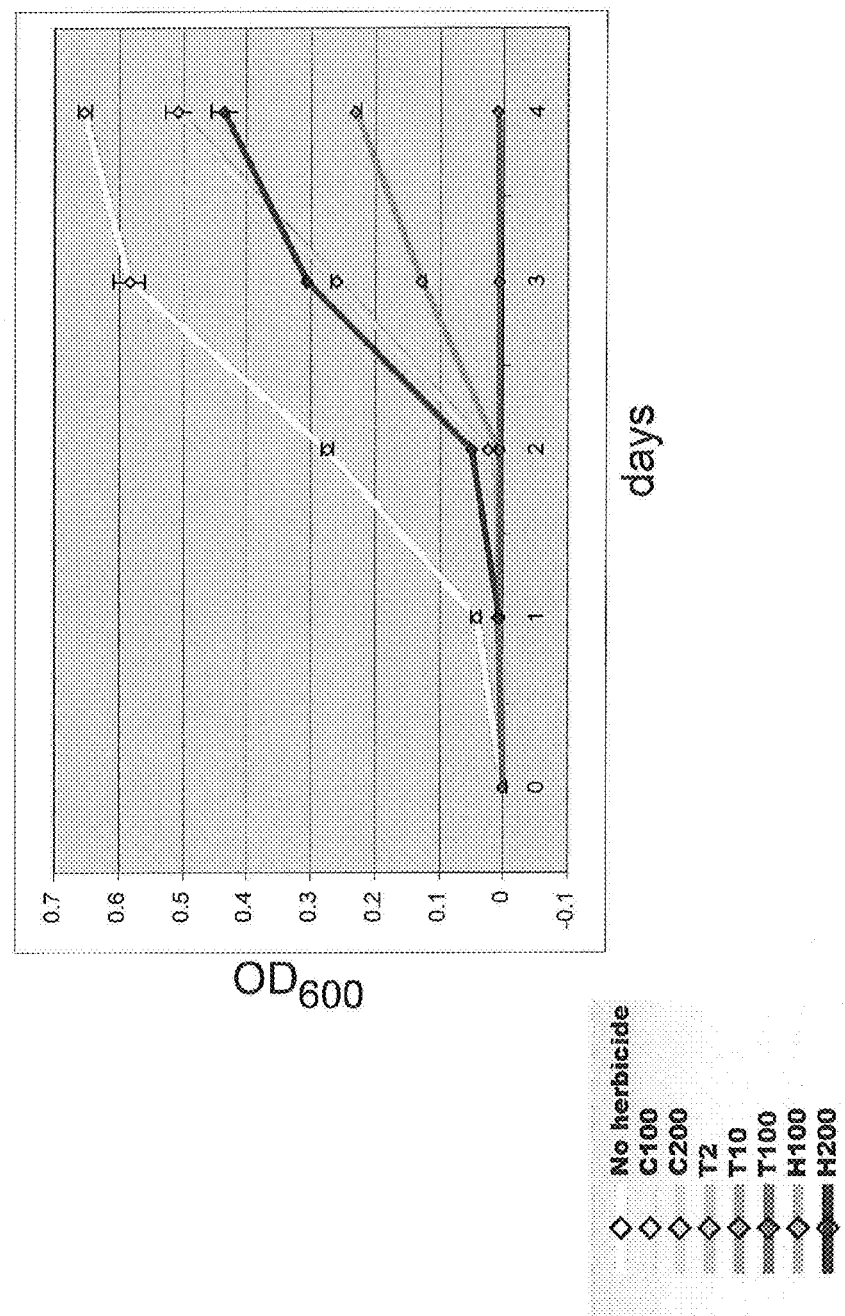
FIG. 51 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 52:
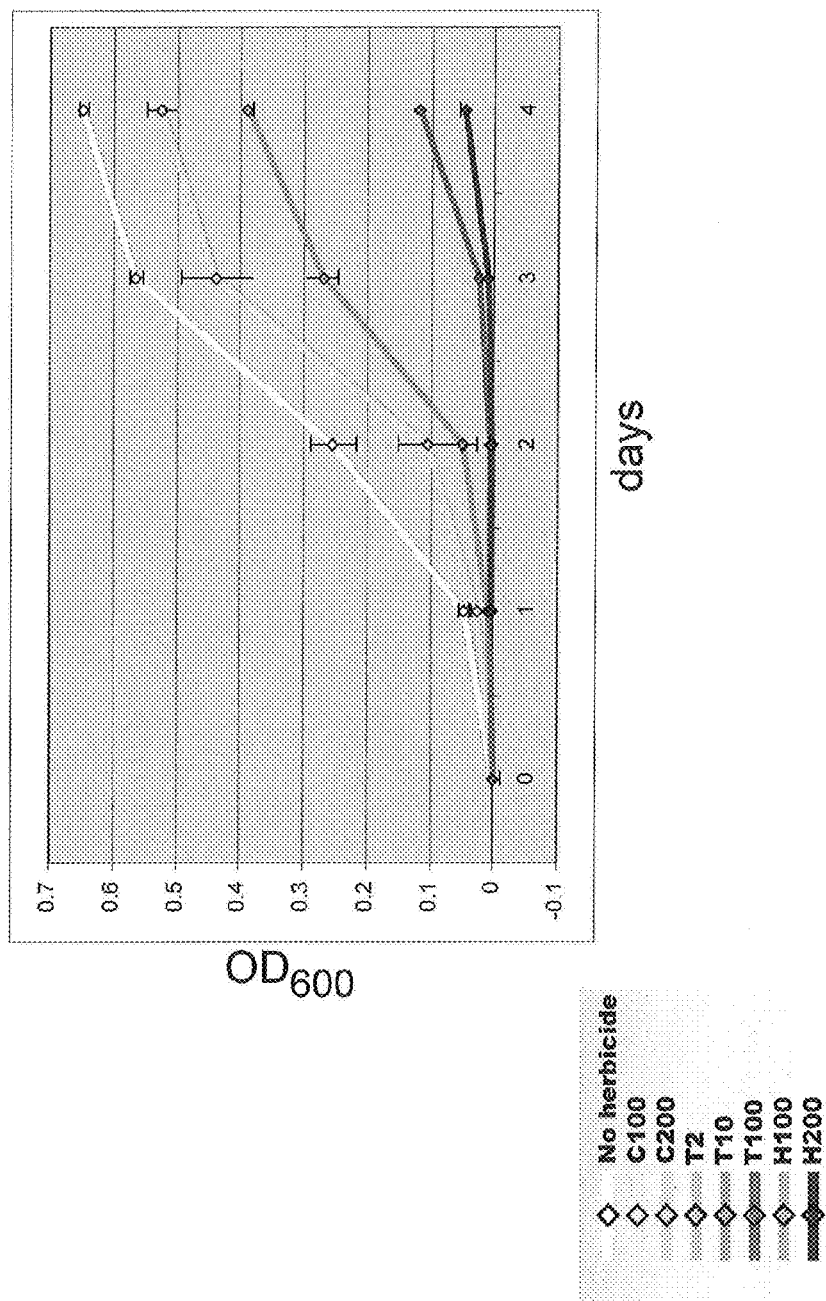
FIG. 52 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 53:
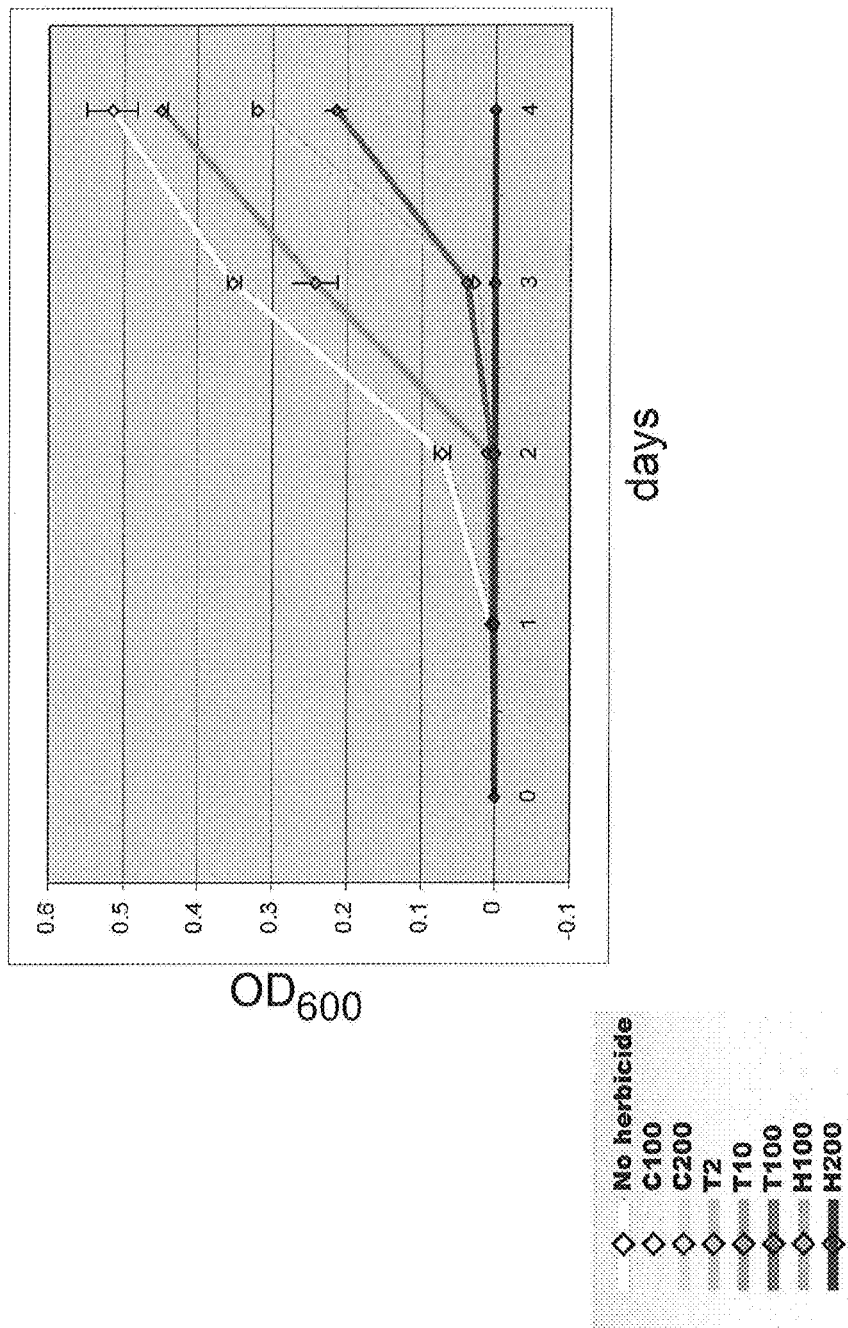
FIG. 53 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 54:
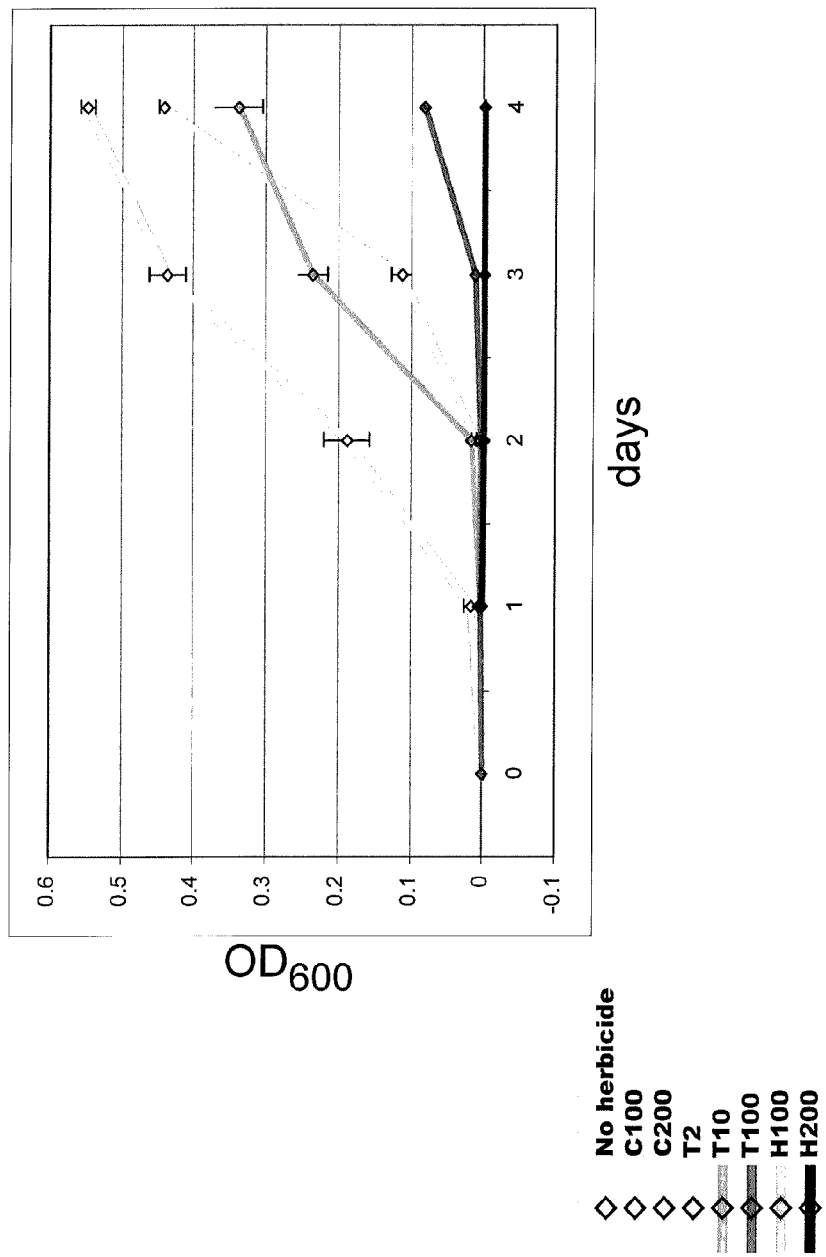
FIG. 54 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 55:
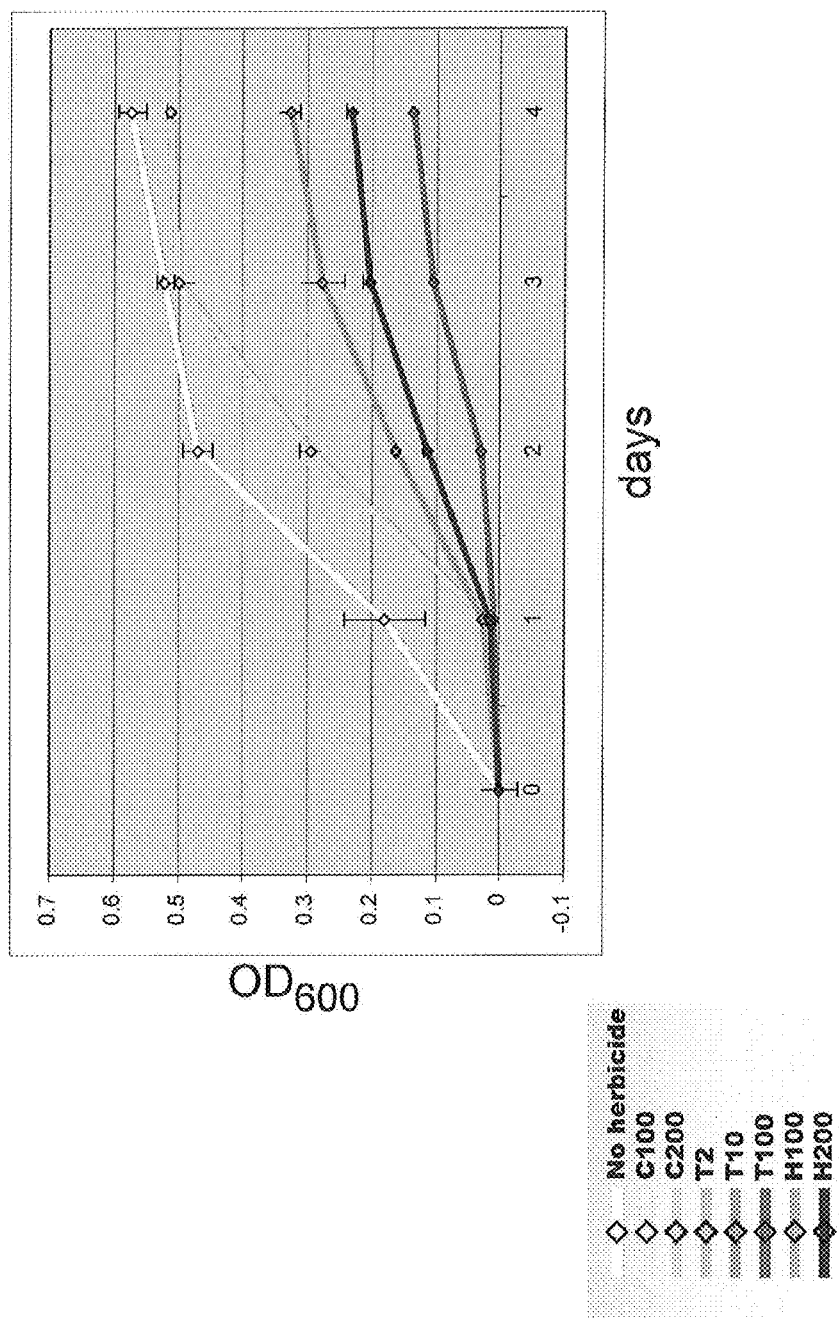
FIG. 55 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 56:
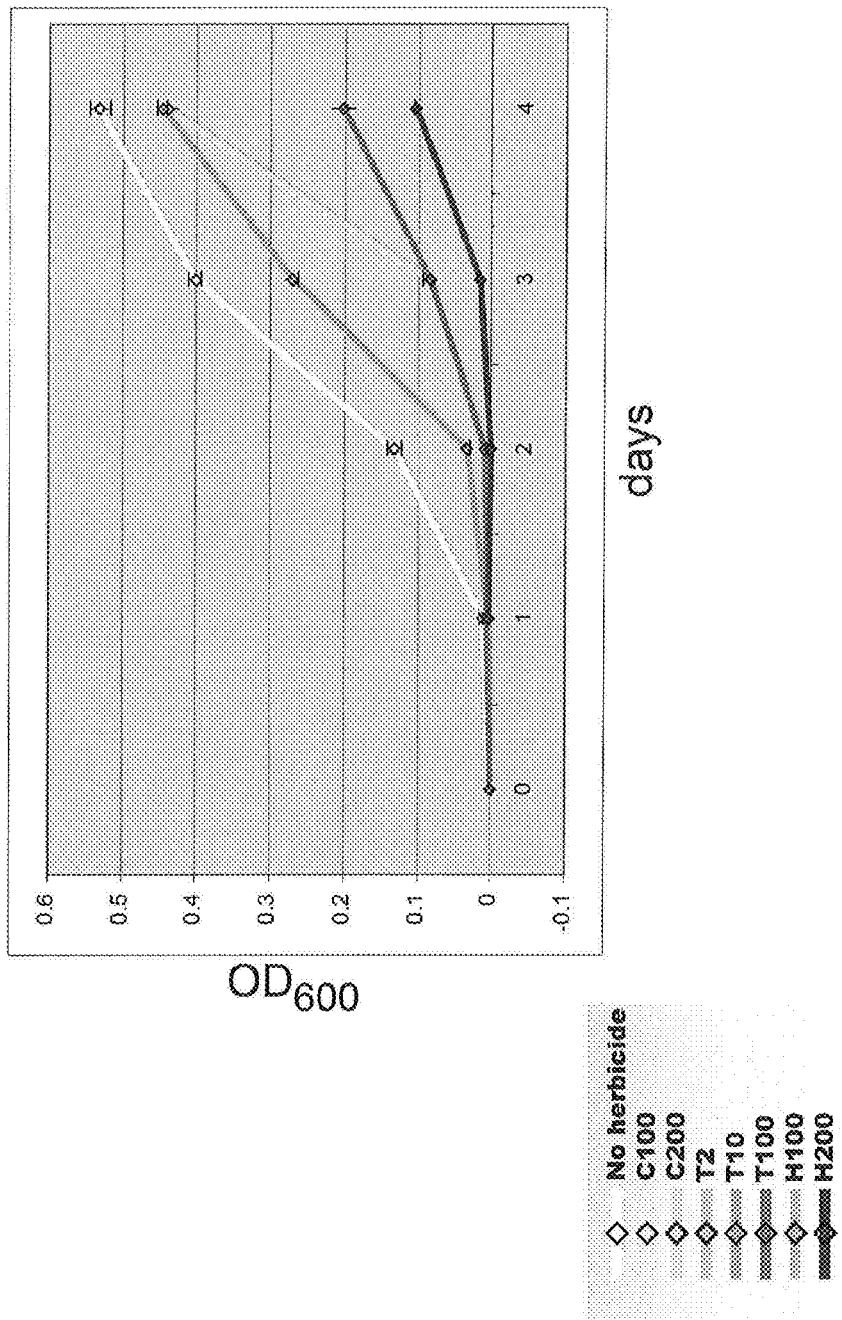
FIG. 56 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 57:
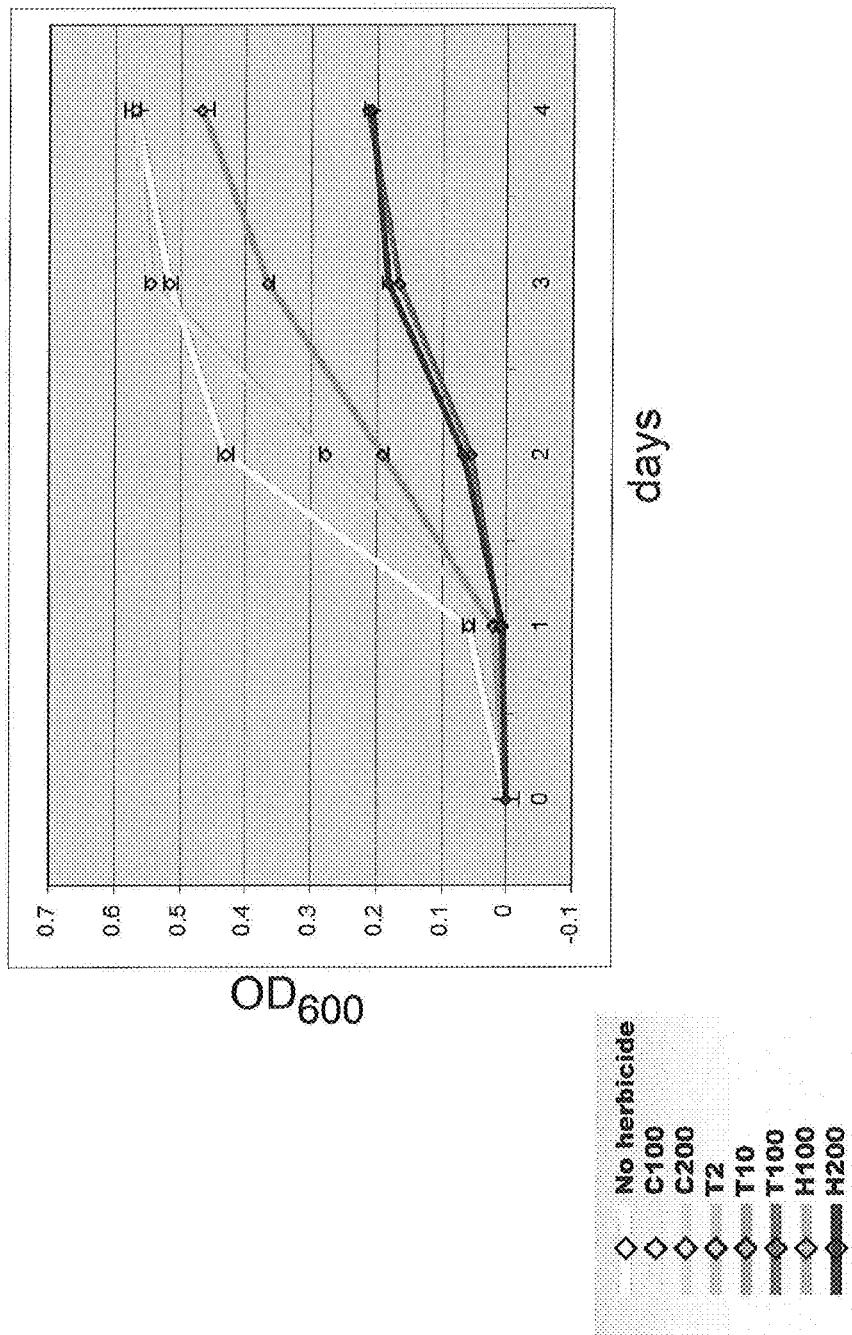
FIG. 57 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 58:
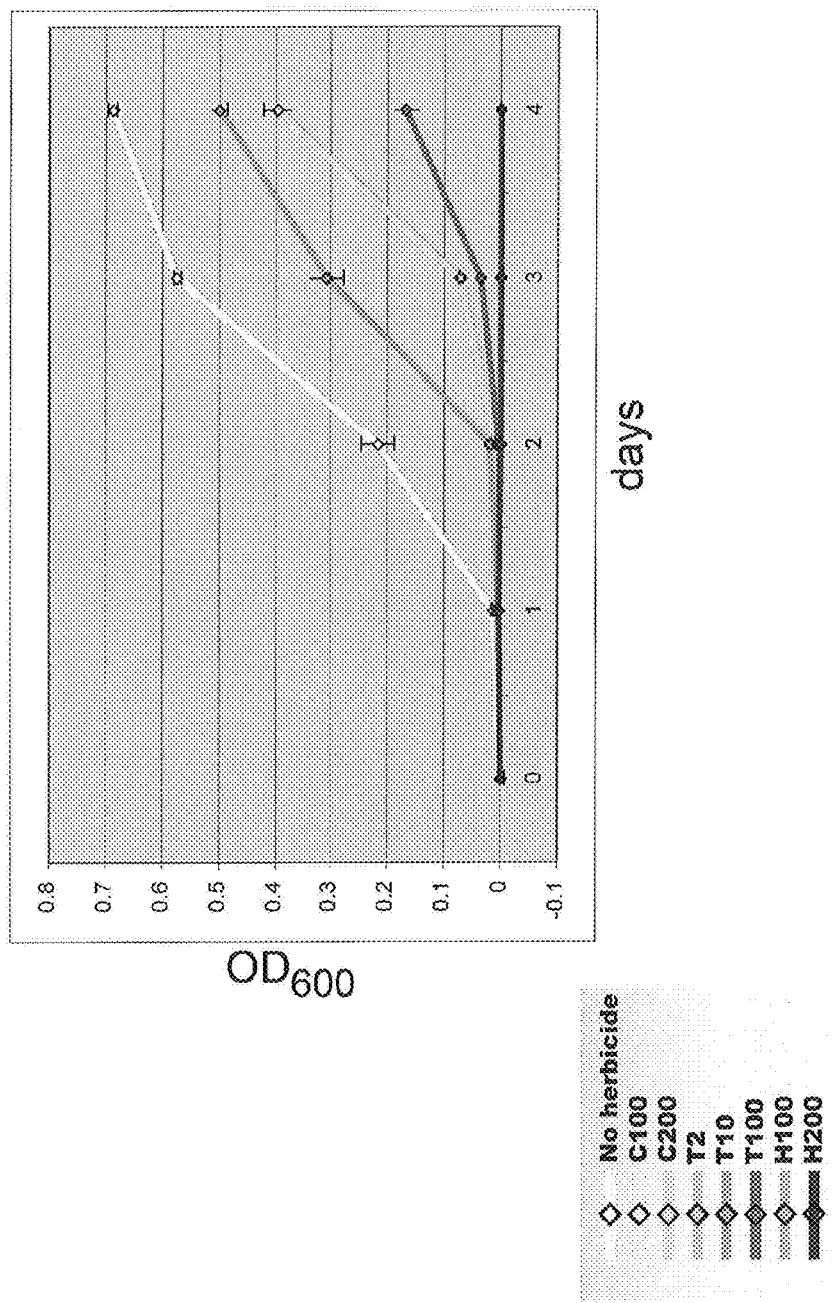
FIG. 58 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 59:
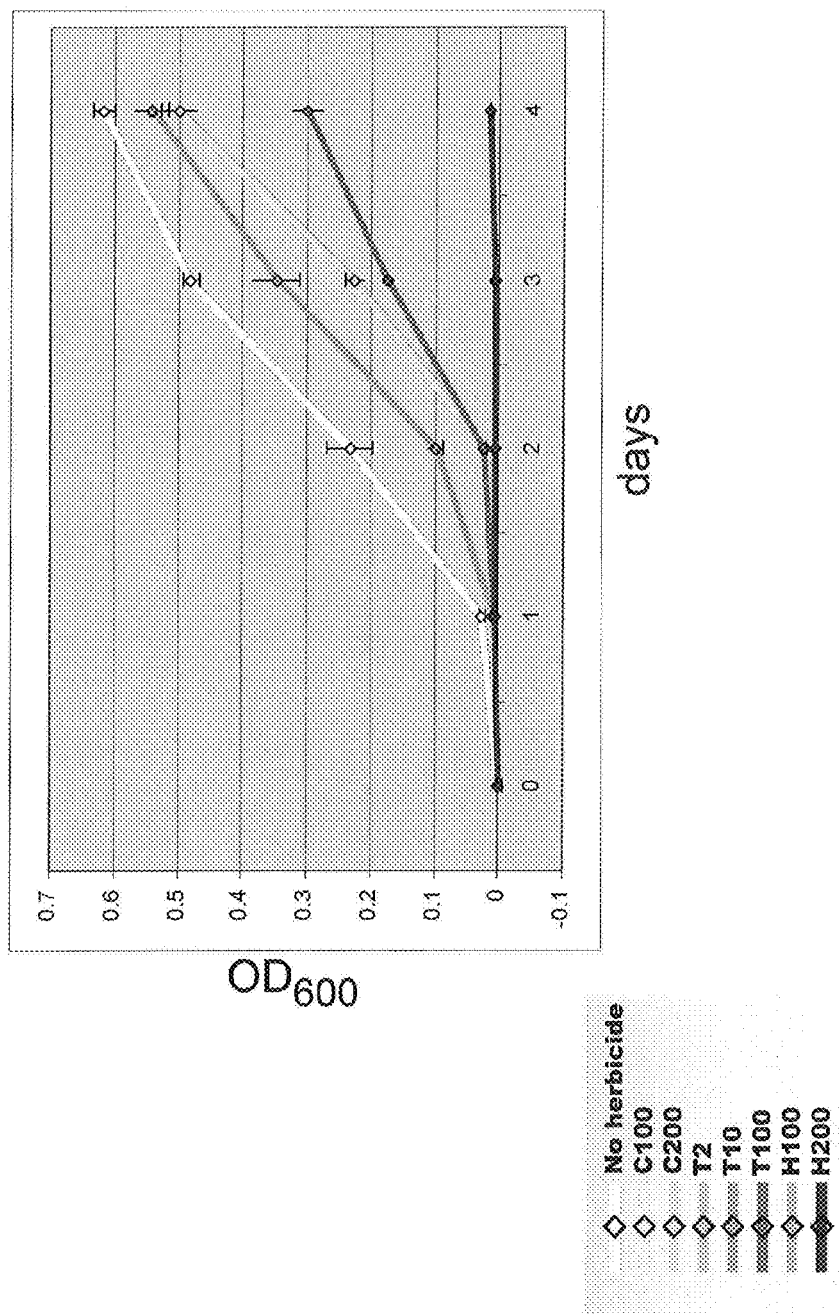
FIG. 59 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 60:
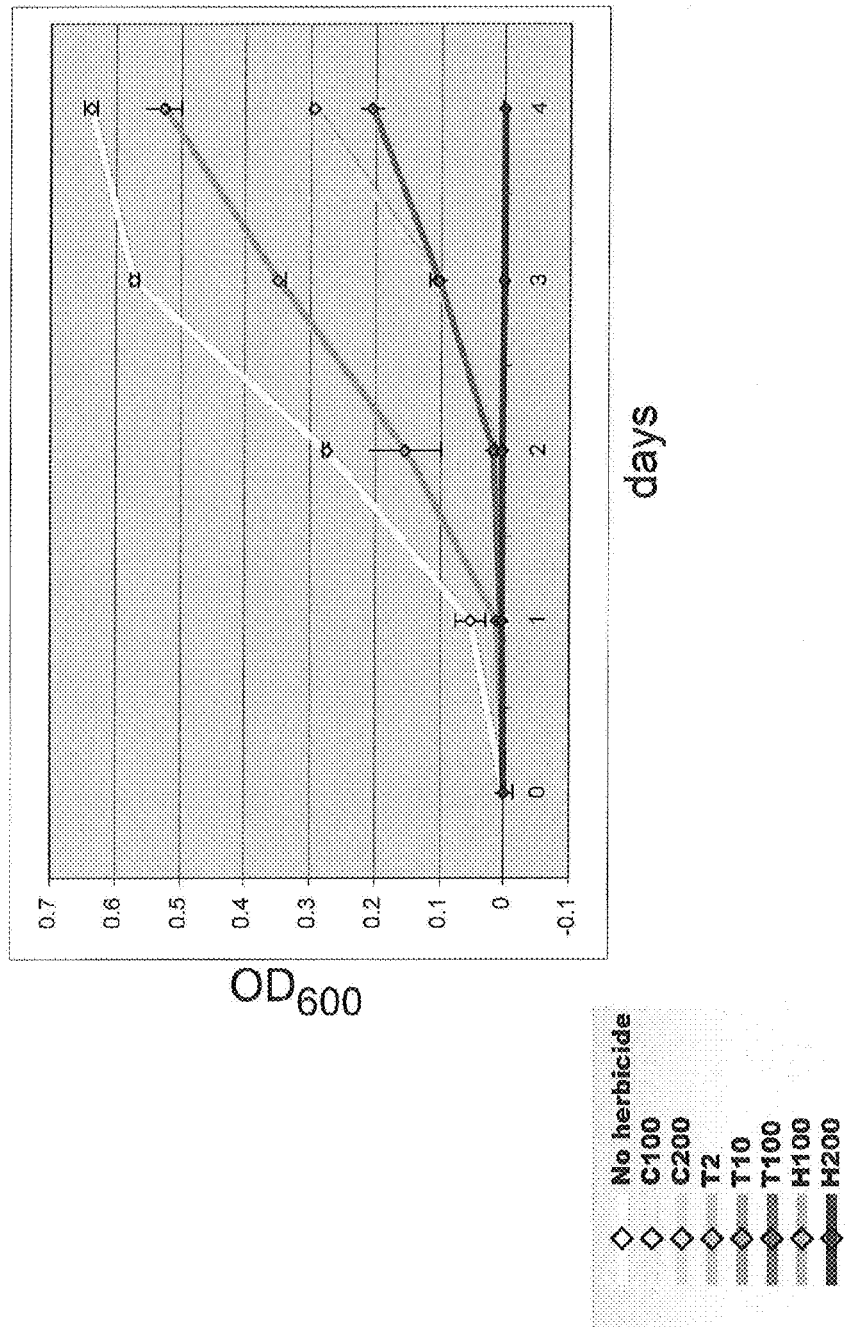
FIG. 60 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 61:
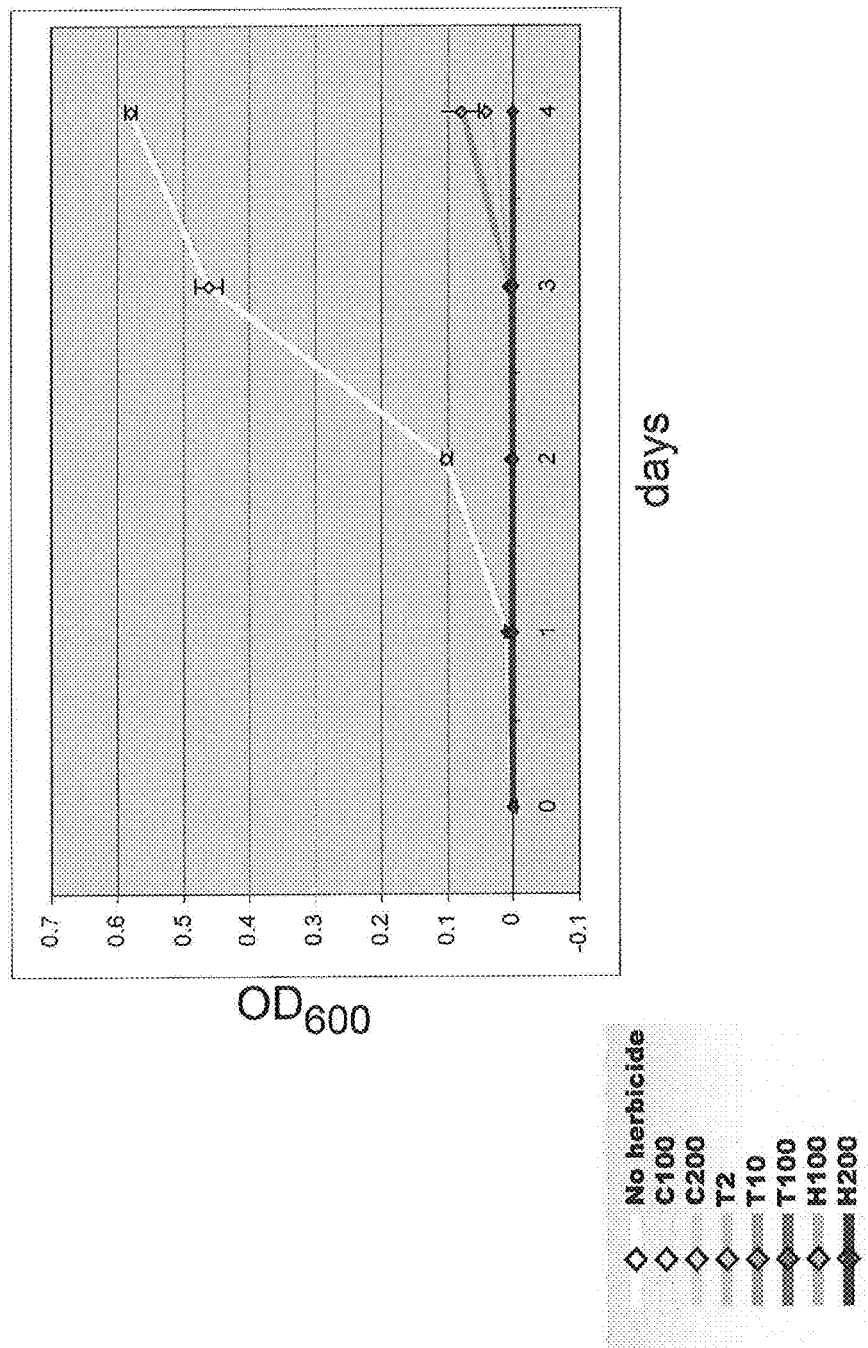
FIG. 61 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 62:
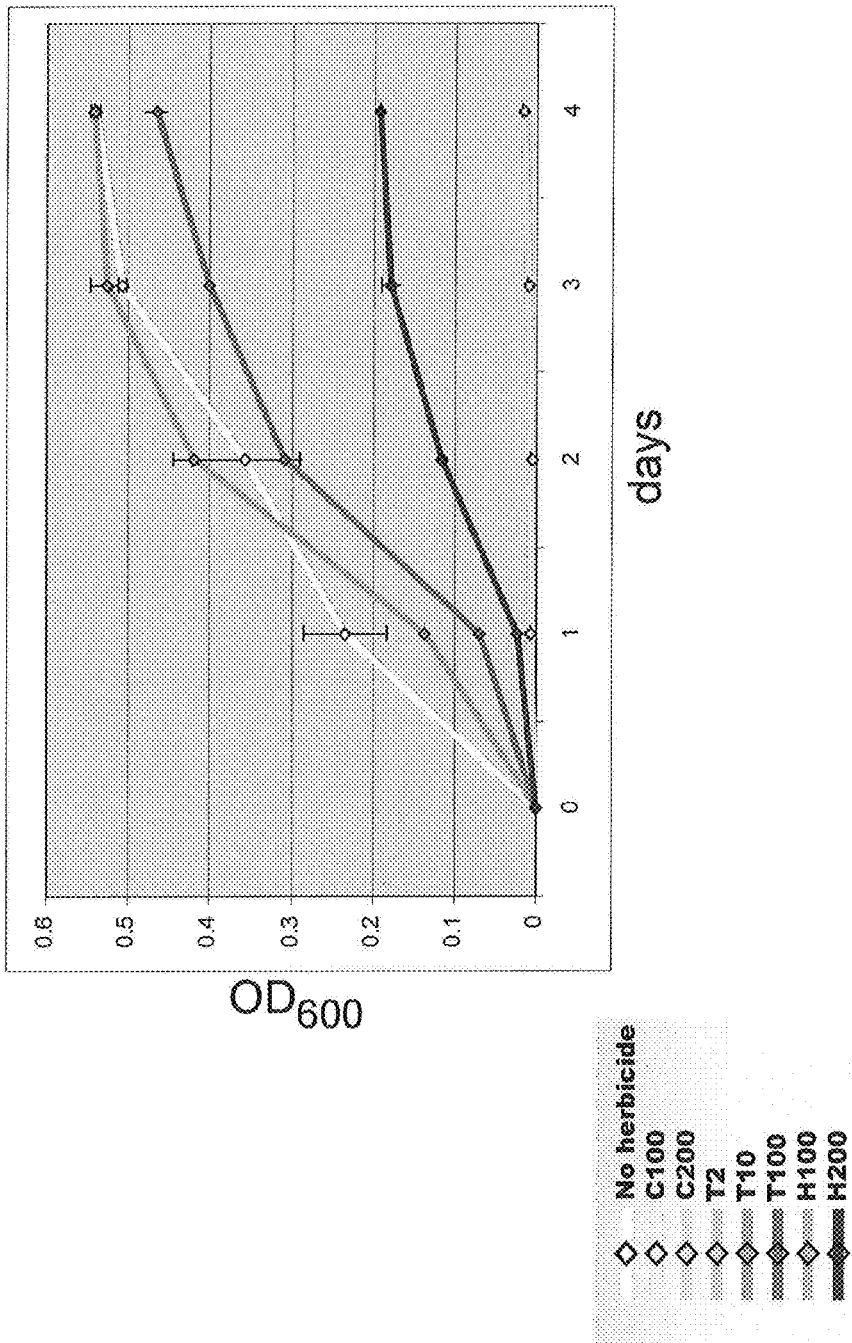
FIG. 62 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 63:
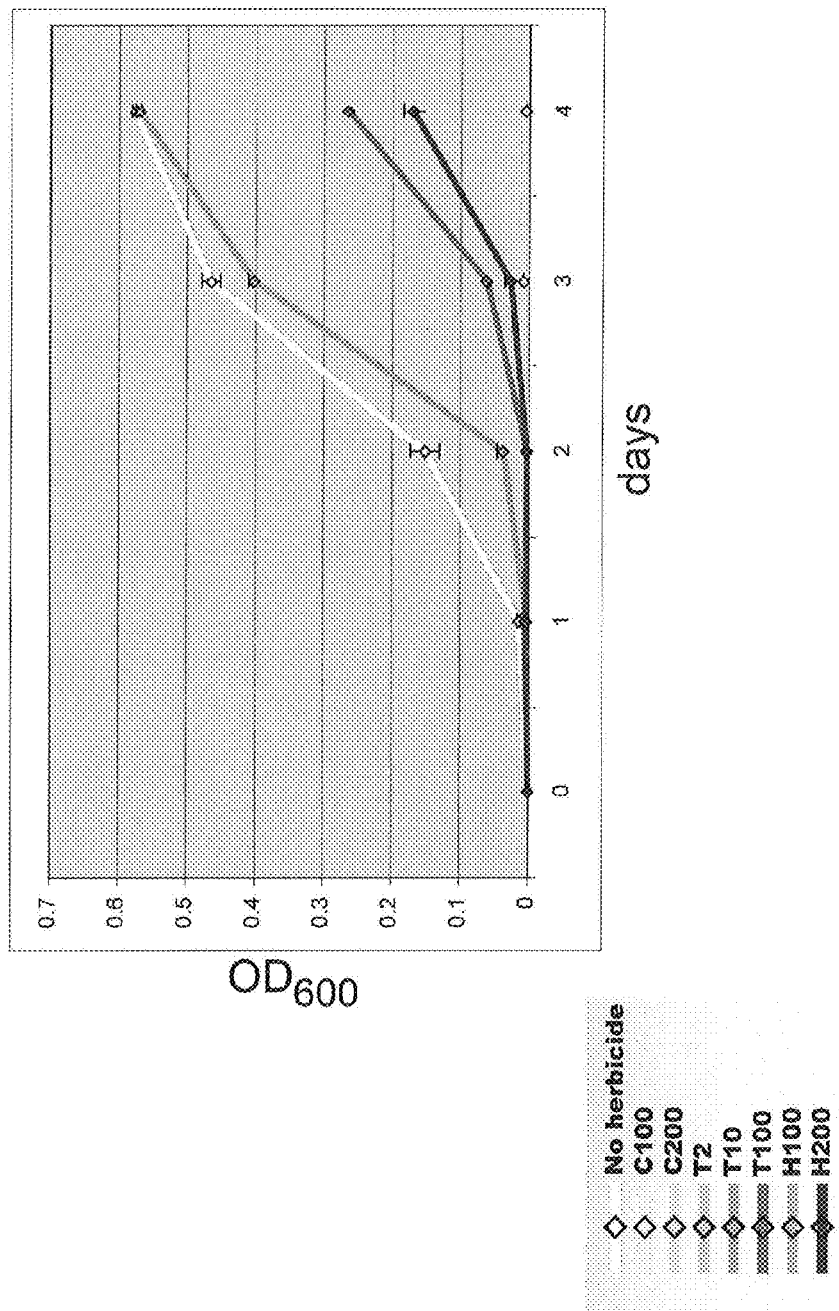
FIG. 63 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is µM concentration. The mutation in the HSR is as indicated.
Figure 64:
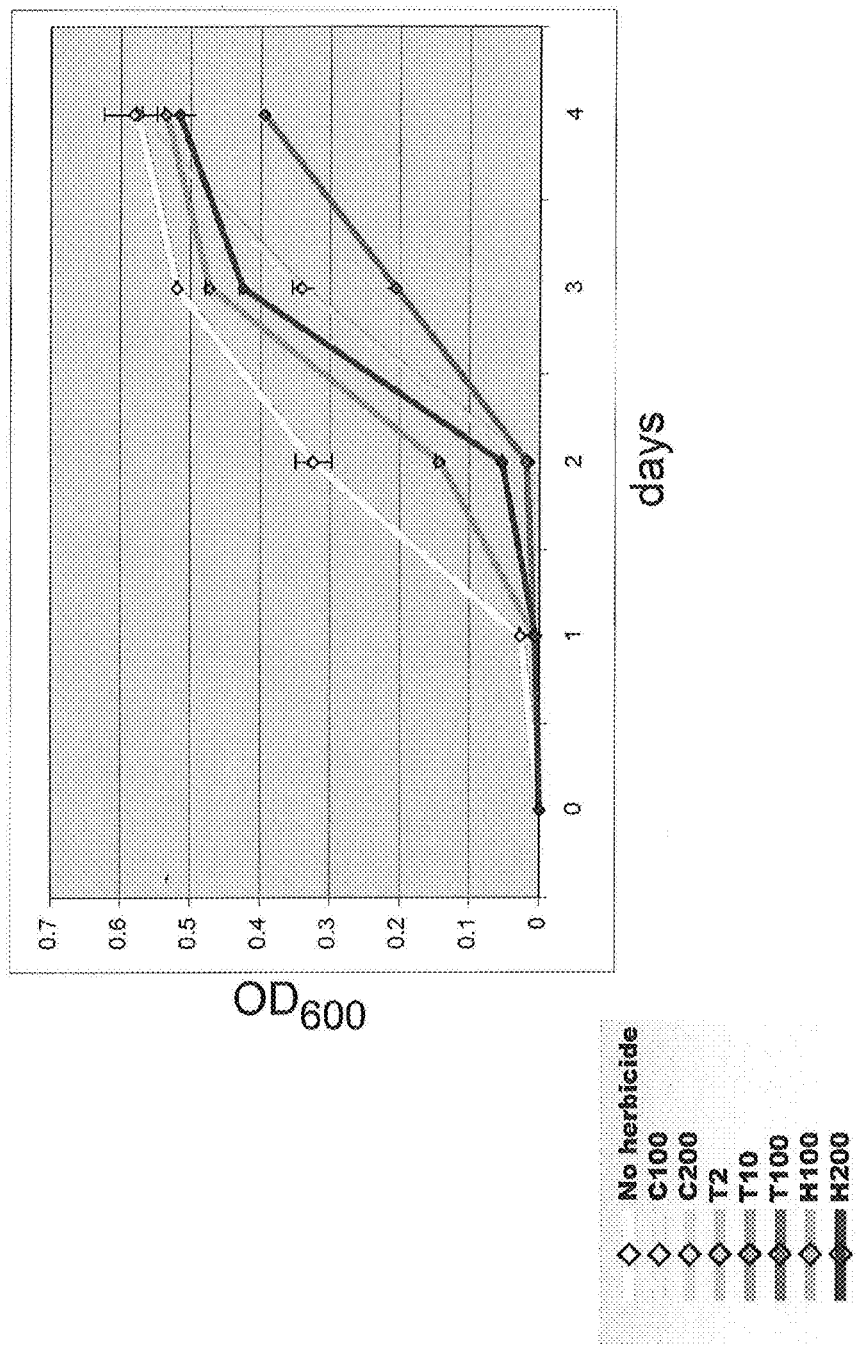
FIG. 64 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 65:
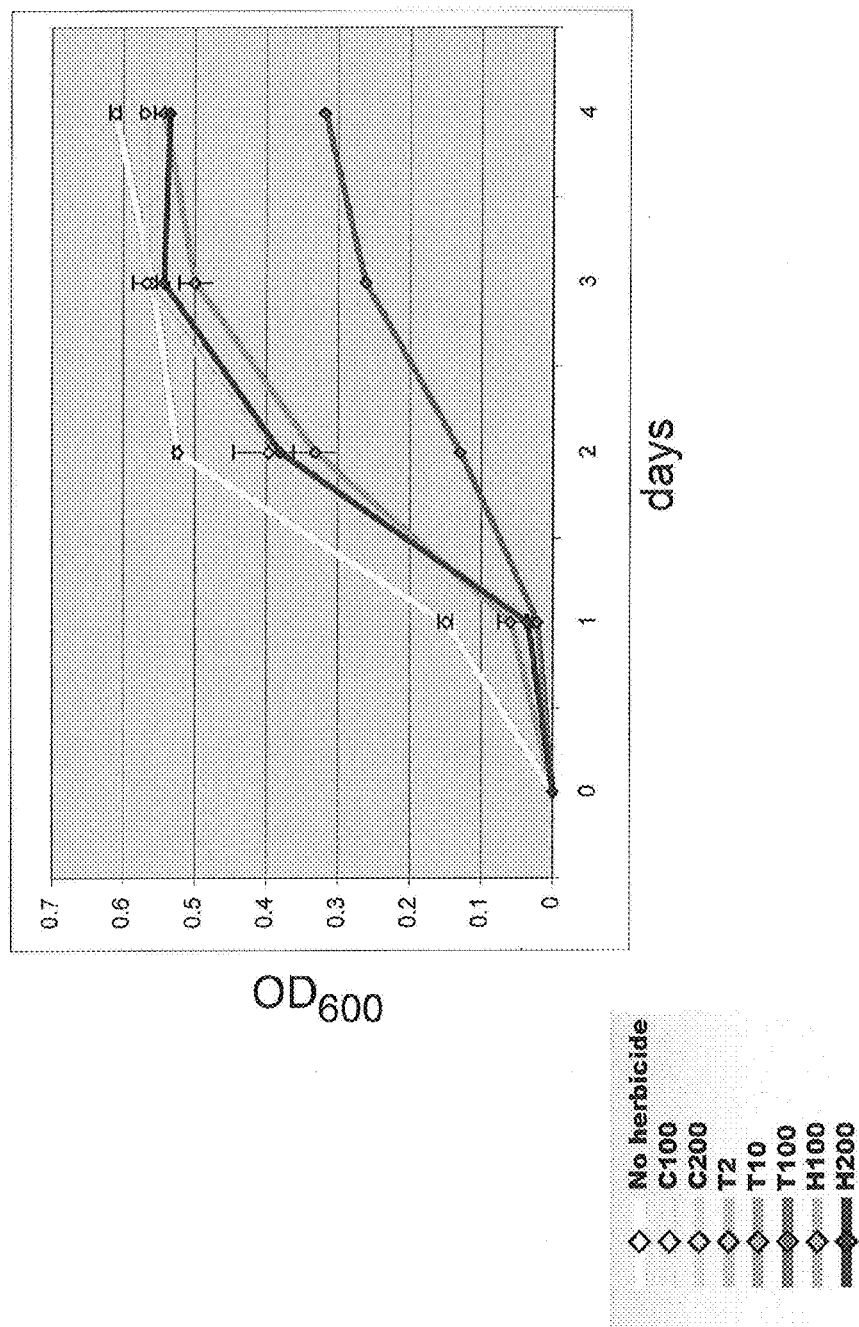
FIG. 65 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 66:
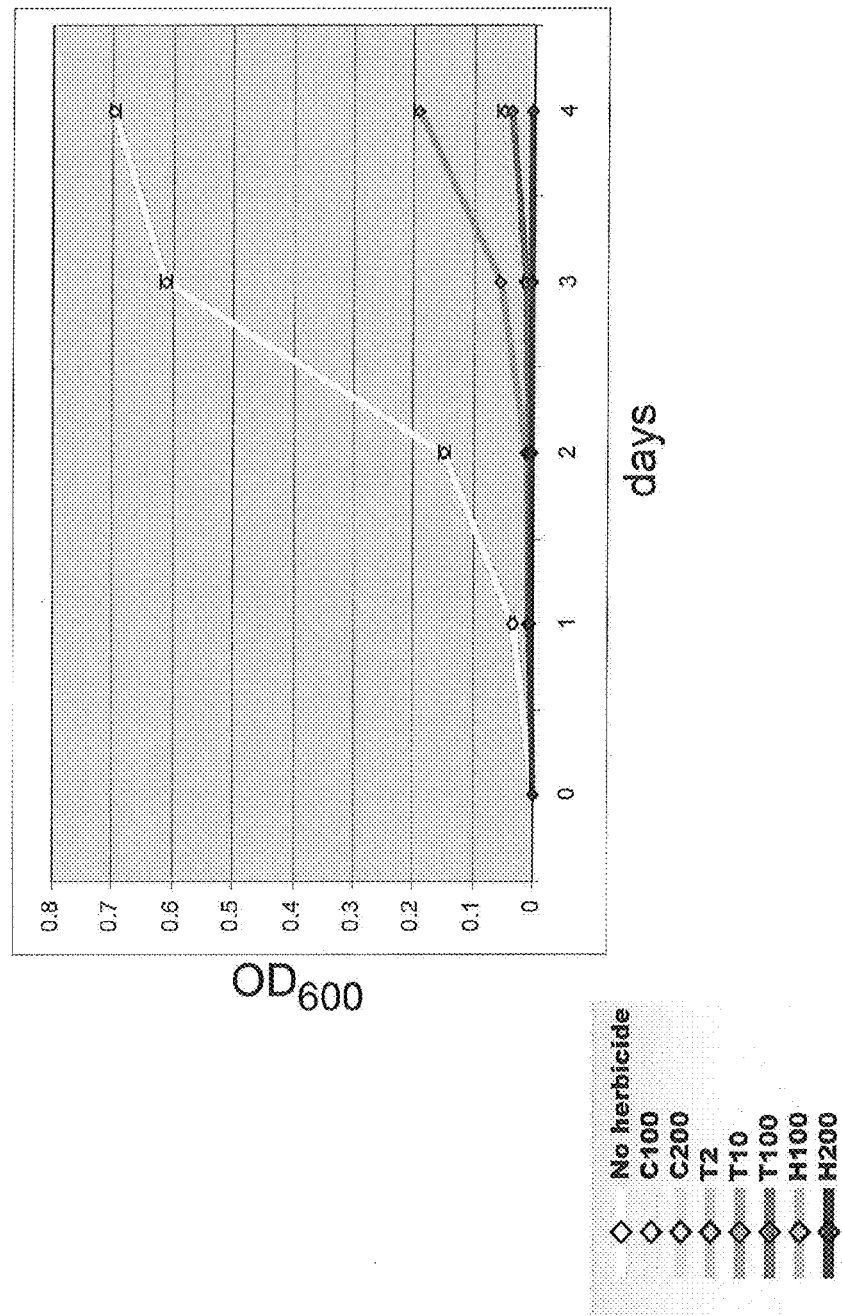
FIG. 66 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 67:
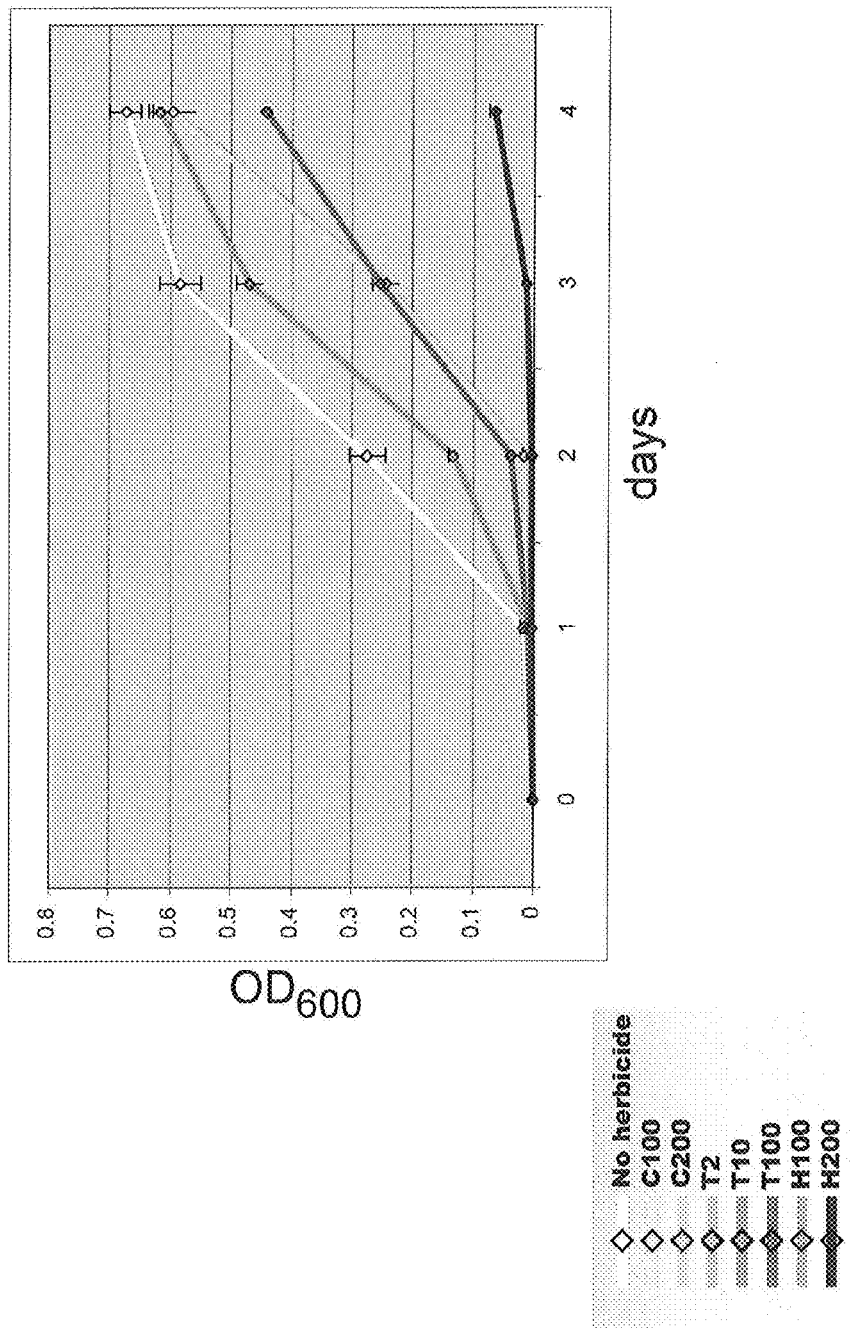
FIG. 67 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 68:
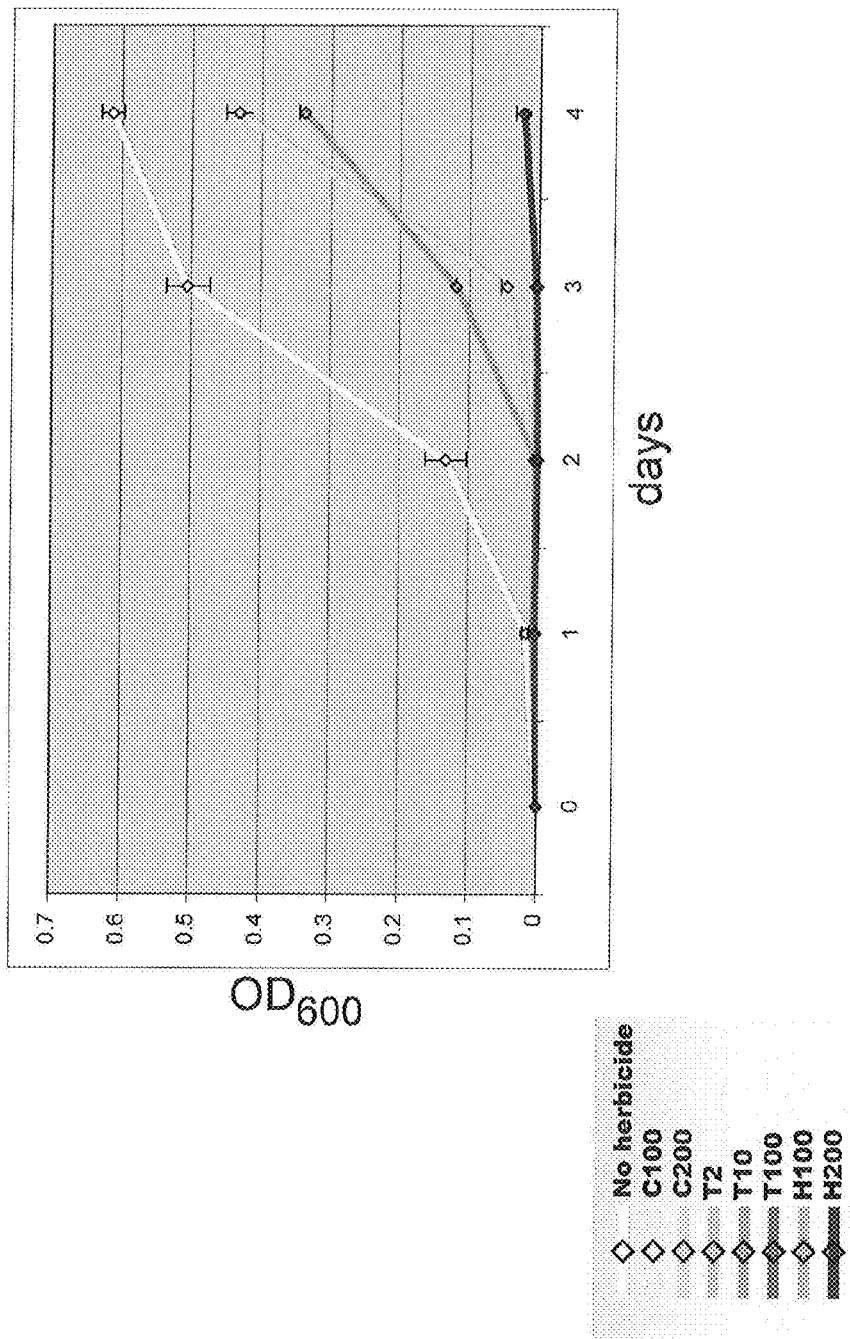
FIG. 68 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 69:
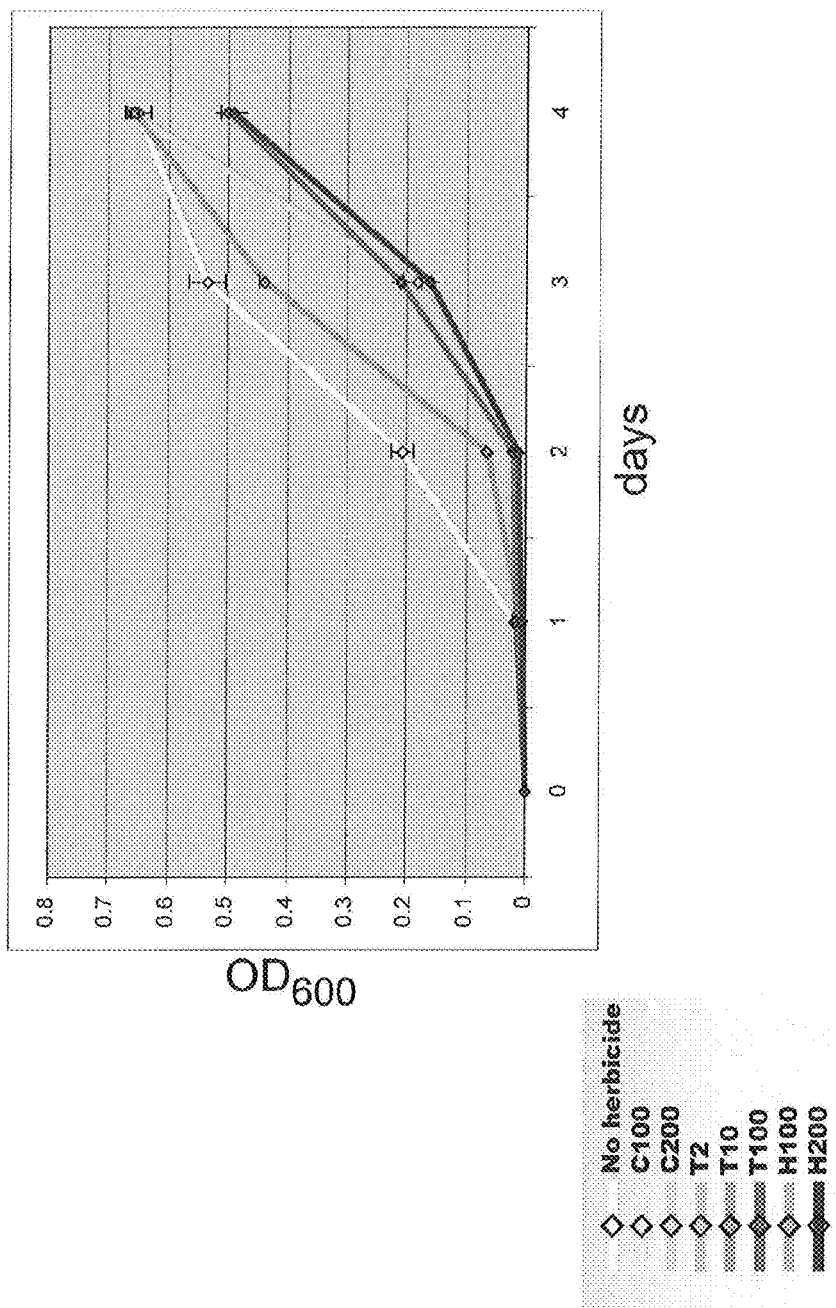
FIG. 69 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 70:
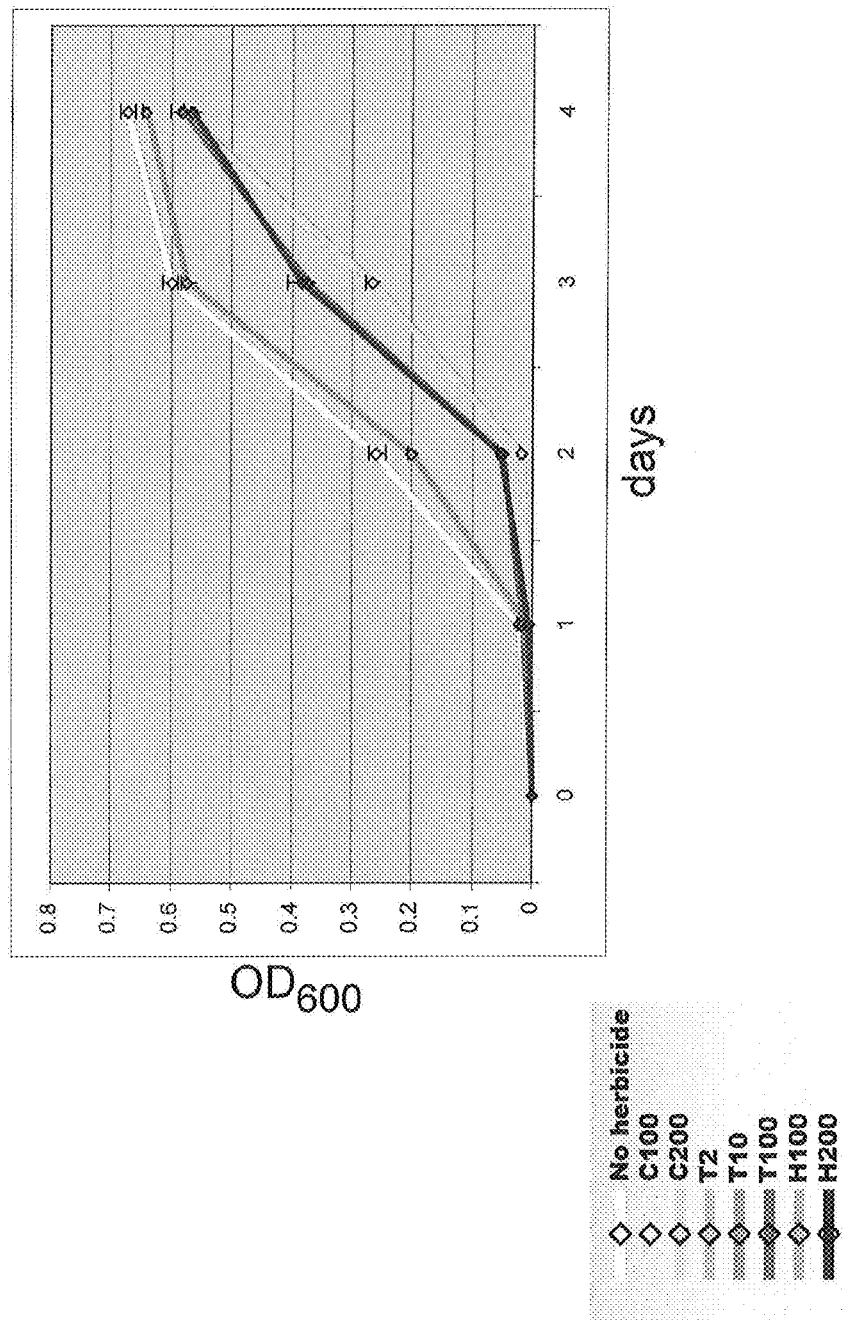
FIG. 70 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 71:
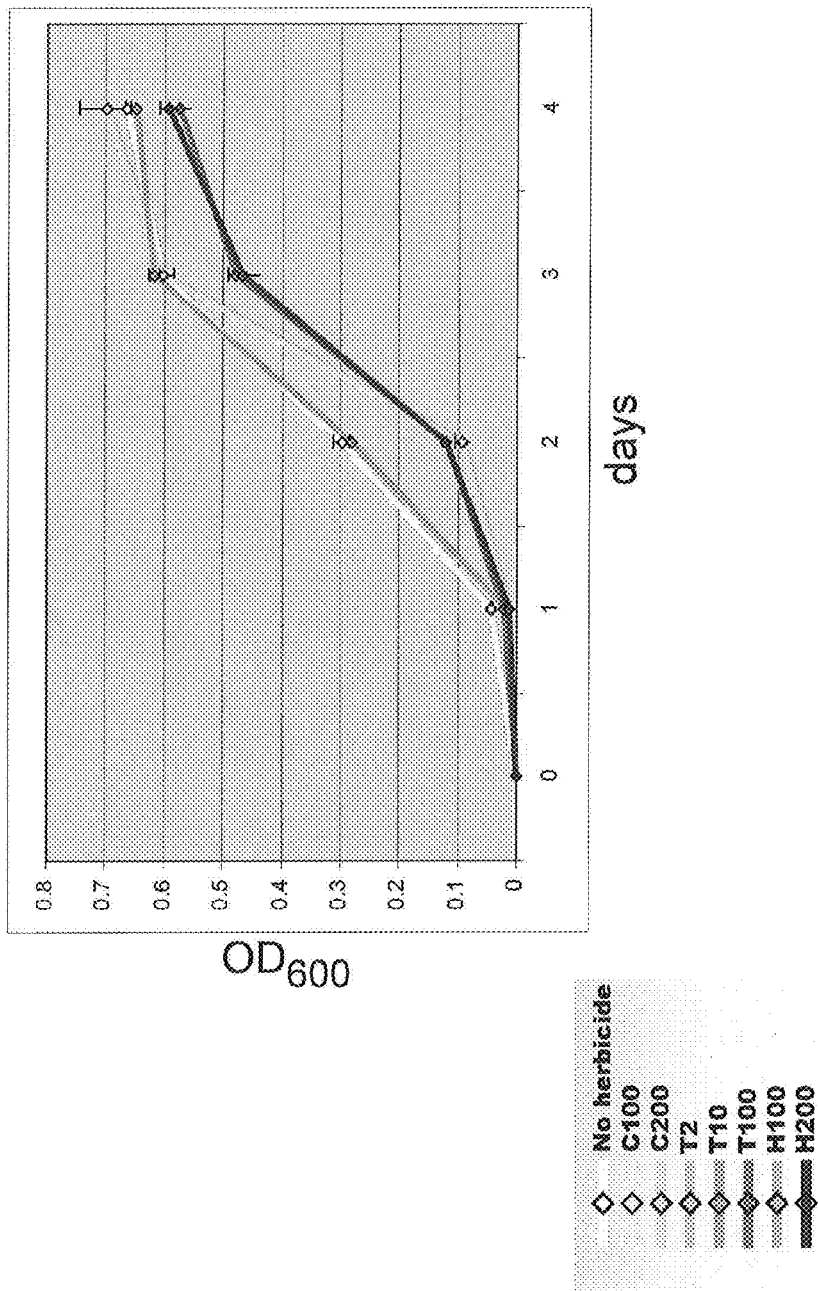
FIG. 71 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 72:
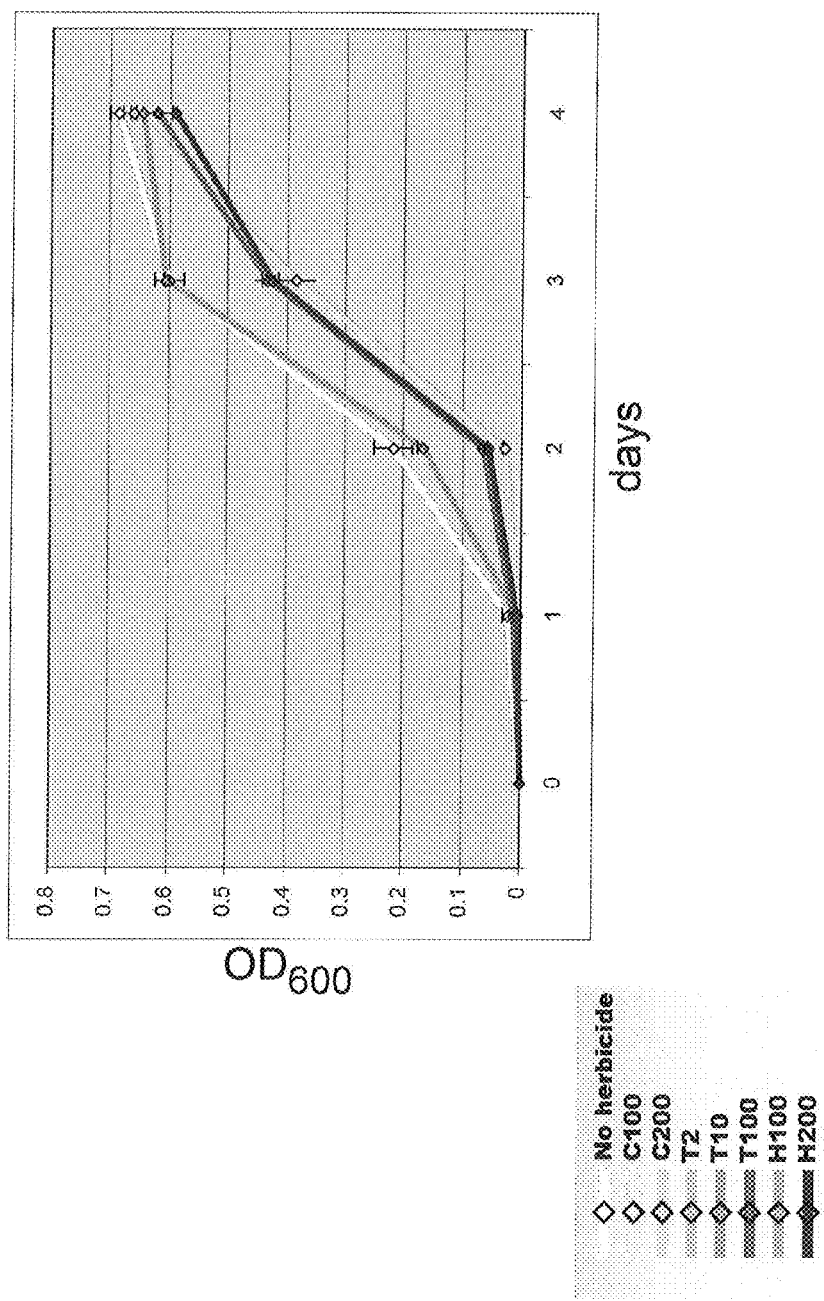
FIG. 72 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 73:
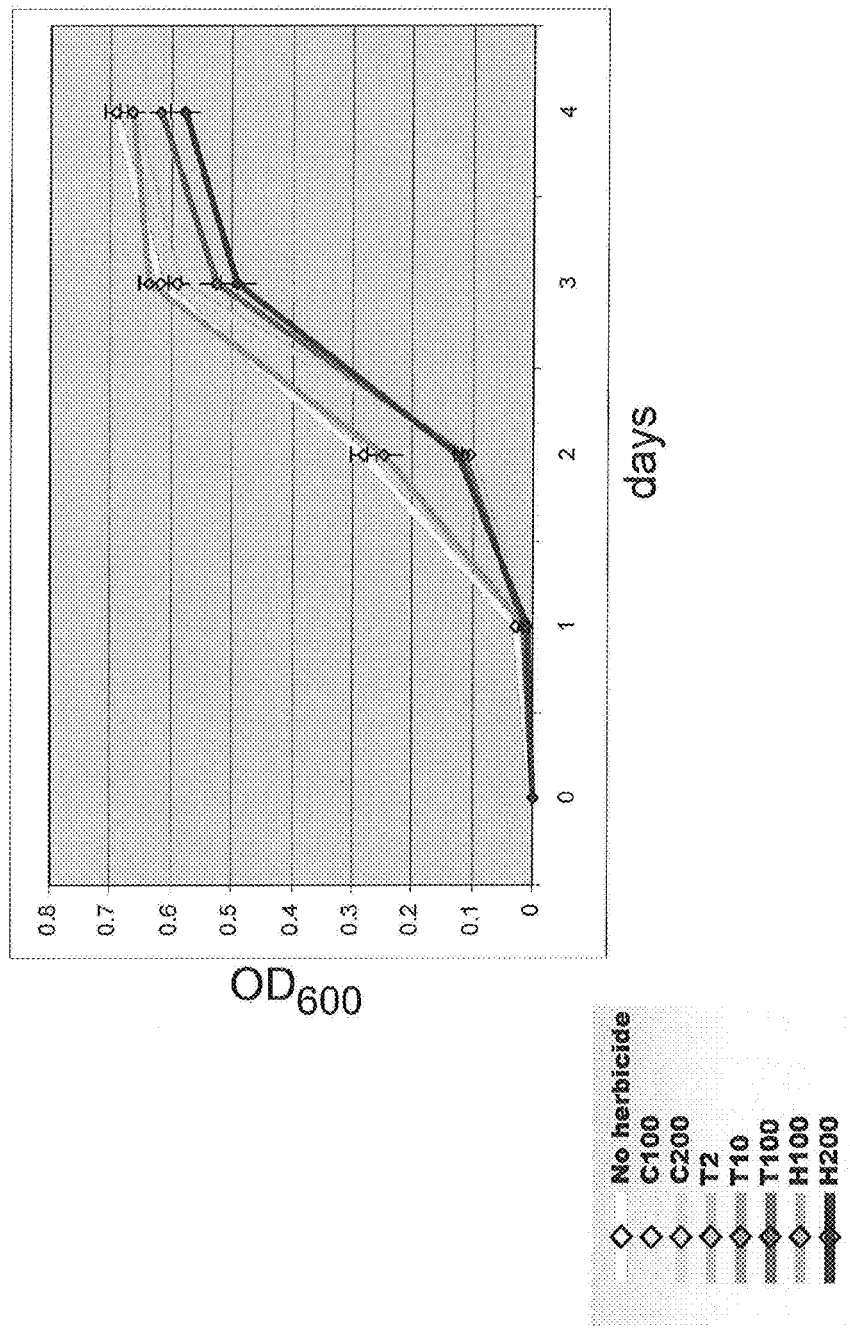
FIG. 73 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 74:
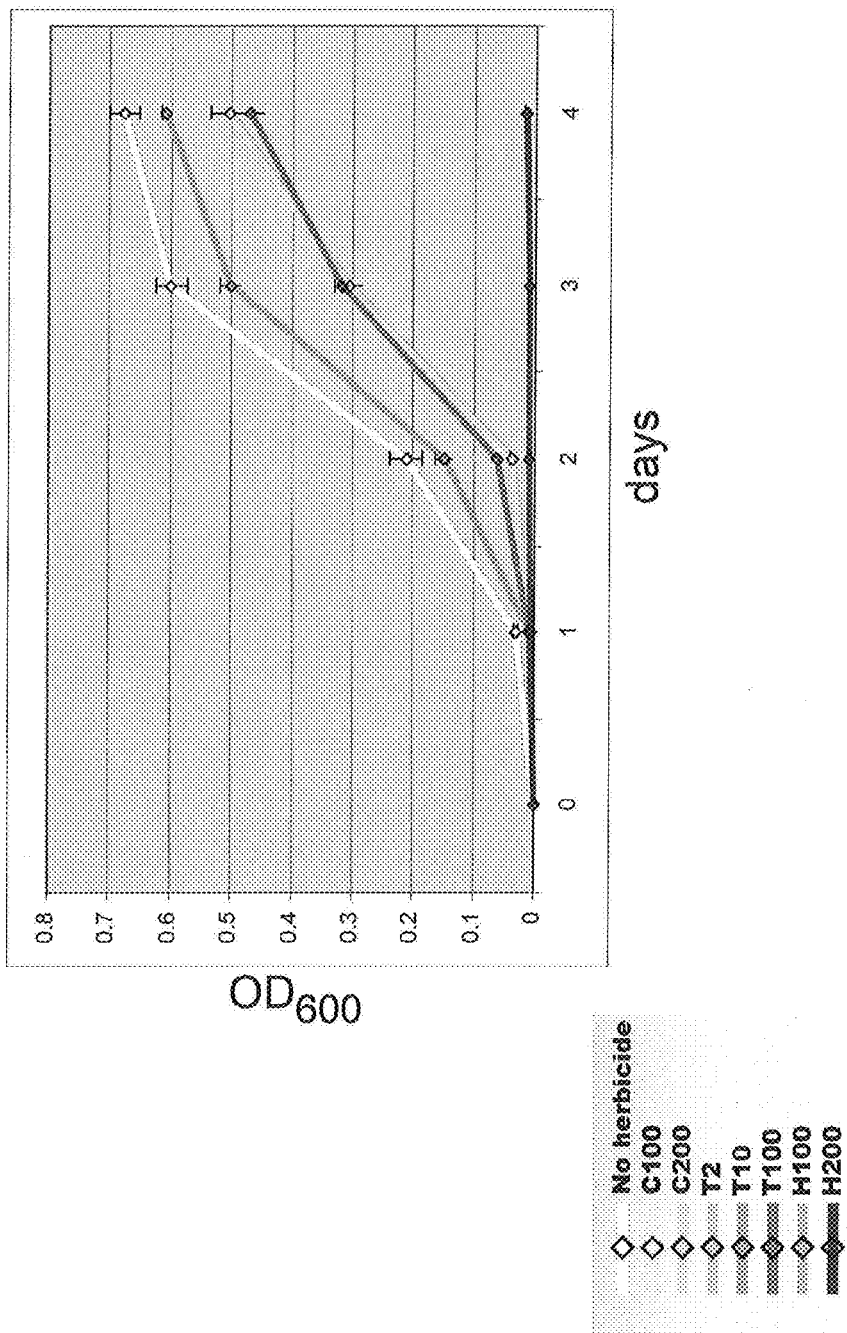
FIG. 74 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 75:
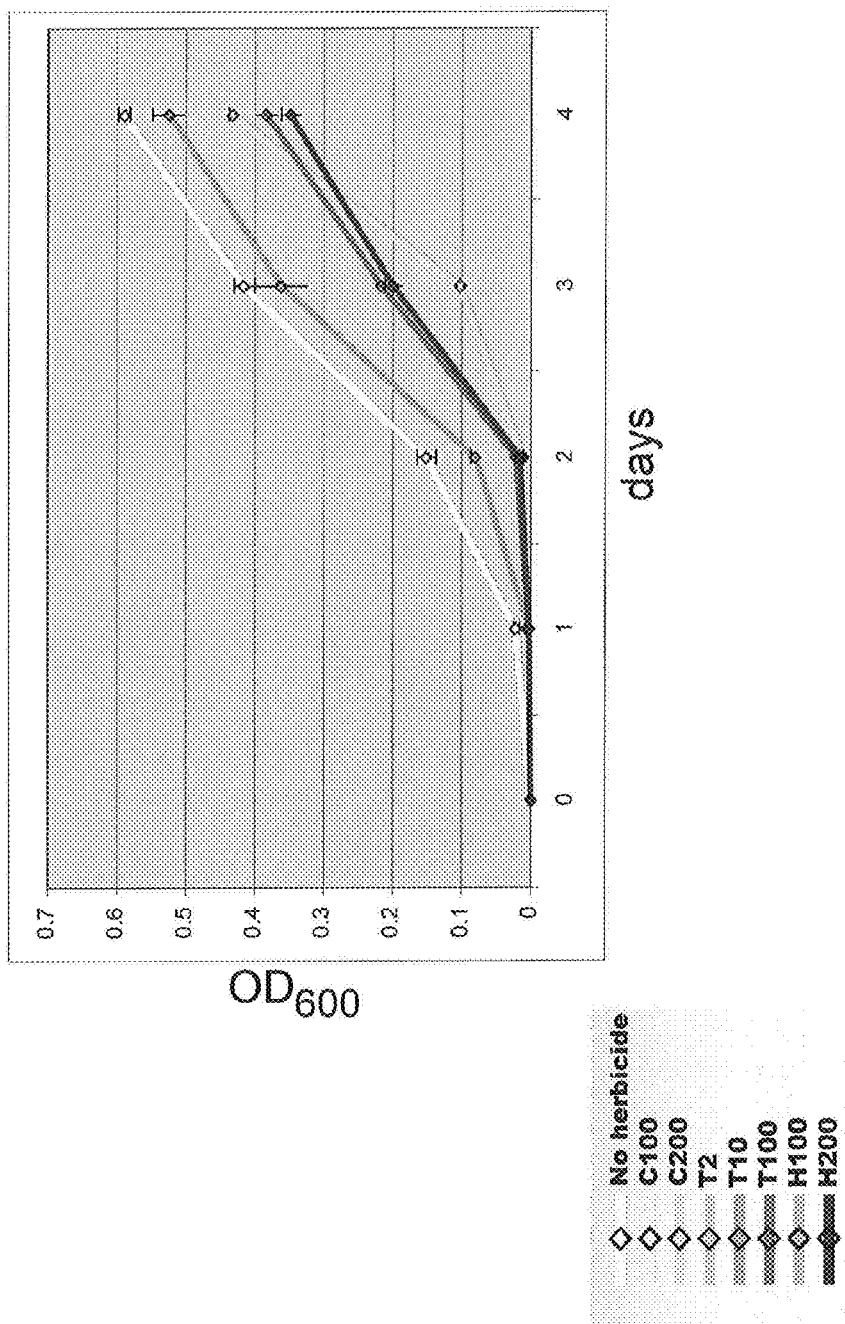
FIG. 75 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 76:
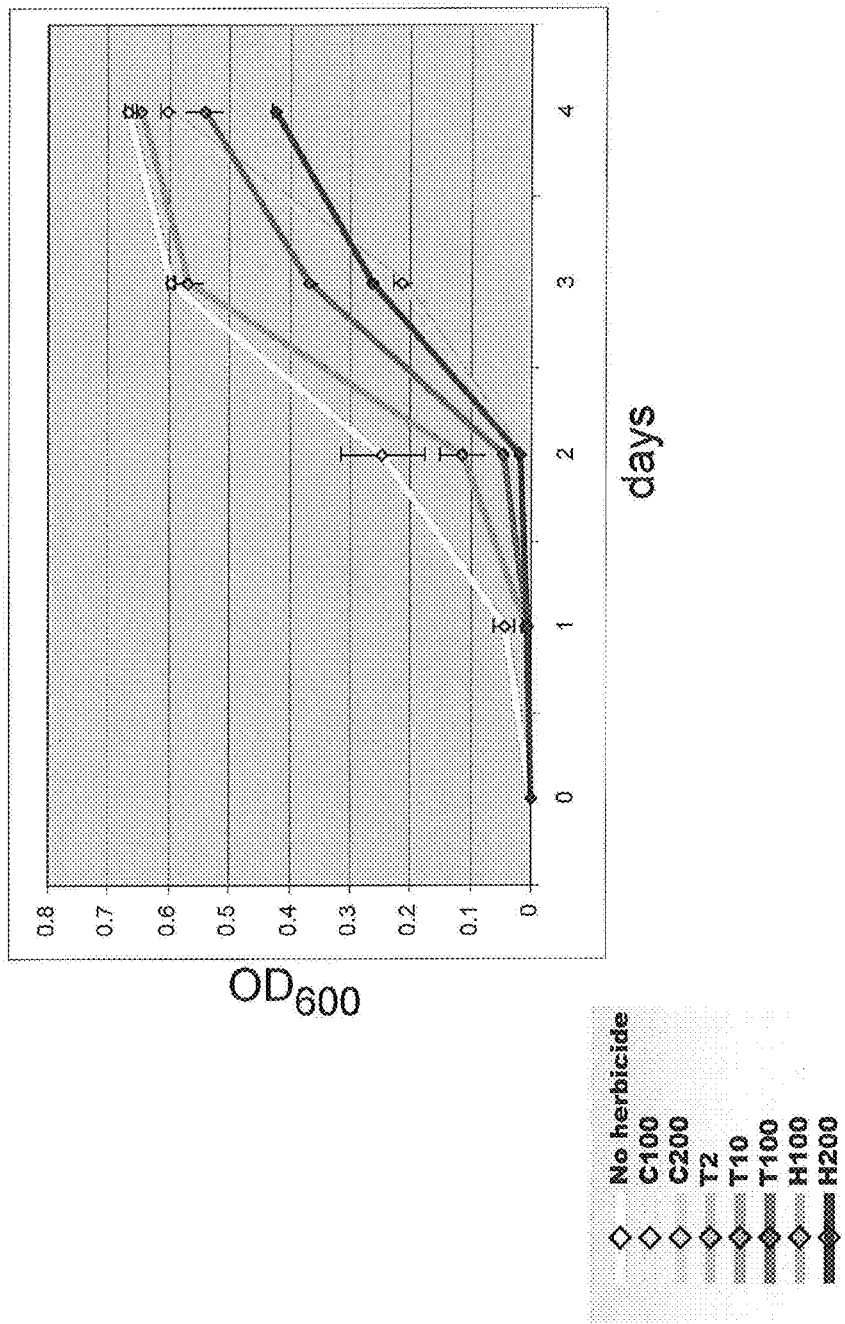
FIG. 76 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 77:
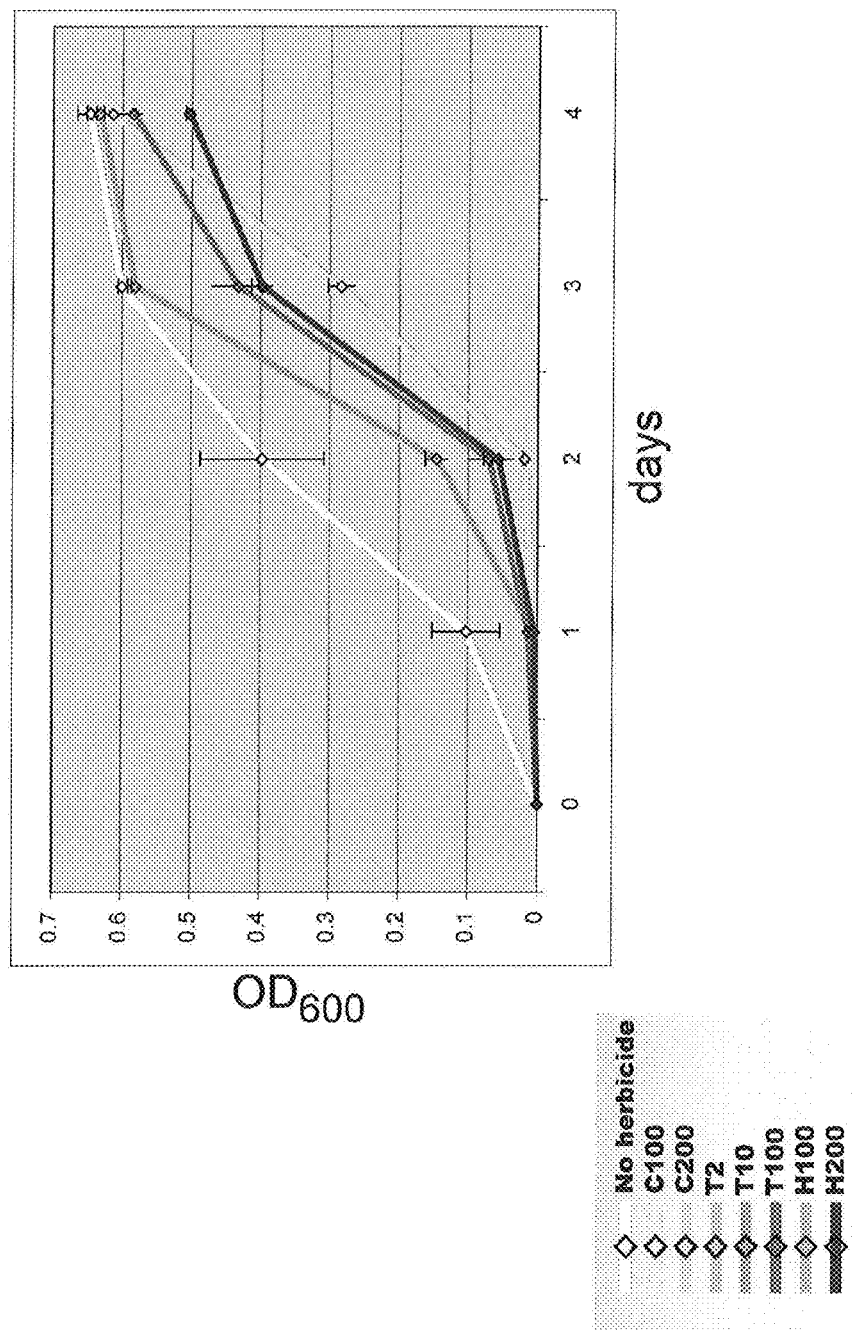
FIG. 77 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 78:
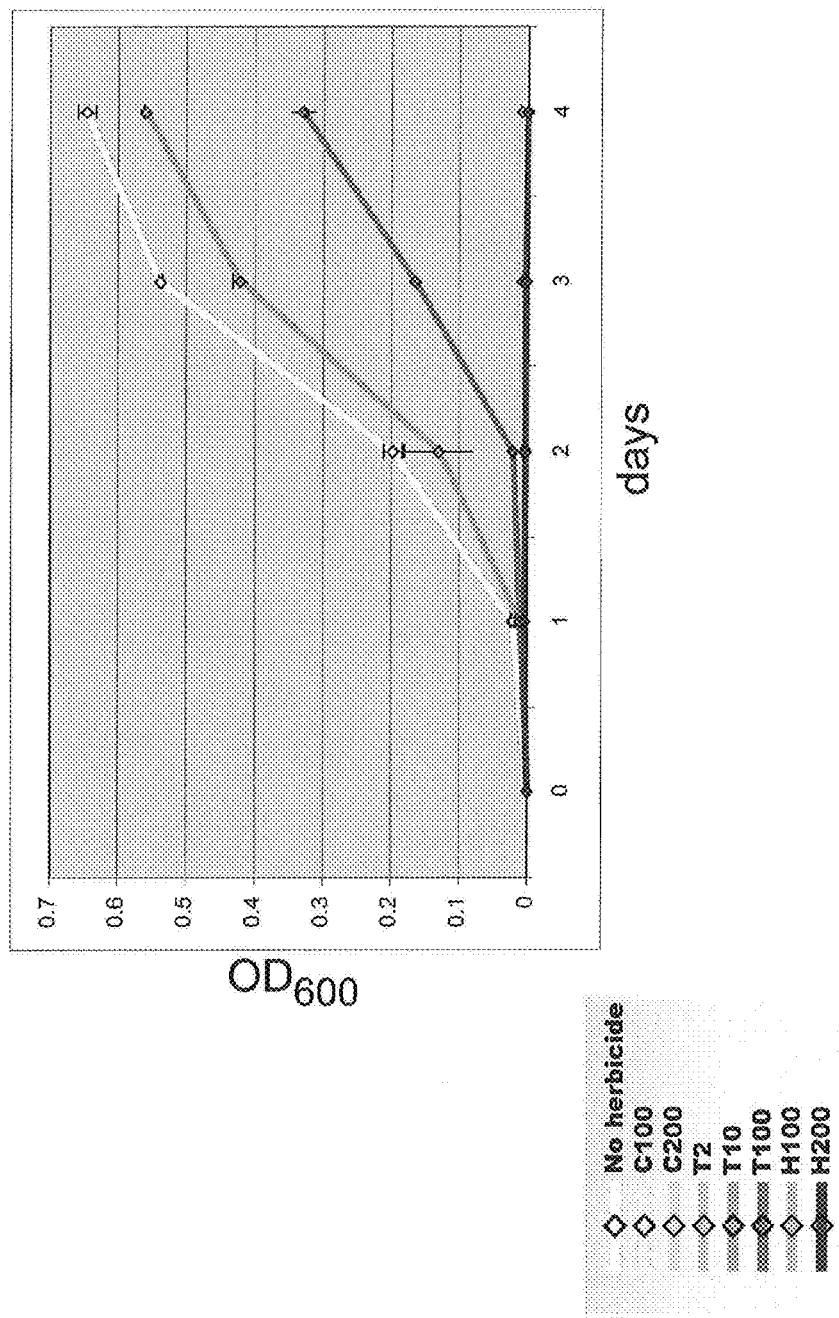
FIG. 78 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 79:
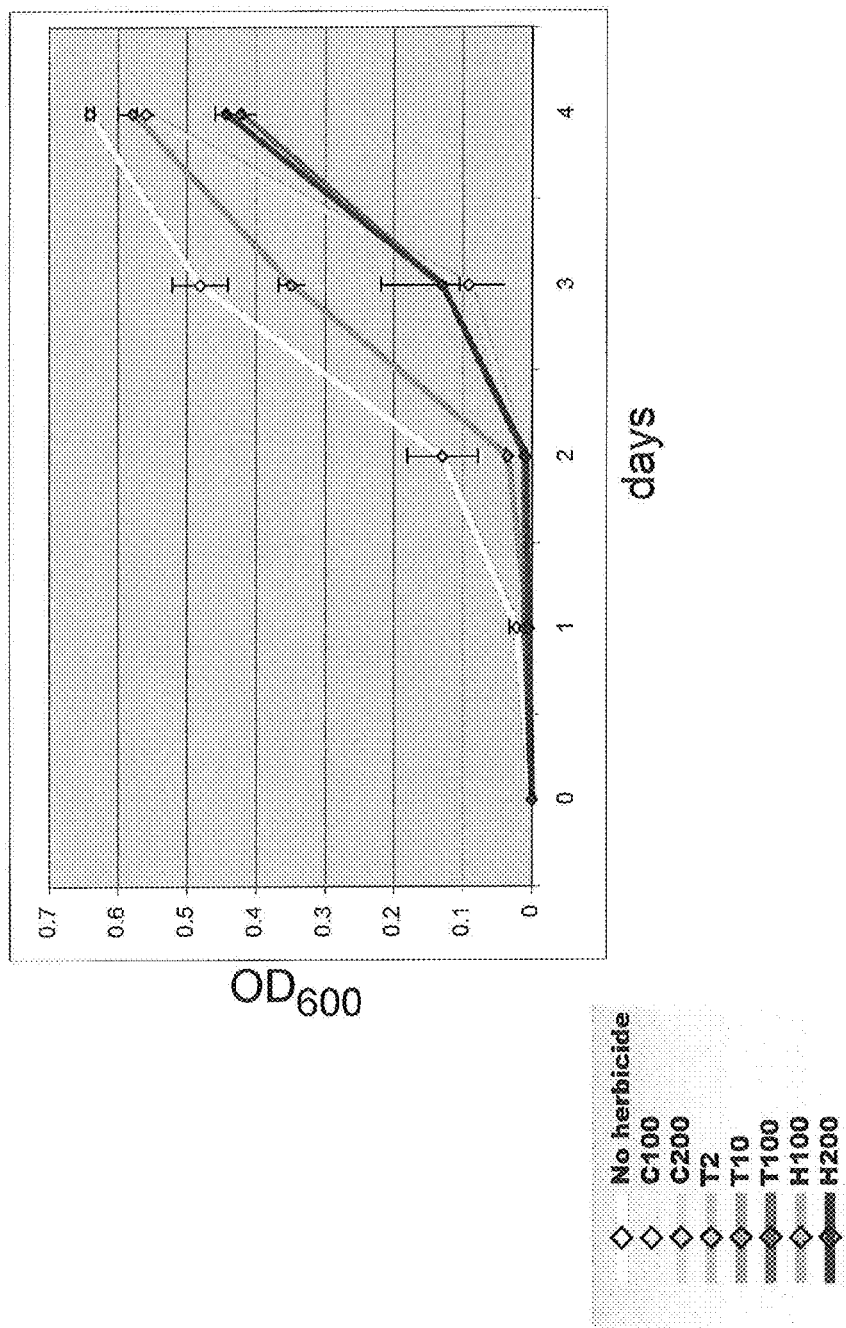
FIG. 79 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim. T=tepraloxydim, and H=haloxyfop. The number is μM concentration. The mutation in the HSR is as indicated.
Figure 80:
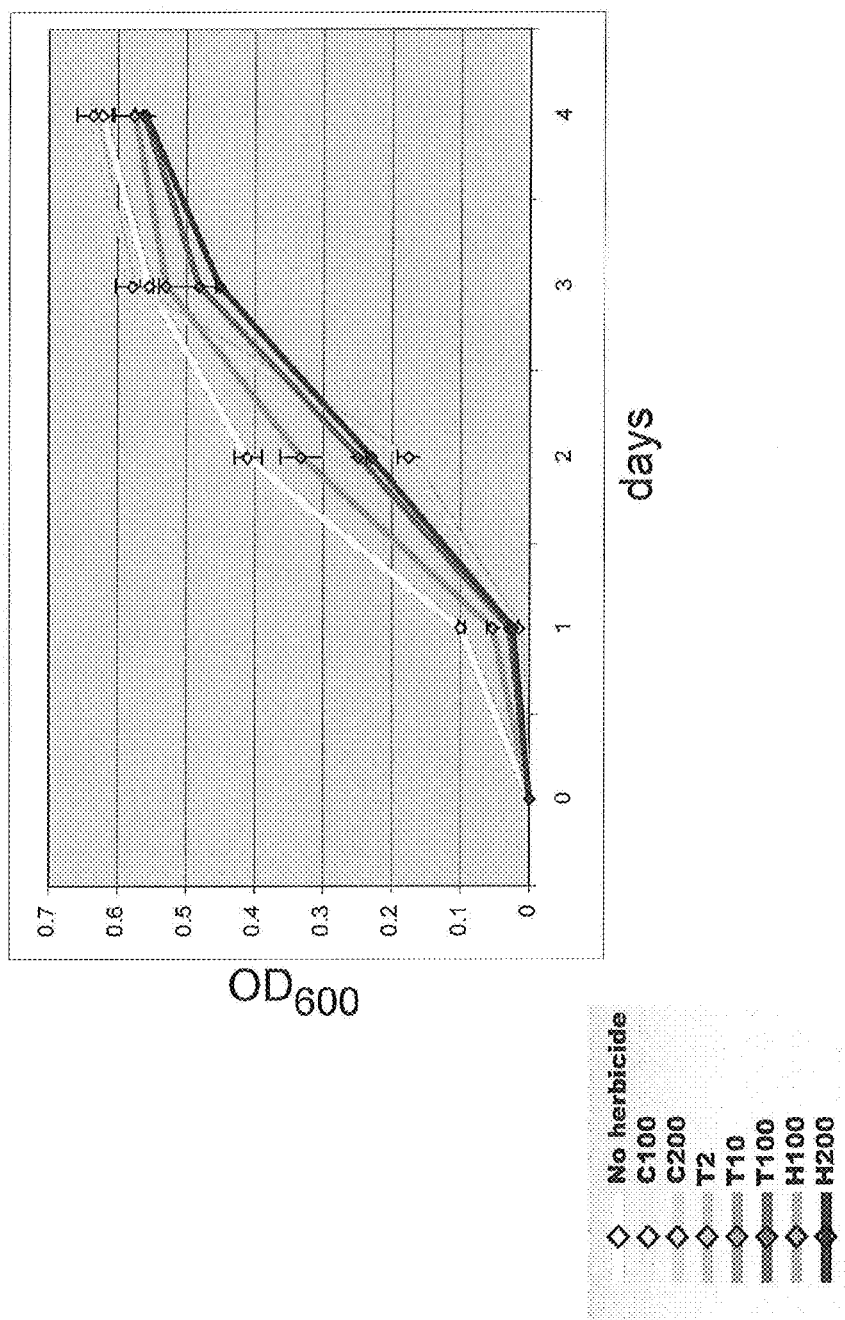
FIG. 80 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 81:
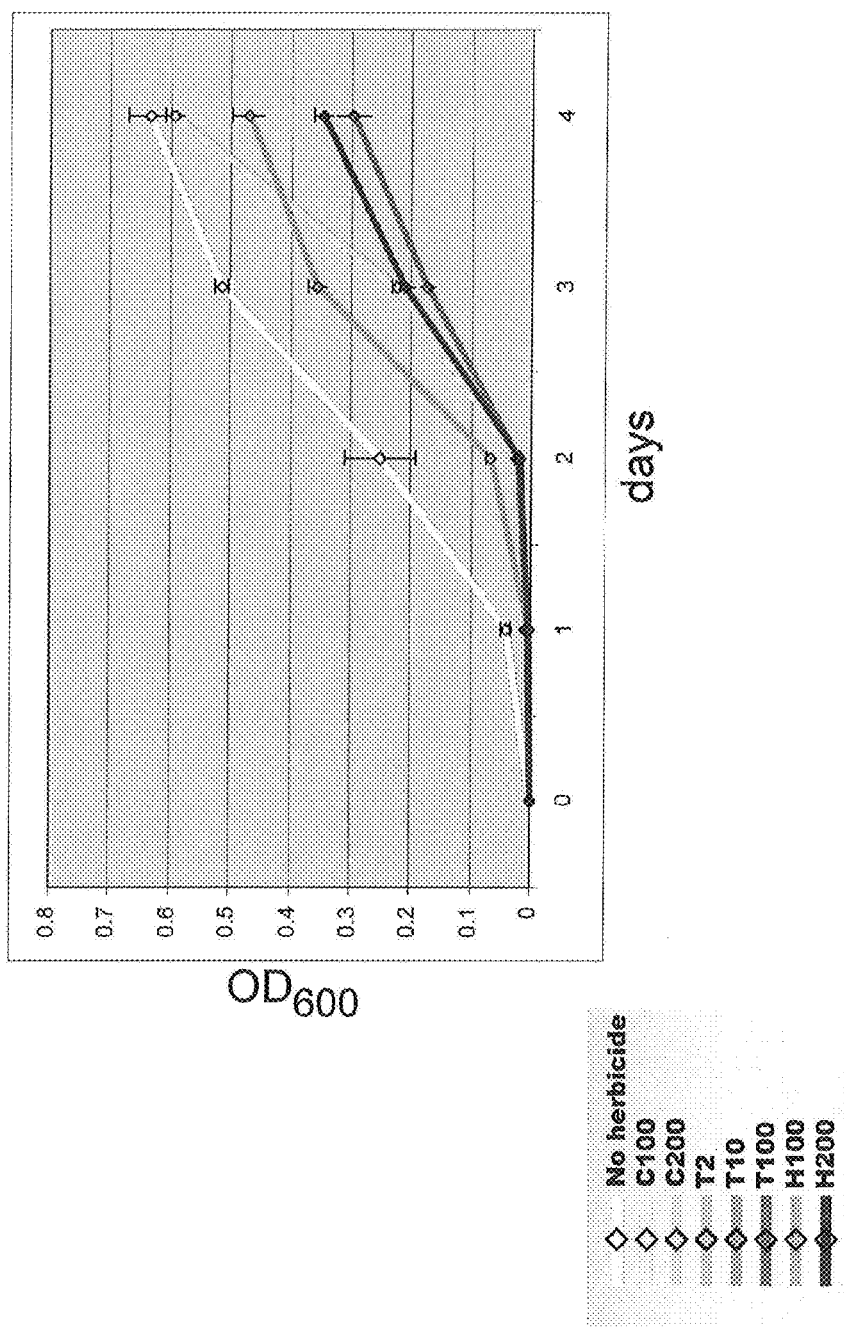
FIG. 81 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 82:
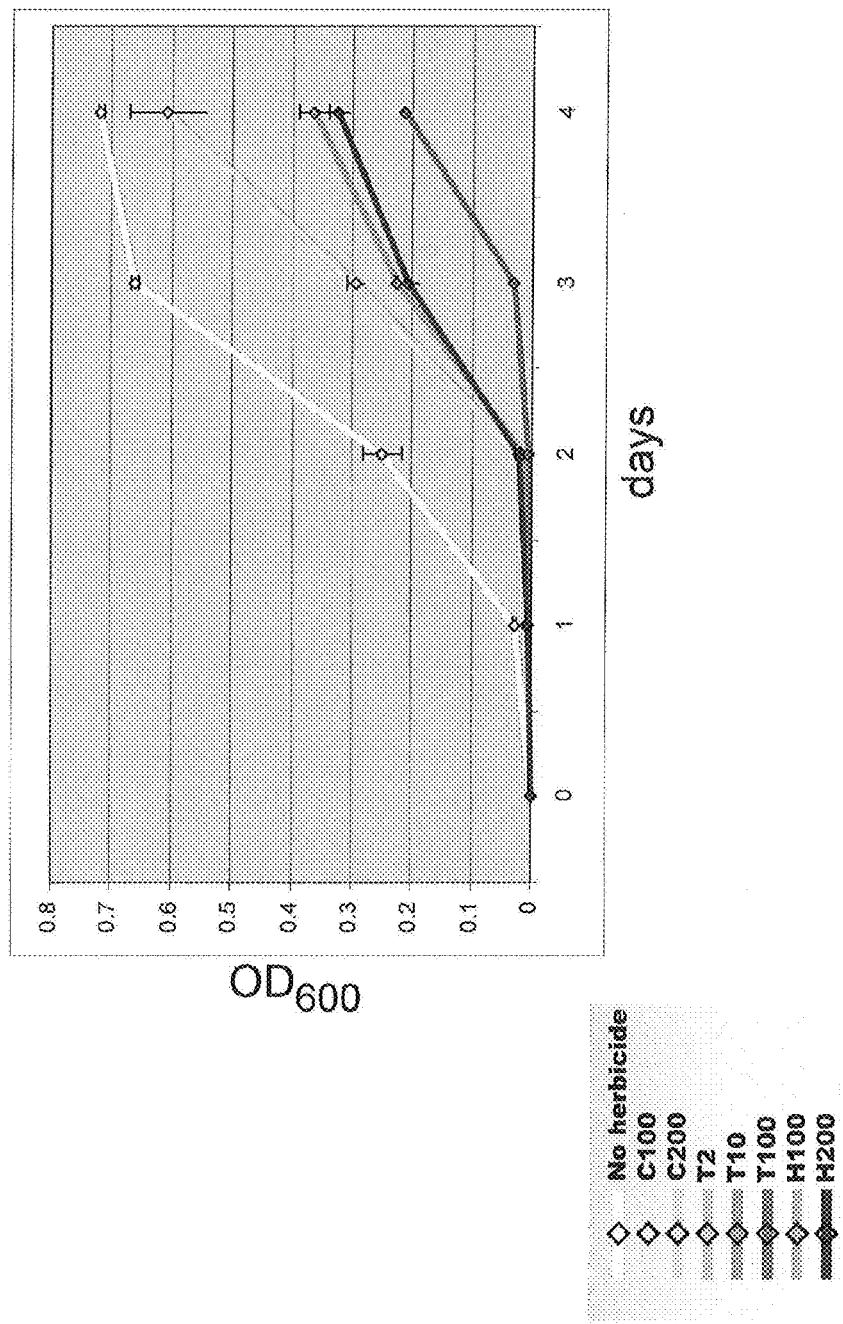
FIG. 82 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 83:
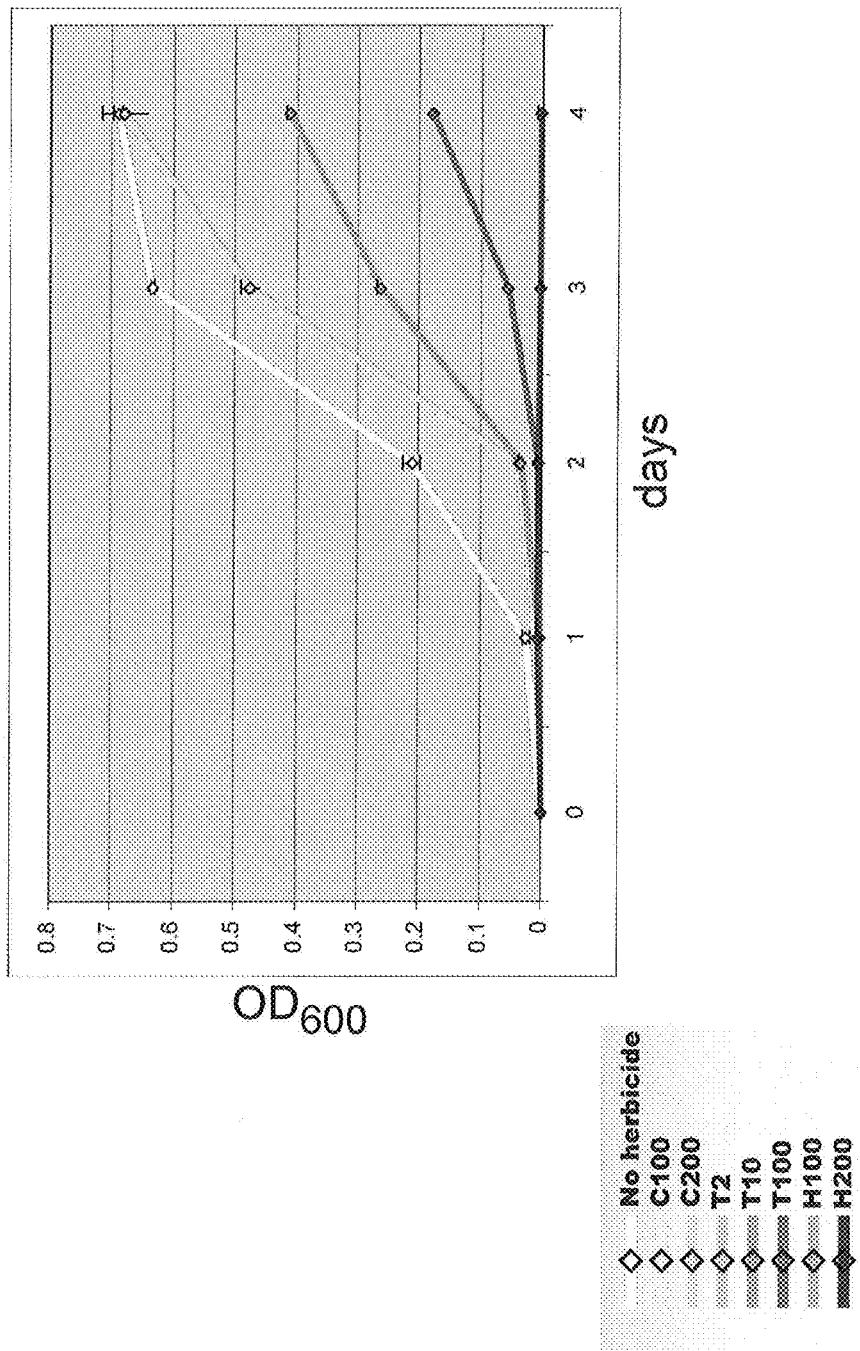
FIG. 83 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 84:
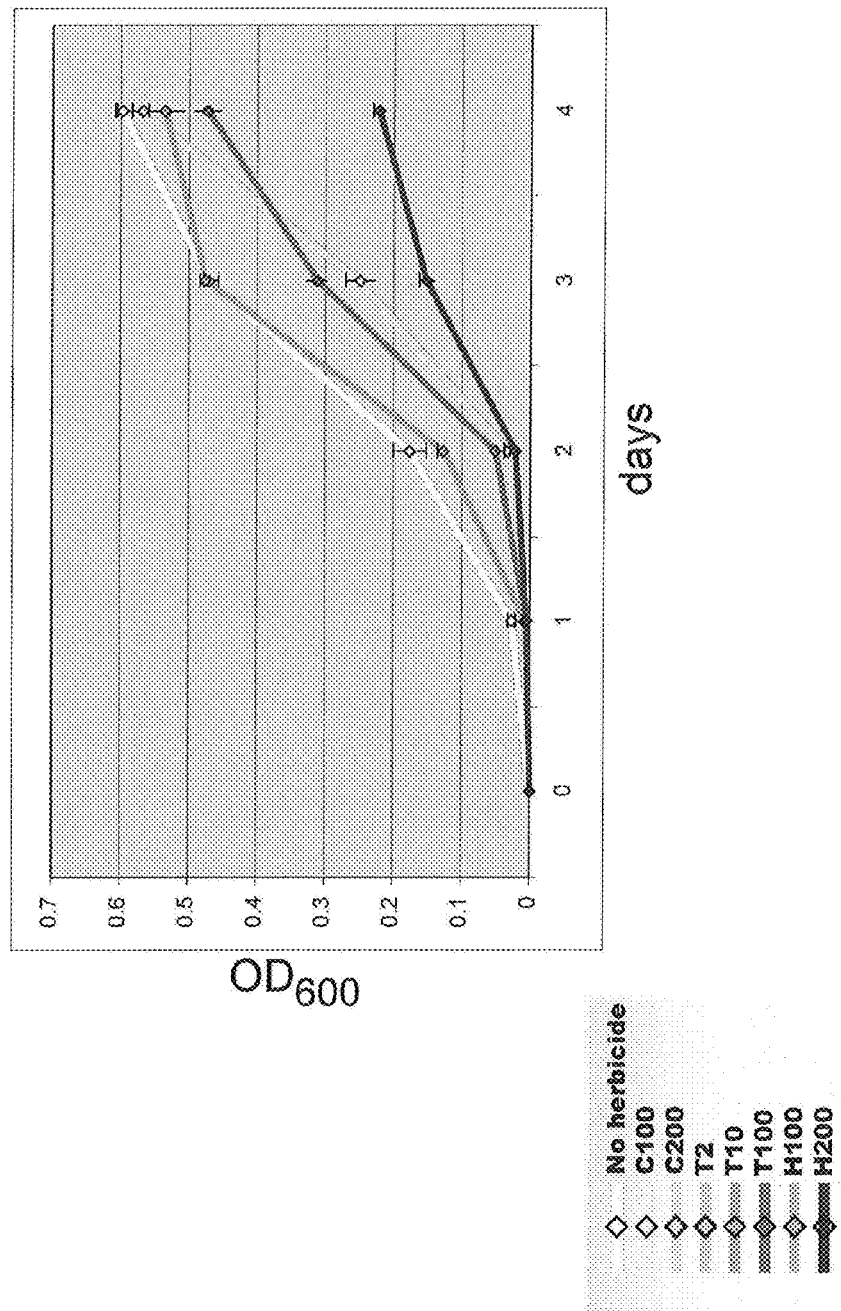
FIG. 84 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 85:
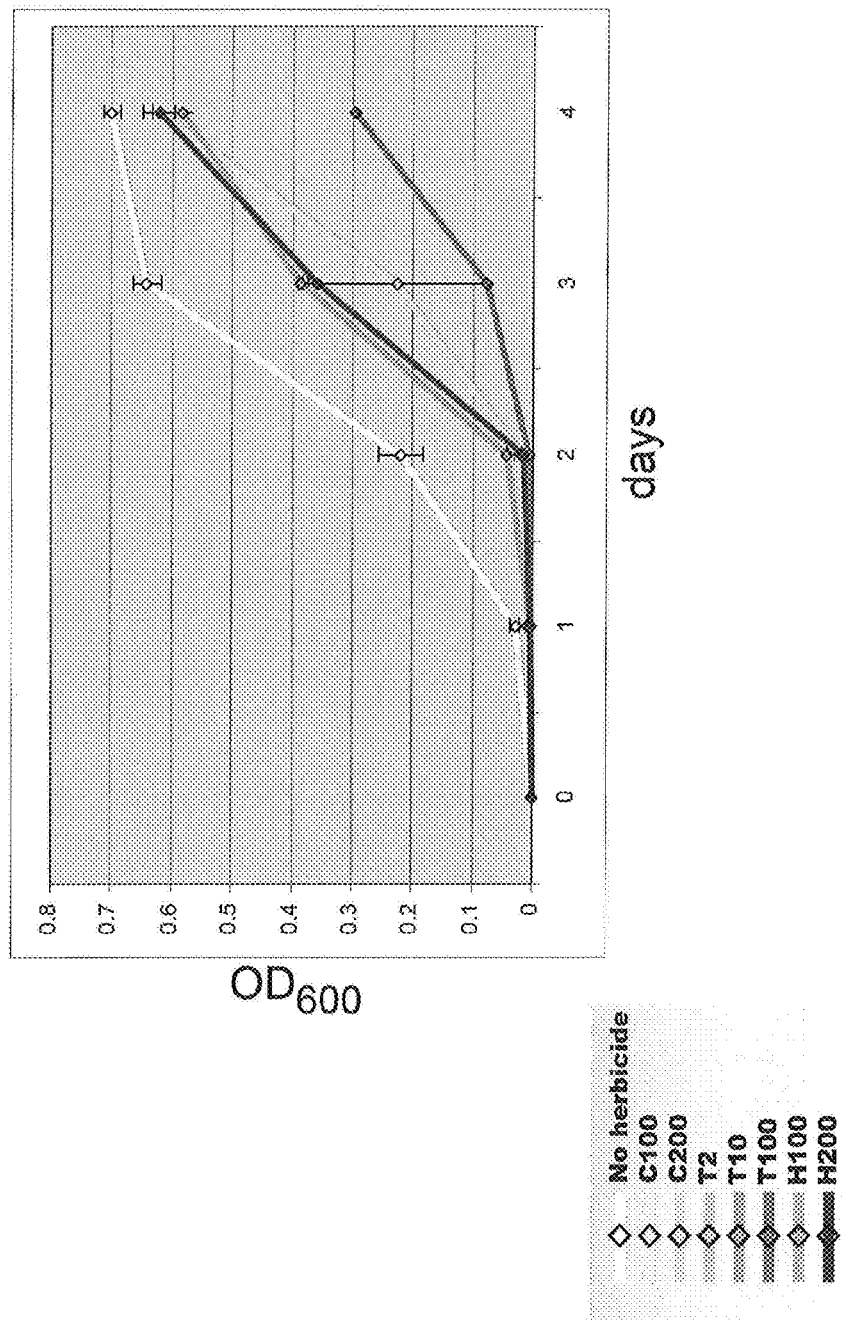
FIG. 85 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 86:
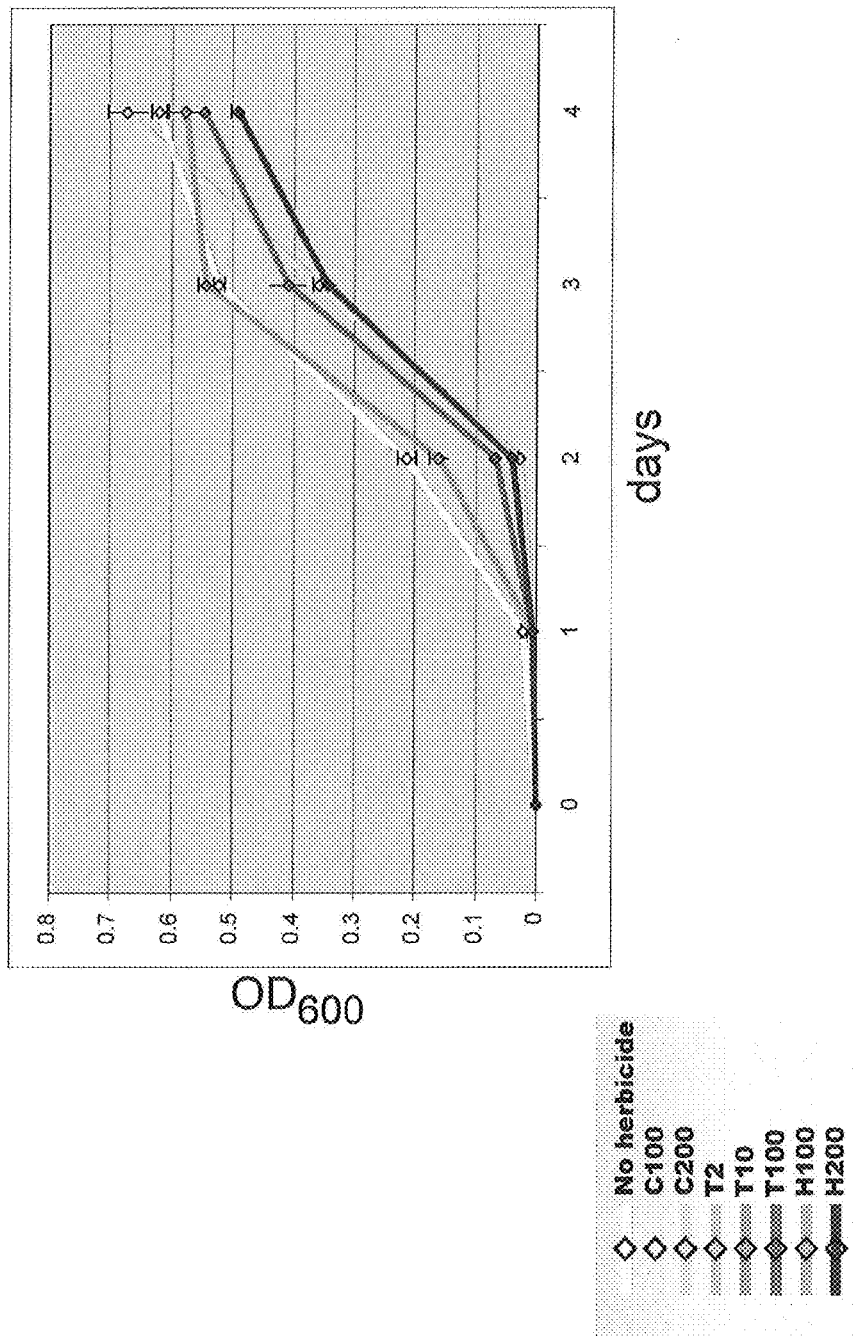
FIG. 86 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 87:
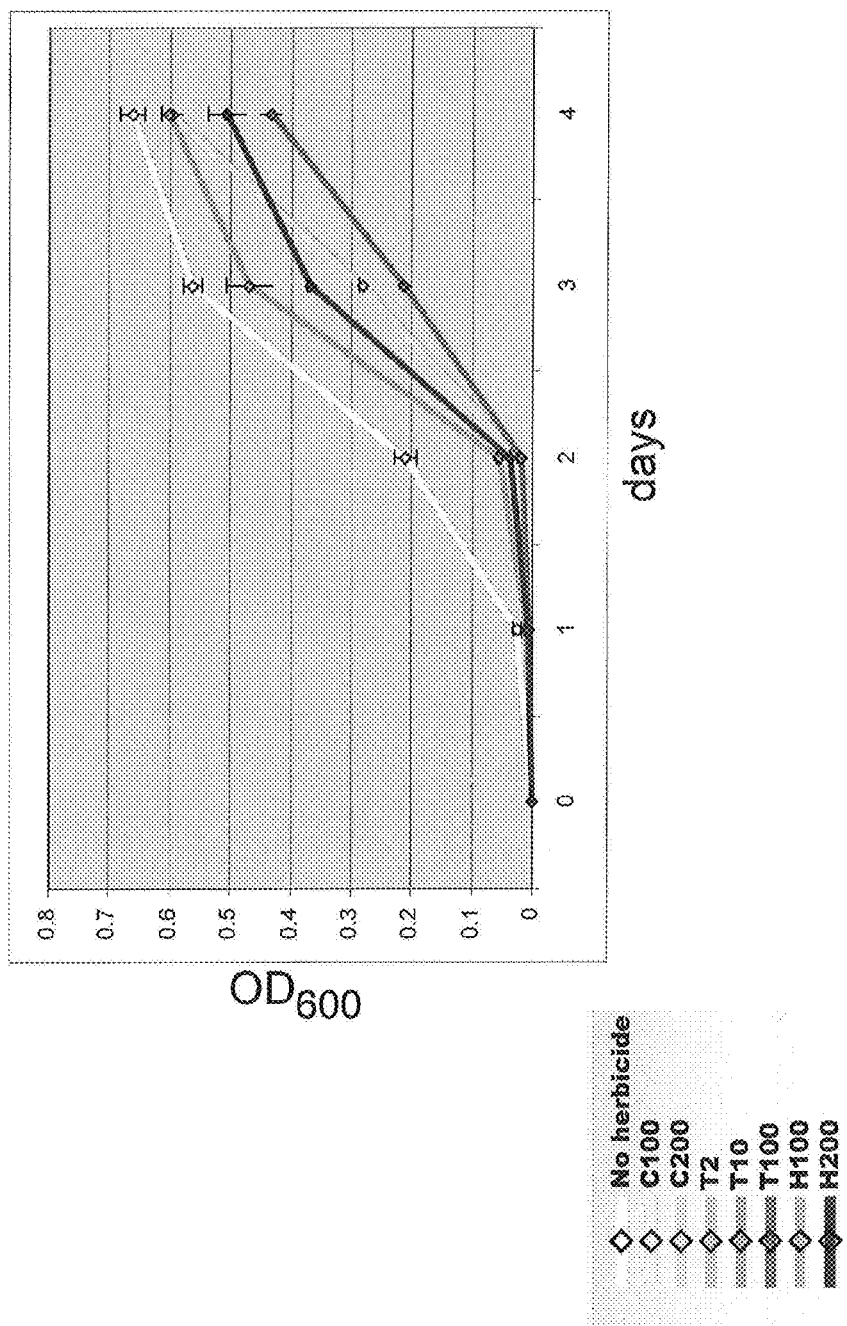
FIG. 87 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 88:
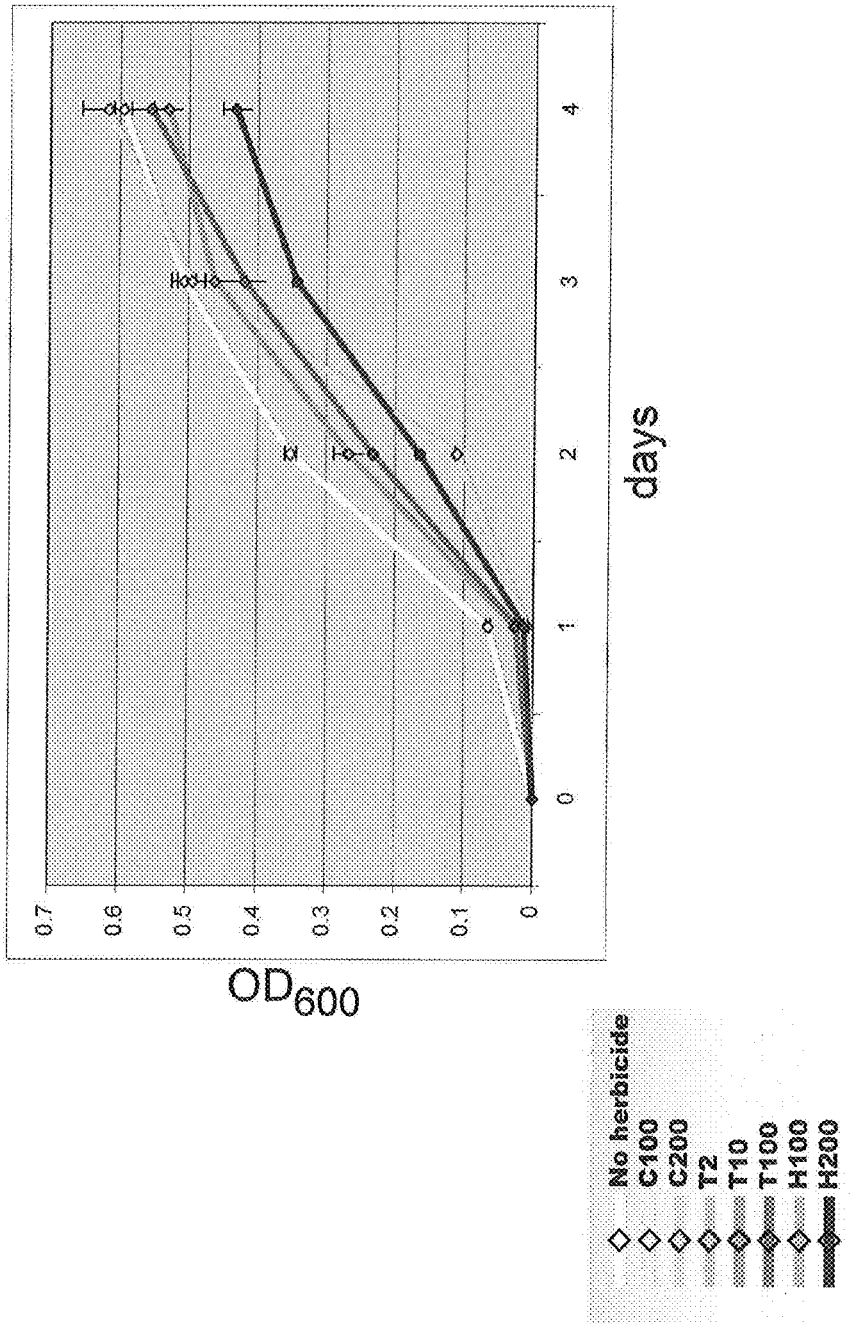
FIG. 88 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 89:
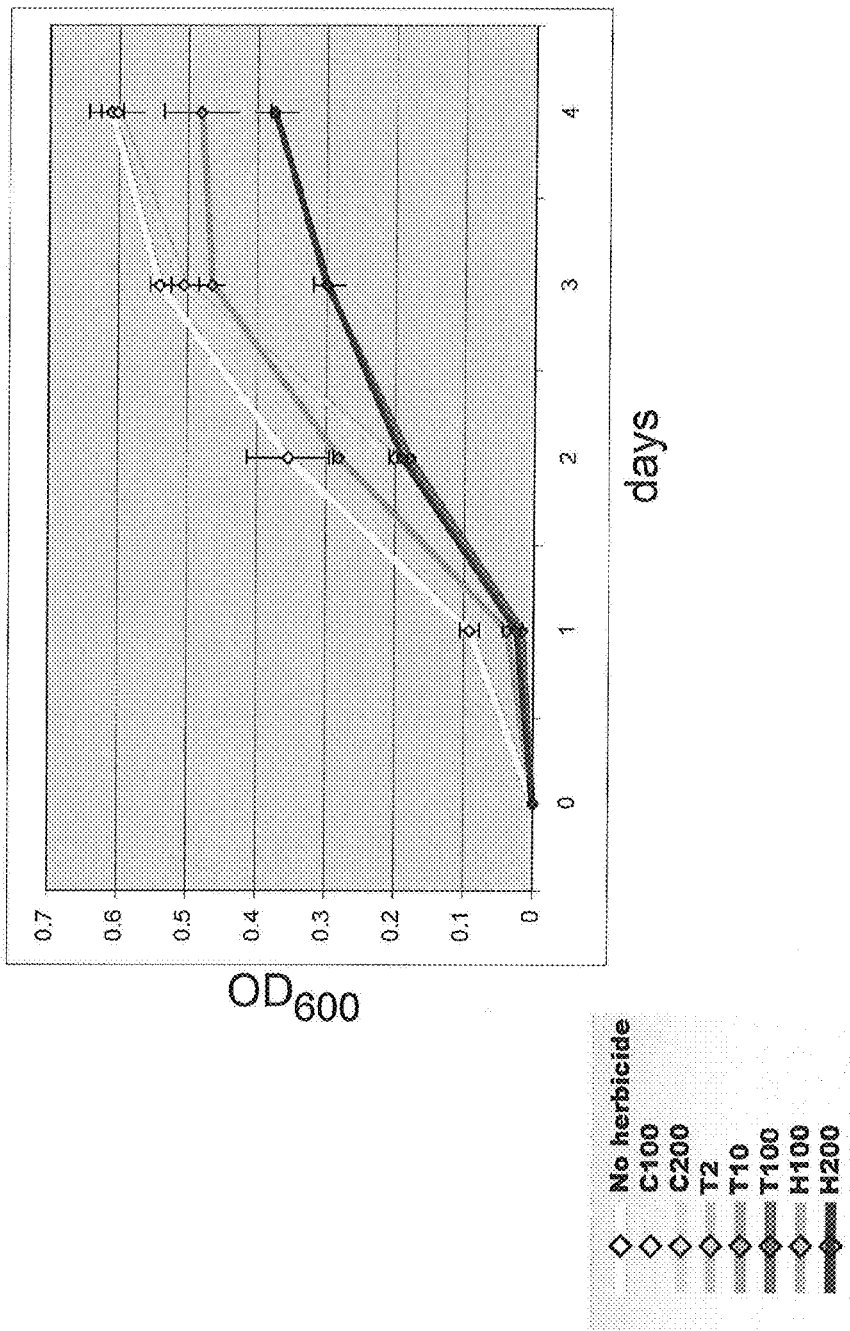
FIG. 89 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 90:
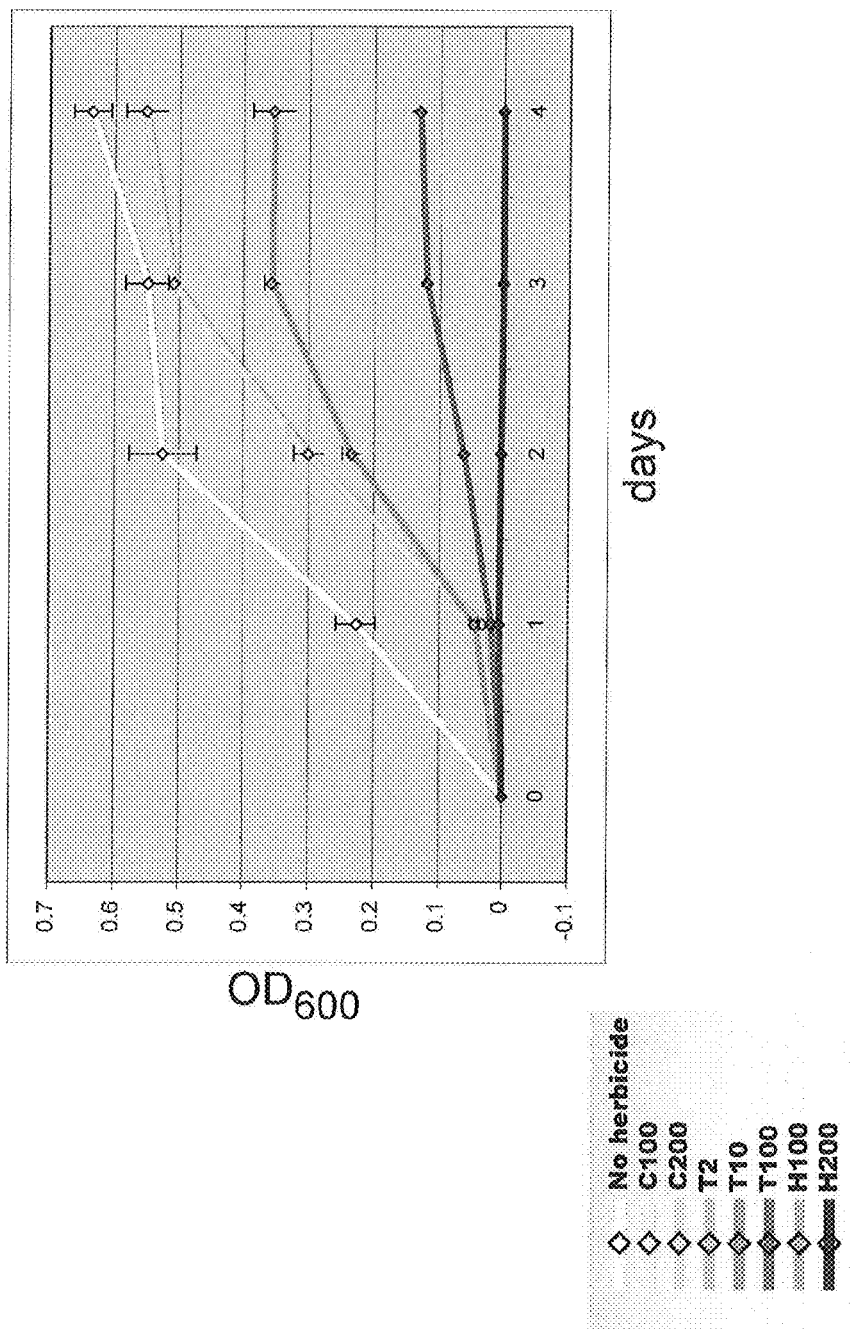
FIG. 90 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 91:
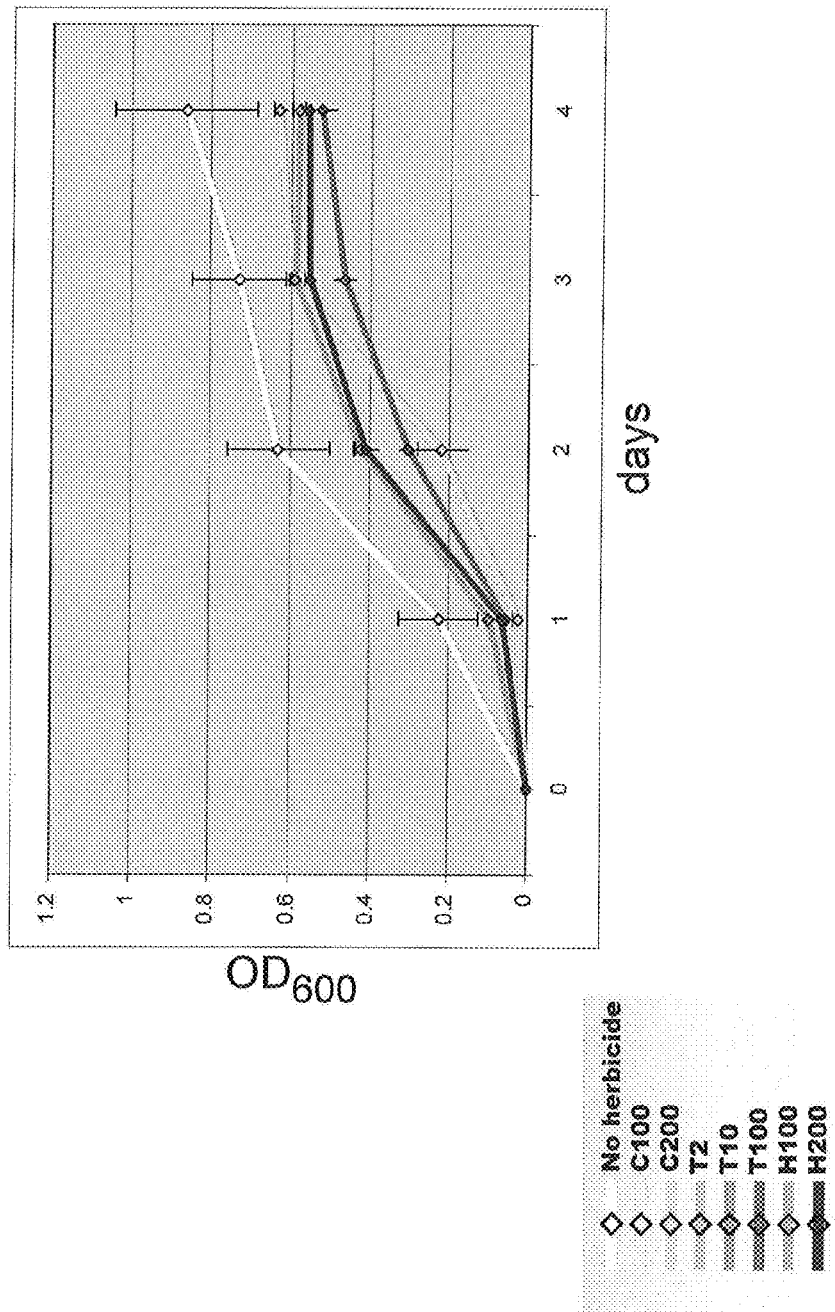
FIG. 91 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 92:
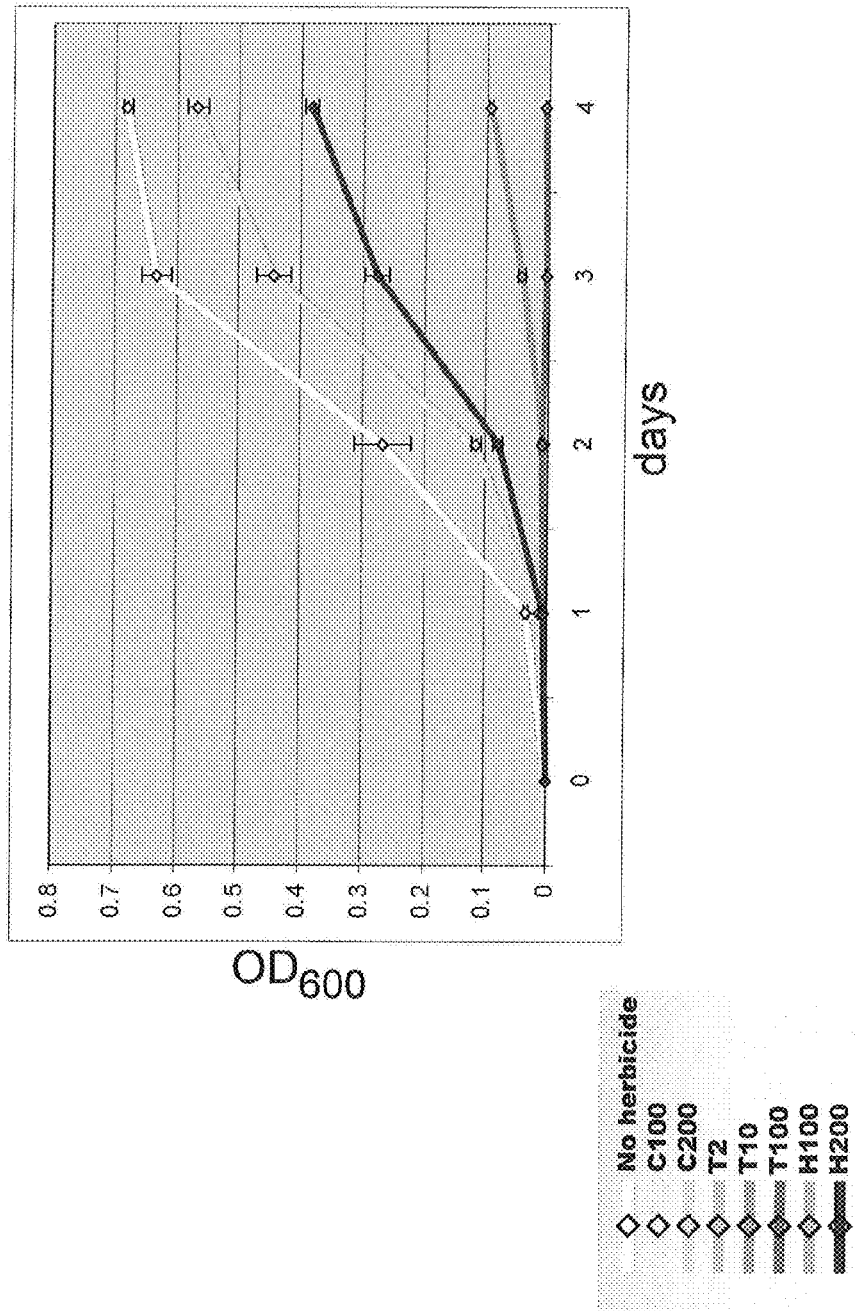
FIG. 92 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.
Figure 93:
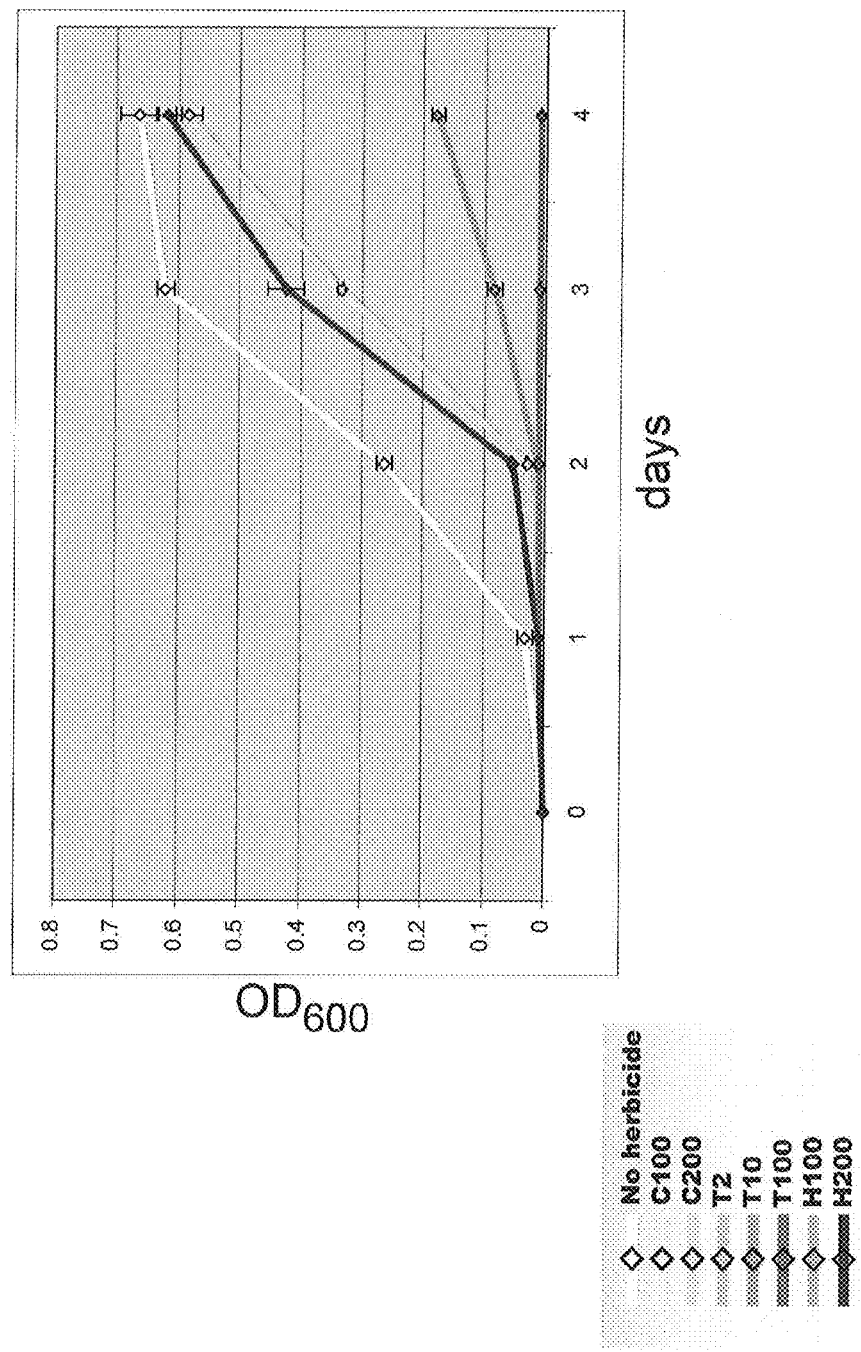
FIG. 93 is line graph showing the growth of yeast expressing a chimeric ACCase gene of the invention grown in the presence of the indicated herbicides. The growth is measured as the $OD_{600nm}$ (y-axis) as a function of time in days. The herbicides used are C=cycloxydim, T=tepraloxydim, and H=haloxyfop. The number is μM concentration. The mutation in the HSR is as indicated.

The OsJACCc60p40 control strain (RTP4107-5b-1) was unable to grow in the presence of any of the herbicides tested here (FIG. 13). All single mutants showed a certain degree of herbicide tolerance. The single mutants W1999G and V2098A were tested in triplicate with three independently obtained strains (FIGS. 14-19). The triplicates produced similar graphs. However, caution should be taken comparing across different strains. We aimed at starting all cultures with the same amount of cells, but the general fitness of cultures may differ depending on how long pre-cultures were in stationary phase prior to dilution into medium with herbicides. Growth should always be judged as relative growth compared to growth in medium without herbicide. The best single mutations conferring DIM resistance are D2078G, V2098A and V2098G. V2075M (and to a lesser extent V2075L) is a good mutation for growth in tepraloxydim medium, but not cycloxydim medium. This mutation has potential to be used in rotation with the I1781L mutation, for which it has been shown that it provides commercial tolerance to cycloxydim, but not tepraloxydim. Haloxyfop resistance is most pronounced in W1999G and C2088R mutants.

We isolated a large number of double mutants in which one mutation was never characterized as a single mutation. Therefore these mutations may not have contributed to resistance. The following table shows the relative change in tolerance to cycloxydim, tepraloxydim and haloxyfop due to the second, uncharacterized mutation as compared to the characterized mutation.

Table of changes in relative resistance to cycloxydim, tepraloxydim and haloxyfop between single mutants that have been fully characterized and double mutants that have an untested mutation in combination with the tested mutations listed.

| untested | tested | cycloxydim | tepraloxydim | haloxyfop |
|---|---|---|---|---|
| S1792L | V2049F | ND | ND | ND |
| Q1824P | D2078G | — | — | — |
| Q1824P | I1781L | — | — | — |
| A1837V | V2075I | ↑↑ | ↑↑ | ↑↑ |
| V1864F | I1781L | — | ↑↑ | ↓↓ (gone) |
| V1864F | W1999G | ↓↓ (gone) | ↑↑ | ↓↓ (gone) |
| W1999C | V2075I | ↑↑ | ↑↑ | ↑↑ |
| W1999I | V2049F | ND | ND | ND |
| W2027R | I1781L | ↓ | ↓↓ | ↓ |
| E2039G | D2078G | — | — | — |
| I2041V | D2078G | ↑↑ | ↑↑ | ↑↑ |
| V2049A | D2078G | ND | ND | ND |
| V2049C | D2078G | ↑ | ↑ | ↓↓ (gone) |
| V2049I | W1999G | — | ↑↑ | — |
| V2049L | V2098A | ↓↓ | ↓↓ | ↓↓ (gone) |
| V2049S | D2078G | ND | ND | ND |
| V2049T | D2078G | ↓ | ↑↑ | ↓↓ (gone) |
| dupIV2075 | I1781L | — | ↑↑ | — |
| S2079F | D2078G | ↓↓ | ↓↓ | ↓↓ |
| S2079P | D2078G | ↓ | ↓ | ↓ |
| K2080E | V2075M | — (none) | ↑↑ | ↑↑ |
| C2088F | V2049F | ND | ND | ND |

| | | | | |
|---|---|---|---|---|
| C2088F | V2098A | ↓ | ↓ | ↓ |
| C2088G | D2078G | — | ↑↑ | ↑ |
| C2088G | V2098G | ↓ | — | — (none) |
| C2088H | V2098A | ↑↑ | ↑↑ | ↑ |
| C2088H | V2098G | — | ↑↑ | ↑ |
| C2088K | V2098A | ↑↑ | — | — |
| C2088L | V2098A | ↑↑ | — | ↑ |
| C2088L | V2098G | ↓ | ↑ | — (none) |
| C2088S | V2098G | ↓ | — | — (none) |
| C2088T | V2098A | ND | ND | ND |
| C2088T | V2098G | — | ↑↑ | — (none) |
| C2088V | V2098G | ↓ | ↑ | ↑ |
| K2095E | V2075M | — (none) | ↑↑ | — |
| V2098C | C2088W | ↓↓ | ↑ | — (none) |

Grey boxes represent double mutants picked up from high concentration tepraloxydim plates (FIGS. 10 and 11).
ND = Not Determined;
— = no change in tolerance;
↓ = decrease in tolerance;
↑ = increase in tolerance.

Mutations Q1824P and E2039G did not seem to change herbicide tolerance and other mutations had a negative effect on herbicide tolerance (W2027R, V2049L, S2079F, S2079P, C2088F and C2088S). Mutations A1837V, V1864F, W1999C, I2041V, V2049C, V2049I, V2049T, duplication V2075, K2080E, C2088G, C2088H, C2088K, C2088L, C2088T, C2088V, K2095E and V2098C increased tolerance to at least one herbicide. In some cases there was an accompanying decrease in tolerance to (an)other herbicide(s) (V1864F, V2049C, V2049T, C2088L, C2088V and V2098C). Most notably the extra presence of V1864F completely eliminated the high tolerance that I1781L and W1999G single mutants displayed for haloxyfop. Such observations are important in light of possible rotation between DIMs or between DIMs and FOPs in cultivated, modified, non-GMO rice in the future. All isolations described here were selected on DIM plates. The V2075G mutant, which was isolated from cycloxydim plates, is the most "FOP-specific" mutation that was isolated. Mutants that are specifically tolerant to FOPs can be obtained by repeating all screenings described here and selecting on FOP plates.

Among the double mutants consisting of two separately-characterized single mutations, I1781L+V2075L, W1999G+V2075L and W1999G+V2098A were found to be fully resistant to ~150-200× the tepraloxydim concentration that completely halts growth of the OsJACCc60p40 control. These three double mutations were also highly resistant to cycloxydim and haloxyfop. Growth curves were made with three independently obtained strains (see Figures) and results were highly reproducible in multiple experiments (data not shown). These three double mutations, together with the V2075M single mutation, have been introduced in fully plastidic rice ACCase and can be used to generate transgenic plants, for example, transgenic corn. A1837V+V2075I, I1781L+V2049F, I1781L+V2098G, W1999G+D2078G, W1999C+V2075I and I2041V+D2078G may be also be used.

Additional double mutants that may be used include, but are not limited to, S1792L+V2049F, N1780D+I1781L, I1781V+V2049F, A1785G+D2078G, A1785G+V2098A, A1785G+V2098G, W1999L+V2049F, V2049A+D2078G, V2049F+C2088F, V2049S+D2078G, A2059G+D2078G, V2075L+C2088W and C2088T+V2098A.

The single mutants V2075L, V2098A and V2098G are the most tepraloxydim resistant single mutants, with V2075L exhibiting lesser tolerance to cycloxydim and V2098G exhibiting more. Double mutants containing W1999G in combination with I1781L and/or V2075L exhibited good tolerance. The double mutant W1999G V2075L is resistant to 100 μM tepraloxydim (compare to I1781L T100). W1999C appears to specifically provide tolerance to only FOPs.

REFERENCES

Beetham P R, Kipp P B, Sawycky X L, Arntzen C J and May G D (1999). A tool for functional plant genomics: Chimeric RNA/DNA oligonucleotides cause in vivo gene-specific mutations. *Proc Natl Acad Sci USA* 96: 8774-8778.

Chugh and Eudes (2008). Study of uptake of cell penetrating peptides and their cargoes in permeabilized wheat immature embryos. *FEBS J* 275: 2403-2014.

Delye C, Zhang X-Q, Chalopin C, Michel S and Powles S B (2003). An isoleucine residue within the carboxyltransferase domain of multidomain acetyl-coenzyme A carboxylase is a major determinant of sensitivity to aryloxyphenoxypropionate but not to cyclohexanedione inhibitors. *Plant Physiol* 132: 1716-1723.

Delye C, Zhang X-Q, Michel S, Matejicek A and Powles S B (2005). Molecular bases for sensitivity to acetyl-coenzyme A carboxylase inhibitors in Black-Grass. *Plant Physiol* 137: 794-806.

Gietz D, St Jean A, Woods R A and Schiestl G H (1992). Improved method for high efficiency transformation of intact yeast cells. *Nucl Acids Res* 20: 1425.

Hasslacher M, Ivessa A S, Paltauf F and Kohlwein S D (1993). Acetyl-CoA carboxylase from yeast is an essential enzyme and is regulated by factors that control phospholipid metabolism. *J Biol Chem* 268 (15):10946-10952.

Joachimiak M, Tevzadze G, Podkowinski J, Haselkorn R and Gornicki P (1997). Wheat cytosolic acetyl-CoA carboxylase complements an ACC1 null mutation in yeast. *Proc Natl Acad Sci USA* 94 (18): 9990-9995.

Liu W, Harrison D K, Chalupska K, Gornicki P, O-Donnell C C, Adkins S W, Haselkorn R and Williams R R (2007). Single-site mutations in the carboxyltransferase domain of plastid acetyl-CoA carboxylase confer resistance to grass-specific herbicides. *Proc Natl Acad Sci USA* 104: 3627-3632.

Mumberg D, Müller R and Funk M (1995). Yeast vectors for the controlled expression of heterologous proteins in different genetic backgrounds. *Gene* 156, 119-122.

Nikolau B J, Ohlrogge J B and Wurtele E S (2003). Plant biotin-containing carboylases. *Arch Biochem Biophys* 414:211-222.

Nikolskaya T, Zagnitko O, Tevzadze G, Haselkorn R, and Gornick P (1999) Herbicide sensitivity determinant of wheat plastid acetyl-CoA carboxylase is located in a 400-amino acid fragment of the carboxyltransferase domain. *Proc Natl Acad Sci USA* 96 (25): 14647-14651.

Podkowinski J, Jelenska J, Sirikhachornkit A, Zuther E, Halekorn R and Gornicki P (2003). Expression of cytosolic and plastid acetyl-coenzyme A carboxylase genes in young wheat plants. *Plant Physiol* 131(2):763-772.

Schneiter R, Hitomi M. Ivessa A S, Fasch E V, Kohlwein S D and Tartakoff A M (1996) A yeast acetyl coenzyme A carboxylase mutant links very-long-chain fatty acid synthesis to the structure and function of the nuclear membrane-pore complex. *Mol Cell Biol* 16: 7161-7172.

Shivrain V K, Burgos N R, Anders M M, Rajguru S N, Moore J and Sales M A (2007). Gene flow between CLEARFIELD® rice and red rice. *Crop Protection* 26: 349-356.

Somers D A (1996). Aryloxyphenoxypropionate- and cyclohexanedione-resistant crops. Duke S O. (Editor) In: Herbicide-Resistant Crops Agricultural, Environmental, Economic, Regulatory and Technical Aspects, Duke S O (Editor), CRC Press, New York, (1996). pp. 175-187188

Tong A H, Evangelista M, Parsons A B, Xu H, Bader G D, Pagé N, Robinson M, Raghibizadeh S, Hogue C W, Bussey H, Andrews B, Tyers M and Boone C (2001). Systematic genetic analysis with ordered arrays of yeast deletion mutants. *Science* 294 (5550): 2364-2368.

Tong A H and Boone C (2006). Synthetic genetic array analysis in *Saccharomyces cerevisiae*. *Methods Mol Biol* 313:171-92.

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference.

We claim:

1. A method of producing an acetyl-CoA carboxylase (ACCase) enzyme that is tolerant to at least one herbicide, comprising:

a. providing a yeast knockout complement comprising an ACCase-deficient yeast into which has been introduced a nucleic acid encoding a chimeric ACCase, said chimeric ACCase comprising an N-terminal region and a C-terminal region, wherein the C-terminal region comprises a wild-type herbicide sensitive sensitivity region (HSR) of a monocot plastidic ACCase of an *Oryza* species, and wherein the chimeric ACCase being herbicide sensitive;

b. mutagenizing said yeast knockout complement under conditions that permit mutagenesis of at least one codon of the nucleic acid encoding the HSR of the chimeric ACCase to form a mutagenized yeast, and growing the mutagenized yeast thereby forming a library of mutagenized yeast colonies;

c. culturing the mutagenized yeast colonies in the presence of at least one ACCase-inhibiting herbicide to form treated colonies; and d. isolating from at least one of said treated colonies at least one mutagenized yeast that grows in the presence of the herbicide, wherein the mutagenized yeast that grows in the presence of the herbicide comprises a mutagenized chimeric ACCase that has a tolerance to the herbicide that is greater than that exhibited by the chimeric ACCase of step (a), wherein the method is a high throughput method in which one trained worker can generate and screen at least 500 different herbicide-sensitive-region (HSR)-variant ACCases, each from its own cell colony, in one month.

2. The method according to claim 1, wherein the nucleic acid encoding the chimeric ACCase is a single-copy plasmid.

3. The method according to claim 1, wherein the herbicide sensitivity region comprises an amino acid sequence corresponding to residues: 1654(Am) to 2204(Am), 1654(Am) to 2130(Am), 1654(Am) to 2098(Am), 1750(Am) to 2204 (Am), 1750(Am) to 2130(Am), 1750(Am) to 2098(Am), 1781 (Am) to 2204(Am), 1781(Am) to 2130 (Am), or 1781(Am) to 2098 (Am), wherein (Am) refers to the amino acid numbering of the plastidic ACCase of *Alopecurus myosuroides*.

4. The method of claim 1, wherein said ACCase-deficient yeast comprises a mutation of the genomic yeast ACCase gene selected from the group consisting of a single point mutations, multiple point mutations, a partial deletion, a partial knockout, a complete deletion and a complete knockout.

5. The method of claim 1, wherein said N-terminal region is derived from a yeast or fungus genus ACCase, the yeast or fungus being selected from the group consisting of *Saccharomyces, Schizosaccharomyces, Candida, Ascomycetes Neurospora, Kluyveromyces, Pichia, Cryptococcus, Chrysosporium, Yarrowia, Arxula*, and *Hansenula*.

6. The method of claim 1, wherein said herbicide is an aryloxyphenoxypropionate (FOP) or cyclohexanedione (DIM) herbicide.

7. The method of claim 6, wherein said FOP herbicide is selected from the group consisting of cyhalofop, quizalofop, diclofop, clodinafop, fluazifop, metamifop, propaquizafop, and fenoxyprop herbicides.

8. The method of claim 6, wherein said DIM herbicide is selected from the group consisting of alloxydim, butroxydim, clethodim, cycloxydim, tepraloxydim, sethoxydim, tralkoxydim, and profoxydim herbicides.

9. The method of claim 1, wherein said herbicide is present at a concentration from about 0.02 μM to about 200 μM.

10. The method of claim 1, wherein said yeast is cultured, in step (c), at a temperature of about 23° C. to about 30° C.

11. The method of claim 1, wherein said yeast is cultured, in step (c), in liquid media.

12. The method of claim 1, wherein said yeast is cultured, in step (c), on solid phase media.

* * * * *